US007767687B2

(12) United States Patent
Oslob et al.

(10) Patent No.: US 7,767,687 B2
(45) Date of Patent: Aug. 3, 2010

(54) PYRIDO PYRIMIDINONES, DIHYDRO PYRIMIDO PYRIMIDINONES AND PTERIDINONES USEFUL AS RAF KINASE INHIBITORS

(75) Inventors: Johan D. Oslob, Sunnyvale, CA (US);
Jiang Zhu, Palo Alto, CA (US);
Kenneth Barr, San Francisco, CA (US);
Jennifer Cossrow, San Mateo, CA (US);
Brian Raimundo, San Francisco, CA (US); Hiroko Tanaka, Foster City, CA (US)

(73) Assignees: Biogen Idec MA Inc., Cambridge, MA (US); Sunesis Pharmaceuticals, Inc., South San Francisco, CA (US)

( * ) Notice: Subject to any disclaimer, the term of this patent is extended or adjusted under 35 U.S.C. 154(b) by 410 days.

(21) Appl. No.: 11/301,311

(22) Filed: Dec. 12, 2005

(65) Prior Publication Data
US 2006/0211702 A1    Sep. 21, 2006

Related U.S. Application Data

(60) Provisional application No. 60/635,644, filed on Dec. 13, 2004, provisional application No. 60/636,740, filed on Dec. 16, 2004.

(51) Int. Cl.
C07D 471/04    (2006.01)
C07D 487/04    (2006.01)
C07D 473/40    (2006.01)
C07D 473/00    (2006.01)
A61K 31/519   (2006.01)
C07D 475/00    (2006.01)

(52) U.S. Cl. .................... 514/264.1; 544/279; 544/264; 544/257

(58) Field of Classification Search ................. 544/279, 544/264; 514/258.1, 275, 264.1
See application file for complete search history.

(56) References Cited

U.S. PATENT DOCUMENTS 6,331,538 B1    12/2001    Domagala et al. ........ 514/224.5

(Continued)

FOREIGN PATENT DOCUMENTS

WO           95/31469        11/1995

(Continued)

OTHER PUBLICATIONS

Erza, et al., "A Peptide Pro-Drug Approach for Improving Bisphosphonate Oral Absorption", J. Med. Chem. (2000), v. 43, pp. 3641-3652.

Gangwar, et al., "Synthesis of a Novel Esterase-Sensitive Cyclic Prodrug of a Hexapeptide Using an (Acyloxy) Alkoxy Promoiety", J. Org. Chem (1997), v. 62, pp. 1356-1362.
Magnuson, et al., "The Raf-1 Serine/Threonine Protein Kinase", Seminars in Cancer Biology (1994), v. 5, pp. 247-253.

(Continued)

*Primary Examiner*—James O Wilson
*Assistant Examiner*—Cecilia M Jaisle
(74) *Attorney, Agent, or Firm*—Andrea L. C. Robidoux; Emilie Porter Huck; Choate, Hall & Stewart LLP

(57)    ABSTRACT

The present invention provides compounds having the formula:

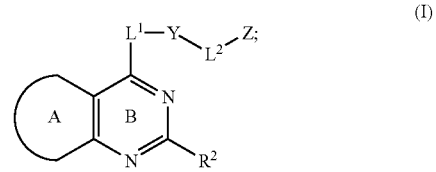

wherein A-B together represent one of the following structures:

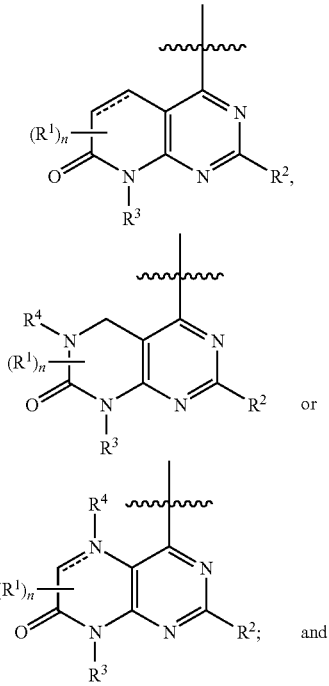

n, $R^1$, $R^2$, $R^3$, $R^4$, $L^1$, $L^2$, Y and Z are as defined in classes and subclasses herein, and pharmaceutical compositions thereof, as described generally and in subclasses herein, which compounds are useful as inhibitors of protein kinase (e.g., RAF), and thus are useful, for example, for the treatment of RAF mediated diseases.

60 Claims, 3 Drawing Sheets

U.S. PATENT DOCUMENTS

| | | |
|---|---|---|
| 6,534,510 B2 | 3/2003 | Barrow et al. .......... 514/255.05 |
| 6,825,199 B2 | 11/2004 | Domagala et al. ...... 514/252.16 |
| 2003/0003634 A1 | 1/2003 | Lowrey et al. .............. 438/133 |
| 2003/0055250 A1 | 3/2003 | Bonnert et al. |
| 2003/0114671 A1 | 6/2003 | Chen .......................... 544/184 |
| 2003/0199526 A1 | 10/2003 | Choquette et al. |
| 2004/0038992 A1 | 2/2004 | Bemis et al. |
| 2004/0044012 A1 | 3/2004 | Dobrusin et al. ......... 514/262.1 |
| 2004/0116697 A1 | 6/2004 | Adams et al. |
| 2004/0142945 A1 | 7/2004 | Barbosa et al. .......... 514/262.1 |
| 2004/0224958 A1 | 11/2004 | Booth et al. ........... 514/252.16 |

FOREIGN PATENT DOCUMENTS

| | | |
|---|---|---|
| WO | WO98/08846 | 3/1998 |
| WO | WO99/21840 | 5/1999 |
| WO | WO99/51613 | 10/1999 |
| WO | WO99/61444 | 12/1999 |
| WO | WO01/55148 A1 | 8/2001 |
| WO | 01/64679 | 9/2001 |
| WO | WO01/70229 A1 | 9/2001 |
| WO | WO02/30934 A1 | 4/2002 |
| WO | 02/076954 | 10/2002 |
| WO | WO02/076954 A1 | 10/2002 |
| WO | WO02/102315 A2 | 12/2002 |
| WO | WO2005/009967 A2 | 2/2005 |

OTHER PUBLICATIONS

Wang, et al., "Synthesis of a Novel Esterase-Sensitive Cyclic Prodrug System for Peptides that Utilizes a "Trimethyl Lock"-Facilitated Lacotonization Reaction", J. Org. Chem (1997), v. 62, pp. 1363-1367.

Lehbauer, et al. "Nucleotides. Part LXIX. Synthesis of phosphoramidite building blocks of isoxanthopterin N8-(2'-deoxy-beta-D-ribonucleosides): new fluorescence markers for oligonucleotide synthesis," Helv. Chim. Acta 84: 2330-2342 (2001).

International Search Report for PCT/US05/44804, mailed on May 17, 2006.

PYRIDO PYRIMIDINONES, DIHYDRO PYRIMIDO PYRIMIDINONES AND PTERIDINONES USEFUL AS RAF KINASE INHIBITORS

PRIORITY

The present application claims priority under 35 U.S.C. 119(e) to U.S. Provisional Patent Application Nos. 60/635,644 filed Dec. 13, 2004 and 60/636,740 filed Dec. 16, 2004; The entire contents of each of these applications are incorporated herein by reference.

BACKGROUND OF THE INVENTION

Cancer results from the deregulation of the normal processes that control cell division, differentiation and apoptotic cell death. Protein kinases play a critical role in this regulatory process. A partial non-limiting list of such kinases includes abl, ATK, bcr-ab1, Blk, Brk, Btk, c-kit, c-met, c-src, CDK1, CDK2, CDK4, CDK6, cRaf1, CSF1R, CSK, EGFR, ErbB2, ErbB3, ErbB4, ERK, Fak, fes, FGFR1, FGFR2, FGFR3, FGFR4, FGFR5, Fgr, FLK4, flt-1, Fps, Frk, Fyn, Hck, IGF-1R, INS-R, Jak, KDR, Lck, Lyn, MEK, p38, PDGFR, PIK, PKC, PYK2, ros, tie.sub.1, tie.sub.2, TRK, Yes and Zap70. In mammalian biology, such protein kinases comprise mitogen activated protein kinase (MAPK) signalling pathways. MAPK signalling pathways are inappropriately activated by a variety of common disease-associated mechanisms such as mutation of ras genes and deregulation of growth factor receptors (Magnuson et al., Seminars in Cancer Biology; 1994 (5), 247-252).

Additionally, protein kinases have been implicated as targets in central nervous system disorders (such as Alzheimer's), inflammatory disorders (such as psoriasis), bone diseases (such as osteoporosis), atheroscleroses, restenosis, thrombosis, metabolic disorders (such as diabetes) and infectious diseases (such as viral and fungal infections).

One of the most commonly studied pathways involving kinase regulation is cellular signalling from receptors at the cell surface to the nucleus. One example of this pathway includes a cascade of kinases in which members of the Growth Factor receptor Tyrosine Kinases (such as EGF-R, PDGF-R, VEGF-R, IGF1-R, the Insulin receptor), deliver signals through phosphorylation to other kinases such as Src Tyrosine kinase, and the Raf, Mek and Erk serine/threonine kinase families. Each of these kinases is represented by several family members which play related, but functionally distinct roles. The loss of regulation of the growth factor signalling pathway is a frequent occurrence in cancer as well as other disease states.

The signals mediated by kinases have also been shown to control growth, death and differentiation in the cell by regulating the processes of the cell cycle. Progression through the eukaryotic cell cycle is controlled by a family of kinases called cyclin dependent kinases (CDKs). The regulation of CDK activation is complex, but requires the association of the CDK with a member of the cyclin family of regulatory subunits. A further level of regulation occurs through both activating and inactivating phosphorylations of the CDK subunit. The coordinate activation and inactivation of different cyclin/CDK complexes is necessary for normal progression through the cell cycle. Both the critical G1-S and G2-M transitions are controlled by the activation of different cyclin/CDK activities. In G1, both cyclin D/CDK4 and cyclin E/CDK2 are thought to mediate the onset of S-phase. Progression through S-phase requires the activity of cyclin A/CDK2 whereas the activation of cyclin A/cdc2 (CDK1) and cyclin B/cdc2 are required for the onset of metaphase. It is not surprising, therefore, that the loss of control of CDK regulation is a frequent event in hyperproliferative diseases and cancer.

Raf protein kinases are key components of signal transduction pathways by which specific extracellular stimuli elicit precise cellular responses in mammalian cells. Activated cell surface receptors activate ras/rap proteins at the inner aspect of the plasmamembrane which in turn recruit and activate Raf proteins. Activated Raf proteins phosphorylate and activate the intracellular protein kinases MEK1 and MEK2. In turn, activated MEKs catalyse phosphorylation and activation of p42/p44 mitogen-activated protein kinase (MAPK). A variety of cytoplasmic and nuclear substrates of activated MAPK are known which directly or indirectly contribute to the cellular response to environmental change. Three distinct genes have been identified in mammals that encode Raf proteins; A-Raf, B-Raf and C-Raf (also known as Raf-1) and isoformic variants that result from differential splicing of mRNA are known.

Inhibitors of Raf kinases have been suggested for use in disruption of tumor cell growth and hence in the treatment of cancers, e.g. histiocytic lymphoma, lung adenocarcinoma, small cell lung cancer and pancreatic and breast carcinoma; and also in the treatment and/or prophylaxis of disorders associated with neuronal degeneration resulting from ischemic events, including cerebral ischemia after cardiac arrest, stroke and multi-infarct dementia and also after cerebral ischemic events such as those resulting from head injury, surgery and/or during childbirth.

Accordingly, there is a great need to develop compounds useful as inhibitors of protein kinases. In particular, it would be desirable to develop compounds that are useful as RAF inhibitors.

SUMMARY OF THE INVENTION

As discussed above, there remains a need for the development of novel therapeutic agents and agents useful for treating disorders mediated by RAF. In certain embodiments, the present invention provides novel compounds having the structure:

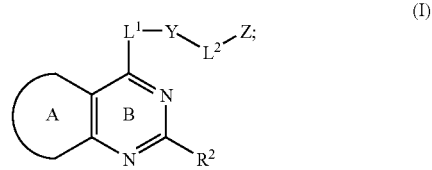

wherein A-B together represent one of the following structures:

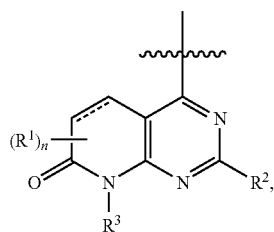

-continued

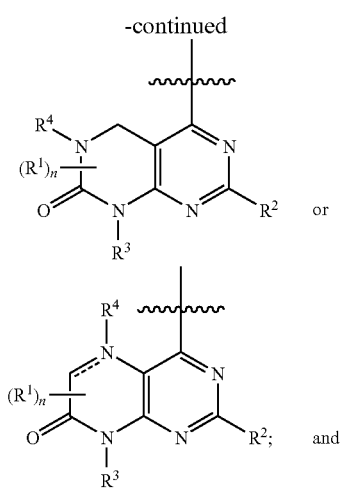

n, $R^1$, $R^2$, $R^3$, $R^4$, $L^1$, $L^2$, Y and Z are as defined in classes and subclasses herein, and pharmaceutical compositions thereof, as described generally and in subclasses herein, which compounds are useful as inhibitors of protein kinase (e.g., RAF), and thus are useful, for example, for the treatment of RAF mediated diseases.

In certain other embodiments, the invention provides pharmaceutical compositions comprising an inventive compound, wherein the compound is present in an amount effective to inhibit RAF activity. In certain other embodiments, the invention provides pharmaceutical compositions comprising an inventive compound and optionally further comprising an additional therapeutic agent. In yet other embodiments, the additional therapeutic agent is an agent for the treatment of cancer.

In yet another aspect, the present invention provides methods for inhibiting kinase activity (e.g., RAF) activity in a patient or a biological sample, comprising administering to said patient, or contacting said biological sample with an effective inhibitory amount of a compound of the invention. In still another aspect, the present invention provides methods for treating any disorder involving RAF activity, comprising administering to a subject in need thereof a therapeutically effective amount of a compound of the invention.

DEFINITIONS

Figure 1:
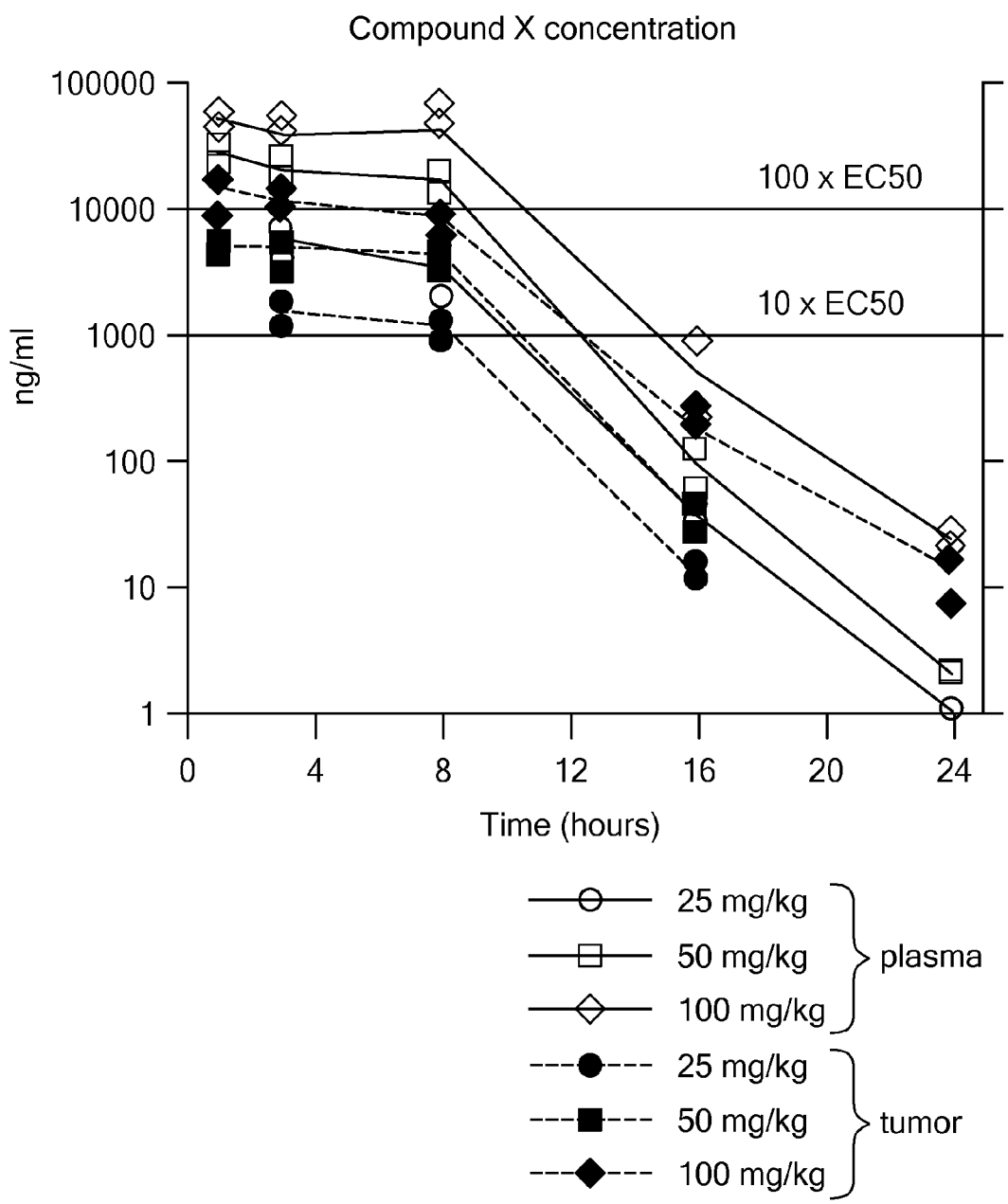
FIG. 1 depicts exemplary compound concentration experiments in mouse plasma (solid lines) and tumor tissue (dashed lines) at 1, 3, 8, 16, and 24 hours following a single oral dose of 25 (blue), 50 (red), or 100 (green) mg/kg compound X.

It is understood that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic, carbon and heteroatom substituents of organic compounds. For purposes of this invention, heteroatoms such as nitrogen may have hydrogen substituents and/or any permissible substituents of organic compounds described herein which satisfy the valencies of the heteroatoms. Combinations of substituents and variables envisioned by this invention are preferably those that result in the formation of stable compounds useful in the treatment and prevention, for example of disorders, as described generally above. Examples of substituents include, but are not limited to aliphatic; heteroaliphatic; alicyclic; heteroalicyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; - or -$GR^{G1}$ wherein G is —O—, —S—, —$NR^{G2}$—, —C(=O)—, —S(=O)—, —$SO_2$—, —C(=O)O—, —C(=O)$NR^{G2}$—, —OC(=O)—, —$NR^{G2}$C(=O)—, —OC(=O)O—, —OC(=O)$NR^{G2}$—, —$NR^{G2}$C(=O)O—, —$NR^{G2}$C(=O)$NR^{G3}$—, —C(=S)—, —C(=S)S—, —SC(=S)—, —SC(=S)S—, —C(=$NR^{G2}$)—, —C(=$NR^{G2}$)O—, —C(=$NR^{G2}$)$NR^{G3}$—, —OC(=$NR^{G2}$)—, —$NR^{G2}$C(=$NR^{G3}$)—, —$NR^{G2}SO_2$—, —$NR^{G2}SO_2NR^{G3}$—, or —$SO_2NR^{G2}$—, wherein each occurrence of $R^{G1}$, $R^{G2}$ and $R^{G3}$ independently includes, but is not limited to, hydrogen, halogen, or an optionally substituted aliphatic, heteroaliphatic, alicyclic, heteroalicyclic, aromatic, heteroaromatic, aryl, heteroaryl, alkylaryl, or alkylheteroaryl moiety. Additional examples of generally applicable substituents are illustrated by the specific embodiments shown in the Examples that are described herein.

The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having about 1-6 carbon atoms.

In certain embodiments, the alkyl, alkenyl and alkynyl groups employed in the invention contain about 1-20 or 2-20 aliphatic carbon atoms. In certain other embodiments, the alkyl, alkenyl, and alkynyl groups employed in the invention contain about 1-10 or 2-10 aliphatic carbon atoms. In yet other embodiments, the alkyl, alkenyl, and alkynyl groups employed in the invention contain about 1-8 or 2-8 aliphatic carbon atoms. In still other embodiments, the alkyl, alkenyl, and alkynyl groups employed in the invention contain about 1-6 or 2-6 aliphatic carbon atoms. In yet other embodiments, the alkyl, alkenyl, and alkynyl groups employed in the invention contain about 1-4 or 2-4 aliphatic carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —$CH_2$-cyclopropyl, cyclobutyl, —$CH_2$-cyclobutyl, cyclopentyl, —$CH_2$-cyclopentyl-n, cyclohexyl, —$CH_2$-cyclohexyl, cyclohexenylethyl, cyclohexanylethyl, norborbyl moieties and the like, which again, may bear one or more substituents.

The term "cycloalkyl", as used herein, refers specifically to cyclic alkyl groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, heteroaliphatic or heterocyclic moieties, may optionally be substituted. An analogous convention applies to other generic terms such as "cycloalkenyl", "cycloalkynyl" and the like.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, i.e., in place of carbon atoms. Thus, a 1-6 atom heteroaliphatic linker having at least one N atom in the heteroaliphatic main chain, as used herein, refers to a $C_{1-6}$ aliphatic chain wherein at least one carbon atom is replaced with a nitrogen atom, and wherein any one or more of the remaining 5 carbon atoms may be replaced by an oxygen, sulfur, nitrogen, phosphorus or silicon atom. As used herein, a 1-atom heteroaliphatic linker having at least one N atom in the heteroaliphatic main chain refers to —NH— or —NR— where R is aliphatic, heteroaliphatic, acyl, aromatic, heteroaromatic or a nitrogen protecting group. Heteroaliphatic moieties may be branched or linear unbranched. In certain embodiments, heteroaliphatic moieties are substituted by independent replacement of one or more of the hydrogen atoms thereon with one or more moieties including, any of the substituents described above.

The term "heteroalicyclic", "heterocycloalkyl" or "heterocyclic", as used herein, refers to compounds which combine the properties of heteroaliphatic and cyclic compounds and include but are not limited to saturated and unsaturated mono- or polycyclic heterocycles such as morpholino, pyrrolidinyl, furanyl, thiofuranyl, pyrrolyl etc., which are optionally substituted with one or more functional groups, as defined herein. In certain embodiments, the term "heterocyclic" refers to a non-aromatic 5-, 6- or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 2 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to an aryl or heteroaryl ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

Additionally, it will be appreciated that any of the alicyclic or heteroalicyclic moieties described above and herein may comprise an aryl or heteroaryl moiety fused thereto. Additional examples of generally applicable substituents are illustrated by the specific embodiments shown in the Examples that are described herein.

In general, the term "aromatic moiety", as used herein, refers to stable substituted or unsubstituted unsaturated mono- or polycyclic hydrocarbon moieties having preferably 3-14 carbon atoms, comprising at least one ring satisfying the Huckel rule for aromaticity. Examples of aromatic moieties include, but are not limited to, phenyl, indanyl, indenyl, naphthyl, phenanthryl and anthracyl.

In general, the term "heteroaromatic moiety", as used herein, refers to stable substituted or unsubstituted unsaturated mono-heterocyclic or polyheterocyclic moieties having preferably 3-14 carbon atoms, comprising at least one ring satisfying the Huckel rule for aromaticity. Examples of heteroaromatic moieties include, but are not limited to, pyridyl, quinolinyl, dihydroquinolinyl, isoquinolinyl, quinazolinyl, dihydroquinazolyl, and tetrahydroquinazolyl.

It will also be appreciated that aromatic and heteroaromatic moieties, as defined herein, may be attached via an aliphatic (e.g., alkyl) or heteroaliphatic (e.g., heteroalkyl) moiety and thus also include moieties such as -(aliphatic)aromatic, -(heteroaliphatic)aromatic, -(aliphatic)heteroaromatic, -(heteroaliphatic)heteroaromatic, -(alkyl)aromatic, (heteroalkyl)aromatic, -(alkyl)heteroaromatic, and -(heteroalkyl)heteroaromatic moieties. Thus, as used herein, the phrases "aromatic or heteroaromatic moieties" and "aromatic, heteroaromatic, -(alkyl)aromatic, -(heteroalkyl)aromatic, -(heteroalkyl)heteroaromatic, and -(heteroalkyl)heteroaromatic" are interchangeable. Substituents include, but are not limited to, any of the previously mentioned substituents resulting in the formation of a stable compound.

In general, the term "aryl" refers to aromatic moieties, as described above, excluding those attached via an aliphatic (e.g., alkyl) or heteroaliphatic (e.g., heteroalkyl) moiety. In certain embodiments of the present invention, "aryl" refers to a mono- or bicyclic carbocyclic ring system having one or two rings satisfying the Huckel rule for aromaticity, including, but not limited to, phenyl, naphthyl, tetrahydronaphthyl, indanyl, indenyl and the like.

Similarly, the term "heteroaryl" refers to heteroaromatic moieties, as described above, excluding those attached via an aliphatic (e.g., alkyl) or heteroaliphatic (e.g., heteroalkyl) moiety. In certain embodiments of the present invention, the term "heteroaryl", as used herein, refers to a cyclic unsaturated radical having from about five to about ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

Substituents for aryl and heteroaryl moieties include, but are not limited to, any of the previously mentioned substitutents, i.e., the substituents recited for aliphatic moieties, or for other moieties as disclosed herein, resulting in the formation of a stable compound.

The terms "alkoxy" (or "alkyloxy"), and "thioalkyl" as used herein refers to an alkyl group, as previously defined, attached to the parent molecular moiety through an oxygen atom ("alkoxy") or through a sulfur atom ("thioalkyl"). In certain embodiments, the alkyl group contains about 1-20 aliphatic carbon atoms. In certain other embodiments, the alkyl group contains about 1-10 aliphatic carbon atoms. In yet other embodiments, the alkyl group contains about 1-8 aliphatic carbon atoms. In still other embodiments, the alkyl group contains about 1-6 aliphatic carbon atoms. In yet other embodiments, the alkyl group contains about 1-4 aliphatic carbon atoms. Examples of alkoxy groups, include but are not limited to, methoxy, ethoxy, propoxy, isopropoxy, n-butoxy, tert-butoxy, neopentoxy and n-hexoxy. Examples of thioalkyl groups include, but are not limited to, methylthio, ethylthio, propylthio, isopropylthio, n-butylthio, and the like.

The term "amine" refers to a group having the structure —N($R_X$)$_2$ wherein each occurrence of $R_X$ is independently hydrogen, or an aliphatic, heteroaliphatic, aromatic or heteroaromatic moiety, or the $R_X$ groups, taken together, may form a heterocyclic moiety.

The term "alkylamino" refers to a group having the structure —NH$R_X$ wherein $R_X$ is alkyl, as defined herein. The term "aminoalkyl" refers to a group having the structure H$_2$N$R_X$—, wherein $R_X$ is alkyl, as defined herein. In certain embodiments, the alkyl group contains about 1-20 or 2-20 aliphatic carbon atoms. In certain other embodiments, the alkyl group contains about 1-10 or 2-10 aliphatic carbon atoms. In yet other embodiments, the alkyl, alkenyl, and alkynyl groups employed in the invention contain about 1-8 or 2-8 aliphatic carbon atoms. In still other embodiments, the alkyl group contains about 1-6 or 2-6 aliphatic carbon atoms. In yet other embodiments, the alkyl group contains about 1-4 or 2-4 aliphatic carbon atoms. Examples of alkylamino include, but are not limited to, methylamino, ethylamino, iso-propylamino and the like.

The terms "halo" and "halogen" as used herein refer to an atom selected from fluorine, chlorine, bromine and iodine.

The term "halogenated" denotes a moiety having one, two, or three halogen atoms attached thereto.

The term "haloalkyl" denotes an alkyl group, as defined above, having one, two, or three halogen atoms attached thereto and is exemplified by such groups as chloromethyl, bromoethyl, trifluoromethyl, and the like.

The term "acyloxy", as used herein, does not substantially differ from the common meaning of this term in the art, and refers to a moiety of structure —OC(O)$R_X$, wherein $R_X$ is a substituted or unsubstituted aliphatic, alicyclic, heteroaliphatic, heteroalicyclic, aryl or heteroaryl moiety.

The term "acyl", as used herein, does not substantially differ from the common meaning of this term in the art, and refers to a moiety of structure —C(O)$R_X$, wherein $R_X$ is a substituted or unsubstituted, aliphatic, alicyclic, heteroaliphatic, heteroalicyclic, aryl or heteroaryl moiety.

The term "imino", as used herein, does not substantially differ from the common meaning of this term in the art, and refers to a moiety of structure —C(=N$R_X$)$R_Y$, wherein $R_X$ is hydrogen or an optionally substituted aliphatic, alicyclic, heteroaliphatic, heteroalicyclic, aryl or heteroaryl moiety; and $R_Y$ is an optionally substituted aliphatic, alicyclic, heteroaliphatic, heteroalicyclic, aryl or heteroaryl moiety.

The term "$C_{1-6}$alkylene", as used herein, refers to a substituted or unsubstituted, linear or branched saturated divalent radical consisting solely of carbon and hydrogen atoms, having from one to six carbon atoms, having a free valence "-" at both ends of the radical.

The term "$C_{2-6}$alkenylene", as used herein, refers to a substituted or unsubstituted, linear or branched unsaturated divalent radical consisting solely of carbon and hydrogen atoms, having from two to six carbon atoms, having a free valence "-" at both ends of the radical, and wherein the unsaturation is present only as double bonds and wherein a double bond can exist between the first carbon of the chain and the rest of the molecule.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heterocyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aromatic", "heteroaromatic", "aryl", "heteroaryl" and the like, used alone or as part of a larger moiety, encompass both substituted and unsubstituted groups.

As used herein, the term "isolated", when applied to the compounds of the present invention, refers to such compounds that are (i) separated from at least some components with which they are associated in nature or when they are made and/or (ii) produced, prepared or manufactured by the hand of man.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety that is susceptible to removal in vivo yielding the parent molecule as the pharmacologically active species. An example of a pro-drug is an ester which is cleaved in vivo to yield a compound of interest. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

The term "RAF-mediated disease" or "RAF-mediated condition", as used herein, means any disease or other deleterious condition in which RAF is known to play a role. The terms "RAF-mediated disease" or "RAF-mediated condition" also mean those diseases or conditions that are alleviated by treatment with an RAF inhibitor. Such conditions include, without limitation, colon, breast, gastric, ovarian, lung, brain, larynx, cervical, renal, lymphatic system, genitourinary tract (including bladder and prostate), stomach, bone, lymphoma, melanoma, glioma, papillary thyroid, neuroblastoma, and pancreatic cancer. The term "RAF-mediated disease", as used herein, means any disease or other deleterious condition or disease in which RAF is known to play a role. Such diseases or conditions include, without limitation, cancers such as colon and breast cancer.

The term "treating" or "treated", as used herein, refers to reversing, alleviating, inhibiting the progress of, or preventing the disease, disorder or condition to which such term applies, or one or more symptoms of such disorder or condition. The term "treatment", as used herein, refers to the act of treating, as "treating" is defined immediately above.

The term "preventing" as used herein means that the compounds of the present invention are useful when administered to a patient who has not been diagnosed as possibly having the disease, disorder or condition at the time of administration, but who would normally be expected to develop the disease, disorder or condition or be at increased risk for the disease, disorder or condition. In certain embodiments, the compounds of the invention will slow the development of disease symptoms, delay the onset of disease, or prevent the individual from developing the disease at all. In certain embodiments, preventing also includes administration of the compounds of the invention to those individuals thought to be predisposed to the disease due to familial history, genetic or chromosomal abnormalities, and/or due to the presence of one or more biological markers for the disease.

As used herein the term "biological sample" includes, without limitation, cell cultures or extracts thereof; biopsied material obtained from an animal (e.g., mammal) or extracts thereof; and blood, saliva, urine, feces, semen, tears, or other body fluids or extracts thereof. For example, the term "biological sample" refers to any solid or fluid sample obtained from, excreted by or secreted by any living organism, including single-celled micro-organisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated). The biological sample can be in any form, including a solid material such as a tissue, cells, a cell pellet, a cell extract, cell homogenates, or cell fractions; or a biopsy, or a biological fluid. The biological fluid may be obtained from any site (e.g. blood, saliva (or a mouth wash containing buccal cells), tears, plasma, serum, urine, bile, cerebrospinal fluid, amniotic fluid, peritoneal fluid, and pleural fluid, or cells therefrom, aqueous or vitreous humor, or any bodily secretion), a transudate, an exudate (e.g. fluid obtained from an abscess or any other site of infection or inflammation), or fluid obtained from a joint (e.g. a normal joint or a joint affected by disease such as rheumatoid arthritis, osteoarthritis, gout or septic arthritis). The biological sample can be obtained from any organ or tissue (including a biopsy or autopsy specimen) or may comprise cells (whether primary cells or cultured cells) or medium conditioned by any cell, tissue or organ. Biological samples may also include sections of tissues such as frozen sections taken for histological purposes. Biological samples also include mixtures of biological molecules including proteins, lipids, carbohydrates and nucleic acids generated by partial or complete fractionation of cell or tissue homogenates. Although the sample is preferably taken from a human subject, biological samples may be from any animal, plant, bacteria, virus, yeast, etc. The term animal, as used herein, refers to humans as well as non-human animals, at any stage of development, including, for example, mammals, birds, reptiles, amphibians, fish, worms and single cells. Cell cultures and live tissue samples are considered to be pluralities of animals. In certain exemplary embodiments, the non-human animal is a mammal (e.g., a rodent, a mouse, a rat, a rabbit, a monkey, a dog, a cat, a sheep, cattle, a primate, or a pig). An animal may be a transgenic animal or a human clone. If desired, the biological sample may be subjected to preliminary processing, including preliminary separation techniques.

DETAILED DESCRIPTION OF CERTAIN PREFERRED EMBODIMENTS OF THE INVENTION

As noted above, there has been increasing interest in recent years in the development of protein kinase inhibitors, particularly RAF inhibitors, as therapeutic agents for the treatment of diseases/conditions involving protein kinase-mediated events. In one aspect, the present invention provides RAF inhibitors.

Compounds of this invention include those generally set forth above and described specifically herein, and are illustrated in part by the various classes, subgenera and species disclosed herein. Additionally, the present invention provides pharmaceutically acceptable derivatives of the inventive compounds, and methods of treating a subject using these compounds, pharmaceutical compositions thereof, or either of these in combination with one or more additional therapeutic agents.

1) General Description of Compounds of the Invention

In certain embodiments, the compounds of the invention include compounds of the general formula (I) as further defined below:

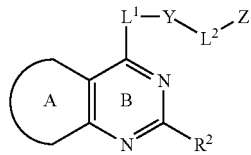

and pharmaceutically acceptable derivatives thereof;

wherein A-B together represent one of the following structures:

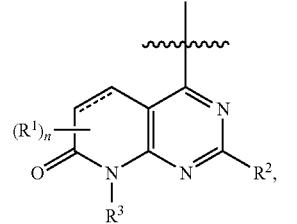

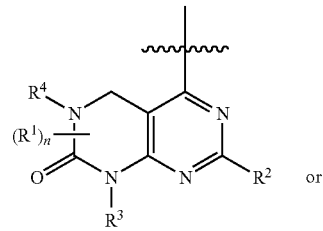

or

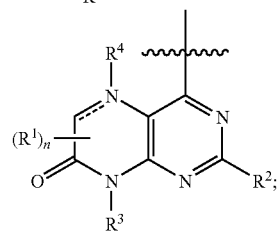

----- represents a single or double bond as valency permits;

n is an integer from 0-4 as valency permits;

$R^1$ and $R^2$ are independently hydrogen, halogen, cyano, nitro, or an aliphatic, heteroaliphatic, alicyclic, heteroalicyclic, aromatic or heteroaromatic moiety;

$R^3$ is hydrogen, a nitrogen protecting group, or an aliphatic, heteroaliphatic, alicyclic, heteroalicyclic, aromatic or heteroaromatic moiety;

$R^4$ is hydrogen, a nitrogen protecting group, or an aliphatic, heteroaliphatic, alicyclic, heteroalicyclic, aromatic or heteroaromatic moiety; or is absent when ----- is a double bond;

$L^1$ is —O—, —S—, —NR$^{L1A}$— or a substituted or unsubstituted $C_{1-6}$alkylene or $C_{2-6}$alkenylene chain wherein up to two non-adjacent methylene units are independently optionally replaced by —C(=O)—, —CO$_2$—, —C(=O)C(=O)—, —C(=O)NR$^{L1A}$—, —OC(=O)—, —OC(=O)NR$^{L1A}$—, —NR$^{L1A}$NR$^{L1B}$—, —NR$^{L1A}$NR$^{L1B}$C(=O)—, —NR$^{L1A}$C(=O)—, —NR$^{L1A}$CO$_2$—, —NR$^{L1A}$C(=O)NR$^{L1B}$—, —S(=O)—, —SO$_2$—, —NR$^{L1A}$SO$_2$—, —SO$_2$NR$^{L1A}$—, —NR$^{L1A}$SO$_2$NR$^{L1B}$—, —O—, —S— or —NR$^{L1A}$—; wherein each occurrence of $R^{L1A}$ and $R^{L1B}$ is independently hydrogen, alkyl, heteroalkyl, heterocyclyl, aromatic, heteroaromatic or acyl;

$L^2$ is absent, —O—, —S—, —NR$^{L2A}$—, a heteroalicyclic or heteroaromatic moiety, or a substituted or unsubstituted $C_{1-6}$alkylene or $C_{2-6}$alkenylene chain wherein up to two non-adjacent methylene units are independently optionally replaced by —C(=O)—, —CO$_2$—, —C(=O)C(=O)—, —C(=O)NR$^{L2A}$—, —OC(=O)—, —OC(=O)NR$^{L2A}$—, —NR$^{L2A}$NR$^{L2A}$NR$^{L2B}$—, —NR$^{L2A}$NR$^{L2B}$C(=O)—, —NR$^{L2A}$C(=O)—, —NR$^{L2A}$CO$_2$—, —NR$^{L2A}$C(=O)NR$^{L2B}$—, —S(=O)—, —SO$_2$—, —NR$^{L2A}$SO$_2$—, —SO$_2$NR$^{L2A}$—, —NR$^{L2A}$SO$_2$NR$^{L2B}$—, —O—, —S—, or —NR$^{L2A}$—; wherein each occurrence of $R^{L2A}$ and $R^{L2B}$ is independently hydrogen, alkyl, heteroalkyl, heterocyclyl, aromatic, heteroaromatic or acyl;

Y is an carbocyclic, heterocyclic, aryl or heteroaryl moiety; and

Z is an aliphatic, heteroaliphatic, alicyclic, heteroalicyclic, aromatic or heteroaromatic moiety.

In certain embodiments, the following groups do not occur simultaneously as defined: A-B together represent

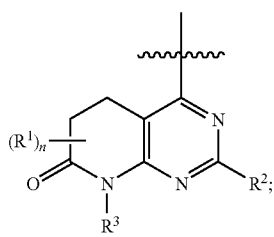

$L^1$ is -Oalkyl-, —N(R)alkyl-, -Salkyl-, -Oalkenyl-, —N(R)alkenyl-, or -Salkenyl-, wherein R is hydrogen, alkyl, alkenyl, aryl, (aryl)alkyl, heteroaryl, (heteroaryl)alkyl, cycloalkyl, (cycloalkyl)alkyl, heterocyclyl or (heterocyclyl)alkyl; and $R^2$ is —NR$^{2A}$R$^{2B}$ wherein $R^{2A}$ is hydrogen or alkyl; and $R^{2B}$ is optionally substituted heteroaryl, heterocyclyl or aryl.

In certain embodiments, the following groups do not occur simultaneously as defined: $L^1$ is —N(R$^{L1}$)—, wherein $R^{L1}$ is hydrogen or $C_{1-6}$alkyl; n is 0-3; $R^1$ is —(CR$^{1A}$CR$^{1B}$)$_q$X(CR$^{1A}$CR$^{1B}$)$_t$ wherein X is absent, —N(R$^{1C}$)—, —NH—, —O—, —C(=O)—, —N(R$^{1C}$)C(=O)—, —C(=O)N(R$^{1C}$)—, —C(=O)(cis or trans alkenyl)-, —N(R$^{1C}$)C(=O)(cis or trans alkenyl)-, —C(=O)alkynyl-, —N(R$^{1C}$)C(=O)alkynyl-, —N(R$^{1C}$)C(=O)alkynylN(R$^{1C}$)—, —N(R$^{1C}$)C(=O)N(R$^{1C}$)—, —N(R$^{1C}$)S(=O)$_j$—, —S(=O)$_j$N(R$^{1C}$)— or —S(=O)$_j$—; and —Y-L$^2$-Z together represent a moiety having the structure:

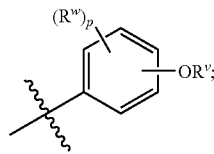

wherein p is 0-4; $R^v$ is optionally substituted phenyl or an optionally substituted 4- to 6-membered heterocyclic ring, wherein said heterocyclic group is optionally fused to an optionally substituted benzene or $C_{5-8}$cycloalkyl group; and $R^w$ is halogen, cyano, nitro, —OCF$_3$, —CF$_3$, hydroxy, $C_{3-8}$cycloalkyl, $C_{1-6}$alkoxy, $C_{1-10}$alkyl, $C_{2-6}$alkenyl, $C_{2-6}$alkynyl, —C(=O)R$^u$, —C(=O)OR$^u$, —OC(=O)R$^u$, —NR$^u$C(=O)R$^s$, —NR$^u$S(=O)$_2$NR$^s$R$^3$, —NR$^u$C(=O)NR$^s$R$^3$, —NR$^u$C(=O)OR$^s$, —C(=O)NR$^s$R$^3$, —NR$^s$R$^3$, —S(=O)$_2$NR$^s$R$^3$, —S(=O)$_j$C$_{1-6}$alkyl-, —(CR$^{w1}$R$^{w2}$)$_t$(C$_{6-10}$aryl)-, —(CR$^{w1}$R$^{w2}$)$_t$(4 to 10 membered heterocyclic)-, —(CR$^{w1}$R$^{w2}$)$_q$C(=O)(CR$^{w1}$R$^{w2}$)$_t$(C$_{6-10}$aryl)-, —(CR$^{w1}$R$^{w2}$)$_q$C(=O)(CR$^{w1}$R$^{w2}$)$_t$(4 to 10 membered heterocyclic)-, —(CR$^{w1}$R$^{w2}$)$_q$O(CR$^{w1}$R$^{w2}$)$_t$(C$_{6-10}$aryl)-, —(CR$^{w1}$R$^{w2}$)$_q$O(CR$^{w1}$R$^{w2}$)$_t$(4 to 10 membered heterocyclic)-, —(CR$^{w1}$R$^{w2}$)$_q$S(=O)$_j$(CR$^{w1}$R$^{w2}$)$_t$(C$_{6-10}$aryl)- or —(CR$^{w1}$R$^{w2}$)$_q$S(=O)$_j$(CR$^{w1}$R$^{w2}$)$_t$(4 to 10 membered heterocyclic)-; wherein j is 0-2; and q and t are independently 0-5.

In certain embodiments, A-B together represent

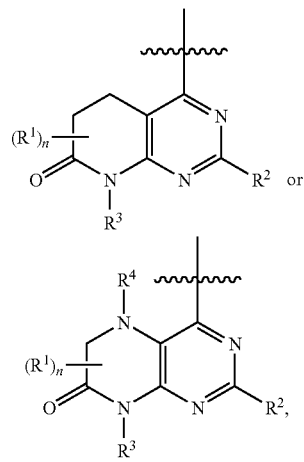

and $R^3$ is not an aryl or heteroaryl moiety.

In certain embodiments, the present invention defines particular classes of compounds which are of special interest. For example, one class of compounds of special interest includes compounds of formula ($I^4$):

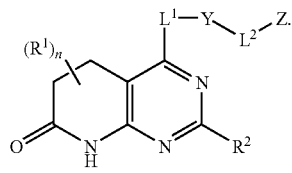

Another class of compounds of special interest includes compounds of formula ($I^B$):

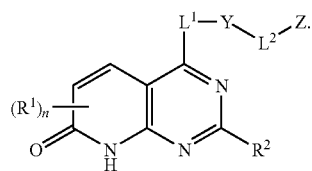

Another class of compounds of special interest includes compounds of formula ($I^C$):

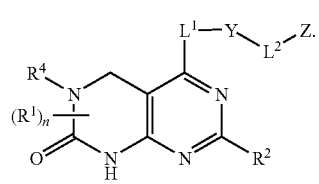

Another class of compounds of special interest includes compounds of formula ($I^D$):

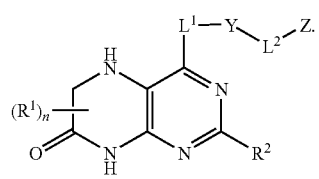

Another class of compounds of special interest includes compounds of formula ($I^E$):

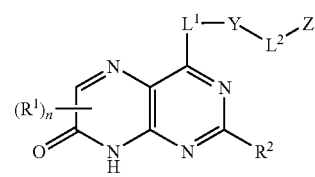

Another class of compounds of special interest includes compounds of formula ($I^F$):

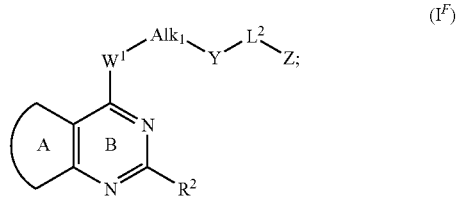

wherein $W^1$ is —O—, —S—, —N($R^{W1}$)—, —C(=O)—, —N($R^{W1}$)C(=O) or —C(=O)N($R^{W1}$)—, where $R^{W1}$ is hydrogen, aliphatic, heteroaliphatic, alicyclic, heteroalicyclic, aromatic, heteroaromatic, or acyl; and $Alk_1$ is a $C_{1-6}$alkylene or $C_{2-6}$alkenylene moiety.

Another class of compounds of special interest includes compounds of formula ($I^G$):

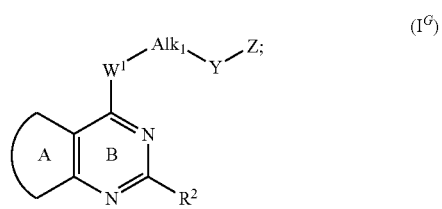

wherein $W^1$ is —O—, —S—, —N($R^{W1}$)—, —C(=O)—, —N($R^{W1}$)C(=O) or —C(=O)N($R^{W1}$)—, where $R^{W1}$ is hydrogen, aliphatic, heteroaliphatic, alicyclic, heteroalicyclic, aromatic, heteroaromatic, or acyl; and $Alk_1$ is a $C_{1-6}$alkylene or $C_{2-6}$alkenylene moiety.

Another class of compounds of special interest includes compounds of formula ($I^H$):

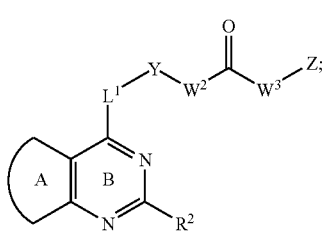

wherein $W^2$ and $W^3$ are independently absent, —O— or —N($R^W$)—, where $R^W$ is hydrogen, aliphatic, heteroaliphatic, alicyclic, heteroalicyclic, aromatic or heteroaromatic.

A number of important subclasses of each of the foregoing classes deserve separate mention; these subclasses include subclasses of the foregoing classes in which:

i) each occurrence of $R^1$ is independently hydrogen, halogen, —CN, —NO$_2$, —C(=O)$R^{1A}$, —C(=O)O$R^{1A}$, —C(=O)N$R^{1A}R^{1B}$, —S(=O)$_2R^{1C}$, —P(=O)($R^{1C}$)$_2$, alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl; wherein $R^{1A}$ and $R^{1B}$ are independently hydrogen, alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl; or taken together with the nitrogen atom to which they are attached form a 5-6-membered heterocyclic ring; and each occurrence of $R^{1C}$ is independently alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl;

ii) each occurrence of $R^1$ is independently hydrogen, halogen, $-NO_2$, $-CN$, $-C(=O)OR^{1A}$, $-S(=O)_2R^{1C}$, $-P(=O)(R^{1C})_2$, alkyl, alkenyl, alkynyl, heteroalkyl, heteroalkenyl, heteroalkynyl, heterocyclyl, aryl or heteroaryl; wherein $R^{1A}$ is hydrogen or $C_{1-6}$alkyl; and each occurrence of $R^{1C}$ is independently $C_{1-6}$alkyl;

iii) each occurrence of $R^1$ is independently hydrogen, halogen, $-NO_2$, $-CN$, $C_{1-5}$alkyl, $C_{1-5}$alkoxy, $C_{1-5}$alkylamino, di$C_{1-5}$alkylamino, amino$C_{1-5}$alkyl, $C_{1-5}$alkylamino$C_{1-5}$alkyl or di$C_{1-5}$alkylamino$C_{1-5}$alkyl;

iv) at least one occurrence of $R^1$ is F;

v) each occurrence of $R^1$ is hydrogen;

vi) n is 1 and $R^1$ is as defined in any one of subsets i)-iii) above;

vii) $R^2$ is hydrogen, halogen, cyano, nitro, or an alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl moiety;

viii) $R^2$ is $C_{1-3}$alkyl or $C_{1-3}$alkoxy;

ix) $R^2$ is methyl or $-CF_3$;

x) $R^2$ is halogen;

xi) $R^2$ is hydrogen;

xii) $R^3$ is hydrogen, $-C(=O)R^{1A}$, $-C(=O)OR^{1A}$, $-C(=O)NR^{1A}R^{1B}$, $-S(=O)_2R^{1C}$, alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl; wherein $R^{1A}$ and $R^{1B}$ are independently hydrogen, alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl; or taken together with the nitrogen atom to which they are attached form a 5-6-membered heterocyclic ring; and each occurrence of $R^{1C}$ is independently alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl;

xiii) $R^3$ is hydrogen, $-C(=O)R^{1A}$, lower alkyl, lower alkenyl, heterocyclyl, aryl or heteroaryl; wherein $R^{1A}$ is hydrogen, or lower alkyl, aryl, or heteroaryl;

xiv) $R^3$ is hydrogen or lower alkyl;

xv) $R^3$ is hydrogen or methyl;

xvi) $R^3$ is hydrogen;

xvii) $L^1$ is a 2-8 atom heteroaliphatic linker having at least one N, O or S atom in the heteroaliphatic main chain;

xviii) $L^1$ is a 2-8 atom heteroaliphatic linker having at least one N or O atom in the heteroaliphatic main chain;

xix) $L^1$ is a 2-8 atom heteroaliphatic linker having at least one N atom in the heteroaliphatic main chain;

xx) $L^1$ is $-W^1$-$Alk_1$-; wherein $W^1$ is $-O-$, $-S-$, $-N(R^{W1})-$, $-C(=O)-$, $-N(R^{W1})C(=O)$ or $-C(=O)N(R^{W1})-$, where $R^{W1}$ is hydrogen, aliphatic, heteroaliphatic, alicyclic, heteroalicyclic, aromatic, heteroaromatic, or acyl; and $Alk_1$ is a $C_{1-6}$alkylene or $C_{2-6}$alkenylene moiety;

xxi) $L^1$ is $-W^1$-$Alk_1$-; wherein $W^1$ is $-O-$, $-S-$, $-N(R^{W1})-$, $-C(=O)-$, $-N(R^{W1})C(=O)$ or $-C(=O)N(R^{W1})-$, where $R^{W1}$ is hydrogen, alkyl, cycloalkyl, heteroalkyl, aryl, heteroaryl, -(alkyl)aryl, -(alkyl)heteroaryl or acyl; and $Alk_1$ is a substituted or unsubstituted $C_{1-6}$alkylene or $C_{2-6}$alkenylene chain wherein up to two non-adjacent methylene units are independently optionally replaced by $-C(=O)-$, $-CO_2-$, $-C(=O)C(=O)-$, $-C(=O)NR^{L1A}-$, $-OC(=O)-$, $-OC(=O)NR^{L1A}-$, $-NR^{L1A}NR^{L1B}-$, $-NR^{L1A}NR^{L1B}C(=O)-$, $-NR^{L1A}C(=O)-$, $-NR^{L1A}CO_2-$, $-NR^{L1A}C(=O)NR^{L1B}-$, $-S(=O)-$, $-SO_2-$, $-NR^{L1A}SO_2-$, $-SO_2NR^{L1A}-$, $-NR^{L1A}SO_2NR^{L1B}-$, $-O-$, $-S-$, or $-NR^{L1A}-$; wherein each occurrence of $R^{L1A}$ and $R^{L1B}$ is independently hydrogen, alkyl, heteroalkyl, heterocyclyl, aromatic, heteroaromatic or acyl;

xxii) $L^1$ is $-W^1$-$Alk_1$-; wherein $W^1$ is $-O-$, $-S-$, $-N(R^{W1})-$, $-C(=O)-$, $-N(R^{W1})C(=O)$ or $-C(=O)N(R^{W1})-$, where $R^{W1}$ is hydrogen, lower alkyl, $C_{3-6}$cycloalkyl, lower heteroalkyl, aryl, heteroaryl, -(alkyl)aryl, -(alkyl)heteroaryl or acyl; and $Alk_1$ is a substituted or unsubstituted $C_{1-6}$alkylene or $C_{2-6}$alkenylene chain wherein up to two non-adjacent methylene units are independently optionally replaced by $-C(=O)-$, $-CO_2-$, $-C(=O)C(=O)-$, $-C(=O)NR^{L1A}-$, $-OC(=O)-$, $-OC(=O)NR^{L1A}-$, $-NR^{L1A}NR^{L1B}-$, $-NR^{L1A}NR^{L1B}C(=O)-$, $-NR^{L1A}C(=O)-$, $-NR^{L1A}CO_2-$, $-NR^{L1A}C(=O)NR^{L1B}-$, $-S(=O)-$, $-SO_2-$, $-NR^{L1A}SO_2-$, $-SO_2NR^{L1A}-$, $-NR^{L1A}SO_2NR^{L1B}-$, $-O-$, $-S-$, or $-NR^{L1A}-$; wherein each occurrence of $R^{L1A}$ and $R^{L1B}$ is independently hydrogen, lower alkyl, lower heteroalkyl, heterocyclyl, aryl, heteroaryl or acyl;

xxiii) Compounds of subset xx) above wherein $W^1$ is S;

xxiv) Compounds of subset xx) above wherein $W^1$ is O or $NR^{W1}$;

xxv) Compounds of subset xx) above wherein $W^1$ is $-C(=O)-$ or $-C(=O)N(R^{W1})-$;

xxvi) $L^1$ is $-O$-$Alk_1$-; wherein $Alk_1$ is a substituted or unsubstituted $C_{1-2}$alkylidene chain;

xxvii) $L^1$ is $-O$-cyclopropyl-;

xxviii) $L^1$ is $-O-CH_2CH_2-$;

xxix) $L^1$ is $-O-CH(R^{L1C})-$, wherein $R^{L1C}$ is hydrogen or lower alkyl;

xxx) $L^1$ is $-O-CH_2-$;

xxxi) $L^1$ is $-O-CH(Me)-$;

xxxii) $L^1$ is $-NR^{W1}$-$Alk_1$-; wherein $R^{W1}$ is hydrogen, lower alkyl, $C_{3-6}$cycloalkyl, lower heteroalkyl, aryl, heteroaryl, -(alkyl)aryl, -(alkyl)heteroaryl or acyl; and $Alk_1$ is a substituted or unsubstituted $C_{2-6}$alkylidene chain wherein up to two non-adjacent methylene units are independently optionally replaced by $-C(=O)-$, $-S(=O)-$, $-SO_2-$, $-O-$, $-S-$, or $-NR^{L1A}-$; wherein $R^{L1A}$ is hydrogen or lower alkyl;

xxxiii) $L^1$ is $-NR^{W1}$-$Alk_1$-; wherein $R^{W1}$ is hydrogen or lower alkyl; and $Alk_1$ is a substituted or unsubstituted $C_{1-2}$alkylidene chain;

xxxiv) $L^1$ is $-NH$-cyclopropyl-;

xxxv) $L^1$ is $-NH-CH_2CH_2-$;

xxxvi) $L^1$ is $-NH-CH(R^{L1C})-$, wherein $R^{L1C}$ is hydrogen or lower alkyl;

xxxvii) $L^1$ is $-NH-CH_2-$;

xxxviii) $L^1$ is $-NH-CH(Me)-$;

xxxix) $L^1$ is $-C(=O)$-$Alk_1$-; wherein $Alk_1$ is a substituted or unsubstituted $C_{2-6}$alkylidene chain wherein up to two non-adjacent methylene units are independently optionally replaced by $-C(=O)-$, $-S(=O)-$, $-SO_2-$, $-O-$, $-S-$, or $-NR^{L1A}-$; wherein $R^{L1A}$ is hydrogen or lower alkyl;

xl) $L^1$ is $-C(=O)$-$Alk_1$-; wherein $Alk_1$ is a substituted or unsubstituted $C_{1-2}$alkylidene chain;

xli) $L^1$ is $-C(=O)$-cyclopropyl-;

xlii) $L^1$ is $-C(=O)-CH_2CH_2-$;

xliii) $L^1$ is —C(=O)—CH($R^{L1C}$)—, wherein $R^{L1C}$ is hydrogen or lower alkyl;

xliv) $L^1$ is —C(=O)—CH$_2$—;

xlv) $L^1$ is —C(=O)—CH(Me)—;

xlvi) $L^1$ is —C(=O)NR$^{W1}$-Alk$_1$-; wherein $R^{W1}$ is hydrogen, lower alkyl, $C_{3-6}$cycloalkyl, lower heteroalkyl, aryl, heteroaryl, -(alkyl)aryl, -(alkyl)heteroaryl or acyl; and Alk$_1$ is a substituted or unsubstituted $C_{2-6}$alkylidene chain wherein up to two non-adjacent methylene units are independently optionally replaced by —C(=O)—, —S(=O)—, —SO$_2$—, —O—, —S—, or —NR$^{L1A}$—; wherein $R^{L1A}$ is hydrogen or lower alkyl;

xlvii) $L^1$ is —C(=O)NR$^{W1}$-Alk$_1$-; wherein $R^{W1}$ is hydrogen or lower alkyl; and Alk$_1$ is a substituted or unsubstituted $C_{1-2}$alkylidene chain;

xlviii) $L^1$ is —C(=O)NH-cyclopropyl-;

xlix) $L^1$ is —C(=O)NH—CH$_2$CH$_2$—;

l) $L^1$ is —C(=O)NH—CH($R^{L1C}$)—, wherein $R^{L1C}$ is hydrogen or lower alkyl;

li) $L^1$ is —C(=O)NH—CH$_2$—;

lii) $L^1$ is —C(=O)NH—CH(Me)—;

liii) Y is a saturated or unsaturated cyclic ring system optionally comprising one or more heteroatoms selected from S, N and O;

liv) Y is a saturated or unsaturated monocyclic cyclic ring system optionally comprising one or more heteroatoms selected from S, N and O;

lv) Y is a saturated or unsaturated 5- to 6-membered monocyclic cyclic ring;

lvi) Y is an unsaturated 5-membered monocyclic cyclic ring system comprising one or more heteroatoms selected from S, N and O;

lvii) Y is an unsaturated 6-membered monocyclic cyclic ring system comprising one or more heteroatoms selected from S, N and O;

lviii) Y is a cycloalkyl, cycloalkenyl, heterocyclic, aryl or heteroaryl moiety;

lix) Y is a 5-6 membered cycloalkyl, 5-6 membered cycloalkenyl, 5-6 membered heterocyclic, 6-membered aryl or 6-membered heteroaryl moiety;

lx) Y is one of:

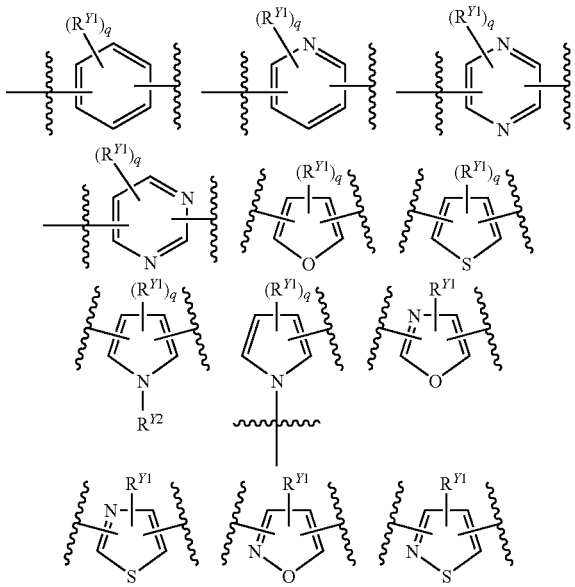

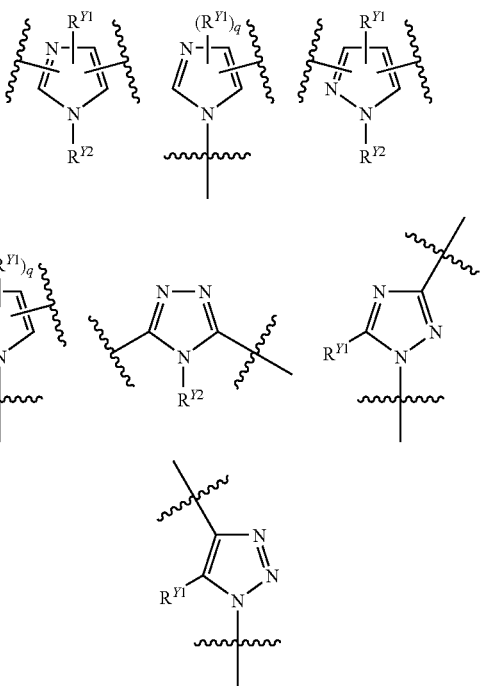

wherein q is an integer from 0 to 3; each occurrence of $R^{Y1}$ is independently hydrogen, alkyl, heteroalkyl, aryl, heteroaryl, -(alkyl)aryl or -(alkyl)heteroaryl, —OR$^{Y3}$, —SR$^{Y3}$, —NR$^{Y2}$R$^{Y3}$, —SO$_2$NR$^{Y2}$R$^{Y3}$, —C(=O)NR$^{Y2}$R$^{Y3}$, halogen, —CN, —NO$_2$, —C(=O)OR$^{Y3}$, —N(R$^{Y2}$)C(=O)R$^{Y3}$, wherein each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or $R^{Y2}$ and $R^{Y3}$ taken together with the nitrogen atom to which they are attached form a 5-6 membered heterocyclic ring;

lxi) Y is one of:

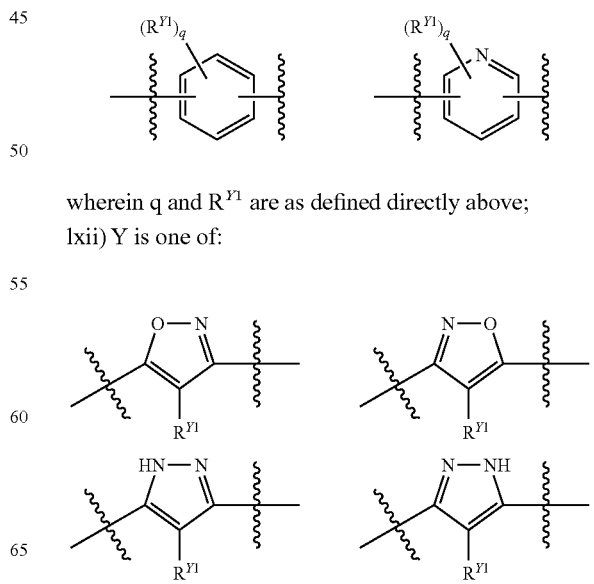

wherein q and $R^{Y1}$ are as defined directly above;

lxii) Y is one of:

-continued

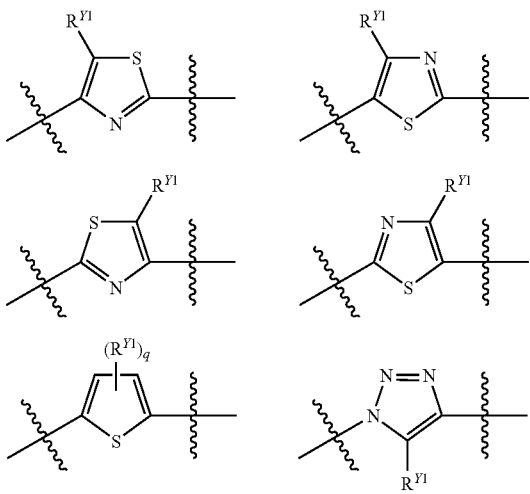

wherein q is 0-3; and $R^{Y1}$ is hydrogen, halogen or lower alkyl;

lxiii) Y is one of:

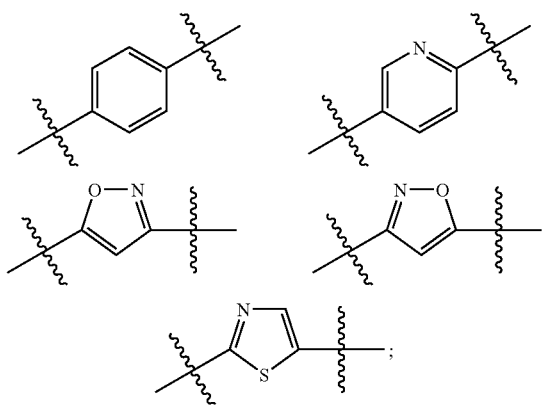

lxiv) Y is one of:

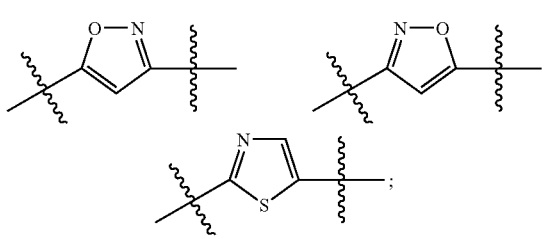

lxv) Y is:

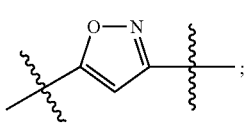

lxvi) Y is:

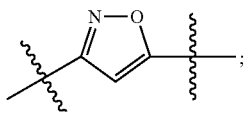

lxvii) Y is:

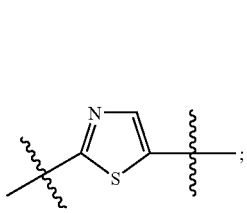

lxviii) $L^2$ is absent, —O—, —S—, —$NR^{L2A}$—, a heterocyclic or heteroaryl moiety, or a substituted or unsubstituted $C_{1-6}$alkylene or $C_{2-6}$alkenylene chain wherein up to two non-adjacent methylene units are independently optionally replaced by —C(=O)—, —$CO_2$—, —C(=O)C(=O)—, —C(=O)$NR^{L2A}$—, —OC(=O)—, —OC(=O)$NR^{L2A}$—, —$NR^{L2A}NR^{L2B}$—, —$NR^{L2A}NR^{L2B}$C(=O)—, —$NR^{L2A}$C(=O)—, —$NR^{L2A}CO_2$—, —$NR^{L2A}$C(O)$NR^{L2B}$—, —S(=O)—, —$SO_2$—, —$NR^{L2A}SO_2$—, —$SO_2NR^{L2A}$—, —$NR^{L2A}SO_2NR^{L2B}$—, —O—, —S—, or —$NR^{L2A}$—; wherein each occurrence of $R^{L2A}$ and $R^{L2B}$ is independently hydrogen, alkyl, heteroalkyl, heterocyclyl, aromatic, heteroaromatic or acyl;

lxix) $L^2$ is a 2-6 atom heteroaliphatic linker having at least one N atom in the heteroaliphatic main chain;

lxx) $L^2$ is —O—, —S—, —$NR^{L2A}$—, —C(=O)$NR^{L2A}$—, —OC(=O)$NR^{L2A}$—, —$NR^{L2A}NR^{L2B}$—, —$NR^{L2A}NR^{L2B}$C(=O)—, —$NR^{L2A}$C(=O)—, —$NR^{L2A}$C(=O)O—, —$NR^{L2A}$C(=O)$NR^{L2B}$—, —$NR^{L2A}SO_2$—, —$SO_2NR^{L2A}$—, —$NR^{L2A}SO_2NR^{L2B}$—, or a substituted or unsubstituted $C_{1-6}$alkylene or $C_{2-6}$alkenylene chain interrupted with at least one nitrogen atom wherein up to two non-adjacent methylene units are independently optionally replaced by —C(=O)—, —$CO_2$—, —C(=O)C(=O)—, —C(=O)$NR^{L2A}$—, —OC(=O)—, —OC(=O)$NR^{L2A}$—, —$NR^{L2A}NR^{L2B}$—, —$NR^{L2A}NR^{L2B}$C(=O)—, —$NR^{L2A}$C(=O)—, —$NR^{L2A}CO_2$—, —$NR^{L2A}$C(=O)$NR^{L2B}$—, —S(=O)—, —$SO_2$—, —$NR^{L2A}SO_2$—, —$SO_2NR^{L2A}$—, —$NR^{L2A}SO_2NR^{L2B}$—, —O—, —S—, or —$NR^{L2A}$—; wherein each occurrence of $R^{L2A}$ and $R^{L2B}$ is independently hydrogen, alkyl, heteroalkyl, heterocyclyl, aromatic, heteroaromatic or acyl;

lxxi) $L^2$ is —O—, —S—, —$NR^{L2A}$—, —C(=O)$NR^{L2A}$—, —OC(=O)$NR^{L2A}$, —$NR^{L2A}NR^{L2B}$—, —$NR^{L2A}NR^{L2B}$C(=O)—, —$NR^{L2A}$C(=O)—, —$NR^{L2A}CO_2$—, —$NR^{L2A}$C(=O)$NR^{L2B}$—, —$NR^{L2A}SO_2$—, —$SO_2NR^{L2A}$—, —$NR^{L2A}SO_2NR^{L2B}$—, or a substituted or unsubstituted $C_{1-6}$alkylene or $C_{2-6}$alkenylene chain interrupted with at least one nitrogen atom wherein up to two non-adjacent methylene units are independently optionally replaced by —C(=O)—, —$CO_2$—, —C(=O)C(=O)—, —C(=O)$NR^{L2A}$—, —OC(=O)—, —OC(=O)$NR^{L2A}$, —$NR^{L2A}NR^{L2B}$—, —$NR^{L2A}NR^{L2B}$C(=O)—, —$NR^{L2A}$C(=O)—, —$NR^{L2A}CO_2$—, —$NR^{L2A}$C(O)$NR^{L2B}$—, —S(=O)—, —$SO_2$—, —$NR^{L2A}SO_2$—, —$SO_2NR^{L2A}$—, —$NR^{L2A}SO_2NR^{L2B}$—, —O—, —S—, or —$NR^{L2A}$—; wherein each occurrence of $R^{L2A}$ and $R^{L2B}$ is independently hydrogen, lower alkyl, lower heteroalkyl, heterocyclyl, aryl, heteroaryl or acyl;

lxxii) $L^2$ is —O—, —S—, —NR$^{L2A}$—, —C(=O)NR$^{L2A}$—, —NR$^{L2A}$C(=O)—, —OC(=O)NR$^{L2A}$—, —NR$^{L2A}$CO$_2$—, or —NR$^{L2A}$C(=O)NR$^{L2B}$—, wherein each occurrence of R$^{L2A}$ and R$^{L2B}$ is independently hydrogen, lower alkyl, lower heteroalkyl, heterocyclyl, aryl, heteroaryl or acyl;

lxxiii) $L^2$ is —C(=O)NR$^{L2A}$—, —NR$^{L2A}$C(=O)—, or —NR$^{L2A}$C(=O)NR$^{L2B}$—, wherein each occurrence of R$^{L2A}$ and R$^{L2B}$ is independently hydrogen, lower alkyl, lower heteroalkyl, heterocyclyl, aryl, heteroaryl or acyl;

lxxiv) $L^2$ is —C(=O)NH—, —NHC(=O)—, —OC(=O)NH—, —NHC(=O)O— or —NHC(=O)NH—;

lxxv) $L^2$ is —C(=O)NH—;

lxxvi) $L^2$ is —NHC(=O)—;

lxxvii) $L^2$ is —NHC(=O)NH—;

lxxviii) $L^2$ is absent;

lxxix) $L^2$ is a saturated or unsaturated 5- to 6-membered monocyclic cyclic ring;

lxxx) $L^2$ is a 5- to 6-membered heterocyclic moiety;

lxxxi) $L^2$ is a 5-membered heterocyclic moiety;

lxxxii) $L^2$ is a 6-membered heterocyclic moiety;

lxxxiii) $L^2$ is a 5-membered heterocyclic moiety comprising one or more nitrogen atoms;

lxxxiv) $L^2$ is a 5-membered unsaturated heterocyclic moiety comprising one or more nitrogen atoms;

lxxxv) $L^2$ is one of:

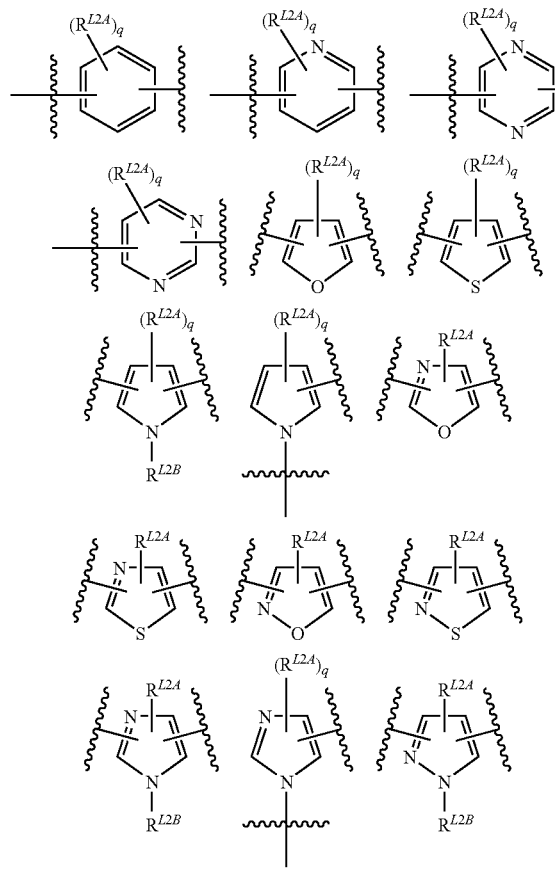

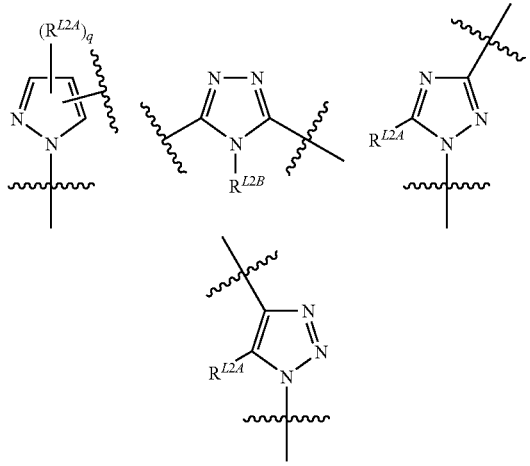

wherein q is an integer from 0 to 3; each occurrence of R$^{L2A}$ is independently hydrogen, alkyl, heteroalkyl, aryl, heteroaryl, -(alkyl)aryl or -(alkyl)heteroaryl, —OR$^{L2C}$, —SR$^{L2C}$, —NR$^{L2B}$R$^{L2C}$, —SO$_2$NR$^{L2B}$R$^{L2C}$, —C(=O)NR$^{L2B}$R$^{L2C}$, halogen, —CN, —NO$_2$, —C(=O)OR$^{L2C}$, —N(R$^{L2B}$)C(=O)R$^{L2C}$, wherein each occurrence of R$^{L2B}$ and R$^{L2C}$ is independently hydrogen, lower alkyl, lower heteroalkyl, aryl, heteroaryl, -(alkyl)aryl, -(alkyl)heteroaryl or acyl, or R$^{L2B}$ and R$^{L2C}$ taken together with the nitrogen atom to which they are attached form a 5-6 membered heterocyclic ring;

lxxxvi) $L^2$ is one of:

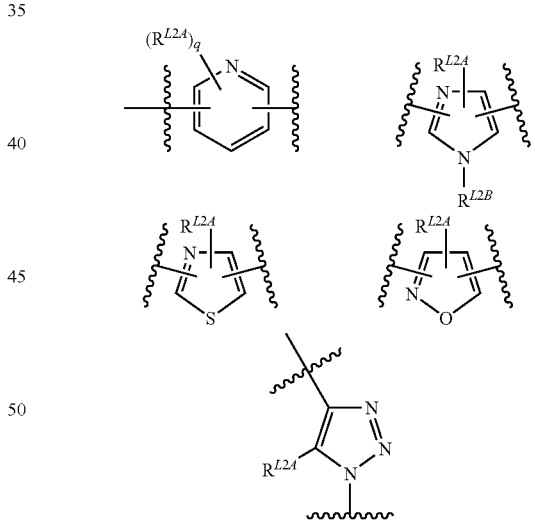

wherein q, R$^{L2A}$ and R$^{L2B}$ are as defined directly above;

lxxxvii) $L^2$ is:

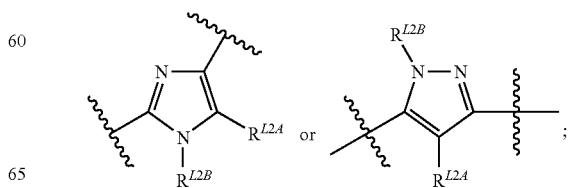

lxxxviii) L² is:

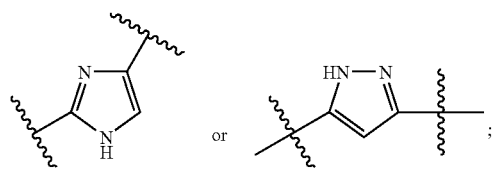

or

;

lxxxix) Z is an alkyl, alkenyl, alkynyl, cycloalkyl, cycloalkenyl, heteroalkyl, heteroalkenyl, heteroalkynyl, heterocyclyl, aryl or heteroaryl moiety;

xc) Z is a branched alkyl, alkenyl, alkynyl, heteroalkyl or heteroalkenyl moiety;

xci) Z is one of:

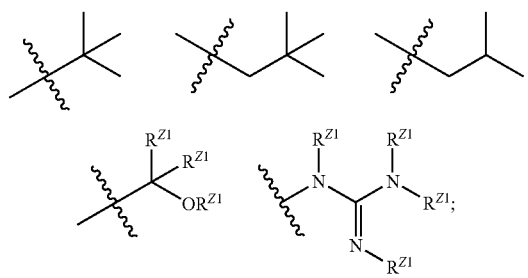

wherein each occurrence of $R^{Z1}$ is independently hydrogen, lower alkyl, lower alkenyl, aryl, heteroaryl or acyl;

xcii) Z is a cycloalkyl, cycloalkenyl, heterocyclyl, aryl or heteroaryl moiety;

xciii) Z is a cycloalkyl, cycloalkenyl, heterocyclyl, aryl or heteroaryl moiety;

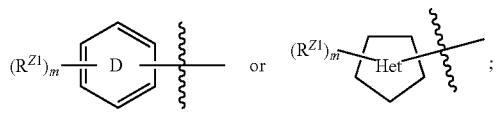

wherein the "D" cyclic moiety is a 6-membered aromatic ring comprising from 0-4 nitrogen atoms; the "Het" moiety represents a fully or partially saturated or unsaturated 5-membered ring comprising 1-4 heteroatoms selected from N, O and S; m is an integer from 0-6; and each occurrence of $R^{Z1}$ is independently hydrogen, alkyl, heteroalkyl, aryl, heteroaryl, -(alkyl)aryl, -(alkyl)heteroaryl, —$OR^{Z2}$, —$SR^{Z2}$, —$N(R^{Z2})_2$, —$SO_2N(R^{Z2})_2$, —$SO_2R^{Z4}$, —C(=O)$N(R^{Z2})_2$, halogen, —CN, —$NO_2$, —C(=O)$OR^{Z2}$, —$N(R^{Z2})$C(=O)$R^{Z3}$ or —$N(R^{Z2})SO_2R^{Z4}$; wherein each occurrence of $R^{Z2}$ and $R^{Z3}$ is independently hydrogen, lower alkyl, lower heteroalkyl, aryl, heteroaryl, -(alkyl)aryl, -(alkyl)heteroaryl, acyl; or any two occurrences of $R^{Z2}$, taken together with the nitrogen atom to which they are attached (e.g., $N(R^{Z2})_2$), form a substituted or unsubstituted heterocyclic moiety; and $R^{Z4}$ is alkyl, heteroalkyl, aryl, heteroaryl, -(alkyl)aryl, or -(alkyl)heteroaryl; and wherein any two adjacent occurrence of $R^{Z1}$ may form a fused 5- to 6-membered aryl, heteroaryl or heterocyclic ring;

xciv) Z is one of:

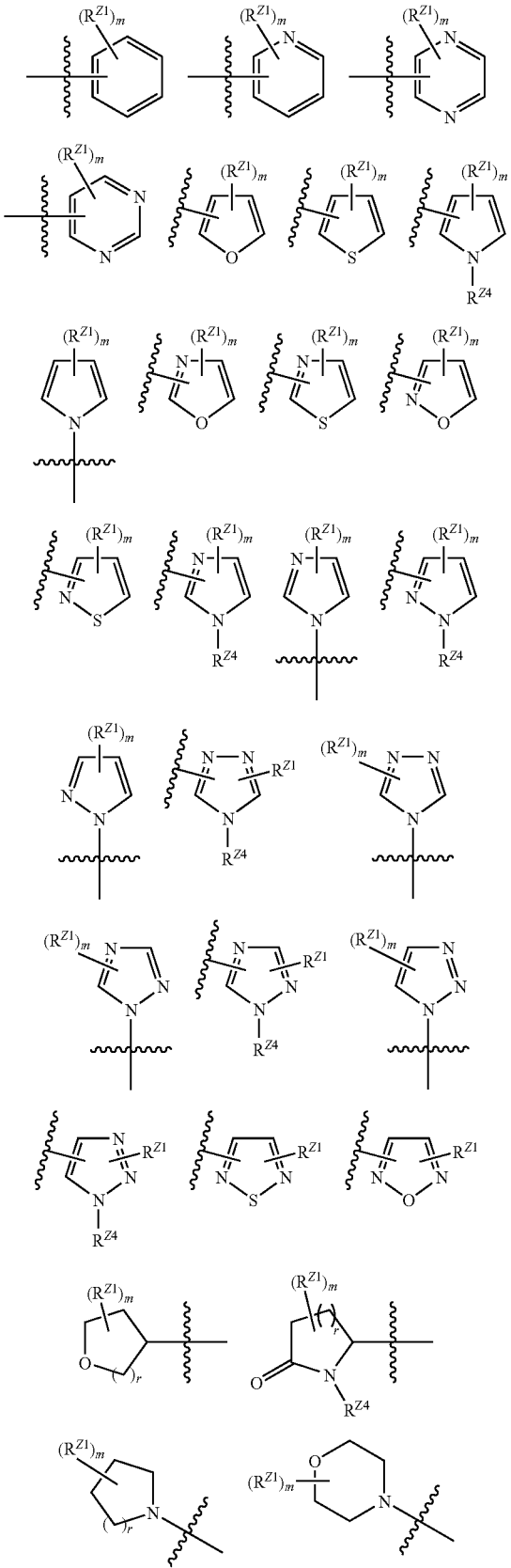

-continued

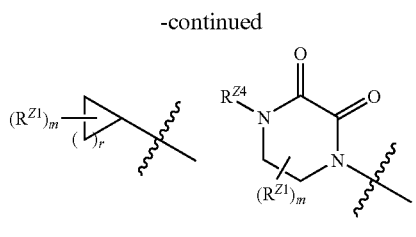

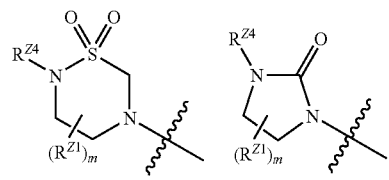

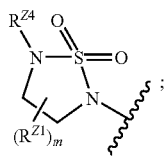

wherein m is an integer from 0 to 3; r is an integer from 1 to 4; each occurrence of $R^{Z1}$ is independently hydrogen, alkyl, heteroalkyl, aryl, heteroaryl, -(alkyl)aryl or -(alkyl)heteroaryl, $-OR^{Z2}$, $-SR^{Z2}$, $-NR^{Z2}R^{Z3}$, $-SO_2NR^{Z2}R^{Z3}$, $-SO_2R^{Z1}$, $-C(=O)NR^{Z2}R^{Z3}$, halogen, $-CN$, $-NO_2$, $-C(=O)OR^{Z3}$, $-N(R^{Z2})C(=O)R^{Z3}$, wherein each occurrence of $R^{Z2}$ and $R^{Z3}$ is independently hydrogen, lower alkyl, lower heteroalkyl, aryl, heteroaryl, -(alkyl)aryl, -(alkyl)heteroaryl or acyl, or $R^{Z2}$ and $R^{Z3}$ taken together with the nitrogen or carbon atom to which they are attached form a 5-6 membered heterocyclic, aryl or heteroaryl ring; and $R^{Z4}$ is hydrogen, lower alkyl, lower heteroalkyl, aryl, heteroaryl, -(alkyl)aryl, -(alkyl)heteroaryl or acyl;

xcv) Z is one of:

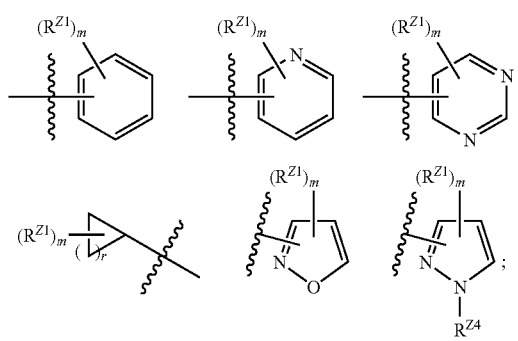

xcvi) Z is one of:

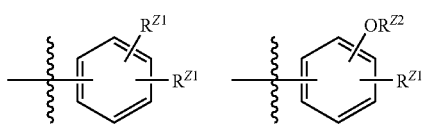

-continued

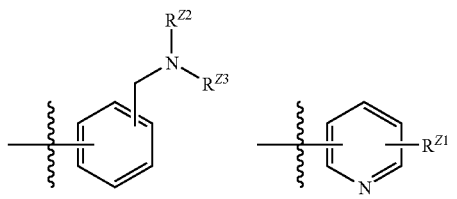

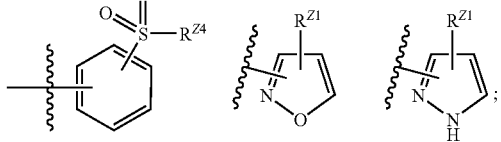

wherein each occurrence of $R^{Z1}$ is independently hydrogen, halogen, lower alkyl or lower haloalkyl; $R^{Z2}$ and $R^{Z3}$ are independently hydrogen, lower alkyl, lower heteroalkyl, acyl, or $R^{Z2}$ and $R^{Z3}$ taken together with the nitrogen atom to which they are attached for a 5-6 membered heterocyclic ring; and $R^{Z4}$ is lower alkyl or lower haloalkyl;

xcvii) Z is one of:

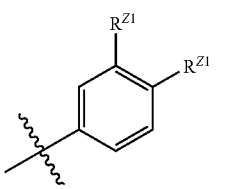 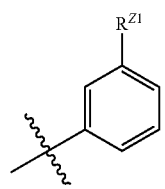

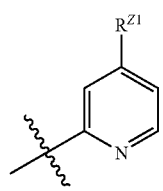 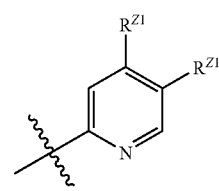

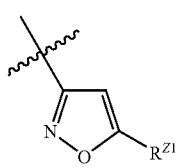 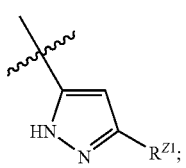

wherein each occurrence of $R^{Z1}$ is independently halogen, lower alkyl or lower haloalkyl;

xcviii) Z is one of:

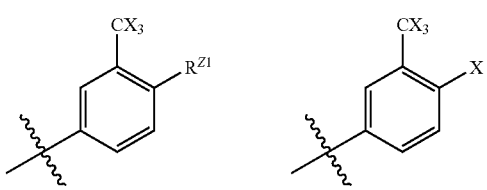

-continued

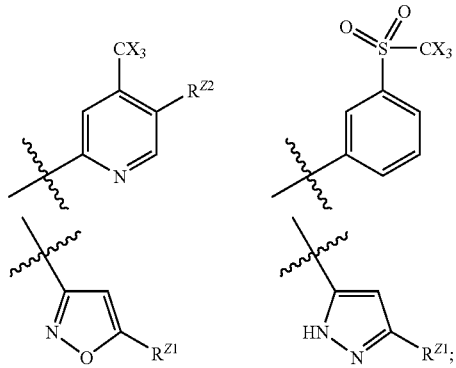

wherein X is halogen; $R^{Z1}$ is substituted or unsubstituted lower alkyl; and $R^{Z2}$ is hydrogen, halogen or substituted or unsubstituted lower alkyl;

xcix) Z is one of:

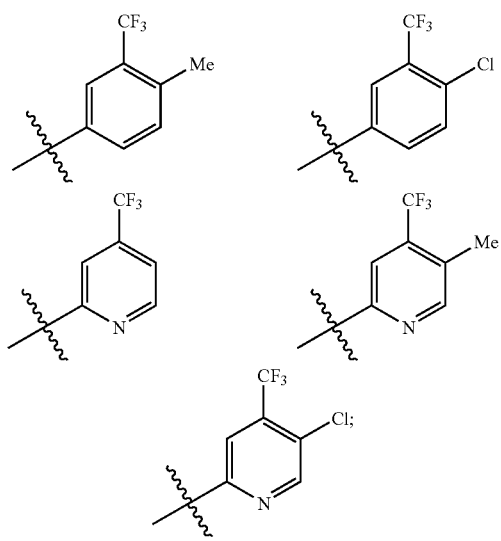

c) Z is an optionally substituted bicyclic heterocycle;
ci) Z is a moiety having one of the following structures:

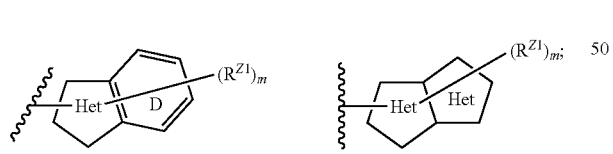

wherein the "D" cyclic moiety is a 6-membered aromatic ring comprising from 0-4 nitrogen atoms; each "Het" moiety independently represents a fully or partially saturated or unsaturated 5-membered ring comprising 1-4 heteroatoms selected from N, O and S; m is an integer from 0-6; and each occurrence of $R^{Z1}$ is independently hydrogen, alkyl, heteroalkyl, aryl, heteroaryl, -(alkyl)aryl, -(alkyl)heteroaryl, —$OR^{Z2}$, —$SR^{Z2}$, —$N(R^{Z2})_2$, —$SO_2N(R^{Z2})_2$, —$SO_2R^{Z4}$, —$C(=O)N(R^{Z2})_2$, halogen, —CN, —$NO_2$, —$C(=O)OR^{Z2}$, —$N(R^{Z2})C(=O)R^{Z3}$ or —$N(R^{Z2})SO_2R^{Z4}$; wherein each occurrence of $R^{Z2}$ and $R^{Z3}$ is independently hydrogen, lower alkyl, lower heteroalkyl, aryl, heteroaryl, -(alkyl)aryl, -(alkyl) heteroaryl, acyl; or any two occurrences of $R^{Z2}$, taken together with the nitrogen atom to which they are attached (e.g., $N(R^{Z2})_2$), form a substituted or unsubstituted heterocyclic moiety; and $R^{Z4}$ is alkyl, heteroalkyl, aryl, heteroaryl, -(alkyl)aryl, or -(alkyl)heteroaryl; and wherein any two adjacent occurrence of $R^{Z1}$ may form a fused 5- to 6-membered aryl, heteroaryl or heterocyclic ring;

cii) Z is a moiety having one of the following structures:

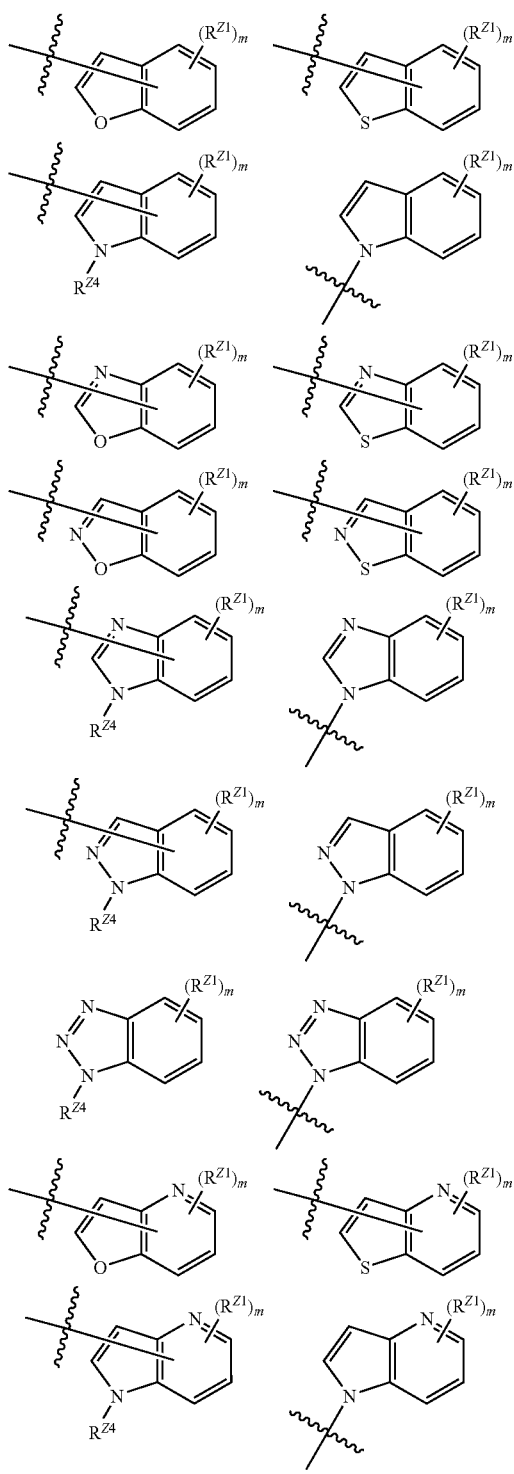

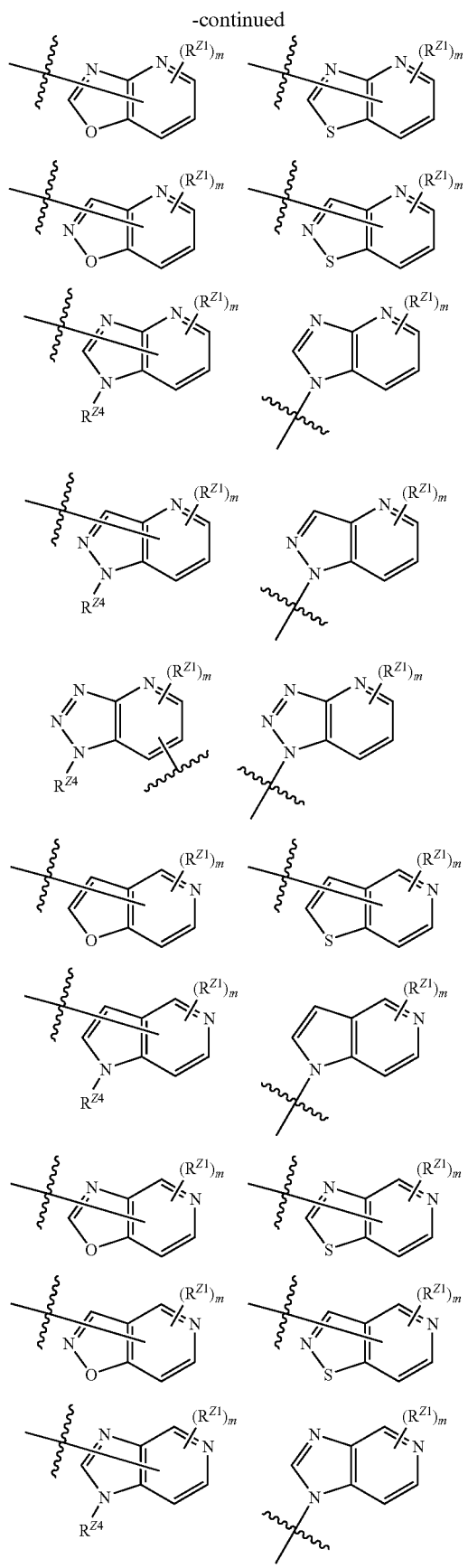
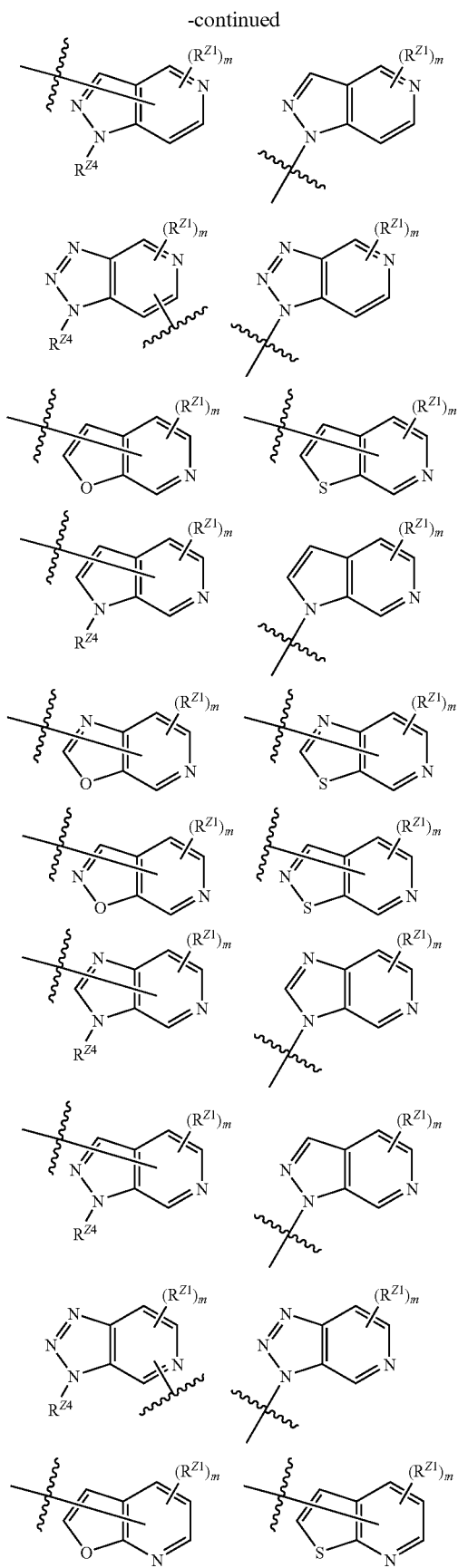

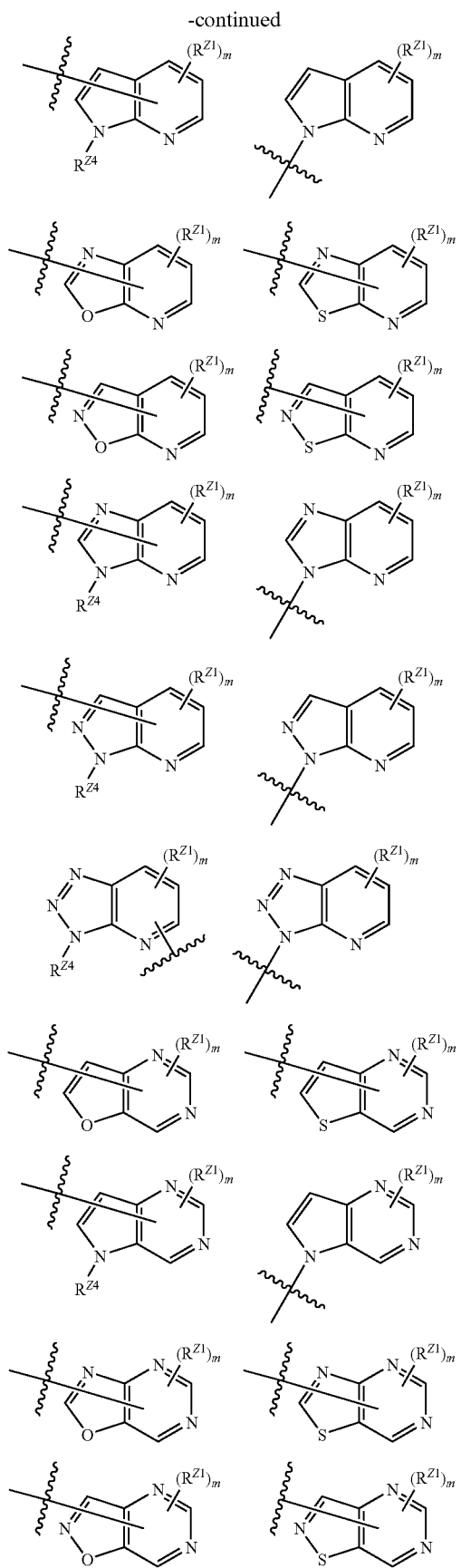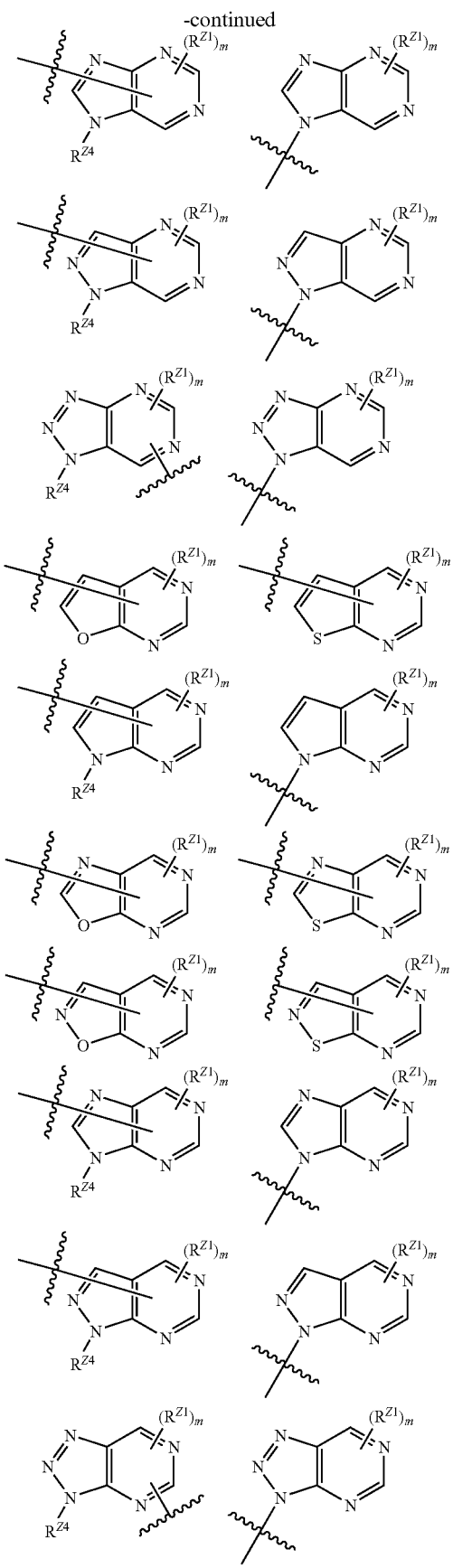

-continued
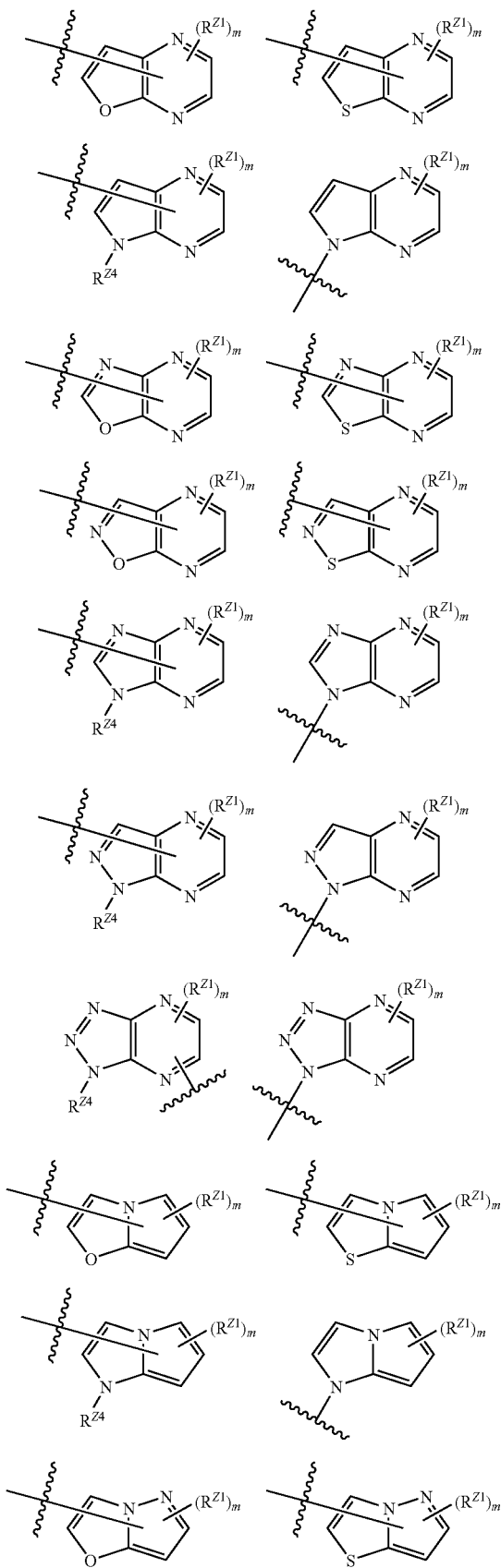
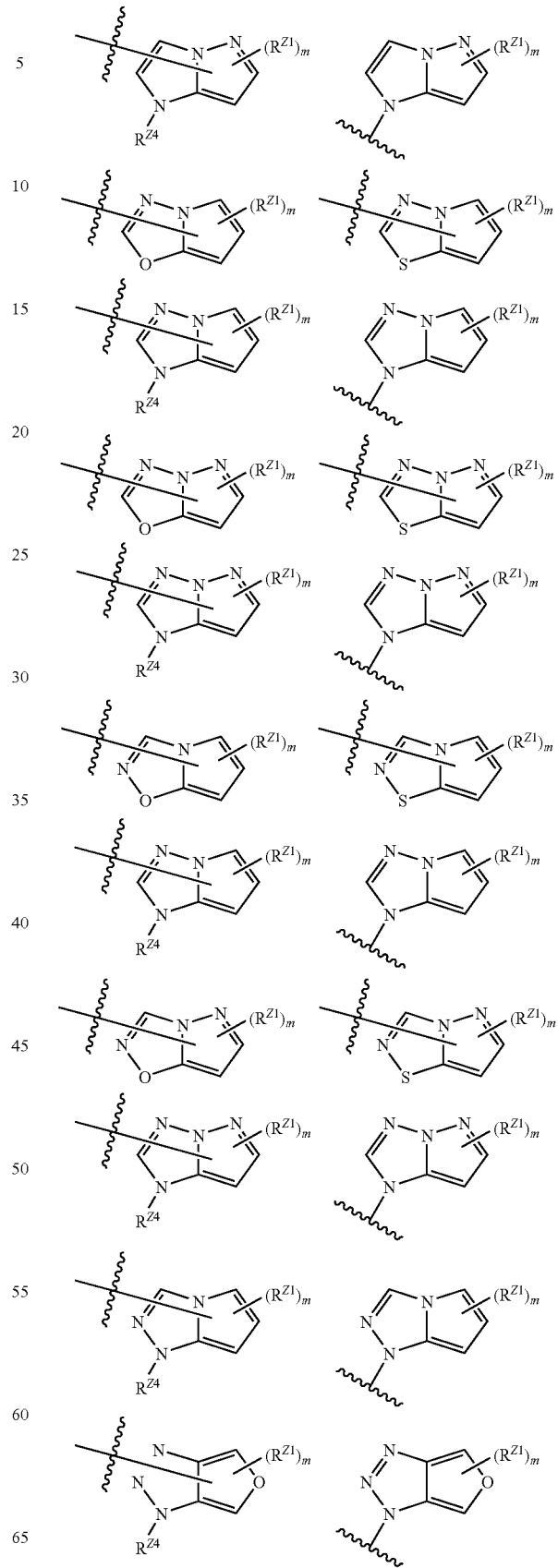

-continued

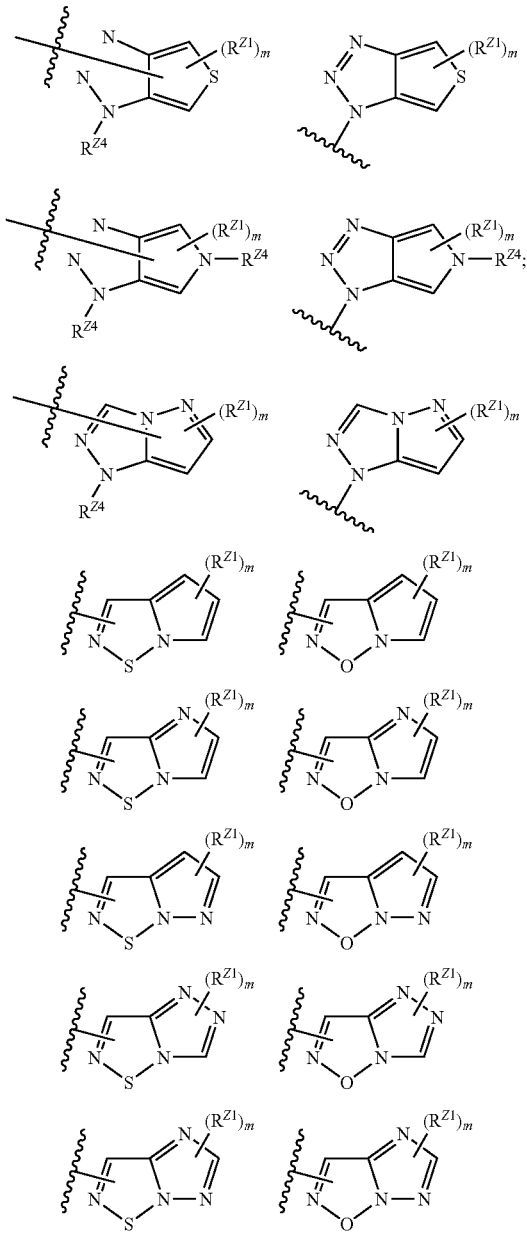

wherein m is an integer from 0 to 3; each occurrence of $R^{Z1}$ is independently hydrogen, alkyl, heteroalkyl, aryl, heteroaryl, -(alkyl)aryl or -(alkyl)heteroaryl, —$OR^{Z2}$, —$SR^{Z2}$, —$NR^{Z2}R^{Z3}$, —$SO_2NR^{Z2}R^{Z3}$, —$SO_2R^{Z1}$, —C(=O)$NR^{Z2}R^{Z3}$, halogen, —CN, —$NR_2$, —C(=O)$R^{Z3}$, —N($R^{Z2}$)C(=O)$R^{Z3}$, wherein each occurrence of $R^{Z2}$ and $R^{Z3}$ is independently hydrogen, lower alkyl lower heteroalkyl, aryl, heteroaryl, -(alkyl)aryl, -(alkyl)heteroaryl or acyl, or $R^{Z2}$ and $R^{Z3}$ taken together with the nitrogen or carbon atom to which they are attached form a 5-6 membered heterocyclic, aryl or heteroaryl ring; and $R^{Z4}$ is hydrogen, lower alkyl, lower heteroalkyl, aryl, heteroaryl, -(alkyl)aryl, -(alkyl)heteroaryl or acyl;

ciii) $L^2$ is absent and Z is an optionally substituted bicyclic heterocycle;

civ) $L^2$ is absent and Z is a moiety having one of the following structures:

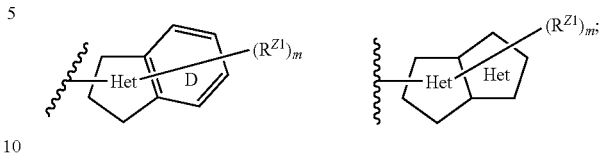

wherein the "D" cyclic moiety is a 6-membered aromatic ring comprising from 0-4 nitrogen atoms; each "Het" moiety independently represents a fully or partially saturated or unsaturated 5-membered ring comprising 1-4 heteroatoms selected from N, O and S; m is an integer from 0-6; and each occurrence of $R^{Z1}$ is independently hydrogen, alkyl, heteroalkyl, aryl, heteroaryl, -(alkyl)aryl, -(alkyl)heteroaryl, —$OR^{Z2}$, —$SR^{Z2}$, —$N(R^{Z2})_2$, —$SO_2N(R^{Z2})_2$, —$SO_2R^{Z4}$, —C(=O)$N(R^{Z2})_2$, halogen, —CN, —$NO_2$, —C(=O)$OR^{Z2}$, —N($R^{Z2}$)C(O)$R^{Z3}$ or —N($R^{Z2}$)$SO_2R^{Z4}$; wherein each occurrence of $R^{Z2}$ and $R^{Z3}$ is independently hydrogen, lower alkyl, lower heteroalkyl, aryl, heteroaryl, -(alkyl)aryl, -(alkyl)heteroaryl, acyl; or any two occurrences of $R^{Z2}$, taken together with the nitrogen atom to which they are attached (e.g., $N(R^{Z2})_2$), form a substituted or unsubstituted heterocyclic moiety; and $R^{Z4}$ is alkyl, heteroalkyl, aryl, heteroaryl, -(alkyl)aryl, or -(alkyl)heteroaryl; and wherein any two adjacent occurrence of $R^{Z1}$ may form a fused 5- to 6-membered aryl, heteroaryl or heterocyclic ring;

cv) $L^2$ is absent and Z is a moiety having one of the following structures:

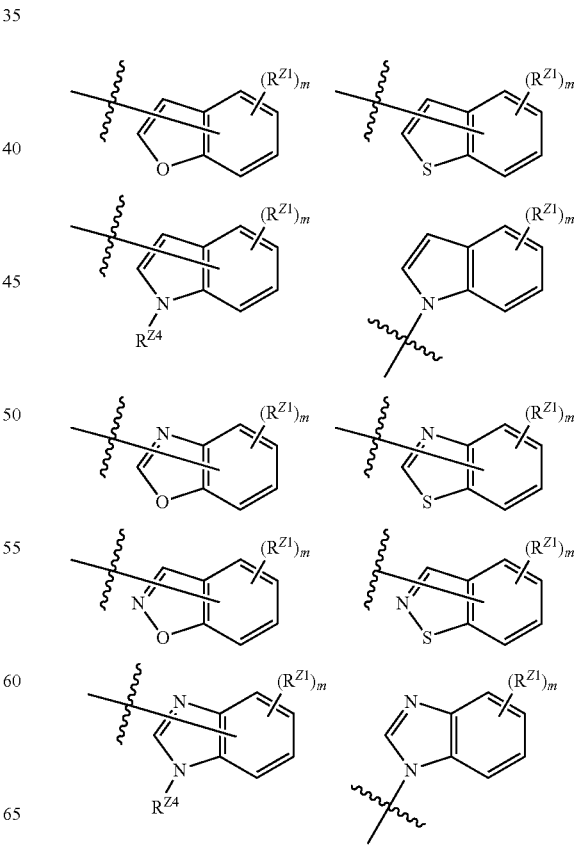

-continued
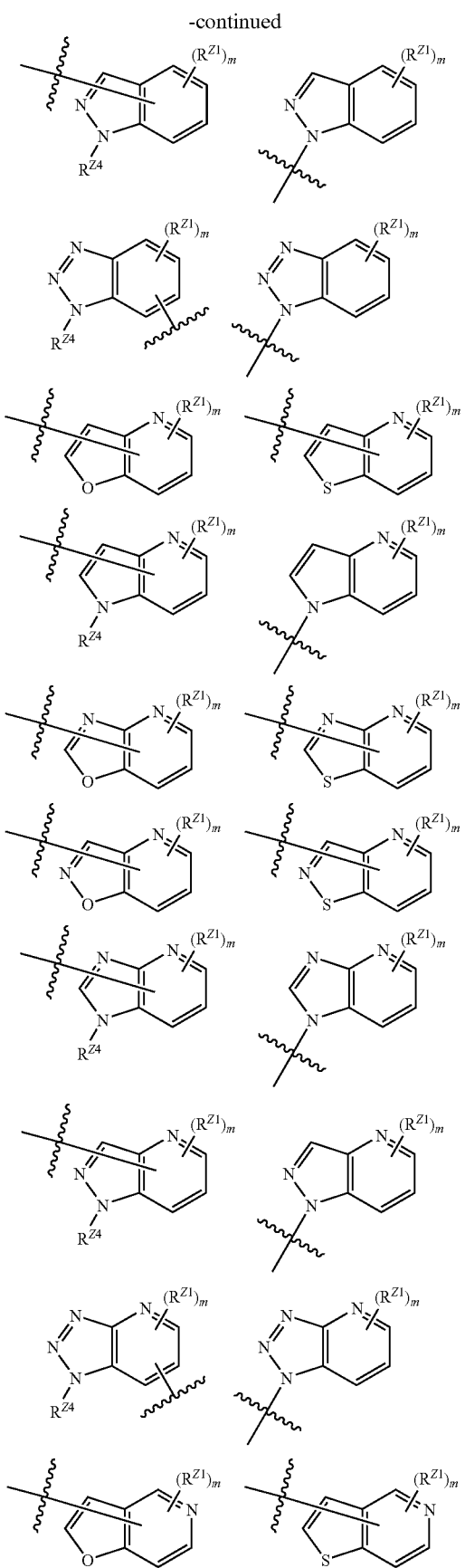
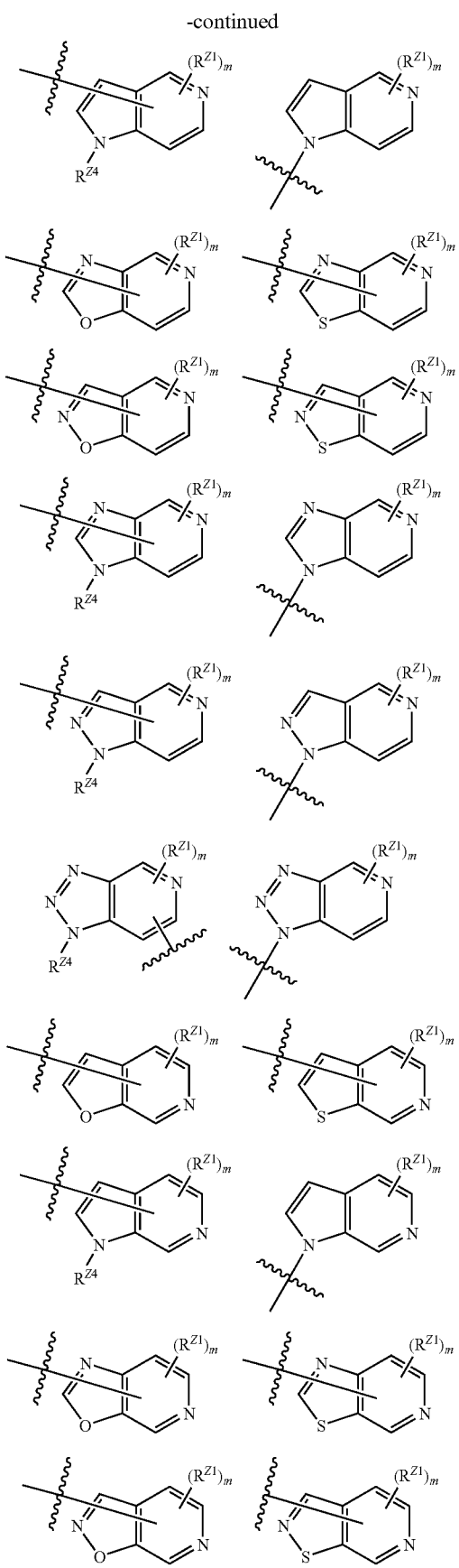

-continued
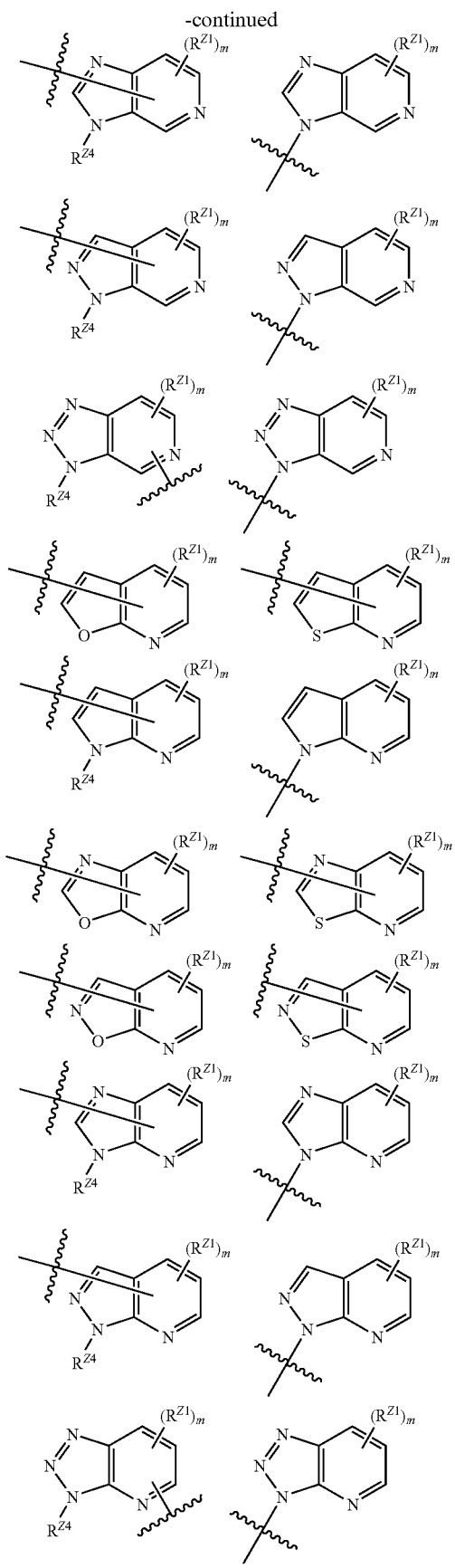
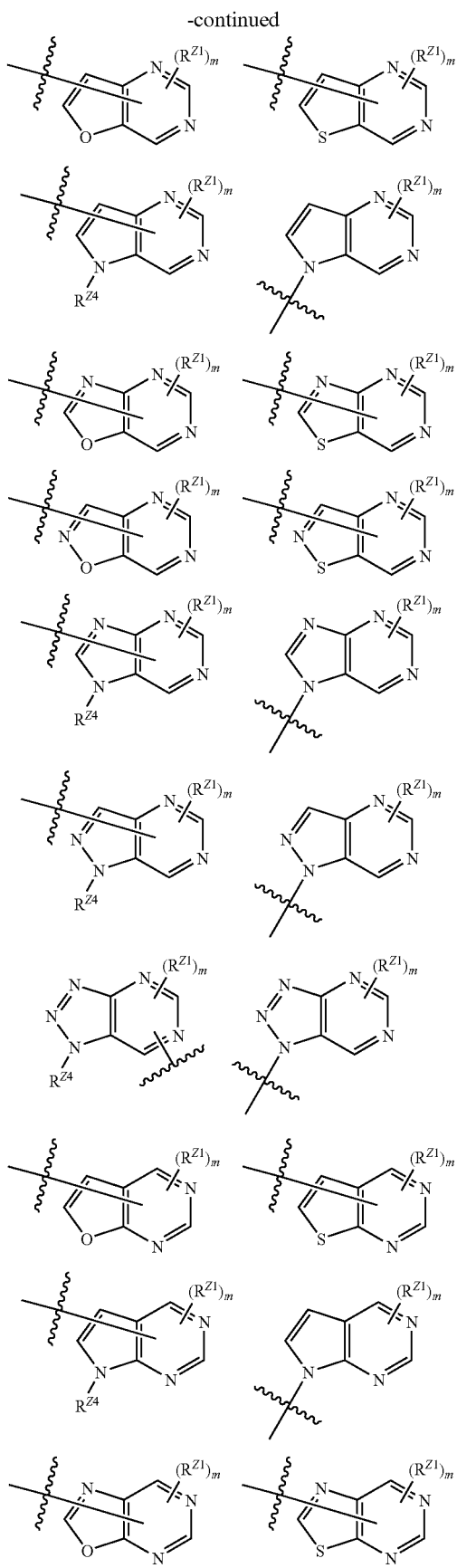

-continued
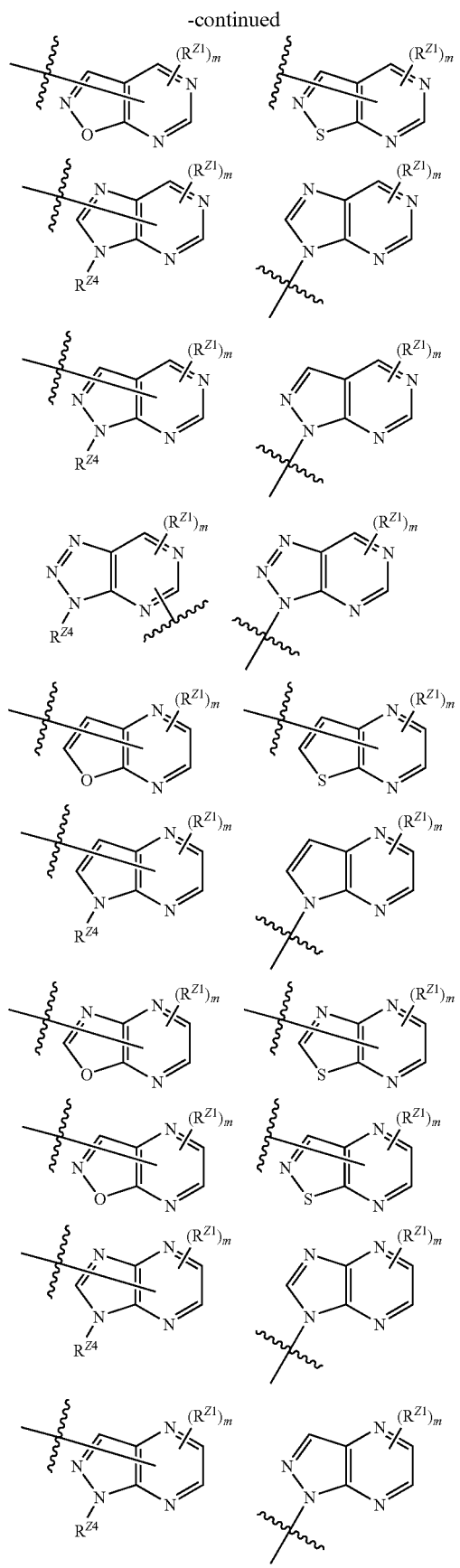
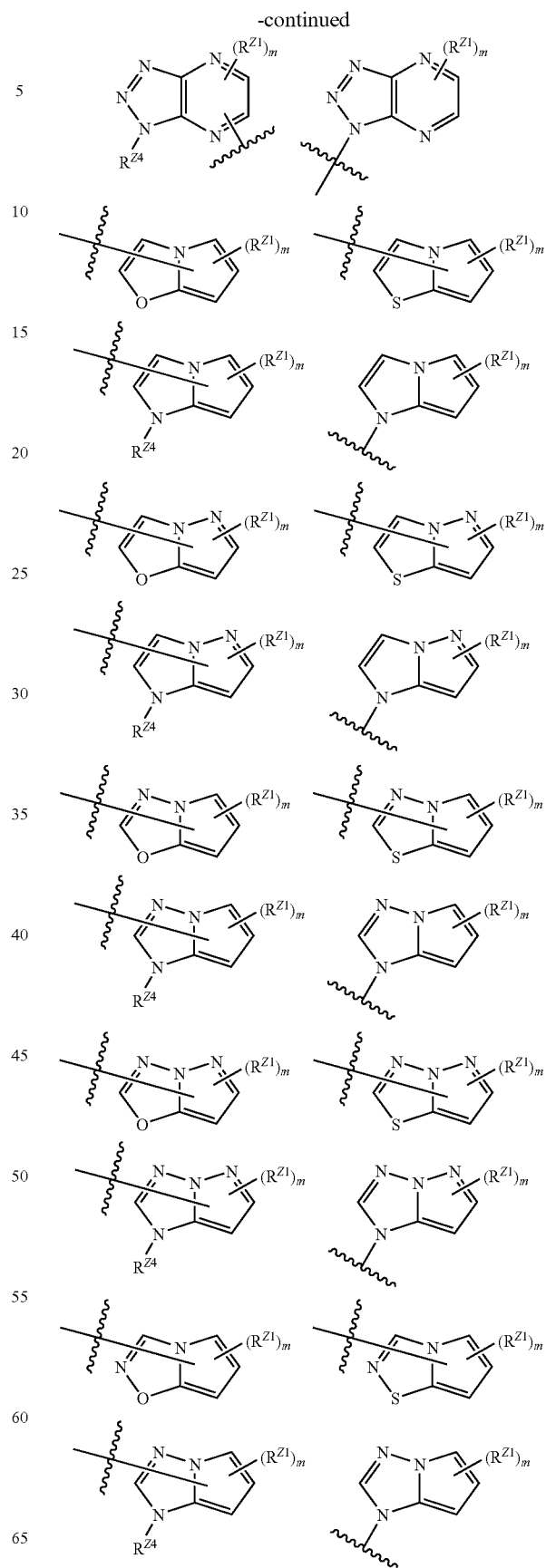

-continued

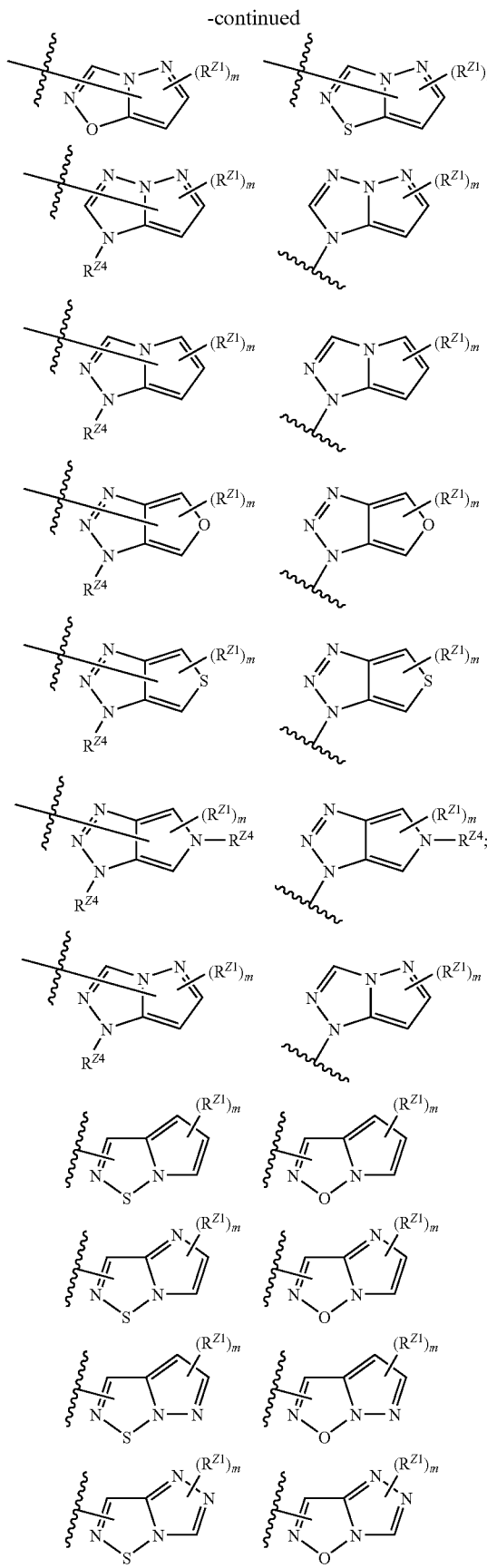
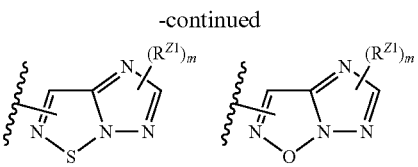

wherein m is an integer from 0 to 3; each occurrence of $R^{Z1}$ is independently hydrogen, alkyl, heteroalkyl, aryl, heteroaryl, -(alkyl)aryl or -(alkyl)heteroaryl, $-OR^{Z2}$, $-SR^{Z2}$, $-NR^{Z2}R^{Z3}$, $-SO_2NR^{Z2}R^{Z3}$, $-SO_2R^{Z1}$, $-C(=O)NR^{Z2}R^{Z3}$, halogen, $-CN$, $-NO_2$, $-C(=O)OR^{Z3}$, $-N(R^{Z2})C(=O)R^{Z3}$, wherein each occurrence of $R^{Z2}$ and $R^{Z3}$ is independently hydrogen, lower alkyl, lower heteroalkyl, aryl, heteroaryl, -(alkyl)aryl, -(alkyl)heteroaryl or acyl, or $R^{Z2}$ and $R^{Z3}$ taken together with the nitrogen or carbon atom to which they are attached form a 5-6 membered heterocyclic, aryl or heteroaryl ring; and $R^{Z4}$ is hydrogen, lower alkyl, lower heteroalkyl, aryl, heteroaryl, -(alkyl)aryl, -(alkyl)heteroaryl or acyl;

cvi) $L^2$ is absent and Z is a moiety having one of the following structures:

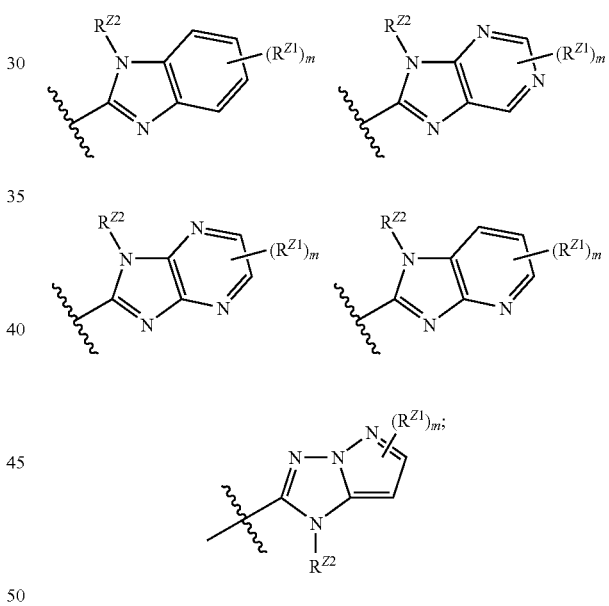

wherein m is an integer from 0-4; and each occurrence of $R^{Z1}$ is independently hydrogen, alkyl, heteroalkyl, aryl, heteroaryl, -(alkyl)aryl, -(alkyl)heteroaryl, $-OR^{Z2}$, $-SR^{Z2}$, $-N(R^{Z2})_2$, $-SO_2N(R^{Z2})_2$, $-SO_2R^{Z4}$, $-C(=O)N(R^{Z2})_2$, halogen, $-CN$, $-NO_2$, $-C(=O)OR^{Z2}$, $-N(R^{Z2})C(=O)R^{Z3}$ or $-N(R^{Z2})SO_2R^{Z4}$; wherein each occurrence of $R^{Z2}$ and $R^{Z3}$ is independently hydrogen, lower alkyl, lower heteroalkyl, aryl, heteroaryl, -(alkyl)aryl, -(alkyl)heteroaryl, acyl; or any two occurrences of $R^{Z2}$, taken together with the nitrogen atom to which they are attached (e.g., $N(R^{Z2})_2$), form a substituted or unsubstituted heterocyclic moiety; and $R^{Z4}$ is alkyl, heteroalkyl, aryl, heteroaryl, -(alkyl)aryl, or -(alkyl)heteroaryl; and wherein any two adjacent occurrence of $R^{Z1}$ may form a fused 5- to 6-membered aryl, heteroaryl or heterocyclic ring;

cvii) L² is absent and Z is a moiety having one of the following structures:

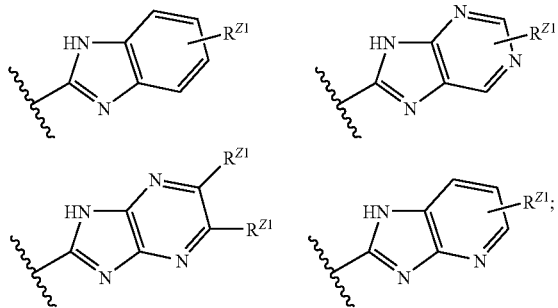

wherein each occurrence of R^{Z1} is independently hydrogen, halogen, lower alkyl, lower heteroalkyl, lower haloalkyl, aryl, heteroaryl, —OR^{Z2}, —SR^{Z2} or —N(R^{Z2})$_2$; wherein each occurrence of R^{Z2} is independently hydrogen, lower alkyl, lower heteroalkyl, aryl, heteroaryl, -(alkyl)aryl, -(alkyl)heteroaryl, acyl; or any two occurrences of R^{Z2}, taken together with the nitrogen atom to which they are attached (e.g., N(R^{Z2})$_2$), form a substituted or unsubstituted heterocyclic moiety;

cviii) L² is absent and Z is a moiety having one of the following structures:

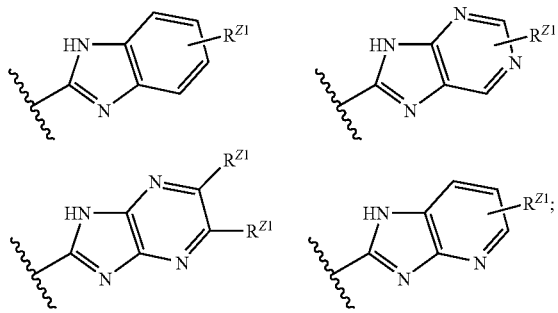

wherein R^{Z1} is independently halogen, lower alkyl or lower haloalkyl;

cix) L² is absent and Z is a moiety having one of the following structures:

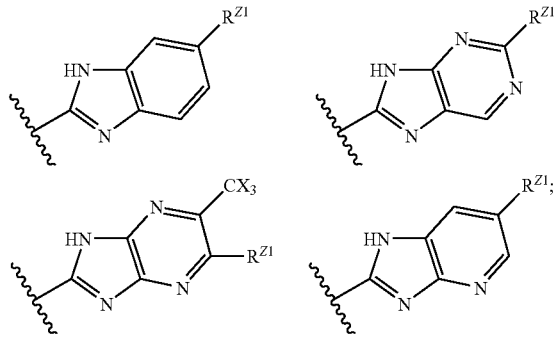

wherein X is halogen and R^{Z1} is halogen, lower alkyl or lower haloalkyl;

cx) L² is absent and Z is a moiety having one of the following structures:

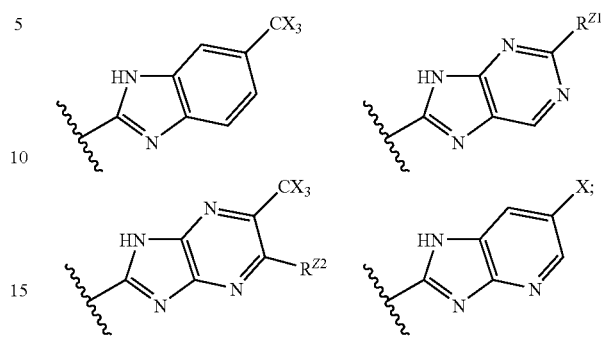

wherein R^{Z1} is lower alkyl; R^{Z2} is —CX$_3$ or lower alkyl; and X is halogen;

cxi) L² is absent and Z is a moiety having one of the following structures:

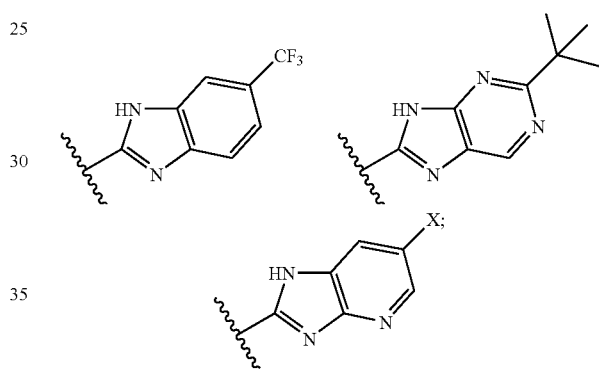

wherein X is F or Cl;

cxii) L² is absent and Z is a moiety having one of the following structures:

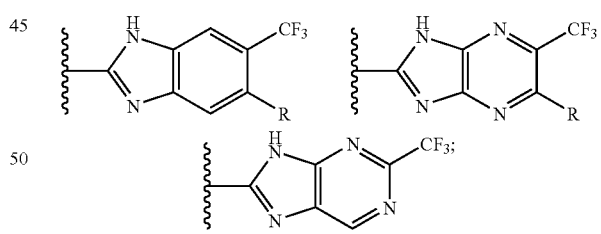

wherein R is —CF$_3$ or tert-butyl;

cxiii) R⁴ is a substituent that enhances water solubility of the compound;

cxiv) R⁴ is hydrogen, —CN, —OR^{4A}, —SR^{4A}, —NR^{4A}R^{4B}, —C(=O)R^{4A}, —C(=O)OR^{4A}, —C(=O)NR^{4A}R^{4B}, —C(=NR^{4A})R^{4B}, —C(=NR^{4A})OR^{4B}, —C(=NR^{4A})NR^{4B}R^{4C}, —S(=O)$_2$R^{4D}, —P(=O)(R^{4D})$_2$, alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl; wherein R^{4A}, R^{4B} and R^{4C} are independently hydrogen, alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl; or taken together with the nitrogen atom to which they are attached form a 5-6-membered heterocyclic ring; and each occurrence of $R^{4D}$ is independently alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl;

cxv) $R^4$ is alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl; each of which bearing a polar substitutent selected from the group consisting of: $-OR^{4A}$, $-SR^{4A}$, $-NR^{4A}R^{4B}$, $-C(=O)OR^{4A}$, $-C(=O)NR^{4A}R^{4B}$, $-C(=NR^{4A})R^{4B}$, $-C(=NR^{4A})OR^{4B}$, $-C(=NR^{4A})NR^{4B}R^{4C}$, $-S(=O)_2R^{4D}$ and $-P(=O)(R^{4D})_2$, wherein each occurrence of $R^{4A}$, $R^{4B}$ and $R^{4C}$ is independently hydrogen, alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl; or taken together with the nitrogen atom to which they are attached form a 5- to 6-membered heterocyclic ring; and each occurrence of $R^{4D}$ is independently alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl;

cxvi) $R^4$ is $C_{1-6}$alkyl$NR^{4A}R^{4B}$, wherein each occurrence of $R^{4A}$ and $R^{4B}$ is independently hydrogen or $C_{1-6}$alkyl; or taken together with the nitrogen atom to which they are attached form a 5- to 6-membered heterocyclic ring;

cxvii) $R^4$ has the structure:

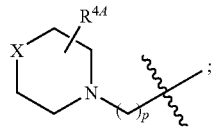

wherein p is an integer from 1-6; X is O, $NR^{4A}$ or $C(R^{4A})_2$; wherein each occurrence of $R^{4A}$ is independently hydrogen or lower alkyl; and/or cxviii) $R^4$ has the structure:

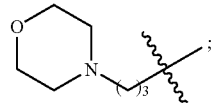

cxix) $R^4$ is absent;

cxx) ----- represents a single bond; and/or cxxi) ----- represents a double bond.

It will be appreciated that for each of the classes and subclasses described above and herein, any one or more occurrences of aliphatic or heteroaliphatic may independently be substituted or unsubstituted, cyclic or acyclic, linear or branched, saturated or unsaturated and any one or more occurrences of aryl, heteroaryl, cycloaliphatic, cycloheteroaliphatic may be substituted or unsubstituted.

The reader will also appreciate that any and all possible combinations of the variables described in i)-through cxxi) above (e.g., $R^1$, $R^2$, $R^3$, $R^4$, $L^1$, $L^2$, Y and Z, among others) are considered part of the invention. Thus, the invention encompasses any and all compounds of formula I generated by taking any possible permutation of variables n, $R^1$, $R^2$, $R^3$, $R^4$, $L^1$, $L^2$, Y and Z, and other variables/substituents (e.g., $R^{L1}$, $R^{L2}$, $R^{Y1}$, $R^{Z1}$ etc.) as further defined for $R^1$, $R^2R^3$, $R^4$, $L^1$, $L^2$, Y and Z, described in i) through cxxi) above.

For example, an exemplary combination of variables described in i) through cxxi) above includes those compounds of Formula I wherein:

----- represents a single bond;

n is 1;

$R^1$ is hydrogen, halogen, $-NO_2$, $-CN$, $-C(=O)OR^{1A}$, $-S(=O)_2R^{1C}$, $-P(=O)(R^{1C})_2$, alkyl, alkenyl, alkynyl, heteroalkyl, heteroalkenyl, heteroalkynyl, heterocyclyl, aryl or heteroaryl; wherein $R^{1A}$ is hydrogen or $C_{1-6}$alkyl; and each occurrence of $R^{1C}$ is independently $C_{1-6}$alkyl;

$R^2$ is hydrogen, halogen, cyano, nitro, or an alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl moiety;

$R^3$ is hydrogen, $-C(=O)R^{1A}$, lower alkyl, lower alkenyl, heterocyclyl, aryl or heteroaryl; wherein $R^{1A}$ is hydrogen, or lower alkyl, aryl, or heteroaryl;

$R^4$ is a substituent that enhances water solubility of the compound;

$L^1$ is $-W^1$-$Alk_1$-; wherein $W^1$ is $-O-$, $-S-$, $-N(R^{W1})-$, $-C(=O)-$, $-N(R^{W1})C(=O)$ or $-C(=O)N(R^{W1})-$, where $R^{W1}$ is hydrogen, lower alkyl, $C_{3-6}$cycloalkyl, lower heteroalkyl, aryl, heteroaryl, -(alkyl)aryl, -(alkyl)heteroaryl or acyl; and $Alk_1$ is a substituted or unsubstituted $C_{1-6}$alkylene or $C_{2-6}$alkenylene chain wherein up to two non-adjacent methylene units are independently optionally replaced by $-C(=O)-$, $-CO_2-$, $-C(=O)C(=O)-$, $-C(=O)NR^{L1A}-$, $-OC(=O)-$, $-OC(=O)NR^{L1A}$, $-NR^{L1A}NR^{L1B}-$, $-NR^{L1A}NR^{L1B}C(=O)-$, $-NR^{L1A}C(=O)-$, $-NR^{L1A}CO_2-$, $-NR^{L1A}C(=O)NR^{L1B}-$, $-S(=O)-$, $-SO_2-$, $-NR^{L1A}SO_2-$, $-SO_2NR^{L1A}-$, $-NR^{L1A}SO_2NR^{L1B}-$, $-O-$, $-S-$, or $-NR^{L1A}-$; wherein each occurrence of $R^{L1A}$ and $R^{L1B}$ is independently hydrogen, lower alkyl, lower heteroalkyl, heterocyclyl, aryl, heteroaryl or acyl;

$L^2$ is $-C(=O)NR^{L2A}-$, $-OC(=O)NR^{L2A}$, $-NR^{L2A}NR^{L2B}-$, $-NR^{L2A}NR^{L2B}C(=O)-$, $-NR^{L2A}C(=O)-$, $-NR^{L2A}C(=O)O-$, $-NR^{L2A}C(=O)NR^{L2B}-$, $-NR^{L2A}SO_2-$, $-SO_2NR^{L2A}-$, $-NR^{L2A}SO_2NR^{L2B}-$, or a substituted or unsubstituted $C_{1-6}$alkylene or $C_{2-6}$alkenylene chain interrupted with at least one nitrogen atom wherein up to two non-adjacent methylene units are independently optionally replaced by $-C(=O)-$, $-CO_2-$, $-C(=O)C(=O)-$, $-C(=O)NR^{L2A}-$, $-OC(=O)-$, $-OC(=O)NR^{L2A}$, $-NR^{L2A}NR^{L2B}-$, $-NR^{L2A}NR^{L2B}C(=O)-$, $-NR^{L2A}C(=O)-$, $-NR^{L2A}CO_2-$, $-NR^{L2A}C(=O)NR^{L2B}-$, $-S(=O)-$, $-SO_2-$, $-NR^{L2A}SO_2-$, $-SO_2NR^{L2A}-$, $-NR^{L2A}SO_2NR^{L2B}-$, $-O-$, $-S-$, or $-NR^{L2A}-$; wherein each occurrence of $R^{L2A}$ and $R^{L2B}$ is independently hydrogen, alkyl, heteroalkyl, heterocyclyl, aromatic, heteroaromatic or acyl;

Y is a saturated or unsaturated cyclic ring system optionally comprising one or more heteroatoms selected from S, N and O;

Z is an alkyl, alkenyl, alkynyl, cycloalkyl, cycloalkenyl, heteroalkyl, heteroalkenyl, heteroalkynyl, heterocyclyl, aryl or heteroaryl moiety.

Other exemplary combinations are illustrated by compounds of the following subgroups:

I. Compounds Having the Structure (and Pharmaceutically Acceptable Derivatives Thereof):

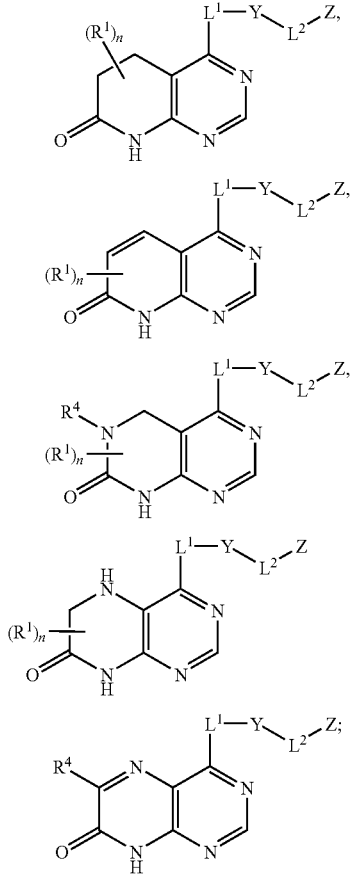

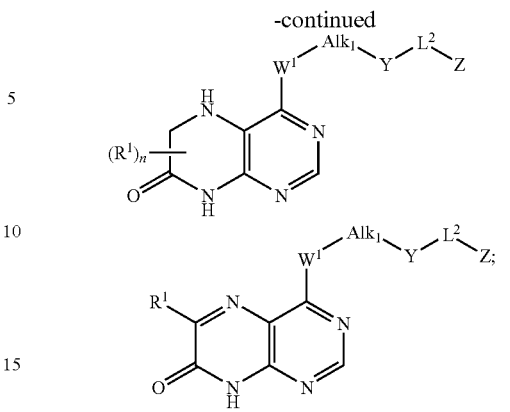

wherein n, $R^1$, $R^4$, $L^1$, $L^2$, Y and Z are as defined generally and in classes and subclasses herein.

II. Compounds Having the Structure (and Pharmaceutically Acceptable Derivatives Thereof):

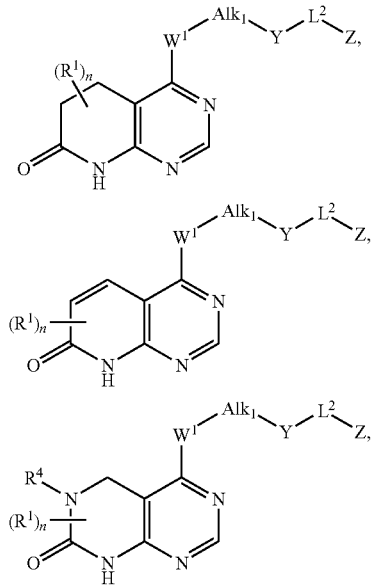

wherein n, $R^1$, $R^4$, $L^2$, Y and Z are as defined generally and in classes and subclasses herein; $W^1$ is —O—, —N($R^{W1}$)—, —C(=O)— or —C(=O)N($R^{W1}$)—, where $R^{W1}$ is hydrogen, alkyl, cycloalkyl, heteroalkyl, aryl, heteroaryl, -(alkyl)aryl, -(alkyl)heteroaryl or acyl; and $Alk_1$ is a substituted or unsubstituted $C_{1-6}$alkylene or $C_{2-6}$alkenylene chain wherein up to two non-adjacent methylene units are independently optionally replaced by —C(=O)—, —CO$_2$—, —C(=O)C(=O)—, —C(=O)NR$^{L1A}$—, —OC(=O)—, —OC(=O)NR$^{L1A}$, —NR$^{L1A}$NR$^{L1B}$—, —NR$^{L1A}$NR$^{L1B}$C(=O)—, —NR$^{L1A}$C(=O)—, —NR$^{L1A}$CO$_2$—, —NR$^{L1A}$C(=O)NR$^{L1B}$—, —S(=O)—, —SO$_2$—, —NR$^{L1A}$SO$_2$—, —SO$_2$NR$^{L1A}$—, —NR$^{L1A}$SO$_2$NR$^{L1B}$—, —O—, —S—, or —NR$^{L1A}$—; wherein each occurrence of $R^{L1A}$ and $R^{L1B}$ is independently hydrogen, alkyl, heteroalkyl, heterocyclyl, aromatic, heteroaromatic or acyl. In certain embodiments, n is 0.

In certain embodiments,

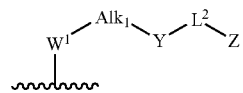

has one of the structures below:

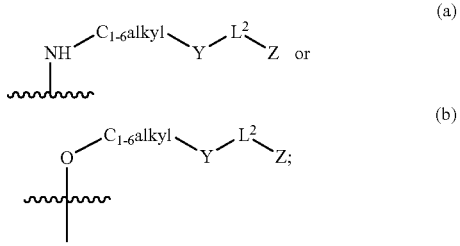

wherein the $C_{1-6}$alkyl moiety may be substituted or unsubstituted.

In certain embodiments,

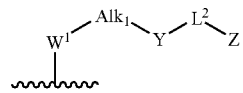

has the structure below:

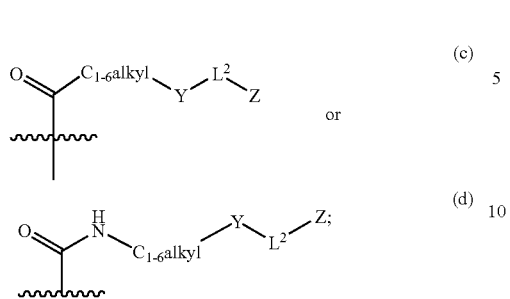

wherein the $C_{1-6}$alkyl moiety may be substituted or unsubstituted.

In certain embodiments, for compounds of formulae (a), (b), (c) and (d), the $C_{1-6}$alkyl moiety is a substituted or unsubstituted $C_{1-2}$alkyl moiety. In certain exemplary embodiments, the $C_{1-6}$alkyl moiety is —CH$_2$—. In certain other exemplary embodiments, the $C_{1-6}$alkyl moiety is —CH(R$^{L1}$)—; wherein R$^{L1}$ is lower alkyl. In certain embodiments, R$^{L1}$ is methyl.

III. Compounds Having the Structure (and Pharmaceutically Acceptable Derivatives Thereof):

wherein n, R$^1$, R$^4$, L$^1$, Y and Z are as defined generally and in classes and subclasses herein; G$_2$ is absent, O or NR$^{G2}$; and R$^{W3}$ and R$^{G2}$ are independently hydrogen, lower alkyl, lower heteroalkyl, aryl, heteroaryl, -(alkyl)aryl, -(alkyl)heteroaryl or acyl.

In certain embodiments, -G$_2$C(=O)N(R$^{W1}$)— is —C(=O)NH—, —OC(=O)NH—, or —NHC(=O)NH—. In certain embodiments, -G$_2$C(=O)N(R$^{W3}$)— is —C(=O)NH—.

IV. Compounds Having the Structure (and Pharmaceutically Acceptable Derivatives Thereof):

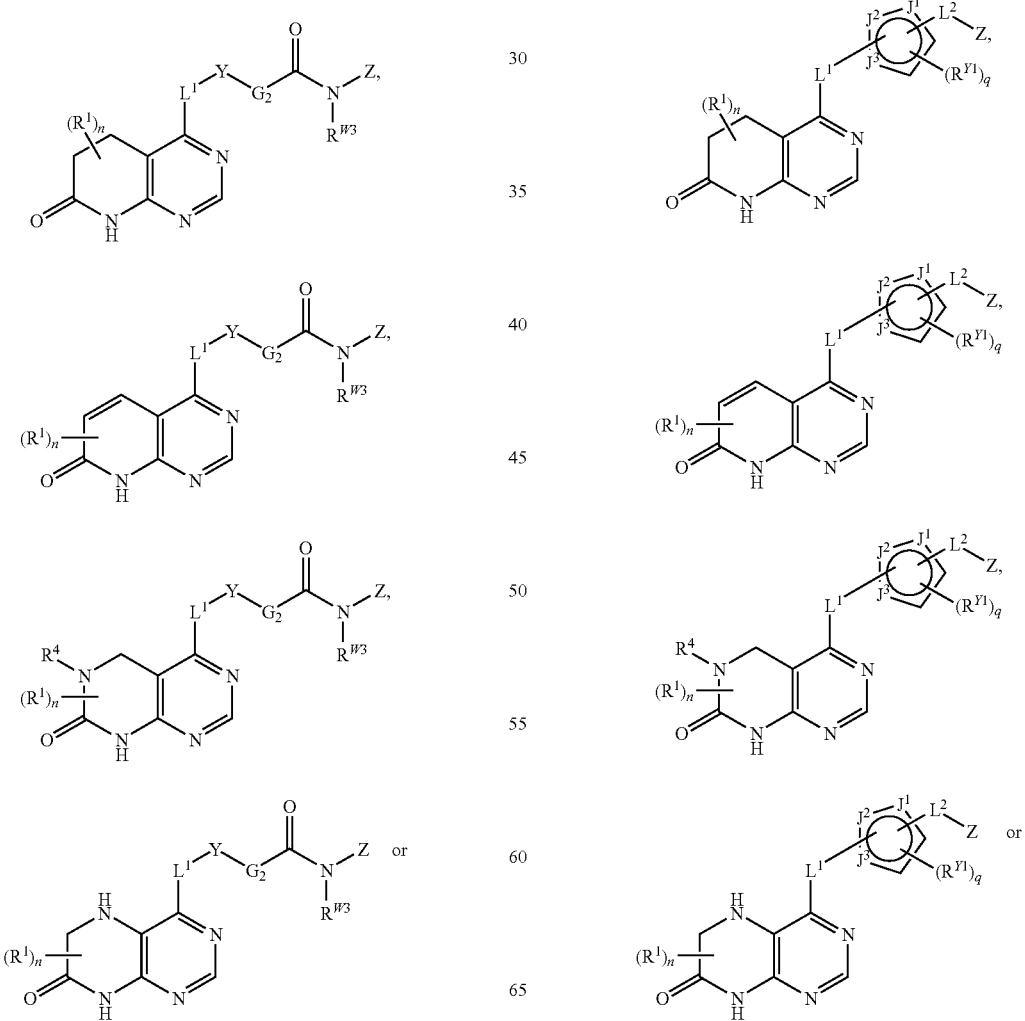

-continued

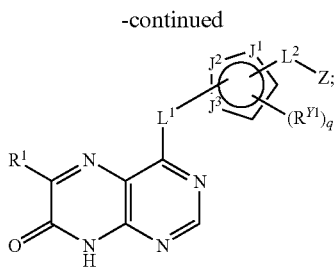

wherein n, $R^1$, $R^4$, $L^1$, $L^2$ and Z are as defined generally and in classes and subclasses herein; q is an integer from 0-2; and $J^1$, $J^2$ and $J^3$ are independently O, S, N, $NR^{Y1}$ or $CR^{Y1}$; wherein each occurrence of $R^{Y1}$ is independently hydrogen, alkyl, heteroalkyl, aryl, heteroaryl, -(alkyl)aryl or -(alkyl)heteroaryl, $-OR^{Y3}$, $-SR^{Y3}$, $-NR^{Y2}R^{Y3}$, $-SO_2NR^{Y2}R^{Y3}$, $-C(=O)NR^{Y2}R^{Y3}$, halogen, $-CN$, $-NO_2$, $-C(=O)OR^{Y3}$, $-N(R^{Y2})C(=O)R^{Y3}$, wherein each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or $R^{Y2}$ and $R^{Y3}$ taken together with the nitrogen atom to which they are attached form a 5-6 membered heterocyclic ring.

In certain embodiments, in compounds of this subclass, the 5-membered ring having the structure:

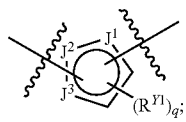

has one of the following structures:

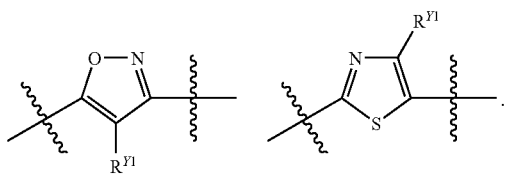

V. Compounds Having the Structure (and Pharmaceutically Acceptable Derivatives Thereof):

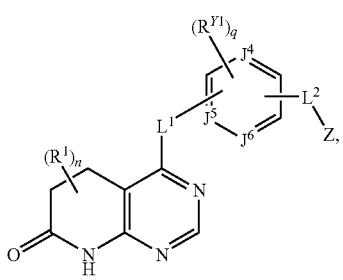

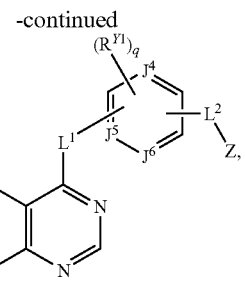

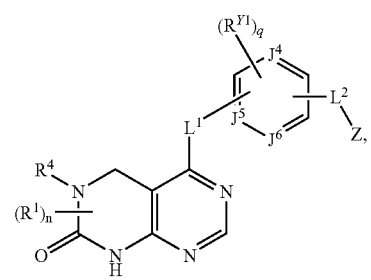

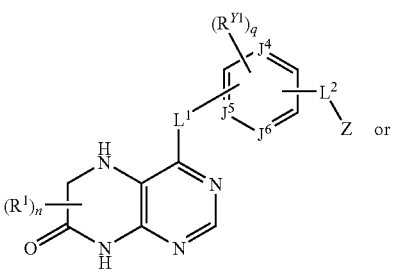

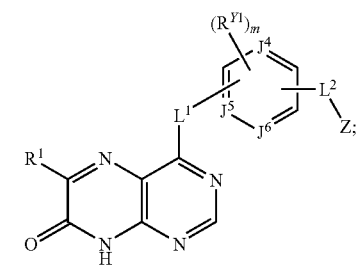

wherein n, $R^1$, $R^4$, $L^1$, $L^2$ and Z are as defined generally and in classes and subclasses herein; q is an integer from 0-3; and $J^4$, $J^5$ and $J^6$ are independently N or $CR^{Y1}$; wherein each occurrence of $R^{Y1}$ is independently hydrogen, alkyl, heteroalkyl, aryl, heteroaryl, -(alkyl)aryl or -(alkyl)heteroaryl, $-OR^{Y3}$, $-SR^{Y3}$, $-NR^{Y2}R^{Y3}$, $-SO_2NR^{Y2}R^{Y3}$, $-C(=O)NR^{Y2}R^{Y3}$, halogen, $-CN$, $-NO_2$, $-C(=O)OR^{Y3}$, $-N(R^{Y2})C(=O)R^{Y3}$, wherein each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or $R^{Y2}$ and $R^{Y3}$ taken together with the nitrogen atom to which they are attached form a 5-6 membered heterocyclic ring.

In certain embodiments, in compounds of this subclass, the 6-membered ring having the structure:

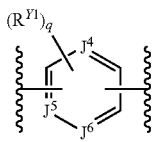

has the structure:

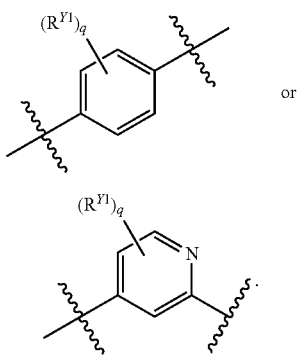

VI. Compounds Having the Structure (and Pharmaceutically Acceptable Derivatives Thereof):

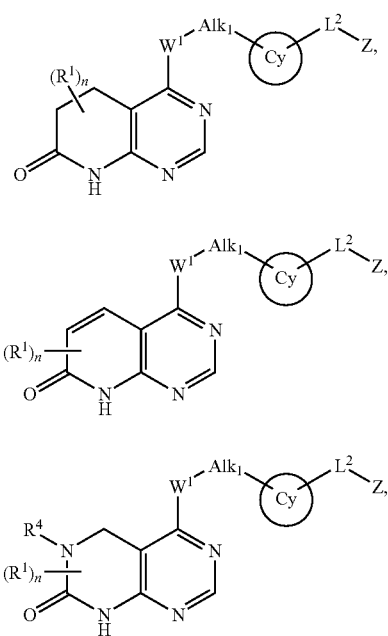

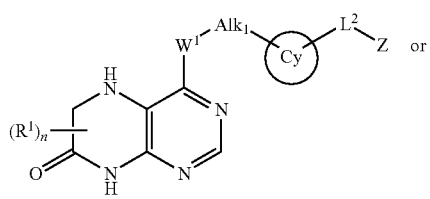

-continued

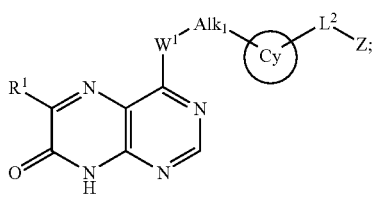

wherein Cy is

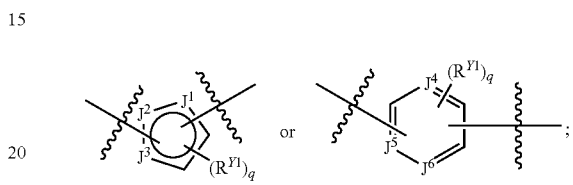

n, $R^1$, $R^4$, $L^2$ and Z are as defined generally and in classes and subclasses herein; $W^1$ is —O—, —N($R^{W1}$)—, —C(=O)— or —C(=O)N($R^{W1}$)—, where $R^{W1}$ is hydrogen, alkyl, cycloalkyl, heteroalkyl, aryl, heteroaryl, -(alkyl)aryl, -(alkyl)heteroaryl or acyl; and $Alk_1$ is a substituted or unsubstituted $C_{1-6}$alkylene or $C_{2-6}$alkenylene chain wherein up to two non-adjacent methylene units are independently optionally replaced by —C(=O)—, —$CO_2$—, —C(=O)C(=O)—, —C(=O)$NR^{L1A}$—, —OC(=O)—, —OC(=O)$NR^{L1A}$—, —$NR^{L1A}NR^{L1B}$—, —$NR^{L1A}NR^{L1B}$C(=O)—, —$NR^{L1A}$C(=O)—, —$NR^{L1A}CO_2$—, —$NR^{L1A}$C(=O)$NR^{L1B}$—, —S(=O)—, —$SO_2$—, —$NR^{L1A}SO_2$—, —$SO_2NR^{L1A}$—, —$NR^{L1A}SO_2NR^{L1B}$—, —O—, —S—, or —$NR^{L1A}$—; wherein each occurrence of $R^{L1A}$ and $R^{L1B}$ is independently hydrogen, alkyl, heteroalkyl, heterocyclyl, aromatic, heteroaromatic or acyl; q is an integer from 0-3; $J^1$, $J^2$ and $J^3$ are independently O, S, N, $NR^{Y1}$ or $CR^{Y1}$; $J^4$, $J^5$ and $J^6$ are independently N or $CR^{Y1}$; wherein each occurrence of $R^{Y1}$ is independently hydrogen, alkyl, heteroalkyl, aryl, heteroaryl, -(alkyl)aryl or -(alkyl)heteroaryl, —$OR^{Y3}$, —$SR^{Y3}$, —$NR^{Y2}R^{Y3}$, —$SO_2NR^{Y2}R^{Y3}$, —C(=O)$NR^{Y2}R^{Y3}$, halogen, —CN, —$NO_2$, —C(=O)$OR^{Y3}$, —N($R^{Y2}$)C(=O)$R^{Y3}$, wherein each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or $R^{Y2}$ and $R^{Y3}$ taken together with the nitrogen atom to which they are attached form a 5-6 membered heterocyclic ring.

In certain embodiments, in compounds of this subclass, the 5-membered ring having the structure:

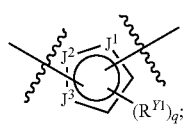

has one of the following structures:

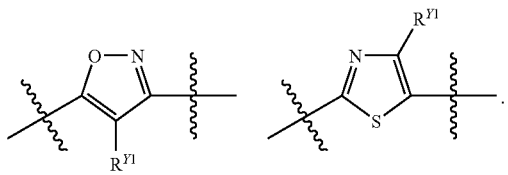

In certain embodiments, in compounds of this subclass, the 6-membered ring having the structure:

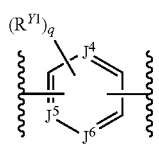

has the structure:

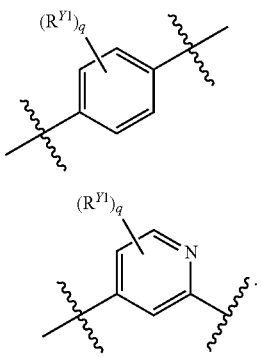

VII. Compounds Having the Structure (and Pharmaceutically Acceptable Derivatives Thereof):

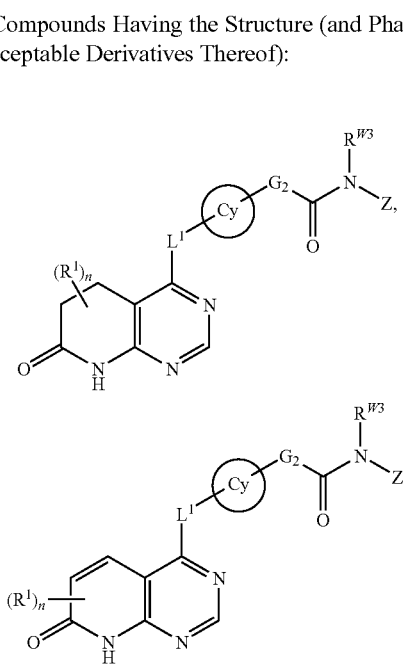

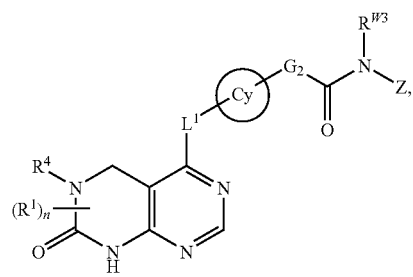

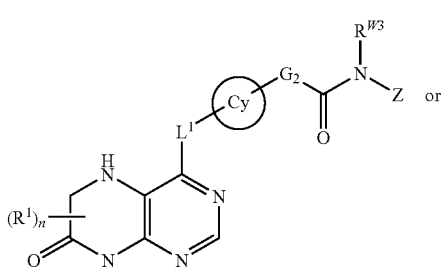

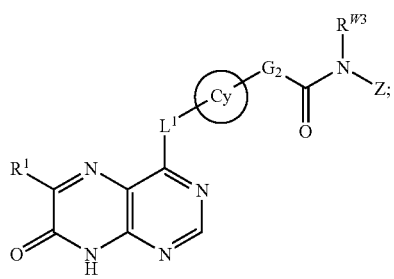

wherein Cy is

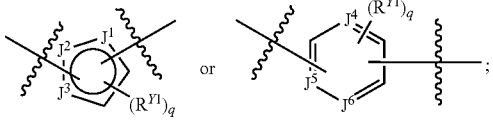

wherein n, $R^1$, $R^4$, $L^1$ and Z are as defined generally and in classes and subclasses herein; q is an integer from 0-3; $J^1$, $J^2$ and $J^3$ are independently O, S, N, $NR^{Y1}$ or $CR^{Y1}$; $J^4$, $J^5$ and independently N or $CR^{Y1}$; wherein each occurrence of $R^{Y1}$ is independently hydrogen, alkyl, heteroalkyl, aryl, heteroaryl, -(alkyl)aryl or -(alkyl)heteroaryl, $-OR^{Y3}$, $-SR^{Y3}$, $-NR^{Y2}R^{Y3}$, $SO_2NR^{Y2}R^{Y3}$, $-C(=O)NR^{Y2}R^{Y3}$, halogen, $-CN$, $-NO_2$, $-C(=O)OR^{Y3}$, $-N(R^{Y2})C(=O)R^{Y3}$, wherein each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or $R^{Y2}$ and $R^{Y3}$ taken together with the nitrogen atom to which they are attached form a 5-6 membered heterocyclic ring; $G_2$ is absent, O or $NR^{G2}$; and $R^{W3}$ and $R^{G2}$ are independently hydrogen, lower alkyl, lower heteroalkyl, aryl, heteroaryl, -(alkyl)aryl, -(alkyl)heteroaryl or acyl.

In certain embodiments, in compounds of this subclass, the 5-membered ring having the structure:

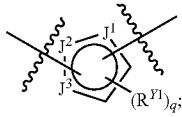

has one of the following structures:

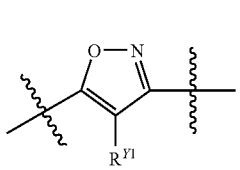 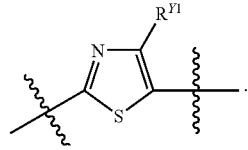

In certain embodiments, in compounds of this subclass, the 6-membered ring having the structure:

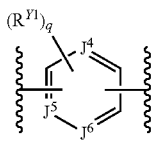

has the structure:

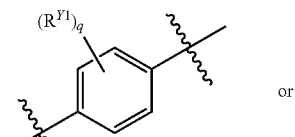 or

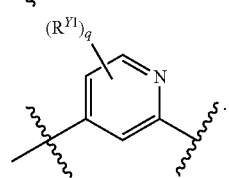

In certain embodiments, -G$_2$C(=O)N(R$^{W3}$)— is —C(=O)NH—, —OC(=O)NH—, or —NHC(=O)NH—. In certain embodiments, -G$_2$C(=O)N(R$^{W3}$)— is —C(=O)NH—.

VIII. Compounds Having the Structure (and Pharmaceutically Acceptable Derivatives Thereof):

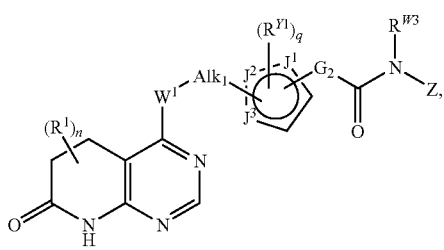

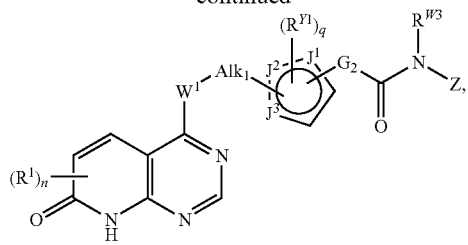

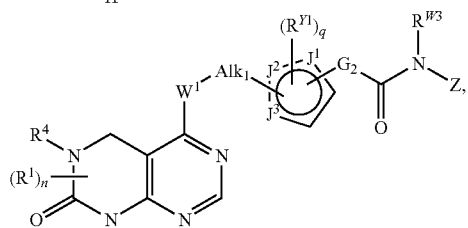

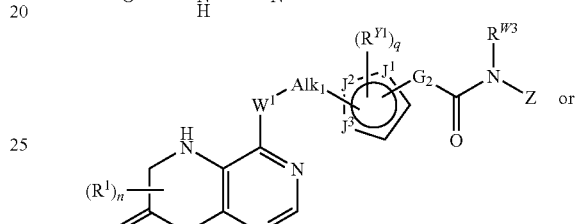

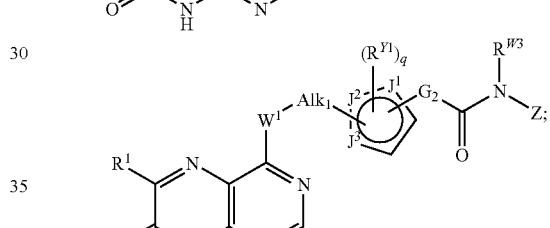

wherein n, R$^1$, R$^4$ and Z are as defined generally and in classes and subclasses herein; W$^1$ is —O—, —N(R$^{W1}$)—, —C(=O)— or —C(=O)N(R$^{W1}$)—, where R$^{W1}$ is hydrogen, alkyl, cycloalkyl, heteroalkyl, aryl, heteroaryl, -(alkyl)aryl, -(alkyl)heteroaryl or acyl; and Alk$_1$ is a substituted or unsubstituted C$_{1-6}$alkylene or C$_{2-6}$alkenylene chain wherein up to two non-adjacent methylene units are independently optionally replaced by —C(=O)—, —CO$_2$—, —C(=O)C(=O)—, —C(=O)NR$^{L1A}$—, —OC(=O)—, —OC(=O)NR$^{L1A}$—, —NR$^{L1A}$NR$^{L1B}$—, —NR$^{L1A}$NR$^{L1B}$C(=O)—, —NR$^{L1A}$C(=O)—, —NR$^{L1A}$CO$_2$—, —NR$^{L1A}$C(=O)NR$^{L1B}$—, —S(=O)—, —SO$_2$—, —NR$^{L1A}$SO$_2$—, —SO$_2$NR$^{L1A}$—, —NR$^{L1A}$SO$_2$NR$^{L1B}$—, —O—, —S—, or —NR$^{L1A}$—; wherein each occurrence of R$^{L1A}$ and R$^{L1B}$ is independently hydrogen, alkyl, heteroalkyl, heterocyclyl, aromatic, heteroaromatic or acyl; q is an integer from 0-3; J$^1$, J$^2$ and J$^3$ are independently O, S, N, NR$^{Y1}$ or CR$^{Y1}$; wherein each occurrence of R$^{Y1}$ is independently hydrogen, alkyl, heteroalkyl, aryl, heteroaryl, -(alkyl)aryl or -(alkyl)heteroaryl, —OR$^{Y3}$, —SR$^{Y3}$, —NR$^{Y2}$R$^{Y3}$, —SO$_2$NR$^{Y2}$R$^{Y3}$, —C(=O)NR$^{Y2}$R$^{Y3}$, halogen, —CN, —NO$_2$, —C('N(R$^{Y2}$)C(=O)R$^{Y3}$, wherein each occurrence of R$^{Y2}$ and R$^{Y3}$ is independently hydrogen, lower alkyl, lower heteroalkyl, aryl, heteroaryl, -(alkyl)aryl, -(alkyl)heteroaryl or acyl, or R$^{Y2}$ and R$^{Y3}$ taken together with the nitrogen atom to which they are attached form a 5-6 membered heterocyclic ring; G$_2$ is absent, O or NR$^{G2}$; and R$^{W3}$ and R$^{G2}$ are independently hydrogen, lower alkyl, lower heteroalkyl, aryl, heteroaryl, -(alkyl)aryl, -(alkyl)heteroaryl or acyl.

In certain embodiments, the 5-membered ring having the structure:

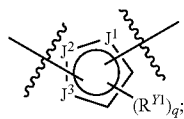

has one of the following structures:

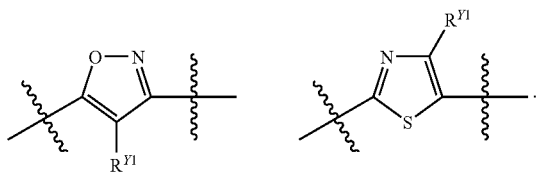

In certain embodiments, —N(R$^{W3}$)C(=O)G$_2$- is —NHC(=O)—, —NHC(=O)O—, or —NHC(=O)NH—.

IX. Compounds Having the Structure (and Pharmaceutically Acceptable Derivatives Thereof):

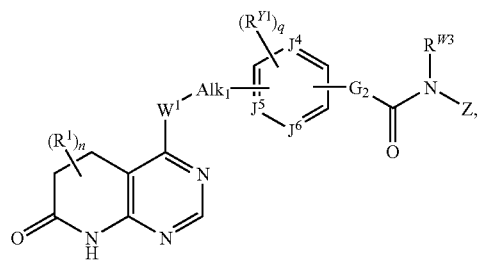

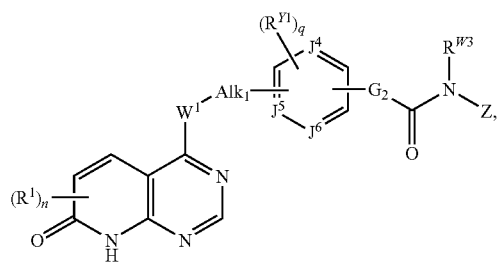

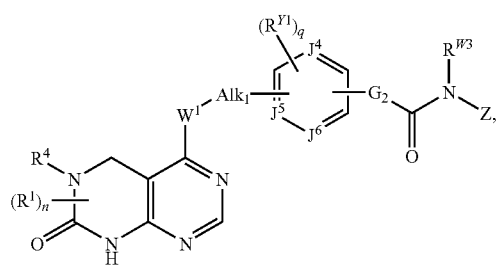

-continued

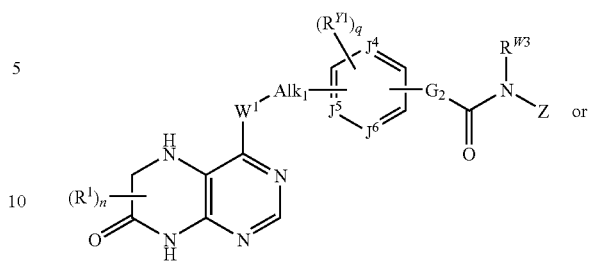

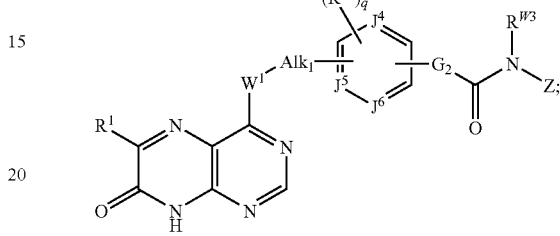

wherein n, R$^1$, R$^4$ and Z are as defined generally and in classes and subclasses herein; W$^1$ is —O—, —N(R$^{W1}$)—, —C(=O)— or —C(=O)N(R$^{W1}$)—, where R$^{W1}$ is hydrogen, alkyl, cycloalkyl, heteroalkyl, aryl, heteroaryl, -(alkyl)aryl, -(alkyl)heteroaryl or acyl; and Alk$_1$ is a substituted or unsubstituted C$_{1-6}$alkylene or C$_{2-6}$alkenylene chain wherein up to two non-adjacent methylene units are independently optionally replaced by —C(=O)—, —CO$_2$—, —C(=O)C(=O)—, —C(=O)NR$^{L1A}$—, —OC(=O)—, —OC(=O)NR$^{L1A}$—, —NR$^{L1A}$NR$^{L1B}$—, —NR$^{L1A}$NR$^{L1B}$C(=O)—, —NR$^{L1A}$C(=O)—, —NR$^{L1A}$CO$_2$—, —NR$^{L1A}$C(=O)NR$^{L1B}$—, —S(=O)—, —SO$_2$—, —NR$^{L1A}$SO$_2$—, —SO$_2$NR$^{L1A}$—, —NR$^{L1A}$SO$_2$NR$^{L1B}$—, —O—, —S—, or —NR$^{L1A}$—; wherein each occurrence of R$^{L1A}$ and R$^{L1B}$ is independently hydrogen, alkyl, heteroalkyl, heterocyclyl, aromatic, heteroaromatic or acyl; q is an integer from 0-3; J$^4$, J$^5$ and J$^6$ are independently N or CR$^{Y1}$; wherein each occurrence of R$^{Y1}$ is independently hydrogen, alkyl, heteroalkyl, aryl, heteroaryl, -(alkyl)aryl or -(alkyl)heteroaryl, —OR$^{Y3}$, —SR$^{Y3}$, —NR$^{Y2}$R$^{Y3}$, —SO$_2$NR$^{Y2}$R$^{Y3}$, —C(=O)NR$^{Y2}$R$^{Y3}$, halogen, —CN, —NO$_2$, —C(=O)OR$^{Y3}$, —N(R$^{Y2}$)C(=O)R$^{Y3}$, wherein each occurrence of R$^{Y2}$ and R$^{Y3}$ is independently hydrogen, lower alkyl, lower heteroalkyl, aryl, heteroaryl, -(alkyl)aryl, -(alkyl)heteroaryl or acyl, or R$^{Y2}$ and R$^{Y3}$ taken together with the nitrogen atom to which they are attached form a 5-6 membered heterocyclic ring; G$_2$ is absent, O or NR$^{G2}$; and R$^{W3}$ and R$^{G2}$ are independently hydrogen, lower alkyl, lower heteroalkyl, aryl, heteroaryl, -(alkyl)aryl, -(alkyl)heteroaryl or acyl.

In certain embodiments, the 6-membered ring having the structure:

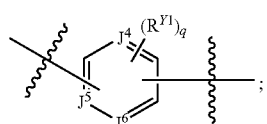

has one of the following structures:

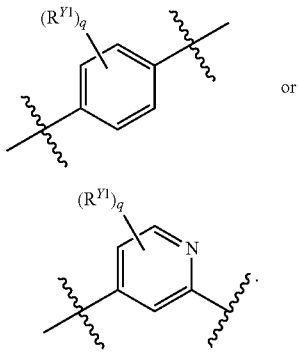

In certain embodiments, —N(R^{W3})C(=O)G_2- is —NHC(=O)—, —NHC(=O)O—, or —NHC(=O)NH—.

X. Compounds Having the Structure (and Pharmaceutically Acceptable Derivatives Thereof):

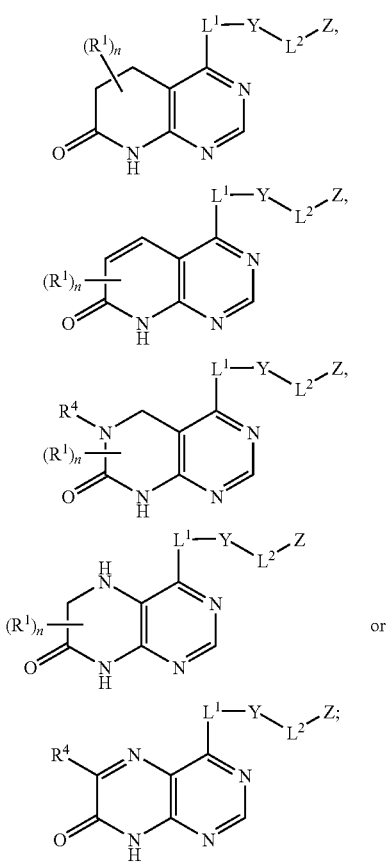

wherein L² is absent and Z is:

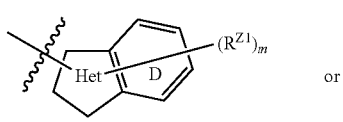

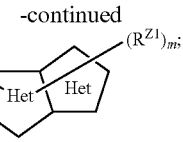

n, $R^1$, $R^4$, $L^1$ and Y are as defined generally and in classes and subclasses herein; the "D" cyclic moiety is a 6-membered aromatic ring comprising from 0-4 nitrogen atoms; each "Het" moiety independently represents a fully or partially saturated or unsaturated 5-membered ring comprising 1-4 heteroatoms selected from N, O and S; m is an integer from 0-6; and each occurrence of $R^{Z1}$ is independently hydrogen, alkyl, heteroalkyl, aryl, heteroaryl, -(alkyl)aryl, -(alkyl)heteroaryl, —$OR^{Z2}$, —$SR^{Z2}$, —$N(R^{Z2})_2$, —$SO_2N(R^{Z2})_2$, —$SO_2R^{Z4}$, —$C(=O)N(R^{Z2})_2$, halogen, —CN, —$NO_2$, —$C(=O)OR^{Z2}$, —$N(R^{Z2})C(=O)R^{Z3}$ or —$N(R^{Z2})SO_2R^{Z4}$; wherein each occurrence of $R^{Z2}$ and $R^{Z3}$ is independently hydrogen, lower alkyl, lower heteroalkyl, aryl, heteroaryl, -(alkyl)aryl, -(alkyl)heteroaryl, acyl; or any two occurrences of $R^{Z2}$, taken together with the nitrogen atom to which they are attached (e.g., $N(R^{Z2})_2$), form a substituted or unsubstituted heterocyclic moiety; and $R^{Z4}$ is alkyl, heteroalkyl, aryl, heteroaryl, -(alkyl)aryl, or -(alkyl)heteroaryl; and wherein any two adjacent occurrence of $R^{Z1}$ may form a fused 5- to 6-membered aryl, heteroaryl or heterocyclic ring.

In certain embodiments, L² is absent and Z is a moiety having one of the following structures:

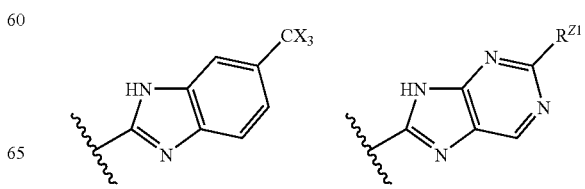

wherein each occurrence of $R^{Z1}$ is independently hydrogen, halogen, lower alkyl, lower heteroalkyl, lower haloalkyl, aryl, heteroaryl, —$OR^{Z2}$, —$SR^{Z2}$ or —$N(R^{Z2})_2$; wherein each occurrence of $R^{Z2}$ is independently hydrogen, lower alkyl, lower heteroalkyl, aryl, heteroaryl, -(alkyl)aryl, -(alkyl)heteroaryl, acyl; or any two occurrences of $R^{Z2}$, taken together with the nitrogen atom to which they are attached (e.g., $N(R^{Z2})_2$), form a substituted or unsubstituted heterocyclic moiety.

In certain embodiments, L² is absent and Z is a moiety having one of the following structures:

-continued

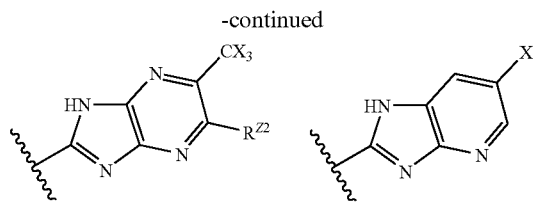

wherein X is halogen, $R^{Z1}$ is halogen, lower alkyl or lower haloalkyl; and $R^{Z2}$ is —$CX_3$ or lower alkyl. In certain exemplary embodiments, $R^{Z1}$ is —$CF_3$ or tert-butyl. In certain exemplary embodiments, X is F or Cl. In certain exemplary embodiments, $R^{Z2}$ is —$CF_3$ or tert-butyl.

In certain embodiments, $L^2$ is absent and Z is a moiety having one of the following structures:

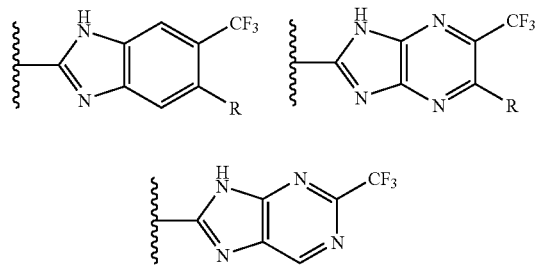

wherein R is —$CF_3$ or tert-butyl.

XI. Compounds Having the Structure (and Pharmaceutically Acceptable Derivatives Thereof):

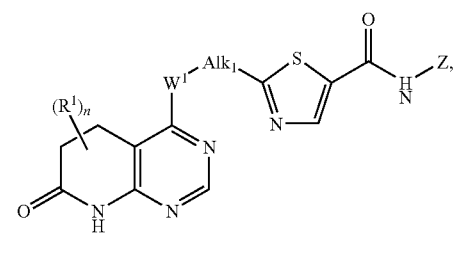

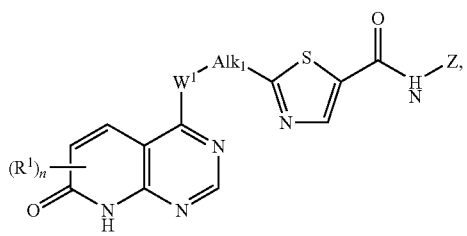

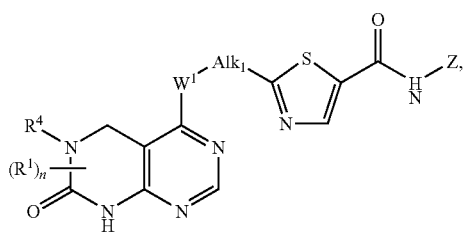

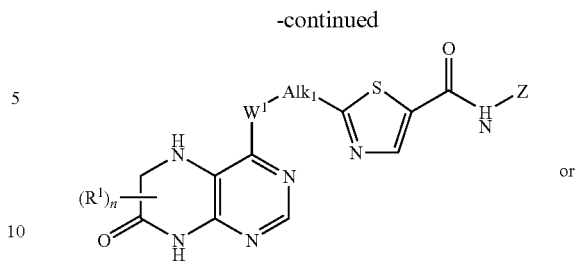

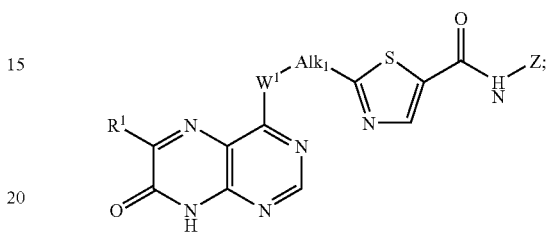

wherein n, $R^1$ and $R^4$ are as defined generally and in classes and subclasses herein; Z is an aryl, heteroaryl or heterocyclic moiety; $W^1$ is —O—, —N($R^{W1}$)—, —C(=O)— or —C(=O)N($R^{W1}$)—, where $R^{W1}$ is hydrogen, alkyl, cycloalkyl, heteroalkyl, aryl, heteroaryl, -(alkyl)aryl, -(alkyl)heteroaryl or acyl; and $Alk_1$ is a substituted or unsubstituted $C_{1-6}$alkylene or $C_{2-6}$alkenylene chain wherein up to two non-adjacent methylene units are independently optionally replaced by —C(=O)—, —$CO_2$—, —C(=O)C(=O)—, —C(=O)$NR^{L1A}$—, —OC(=O)—, —OC(=O)$NR^{L1A}$—, —$NR^{L1A}NR^{L1B}$—, —$NR^{L1A}NR^{L1B}$C(=O)—, —$NR^{L1A}$C(=O)—, —$NR^{L1A}CO_2$—, —$NR^{L1A}$C(=O)$NR^{L1B}$—, —S(=O)—, —$SO_2$—, —$NR^{L1A}SO_2$—, —$SO_2NR^{L1A}$—, —$NR^{L1A}SO_2NR^{L1B}$—, —O—, —S—, or —$NR^{L1A}$—; wherein each occurrence of $R^{L1A}$ and $R^{L1B}$ is independently hydrogen, alkyl, heteroalkyl, heterocyclyl, aromatic, heteroaromatic or acyl.

XII. Compounds Having the Structure (and Pharmaceutically Acceptable Derivatives Thereof):

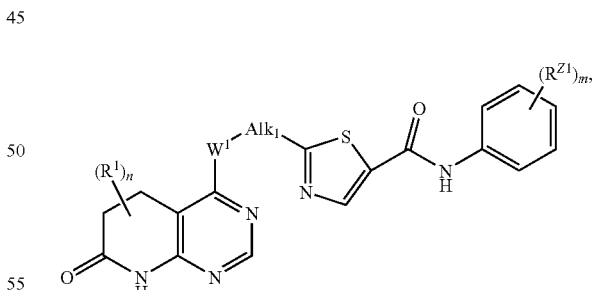

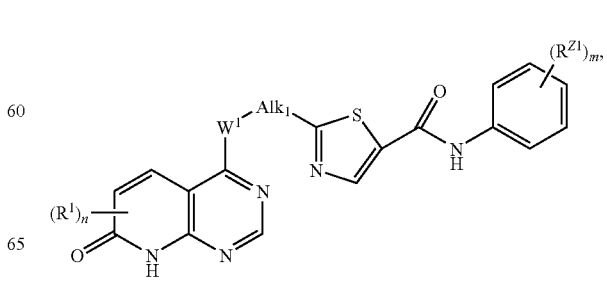

-continued

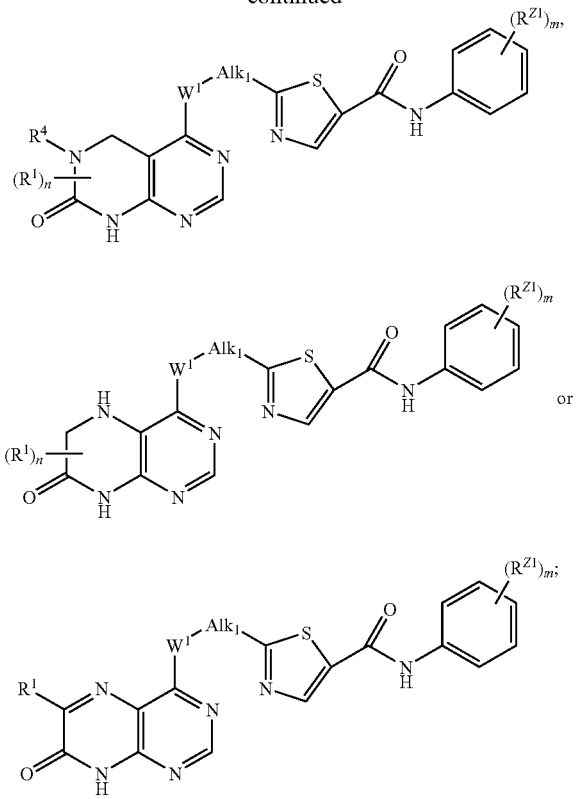

wherein n, $R^1$ and $R^4$ are as defined generally and in classes and subclasses herein; $W^1$ is —O—, —N($R^{W1}$)—, —C(=O)— or —C(=O)N($R^{W1}$)—, where $R^{W1}$ is hydrogen, alkyl, cycloalkyl, heteroalkyl, aryl, heteroaryl, -(alkyl)aryl, -(alkyl)heteroaryl or acyl; and $Alk_1$ is a substituted or unsubstituted $C_{1-6}$alkylene or $C_{2-6}$alkenylene chain wherein up to two non-adjacent methylene units are independently optionally replaced by —C(=O)—, —CO$_2$—, —C(=O)C(=O)—, —C(=O)N$R^{L1A}$—, —OC(=O)—, —OC(=O)N$R^{L1A}$—, —N$R^{L1A}$N$R^{L1B}$—, —N$R^{L1A}$N$R^{L1B}$C(=O)—, —N$R^{L1A}$C(=O)—, —N$R^{L1A}$CO$_2$—, —N$R^{L1A}$C(=O)N$R^{L1B}$—, —S(=O)—, —SO$_2$—, —N$R^{L1A}$SO$_2$—, —SO$_2$N$R^{L1A}$—, —N$R^{L1A}$SO$_2$N$R^{L1B}$—, —O—, —S—, or —N$R^{L1A}$—; wherein each occurrence of $R^{L1A}$ and $R^{L1B}$ is independently hydrogen, alkyl, heteroalkyl, heterocyclyl, aromatic, heteroaromatic or acyl; m is an integer from 0 to 3; each occurrence of $R^{Z1}$ is independently hydrogen, alkyl, heteroalkyl, aryl, heteroaryl, -(alkyl)aryl or -(alkyl)heteroaryl, —O$R^{Z2}$, —S$R^{Z2}$, —N$R^{Z2}R^{Z3}$, —SO$_2$N$R^{Z2}R^{Z3}$, —SO$_2R^{Z4}$, —C(=O)N$R^{Z2}R^{Z3}$, halogen, —CN, —NO$_2$, —C(=O)O$R^{Z3}$, —N($R^{Z2}$)C(=O)$R^{Z3}$, wherein each occurrence of $R^{Z2}$ and $R^{Z3}$ is independently hydrogen, lower alkyl, lower heteroalkyl, aryl, heteroaryl, -(alkyl)aryl, -(alkyl)heteroaryl or acyl, or $R^{Z2}$ and $R^{Z3}$ taken together with the nitrogen or carbon atom to which they are attached form a 5-6 membered heterocyclic, aryl or heteroaryl ring; and $R^{Z4}$ is alkyl, heteroalkyl, aryl, heteroaryl, -(alkyl)aryl, or -(alkyl)heteroaryl.

In certain embodiments, the compounds have the structure:

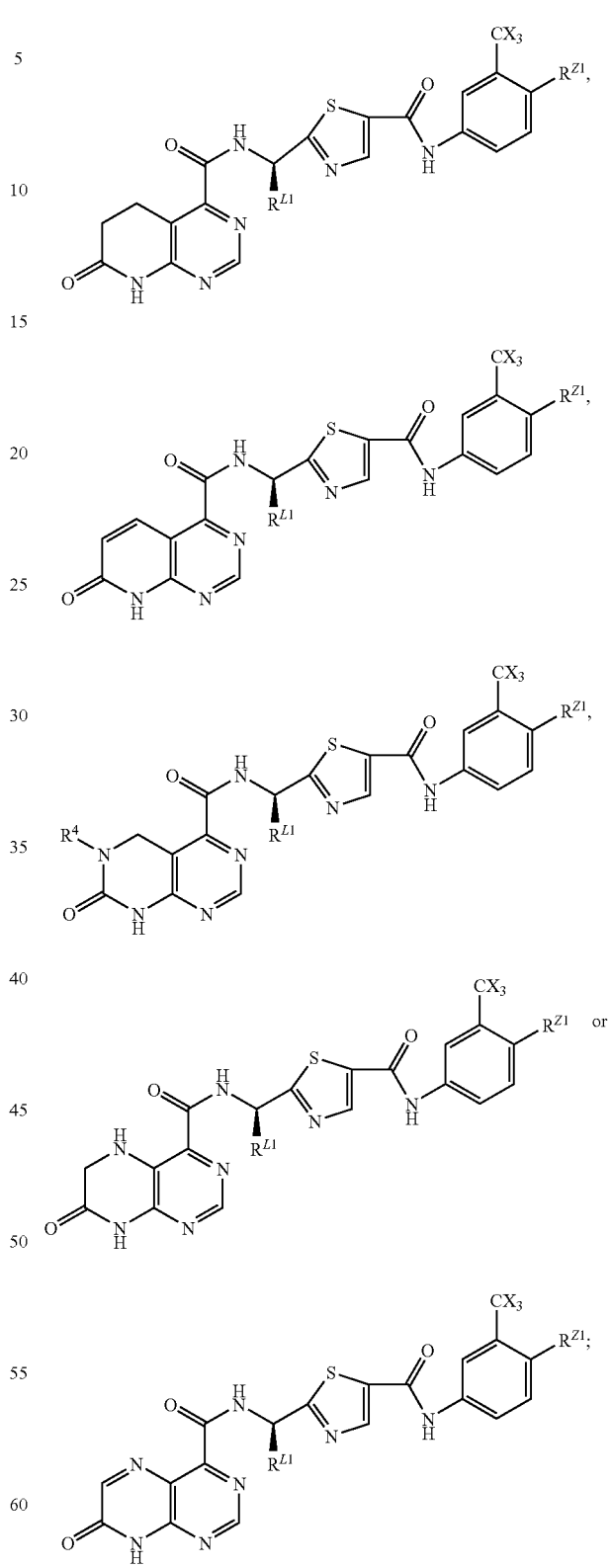

wherein $R^{Z1}$ is halogen or lower alkyl, X is halogen and $R^{L1}$ is lower alkyl. In certain exemplary embodiments, $R^{Z1}$ is Cl or methyl. In certain exemplary embodiments, $R^{L1}$ is methyl.

XIII. Compounds Having the Structure (and Pharmaceutically Acceptable Derivatives Thereof):

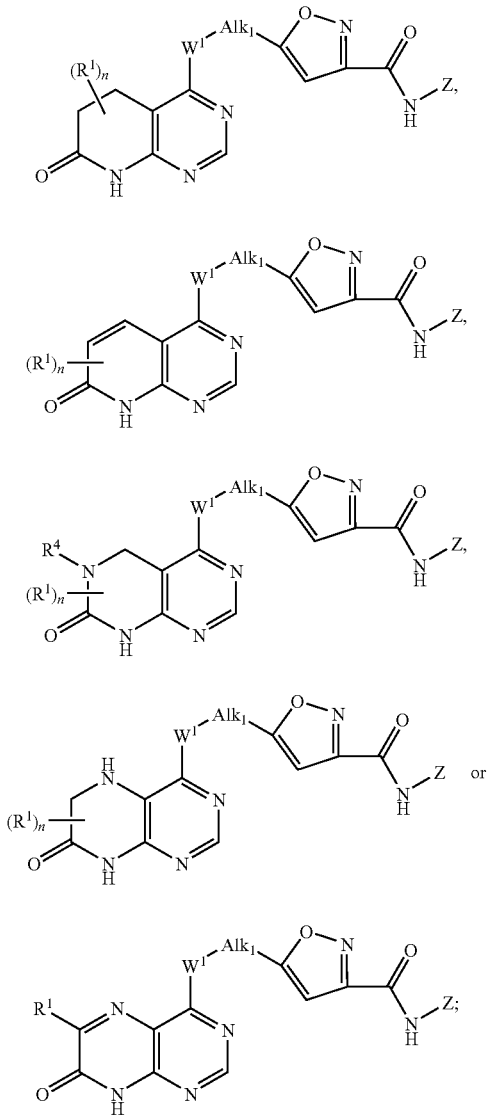

wherein n, $R^1$ and $R^4$ are as defined generally and in classes and subclasses herein; Z is an aryl, heteroaryl or heterocyclic moiety; $W^1$ is —O—, —N($R^{W1}$)—, —C(=O)— or —C(=O)N($R^{W1}$)—, where $R^{W1}$ is hydrogen, alkyl, cycloalkyl, heteroalkyl, aryl, heteroaryl, -(alkyl)aryl, -(alkyl)heteroaryl or acyl; and $Alk_1$ is a substituted or unsubstituted $C_{1-6}$alkylene or $C_{2-6}$alkenylene chain wherein up to two non-adjacent methylene units are independently optionally replaced by —C(=O)—, —$CO_2$—, —C(=O)C(=O)—, —C(=O)$NR^{L1A}$—, —OC(=O)—, —OC(=O)$NR^{L1A}$—, —$NR^{L1A}NR^{L1B}$—, —$NR^{L1A}NR^{L1B}$C(=O)—, —$NR^{L1A}$C(=O)—, —$NR^{L1A}CO_2$—, —$NR^{L1A}$C(=O)$NR^{L1B}$—, —S(=O)—, —$SO_2$—, —$NR^{L1A}SO_2$—, —$SO_2NR^{L1A}$—, —$NR^{L1A}SO_2NR^{L1B}$—, —O—, —S—, or —$NR^{L1A}$—; wherein each occurrence of $R^{L1A}$ and $R^{L1B}$ is independently hydrogen, alkyl, heteroalkyl, heterocyclyl, aromatic, heteroaromatic or acyl.

XIV. Compounds Having the Structure (and Pharmaceutically Acceptable Derivatives Thereof):

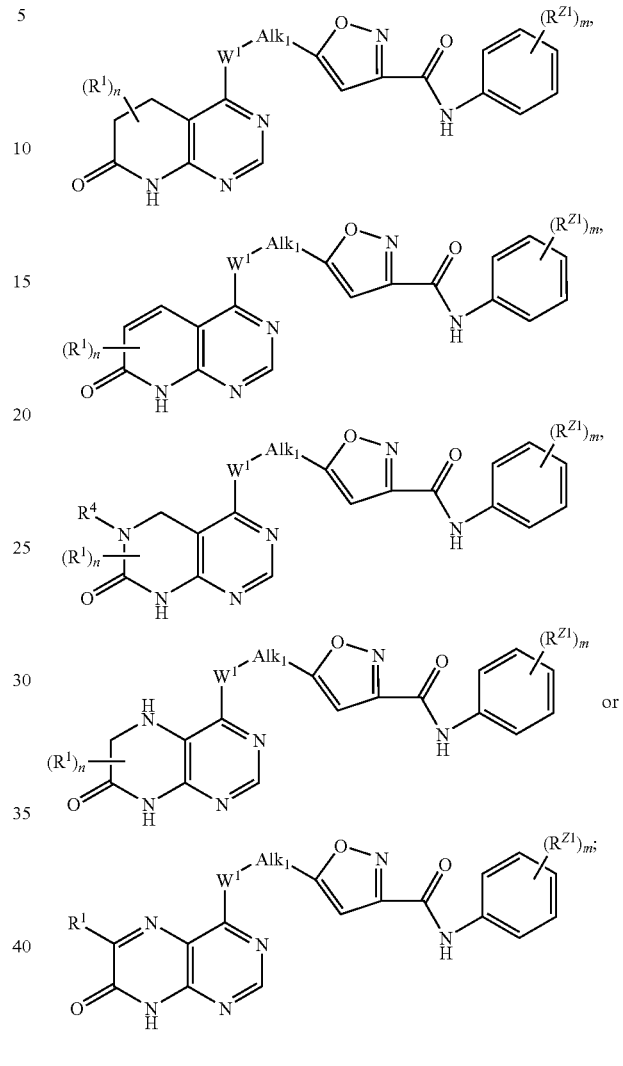

wherein n, $R^1$ and $R^4$ are as defined generally and in classes and subclasses herein; $W^1$ is —O—, —N($R^{W1}$)—, —C(=O)— or —C(=O)N($R^{W1}$)—, where $R^{W1}$ is hydrogen, alkyl, cycloalkyl, heteroalkyl, aryl, heteroaryl, -(alkyl)aryl, -(alkyl)heteroaryl or acyl; and $Alk_1$ is a substituted or unsubstituted $C_{1-6}$alkylene or $C_{2-6}$alkenylene chain wherein up to two non-adjacent methylene units are independently optionally replaced by —C(=O)—, —$CO_2$—, —C(=O)C(=O)—, —C(=O)$NR^{L1A}$—, —OC(=O)—, —OC(=O)$NR^{L1A}$—, —$NR^{L1A}NR^{L1B}$—, —$NR^{L1A}NR^{L1B}$C(=O)—, —$NR^{L1A}$C(=O)—, —$NR^{L1A}CO_2$—, —$NR^{L1A}$C(=O)$NR^{L1B}$—, —S(=O)—, —$SO_2$—, —$NR^{L1A}SO_2$—, —$SO_2NR^{L1A}$—, —$NR^{L1A}SO_2NR^{L1B}$—, —O—, —S—, or —$NR^{L1A}$—; wherein each occurrence of $R^{L1A}$ and $R^{L1B}$ is independently hydrogen, alkyl, heteroalkyl, heterocyclyl, aromatic, heteroaromatic or acyl; m is an integer from 0 to 3; each occurrence of $R^{Z1}$ is independently hydrogen, alkyl, heteroalkyl, aryl, heteroaryl, -(alkyl)aryl or -(alkyl)heteroaryl, —$OR^{Z2}$, —$SR^{Z2}$, —$NR^{Z2}R^{Z3}$, —$SO_2NR^{Z2}R^{Z3}$, —$SO_2R^{Z4}$, —C(=O)$NR^{Z2}R^{Z3}$, halogen, —CN, —$NO_2$, —C(=O)$OR^{Z3}$, —N($R^{Z2}$)C(=O)$R^{Z3}$, wherein each occurrence of $R^{Z2}$ and $R^{Z3}$ is independently hydrogen, lower alkyl, lower heteroalkyl, aryl, heteroaryl, -(alkyl)aryl, -(alkyl)heteroaryl or acyl, or $R^{Z2}$ and $R^{Z3}$ taken together with the nitrogen or carbon atom to which they are attached form a 5-6 membered heterocyclic, aryl or heteroaryl ring; and $R^{Z4}$ is alkyl, heteroalkyl, aryl, heteroaryl, -(alkyl)aryl, or -(alkyl)heteroaryl.

In certain embodiments, the compounds have the structure:

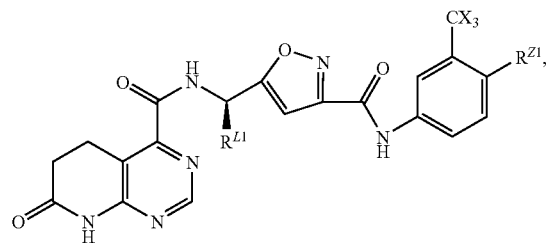

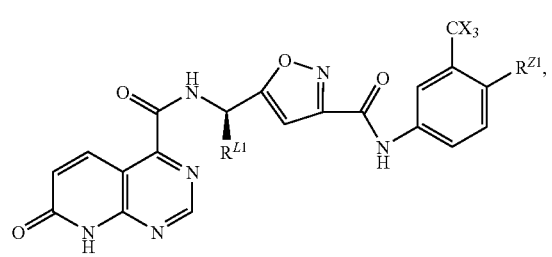

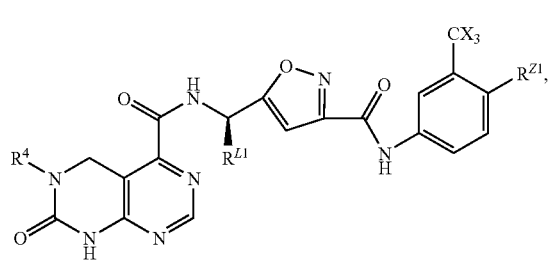

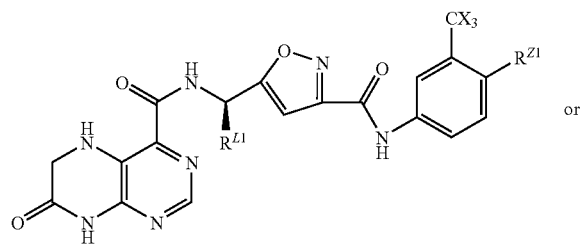

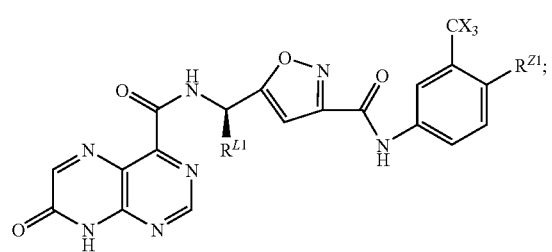

wherein $R^{Z1}$ is halogen or lower alkyl, X is halogen and $R^{L1}$ is lower alkyl. In certain exemplary embodiments, $R^{Z1}$ is Cl or methyl. In certain exemplary embodiments, $R^{L1}$ is methyl.

XV. Compounds Having the Structure (and Pharmaceutically Acceptable Derivatives Thereof):

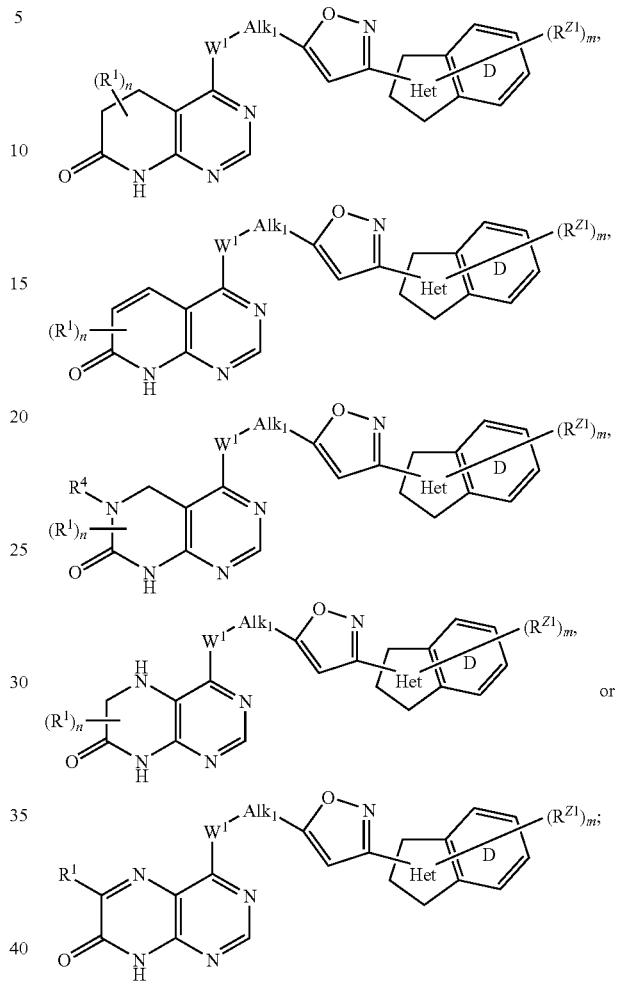

wherein n, $R^1$ and $R^4$ are as defined generally and in classes and subclasses herein; $W^1$ is —O—, —N($R^{W1}$)—, —C(=O)— or —C(=O)N($R^{W1}$)—, where $R^{W1}$ is hydrogen, alkyl, cycloalkyl, heteroalkyl, aryl, heteroaryl, -(alkyl)aryl, -(alkyl)heteroaryl or acyl; and $Alk_1$ is a substituted or unsubstituted $C_{1-6}$alkylene or $C_{2-6}$alkenylene chain wherein up to two non-adjacent methylene units are independently optionally replaced by —C(=O)—, —CO$_2$—, —C(=O)C(=O)—, —C(=O)NR$^{L1A}$—, —OC(=O)—, —OC(=O)NR$^{L1A}$, —NR$^{L1A}$NR$^{L1B}$, —NR$^{L1A}$NR$^{L1B}$(=O)—, —NR$^{L1A}$C(=O)—, —NR$^{L1A}$CO$_2$, —NR$^{L1A}$C(=O)NR$^{L1B}$, —S(=O)—, —SO$_2$—, —NR$^{L1A}$SO$_2$—, —SO$_2$NR$^{L1A}$—, —NR$^{L1A}$SO$_2$NR$^{L1B}$—, —O—, —S—, or —NR$^{L1A}$—; wherein each occurrence of $R^{L1A}$ and $R^{L1B}$ is independently hydrogen, alkyl, heteroalkyl, heterocyclyl, aromatic, heteroaromatic or acyl; the "D" cyclic moiety is a 6-membered aromatic ring comprising from 0-4 nitrogen atoms; each "Het" moiety independently represents a fully or partially saturated or unsaturated 5-membered ring comprising 1-4 heteroatoms selected from N, O and S; m is an integer from 0-6; and each occurrence of $R^{Z1}$ is independently hydrogen, alkyl, heteroalkyl, aryl, heteroaryl, -(alkyl)aryl, -(alkyl)heteroaryl, —OR$^{Z2}$, —SR$^{Z2}$, —N(R$^{Z2}$)$_2$, —SO$_2$N(R$^{Z2}$)$_2$, —SO$_2$R$^{Z4}$, —C(=O)N(R$^{Z2}$)$_2$, halogen, —CN, —NO$_2$, —C(=O)OR$^{Z2}$, —N(R$^{Z2}$)C(=O)R$^{Z3}$ or —N(R$^{Z2}$)SO$_2$R$^{Z4}$; wherein each occurrence of R$^{Z2}$ and R$^{Z3}$ is independently hydrogen, lower alkyl, lower heteroalkyl, aryl, heteroaryl, -(alkyl)aryl, -(alkyl)heteroaryl, acyl; or any two occurrences of R$^{Z2}$, taken together with the nitrogen atom to which they are attached (e.g., N(R$^{Z2}$)$_2$), form a substituted or unsubstituted heterocyclic moiety; and R$^{Z4}$ is alkyl, heteroalkyl, aryl, heteroaryl, -(alkyl)aryl, or -(alkyl)heteroaryl; and wherein any two adjacent occurrence of R$^{Z1}$ may form a fused 5- to 6-membered aryl, heteroaryl or heterocyclic ring.

XVI. Compounds Having the Structure (and Pharmaceutically Acceptable Derivatives Thereof):

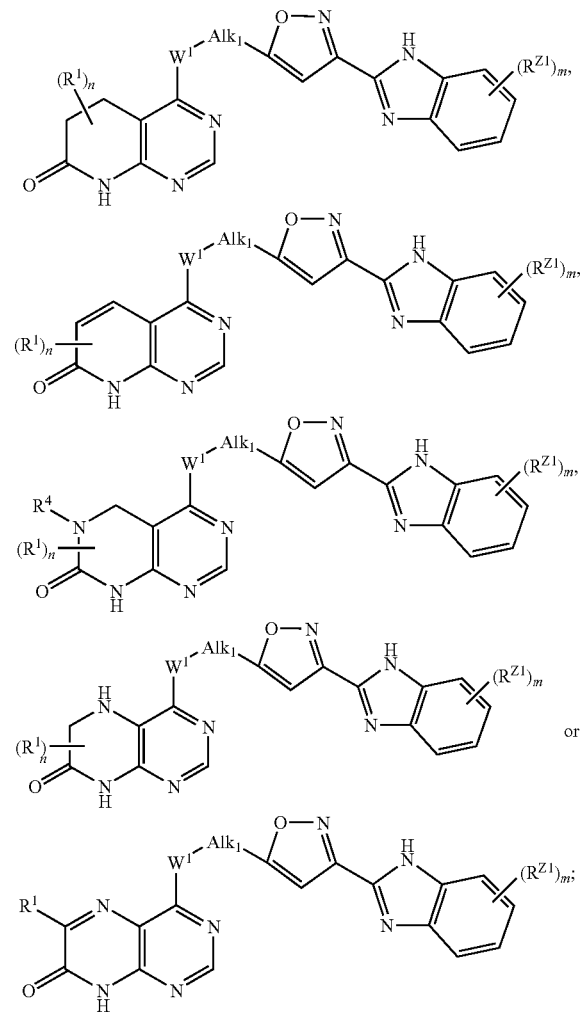

wherein n, R$^1$ and R$^4$ are as defined generally and in classes and subclasses herein; W$^1$ is —O—, —N(R$^{W1}$)—, —C(=O)— or —C(=O)N(R$^{W1}$)—, where R$^{W1}$ is hydrogen, alkyl, cycloalkyl, heteroalkyl, aryl, heteroaryl, -(alkyl)aryl, -(alkyl)heteroaryl or acyl; and Alk$_1$ is a substituted or unsubstituted C$_{1-6}$alkylene or C$_{2-6}$alkenylene chain wherein up to two non-adjacent methylene units are independently optionally replaced by —C(=O)—, —CO$_2$—, —C(=O)C(=O)—, —C(=O)NR$^{L1A}$—, —OC(=O)—, —OC(=O)NR$^{L1A}$, —NR$^{L1A}$NR$^{L1B}$—, —NR$^{L1A}$NR$^{L1B}$C(=O)—, —NR$^{L1A}$C(=O)—, —NR$^{L1A}$CO$_2$—, —NR$^{L1A}$C(=O)NR$^{L1B}$, —S(=O)—, —SO$_2$—, —NR$^{L1A}$SO$_2$—, —SO$_2$NR$^{L1A}$—, —NR$^{L1A}$SO$_2$NR$^{L1B}$—, —O— —S—, or —NR$^{L1A}$—; wherein each occurrence of R$^{L1A}$ and R$^{L1B}$ is independently hydrogen, alkyl, heteroalkyl, heterocyclyl, aromatic, heteroaromatic or acyl; m is an integer from 0 to 3; each occurrence of R$^{Z1}$ is independently hydrogen, alkyl, heteroalkyl, aryl, heteroaryl, -(alkyl)aryl or -(alkyl)heteroaryl, —OR$^{Z2}$, —SR$^{Z2}$, —NR$^{Z2}$R$^{Z3}$, —SO$_2$NR$^{Z2}$R$^{Z3}$, —SO$_2$R$^{Z4}$, —C(=O)NR$^{Z2}$R$^{Z3}$, halogen, —CN, —NO$_2$, —C(=O)OR$^{Z3}$, —N(R$^{Z2}$)C(=O)R$^{Z3}$, wherein each occurrence of R$^{Z2}$ and R$^{Z3}$ is independently hydrogen, lower alkyl, lower heteroalkyl, aryl, heteroaryl, -(alkyl)aryl, -(alkyl)heteroaryl or acyl, or R$^{Z2}$ and R$^{Z3}$ taken together with the nitrogen or carbon atom to which they are attached form a 5-6 membered heterocyclic, aryl or heteroaryl ring; and R$^{Z4}$ is alkyl, heteroalkyl, aryl, heteroaryl, -(alkyl)aryl, or -(alkyl) heteroaryl.

In certain embodiments, the compounds have the structure:

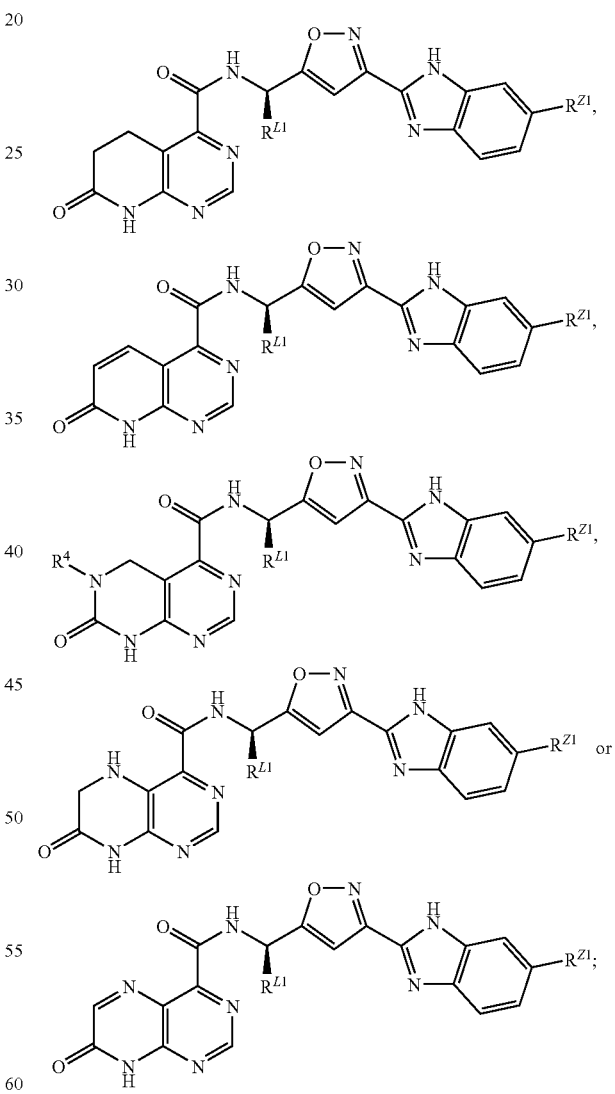

wherein R$^{Z1}$ is lower alkyl, lower diaminoalkyl or lower alkyl and R$^{L1}$ is lower alkyl. In certain exemplary embodiments, R$^{Z1}$ is lower haloalkyl. In certain exemplary embodiments, R$^{Z1}$ is —CF$_3$. In certain exemplary embodiments, R$^{L1}$ is methyl.

XVII. Compounds Having the Structure (and Pharmaceutically Acceptable Derivatives Thereof):

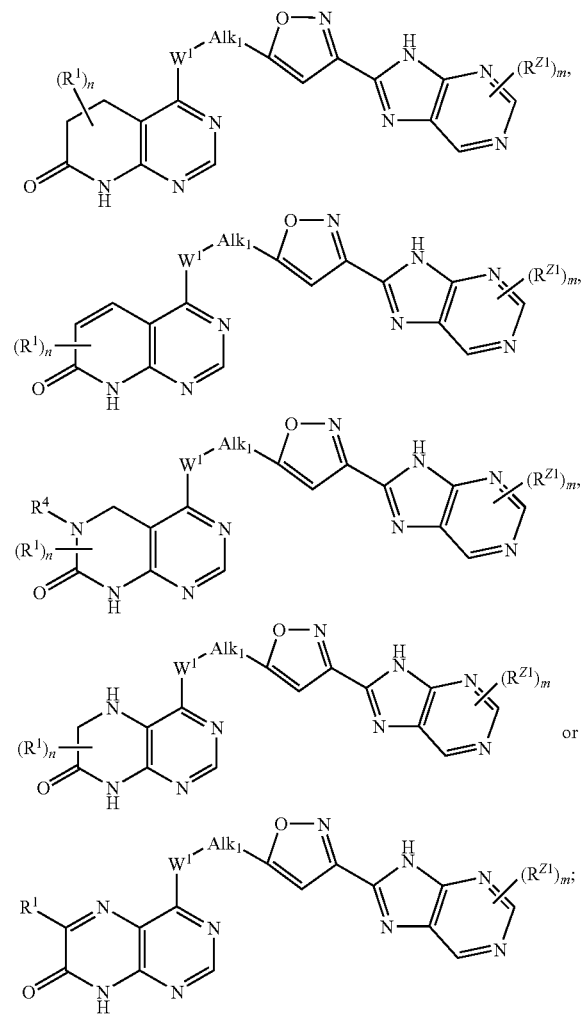

wherein n, $R^1$ and $R^4$ are as defined generally and in classes and subclasses herein; $W^1$ is —O—, —N($R^{W1}$)—, —C(=O)— or —C(=O)N($R^{W1}$)—, where $R^{W1}$ is hydrogen, alkyl, cycloalkyl, heteroalkyl, aryl, heteroaryl, -(alkyl)aryl, -(alkyl)heteroaryl or acyl; and $Alk_1$ is a substituted or unsubstituted $C_{1-6}$alkylene or $C_{2-6}$alkenylene chain wherein up to two non-adjacent methylene units are independently optionally replaced by —C(=O)—, —CO$_2$—, —C(=O)C(=O)—, —C(=O)NR$^{L1A}$—, —OC(=O)—, —OC(=O)NR$^{L1A}$—, —NR$^{L1A}$NR$^{L1B}$—, —NR$^{L1A}$NR$^{L1B}$C(=O)—, —NR$^{L1A}$C(=O)—, —NR$^{L1A}$CO$_2$—, —NR$^{L1A}$C(=O)NR$^{L1B}$—, —S(=O)—, —SO$_2$—, —NR$^{L1A}$SO$_2$—, —SO$_2$NR$^{L1A}$—, —NR$^{L1A}$SO$_2$NR$^{L1B}$—, —O—, —S—, or —NR$^{L1A}$—; wherein each occurrence of $R^{L1A}$ and $R^{L1B}$ is independently hydrogen, alkyl, heteroalkyl, heterocyclyl, aromatic, heteroaromatic or acyl; m is an integer from 0 to 3; each occurrence of $R^{Z1}$ is independently hydrogen, alkyl, heteroalkyl, aryl, heteroaryl, -(alkyl)aryl or -(alkyl)heteroaryl, —OR$^{Z2}$, —SR$^{Z2}$, —NR$^{Z2}$R$^{Z3}$, —SO$_2$NR$^{Z2}$R$^{Z3}$, —SO$_2$R$^{Z4}$, —C(=O)NR$^{Z2}$R$^{Z3}$, halogen, —CN, —NO$_2$, —C(=O)OR$^{Z3}$, —N(R$^{Z2}$)C(=O)R$^{Z3}$, wherein each occurrence of $R^{Z2}$ and $R^{Z3}$ is independently hydrogen, lower alkyl, lower heteroalkyl, aryl, heteroaryl, -(alkyl)aryl, -(alkyl)heteroaryl or acyl, or $R^{Z2}$ and $R^{Z3}$ taken together with the nitrogen or carbon atom to which they are attached form a 5-6 membered heterocyclic, aryl or heteroaryl ring; and $R^{Z4}$ is alkyl, heteroalkyl, aryl, heteroaryl, -(alkyl)aryl, or -(alkyl)heteroaryl In certain embodiments, the compounds have the structure:

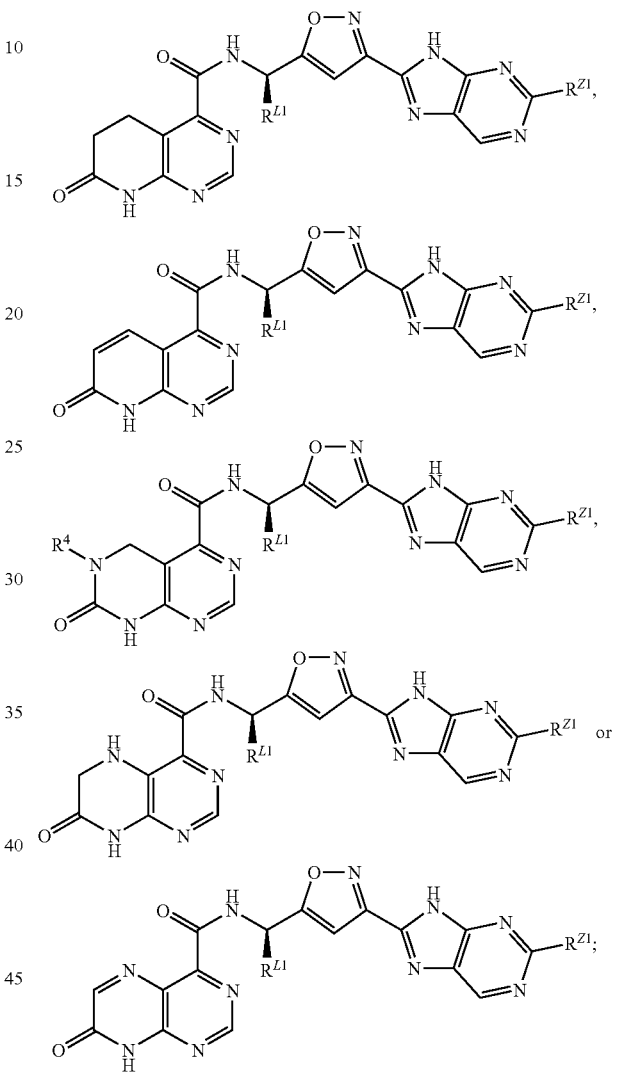

wherein $R^{Z1}$ is lower alkyl or lower alkyl and $R^{L1}$ is lower alkyl. In certain exemplary embodiments, $R^{Z1}$ is lower alkyl. In certain exemplary embodiments, $R^{Z1}$ is t-Bu. In certain exemplary embodiments, $R^{L1}$ is methyl.

In certain embodiments, for compounds of subclasses VI, VIII, IX and XI-XVII above, —$W^1$-$Alk_1$- is —NH—$C_{1-6}$alkyl-, —O—$C_{1-6}$alkyl-, —C(=O)—$C_{1-6}$alkyl- or —C(=O)NH—$C_{1-6}$alkyl-; wherein the $C_{1-6}$alkyl moiety may be substituted or unsubstituted. In certain embodiments, the $C_{1-6}$alkyl moiety is a substituted or unsubstituted $C_{1-2}$alkyl moiety. In certain exemplary embodiments, the $C_{1-6}$alkyl moiety is —CH$_2$—. In certain other exemplary embodiments, the $C_{1-6}$alkyl moiety is —CH(R$^{L1}$)—; wherein $R^{L1}$ is lower alkyl. In certain embodiments, $R^{L1}$ is methyl.

In certain embodiments, for compounds of subclasses XII-XVII above, n is 1 and $R^1$ is hydrogen, halogen, heterocyclyl, aryl or heteroaryl. In certain embodiments, n is 0.

In certain embodiments, for compounds of subclasses XII-XVII above, $R^{Z1}$ is hydrogen, halogen, lower alkyl or lower haloalkyl. In certain embodiments, m is 1 and $R^{Z1}$ is halogen, lower alkyl or lower haloalkyl.

In certain embodiments, for compounds of subclasses I-XVII above, n is 0, 1 or 2. In certain embodiments, n is 0.

In certain embodiments, for compounds of subclasses I-XI above, Z is one of the following structures:

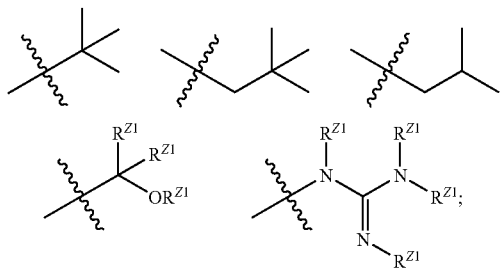

wherein each occurrence of $R^{Z1}$ is independently hydrogen, lower alkyl, lower alkenyl, aryl, heteroaryl or acyl.

In certain embodiments, for compounds of subclasses I-XI above, Z is one of the following structures:

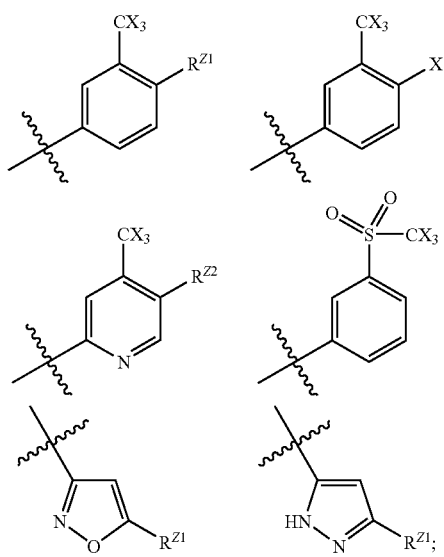

wherein X is halogen; $R^{Z1}$ is substituted or unsubstituted lower alkyl; and $R^{Z2}$ is hydrogen, halogen or substituted or unsubstituted lower alkyl.

In certain embodiments, for compounds of subclasses I-XI above, Z is one of the following structures:

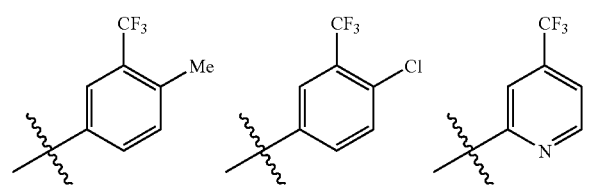

-continued

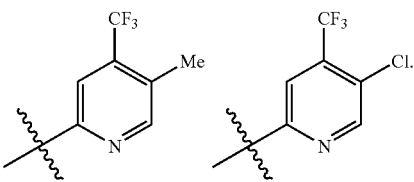

In certain embodiments, for compounds of subclasses I-XI above, $L^2$ is absent and Z is a moiety having one of the following structures:

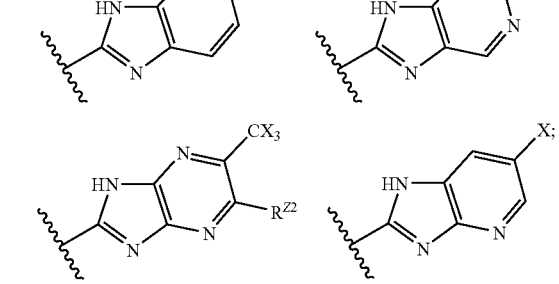

wherein $R^{Z1}$ is lower alkyl; X is halogen; and $R^{Z2}$ is —$CX_3$ or lower alkyl.

In certain embodiments, for compounds of subclasses I-XI above, $L^2$ is absent and Z is a moiety having one of the following structures:

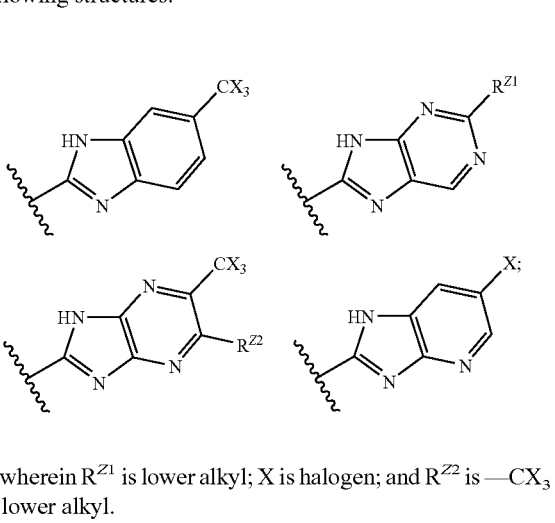

wherein X is F or Cl;

In certain embodiments, for compounds of subclasses I-XI above, $L^2$ is absent and Z is a moiety having one of the following structures:

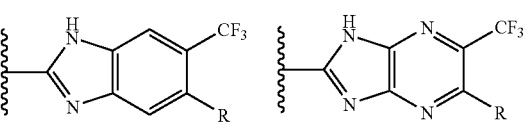

-continued

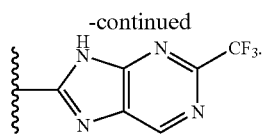

wherein R is —CF$_3$ or tert-butyl;

In certain embodiments, for compounds of subclasses I-XVII above, R$^4$ is a substituent that enhances water solubility of the compound. In certain embodiments, R$^4$ has the structure:

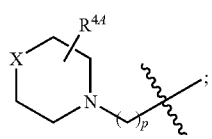

wherein p is an integer from 1-6; X is O, NR$^{4.4}$ or C(R$^{4.4}$)$_2$; wherein each occurrence of R$^{4.4}$ is independently hydrogen or lower alkyl. In certain exemplary embodiments, R$^4$ has the structure:

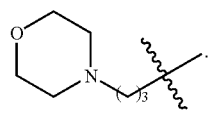

It will also be appreciated that for each of the subgroups I-XVII described above, a variety of other subclasses are of special interest, including, but not limited to those classes described above i)-cxxi) and classes, subclasses and species of compounds described above and in the examples herein.

Some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of the invention may be prepared by crystallization of compound of formula (I) under different conditions and may exist as one or a combination of polymorphs of compound of general formula (I) forming part of this invention. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques. Thus, the present invention encompasses inventive compounds, their derivatives, their tautomeric forms, their stereoisomers, their polymorphs, their pharmaceutically acceptable salts their pharmaceutically acceptable solvates and pharmaceutically acceptable compositions containing them.

2) Synthetic Overview:

The practitioner has a a well-established literature of pyrido-pyrimidinone, pyrimido-pyrimidinone and dihydro pteridinone chemistry to draw upon, in combination with the information contained herein, for guidance on synthetic strategies, protecting groups, and other materials and methods useful for the synthesis of the compounds of this invention, including compounds containing the various R$^1$, R$^2$ and R$^3$ substituents and L$^1$, L$^2$, Y and Z moieties.

The various patent documents and other references cited herein provide helpful background information on preparing compounds similar to the inventive compounds described herein or relevant intermediates. Certain cited patent documents also contain information on formulation, uses, and administration of such compounds which may be of interest. For example, guidance may be found in U.S. Patent Publication Nos.: US 2004/0142945 and US 2003/0114671; and International Application No.: WO 98/08846.

Moreover, the practitioner is directed to the specific guidance and examples provided in this document relating to various exemplary compounds and intermediates thereof.

As described above, the present invention provides novel compounds, specifically compounds having the following general structure:

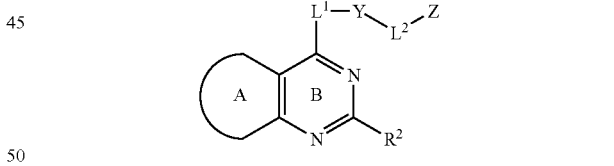

and pharmaceutically acceptable derivatives thereof;

wherein A-B together represent one of the following structures:

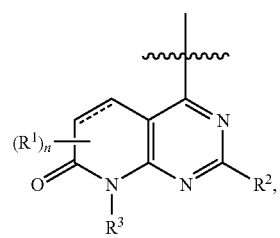

-continued

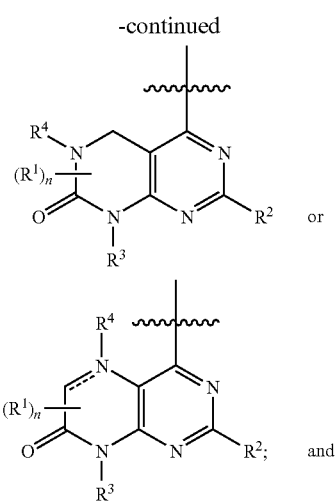

n, $R^1$, $R^2$, $R^3$, $L^1$, $L^2$, Y and Z are as defined in classes and subclasess herein.

In yet another aspect of the invention, methods for producing intermediates useful for the preparation of compounds of formula (I) are provided, embodiments of said methods being depicted generally in Scheme A:

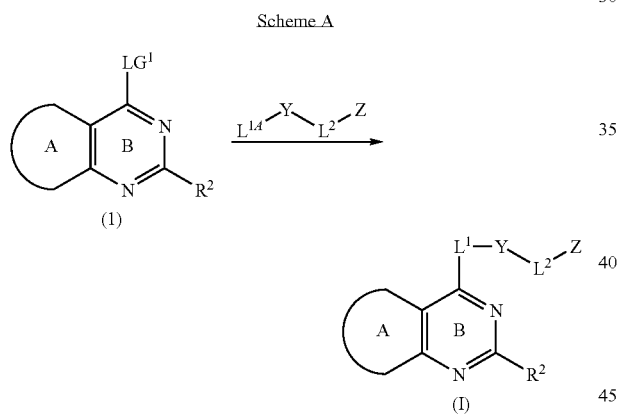

where $LG^1$ is a suitable leaving group and $L^{1A}$ is adapted to displace $LG^1$ upon reaction with pyrido pyrimidinone (1).

In certain embodiments, the methodology may be used to generate inventive compounds of the general formula ($I^B$):

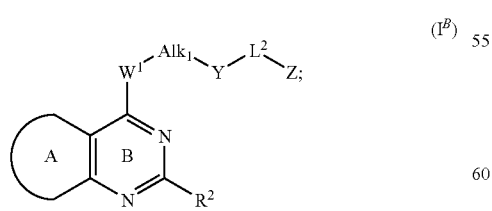

wherein $W^1$ is —O—, —S— or —N($R^{W1}$)— where $R^{W1}$ is hydrogen, aliphatic, heteroaliphatic, alicyclic, heteroalicyclic, aromatic, heteroaromatic, or acyl; and $Alk_1$ is a $C_{1-6}$alkylene or $C_{2-6}$alkenylene moiety.

In yet another aspect of the invention, methods for producing intermediates useful for the preparation of compounds of Formula ($I^B$) wherein $W^1$ is —C(=O)N($R^{W1}$)—, where $R^{W1}$ is as defined above, are provided, embodiments of said methods being depicted generally in Scheme B:

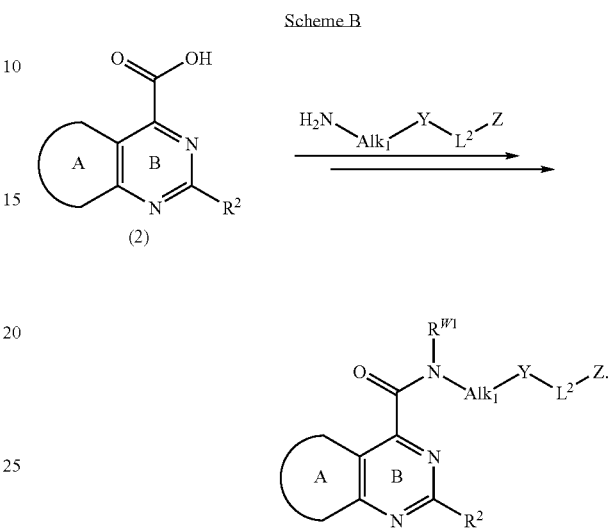

Numerous suitable prodrug moieties, and information concerning their selection, synthesis and use are well known in the art. Examples of prodrug moieties of interest include, among others, prodrug moieties that can be attached to primary or secondary amine-containing functionalities. For instance, prodrug moieties of interest include those that can be attached to group —$NH_2$. Examples of such prodrug moieties include the following:

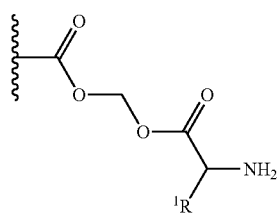

For the synthesis of the prodrug groups, see Borchardt, R. T. et. al., *J. Org. Chem.* 1997, 43, 3641-3652.

$R^1$=all natural, unnatural amino acids

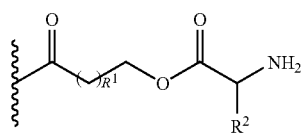

For the synthesis of the prodrug groups, see Zhou, X-X. et. al., PCT WO 99/51613.

$R^1$=C1-C4 alkyl, cycloalkyl, oxyalkyl, aminoalkyl, etc.

$R^2$=all natural, unnatural amino acids

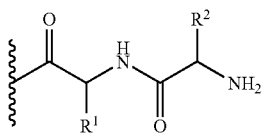

For the synthesis of the prodrug groups, see Ezra, A. et. al., *J. Med. Chem.* 2000, 43, 3641-3652.

$R^1$, $R^2$=all natural, unnatural amino acids

The present invention encompasses any prodrug form of the compounds described herein. Although certain other exemplary prodrug moieties generated from the inventive compounds amino group are detailed herein, it will be appreciated that the present invention is not intended to be limited to these prodrug moieties; rather, a variety of additional prodrug moieties can be readily identified by a person skilled in the relevant art.

3) Pharmaceutical Compositions

As discussed above, the present invention provides compounds that are inhibitors of protein kinases (e.g., RAF kinase), and thus the present compounds are useful for the treatment of diseases, disorders, and conditions including, but not limited to melanoma, leukemia, or cancers such as colon, breast, gastric, ovarian, lung, brain, larynx, cervical, renal, lymphatic system, genitourinary tract (including bladder and prostate), stomach, bone, lymphoma, melanoma, glioma, papillary thyroid, neuroblastoma, and pancreatic cancer. Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

Compounds of the present invention may additionally be useful in the treatment of one or more diseases afflicting mammals which are characterized by cellular proliferation in the areas of blood vessel proliferative disorders, fibrotic disorders, mesangial cell proliferative disorders and metabolic diseases. Blood vessel proliferative disorders include arthritis and restenosis. Fibrotic disorders include hepatic cirrhosis and atherosclerosis. Mesangial cell proliferative disorders include glomerulonephritis, diabetic nephropathy, malignant nephrosclerosis, thrombotic microangiopathy syndromes, organ transplant rejection and glomerulopathies. Metabolic disorders include psoriasis, diabetes mellitus, chronic wound healing, inflammation and neurodegenerative diseases.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a RAF kinase.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

Research Uses

According to the present invention, the inventive compounds may be assayed in any of the available assays known in the art for identifying compounds having protease inhibitory activity. For example, the assay may be cellular or non-cellular, in vivo or in vitro, high- or low-throughput format, etc.

In certain exemplary embodiments, compounds of this invention were assayed for their ability to inhibit protein kinases, more specifically RAF.

Thus, in one aspect, compounds of this invention which are of particular interest include those which:
are inhibitors of protein kinases;
exhibit the ability to inhibit RAF kinase;
are useful for treating mammals (e.g., humans) or animals suffering from an RAF-mediated disease or condition, and for helping to prevent or delay the onset of such a disease/condition;
exhibit a favorable therapeutic profile (e.g., safety, efficacy, and stability).

In certain embodiments, compounds of the invention are RAF kinase inhibitors. In certain exemplary embodiments, inventive compounds are RAF inhibitors. In certain exemplary embodiments, inventive compounds have $^{Cell}IC_{50}$ values≦100 µM. In certain other embodiments, inventive compounds have $^{Cell}IC_{50}$ values≦75 µM. In certain other embodiments, inventive compounds have $^{Cell}IC_{50}$ values≦50 µM. In certain other embodiments, inventive compounds have $^{Cell}IC_{50}$ values≦25 µM. In certain other embodiments, inventive compounds have $^{Cell}IC_{50}$ values≦10 µM. In certain other embodiments, inventive compounds have $^{Cell}IC_{50}$ values≦7.5 µM. In certain other embodiments, inventive compounds have $^{Cell}IC_{50}$ values≦5 µM. In certain other embodiments, inventive compounds have $^{Cell}IC_{50}$ values≦2.5 µM. In certain other embodiments, inventive compounds have $^{Cell}IC_{50}$ values≦1 µM. In certain other embodiments, inventive compounds have $^{Cell}IC_{50}$ values≦800 nM. In certain other embodiments, inventive compounds have $^{Cell}IC_{50}$ values≦600 nM. In certain other embodiments, inventive compounds have $^{Cell}IC_{50}$ values≦500 nM. In certain other embodiments, inventive compounds have $^{Cell}IC_{50}$ values≦300 nM. In certain other embodiments, inventive compounds have $^{Cell}IC_{50}$ values≦200 nM. In certain other embodiments, inventive compounds have $^{Cell}IC_{50}$ values≦100 nM.

In yet another aspect, a method for the treatment or lessening the severity of an RAF-mediated disease or condition is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for treating or lessening the severity of an RAF-mediated disease or condition. The compounds and compositions, according to the method of the present invention, may be administered using any amount and any route of administration effective for treating or lessening the severity of an RAF-mediated disease or condition. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of protein kinases. In one embodiment, the compounds and compositions of the invention are RAF kinase inhibitors, and thus, without wishing to be bound by any particular theory, the compounds and compositions are particularly useful for treating or lessening the severity of a disease, condition, or disorder where activation of RAF kinase is implicated in the disease, condition, or disorder. When activation of RAF kinase is implicated in a particular disease, condition, or disorder, the disease, condition, or disorder may also be referred to as "RAF-mediated disease" or disease symptom. Accordingly, in another aspect, the present invention provides a method for treating or lessening the severity of a disease, condition, or disorder where activation of RAF kinase is implicated in the disease state.

The activity of a compound utilized in this invention as an RAF kinase inhibitor, may be assayed in vitro, in vivo or in a cell line. In vitro assays include assays that determine inhibition of either the phosphorylation activity or ATPase activity of activated RAF. Alternate in vitro assays quantitate the ability of the inhibitor to bind to RAF. Inhibitor binding may be measured by radiolabelling the inhibitor prior to binding, isolating the inhibitor/RAF, complex and determining the amount of radiolabel bound. Alternatively, inhibitor binding may be determined by running a competition experiment where new inhibitors are incubated with RAF bound to known radioligands.

The term "measurably inhibit", as used herein means a measurable change in RAF activity between a sample comprising said composition and a RAF kinase and an equivalent sample comprising RAF kinase in the absence of said composition.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

For example, other therapies, chemotherapeutic agents or other anti-proliferative agents may be combined with the compounds of this invention to treat proliferative diseases and cancer. Examples of therapies or anticancer agents that may be used in combination with the inventive anticancer agents of the present invention include surgery, radiotherapy (in but a few examples, gamma-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide. For a more comprehensive discussion of updated cancer therapies see, The Merck Manual, Seventeenth Ed. 1999, the entire contents of which are hereby incorporated by reference. See also the National Cancer Institute (CNI) website (www.nci.nih.gov) and the Food and Drug Administration (FDA) website for a list of the FDA approved oncology drugs (www.fda.gov/cder/cancer/druglistframe—See Appendix).

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

Another aspect of the invention relates to inhibiting RAF activity in a biological sample or a patient, which method comprises administering to the patient, or contacting said biological sample with a compound of formula I or a composition comprising said compound. The term "biological sample", as used herein, includes, without limitation, cell cultures or extracts thereof, biopsied material obtained from a mammal or extracts thereof, and blood, saliva, urine, feces, semen, tears, or other body fluids or extracts thereof.

Inhibition of RAF kinase activity in a biological sample is useful for a variety of purposes that are known to one of skill in the art. Examples of such purposes include, but are not limited to, blood transfusion, organ-transplantation, biological specimen storage, and biological assays.

Treatment Kit

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

Equivalents

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

EXEMPLIFICATION

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

Example 1

This example describes the synthesis of

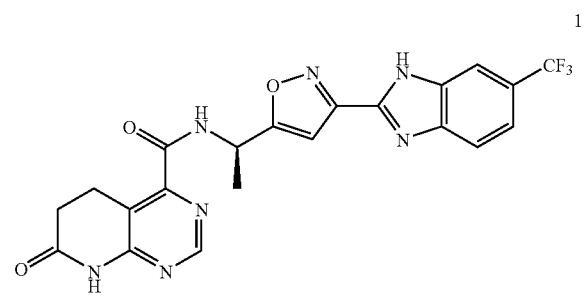

which is prepared according to Scheme A and the protocol below.

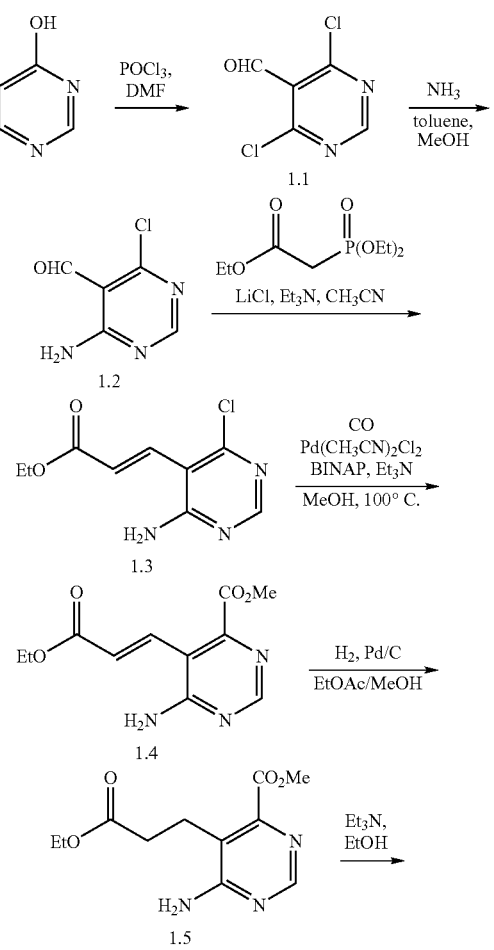

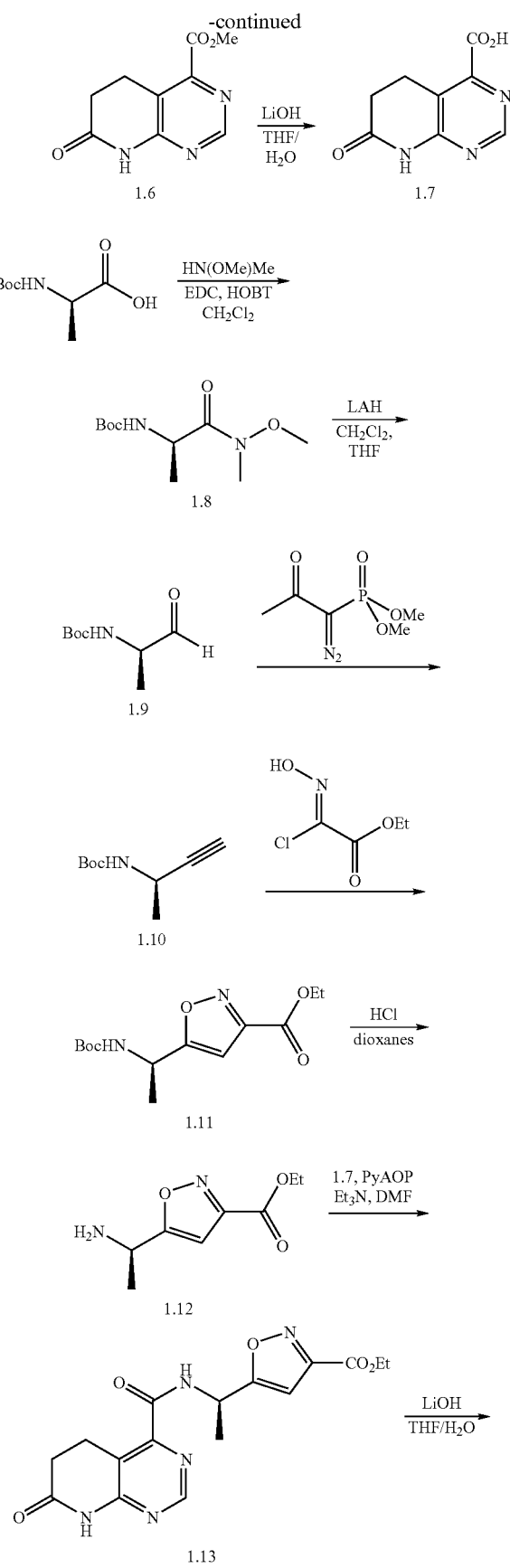

Compound 1.1. To DMF (64 mL) at 0° C. was added POCl₃ (200 mL) dropwise. After 1 hour, 2,4-dihydroxypyrimidine (50 g, 446 mmol) was added. The reaction mixture was stirred at room temperature for 1 hour and then at 110° C. for 3 hours. After cooling to room temperature the solution was poured into ice water portion wise, being careful to keep the mixture from becoming excessively exothermic. The mixture was extracted with ether (8×); the combined organic layer was washed with saturated NaHCO₃, dried over Na₂SO₄, and concentrated in vacuo to provide compound 1.1 (58.6 g, 75%) as a pale yellow solid.

Compound 1.2. To compound 1.1 (19.5 g, 111 mmol) in toluene (220 mL) was added NH₃ (27 mL, 7N in MeOH) and the reaction mixture was heated to 60° C. After 1 hour, a second aliquot of NH₃/MeOH (18 mL) was added and stirring continued for an additional 45 minutes. The mixture was cooled and concentrated in vacuo. The solid was portioned between EtOAc, H₂O using a small amount of MeOH to help dissolve. The aqueous layer was extracted with EtOAc (5×); the combined organic layer was extracted with H₂O, dried over Na₂SO₄, and concentrated to yield compound 1.2 (19 g) that was used without further purification.

Compound 1.3. To compound 1.2 (~19 g, ~111 mmol) in CH₃CN (300 mL) was added (diethoxy-phosphoryl)-acetic acid ethyl ester (28.3 g, 122 mmol), LiCl (9.24 g, 220 mmol), and Et₃N (18.2 mL, 130 mmol). After 7 hours, the mixture was partitioned between EtOAc and water. The aqueous layer was extracted with EtOAc (3×); the combined organic layer was extracted with H₂O, dried over Na₂SO₄, and concentrated in vacuo to provide a brown solid. The resulting solid was suspended in toluene and then filtered to give compound 1.3 (15.6 g, 62% from compound 1.1).

Compound 1.4. Compound 1.3 (664 mg, 2.92 mmol), $PdCl_2(CH_3CN)_2$ (38.1 mg, 0.147 mmol), rac-BINAP (90.7 mg, 0.146 mmol), $Et_3N$ (610 µL, 4.38 mmol) and anhydrous methanol (30 mL) were added to a bomb. Carbon monoxide was purged three times and then the bomb was filled with CO to 50 psi. The reaction mixture was heated in an oil bath at 100° C. overnight. After cooling the reaction mixture, excess CO was vented. Solvents were removed under reduced pressure and the crude material was loaded directly onto a silica gel column. Eluent: hexanes/ethyl acetate (1:1→1:2→1:3→1:4→0:100). Ester 1.4 (557 mg, 78%) was obtained as an approximately 1:1 mixture of ethyl and methyl esters. This compound was further purified by recrystallization from chloroform-hexanes (Final yield: 329 mg, 1.35 mmol, 46%).

Compound 1.5. To compound 1.4 (30 mg, 0.12 mmol) in ethyl acetate/methanol (2 mL, 1:1) was added Pd on carbon (10%, wet, 8.5 mg). The reaction mixture was stirred under an atmosphere of hydrogen (balloon) at room temperature. After one hour, more Pd/C (9.5 mg) was added and the solution was stirred for an additional 4 hours. The reaction mixture was filtered over a pad of silica gel and celite and rinsed thoroughly with methanol. Removal of the solvent at reduced pressure provided compound 1.5 (30 mg, 100%).

Compound 1.6. To compound 1.5 (506 mg, 2 mmol), $Et_3N$ in a sealed tube was added ethanol (5 mL). The reaction mixture was warmed to 80° C. and stirred for 4 hours. After cooling to room temperature, the volatiles were removed in vacuo. The resulting material was suspended in ether/hexanes, filtered, and washed with hexanes to provide compound 1.6.

Compound 1.7. Compound 1.6 (540 mg, <2.61 mmol) was suspended in THF (9 mL) at room temperature. Lithium hydroxide (1 M aqueous solution, 3 mL, 3 mmol) was added. The reaction mixture becomes clear and after stirring for several hours solid precipitates. More lithium hydroxide (0.5 mL of 1 M solution) was added and the reaction mixture was stirred one more hour. The solvents were removed and the crude reaction mixture was suspended in $CH_2Cl_2$. The crude product was filtered and washed thoroughly with $CH_2Cl_2$ until all the color was removed. The solid was collected and 3N—HCl (1.18 mL) was added. The compound was filtered, rinsed with a minimal amount of ethanol, and then rinsed with $CH_2Cl_2$ to provide compound 1.7 (238 mg) as a white solid.

Compound 1.8. To Boc-D-alanine (100 g, 0.53 mol) in $CH_2Cl_2$ (2 L) was added O,N-dimethyl-hydroxylamine hydrochloride (55.2 g, 0.57 mol), EDC (106.7 g, 0.56 mol), HOBT (75.6 g, 0.56 mol), and $Et_3N$ (157 mL, 1.12 mol). The reaction mixture was stirred for 60 hours and then partitioned between $CH_2Cl_2$ and $H_2O$. The organic layer was washed with 1N HCl, 3×$H_2O$, and then dried over $Na_2SO_4$. Concentration of the organic layer provided compound 1.8 (110 g, 90%) as a white solid.

Compound 1.9. To compound 1.8 (16.23 g, 70 mmol) in $CH_2Cl_2$/THF (350 mL, 4:1) at −78° C. was added lithium aluminum hydride (75 mL, 75 mmol, 1.0 M in THF), dropwise, over 45 minutes. After 1 hour at −78° C., the reaction was quenched with aqueous $NaHSO_4$ (110 mL, 110 mmol, 1M solution). The solution was stirred vigorously at room temperature for 1 hour and then partitioned between $CH_2Cl_2$ and $H_2O$. The aqueous layer was extracted with $CH_2Cl_2$ (2×). The combined organic layer was extracted with brine, dried over $NaHSO_4$ and concentrated to give compound 1.9 (13.9 g), which was used without further purification.

Compound 1.10. To compound 1.9 in MeOH (550 mL) was added $K_2CO_3$ (20.7 g, 150 mmol) and (1-diazo-2-oxo-propyl)-phosphonic acid dimethyl ester (14.4 g, 75 mmol). After 1.5 hours, the reaction mixture was concentrated in vacuo. Purification by silica gel chromatography (9:1 hexanes/ethyl acetate) provided compound 1.10 (7.1 g, 60% over two steps) as a white solid.

Compound 1.11. To compound 1.10 (6.7 g, 39.6 mmol) and 2-chloro-2-hydroxyiminoacetic acid ethyl ester (18.1 g, 120 mmol) in DMF at 90° C. (120 mL) was added $Et_3N$ (16.8 mL, 120 mmol) dropwise over 1 hour. The reaction mixture was stirred for 30 minutes, cooled to room temperature, and then concentrated in vacuo. The residue was dissolved in ethyl acetate and $H_2O$. The aqueous layer was extracted with ethyl acetate (2×); the combined organic layer was extracted with 1N HCl, dried over $NaHSO_4$, and concentrated in vacuo. Purification by silica gel chromatography (6:1→3:1 hexanes/ethyl acetate) provided compound 1.11 (8.45 g, 75%).

Compound 1.12. Hydrogen chloride in dioxane (4M solution, 10 mL) was added to compound 1.11 (1.49 g, 5.25 mmol) at room temperature and stirred for 2 hours. Solvent was removed under reduced pressure and the remaining reaction mixture was azeotroped with benzene (1×). Ethyl acetate and saturated sodium bicarbonate solution was added and the product was extracted with ethyl acetate (3×). Solid sodium chloride was added to the aqueous layer and the product was extracted with ethyl acetate. The combined ethyl acetate layers were dried with anhydrous sodium sulfate. Removal of the solvent under reduced pressure afforded compound 1.12 (968 mg), which was used in the next step without further purification.

Compound 1.13. Compound 1.12 (968 mg, 5.25 mmol), compound 1.7 (917 mg, 4.75 mmol) and PyAOP (2.98 g, 5.72 mmol) were dissolved in DMF (15 mL) at room temperature. Diisopropylethylamine (2.1 mL, 12.1 mmol) was added and the reaction mixture was stirred overnight. Ethyl acetate and water was added and the layers were separated. The aqueous layer was extracted with ethyl acetate (2×); the combined organic layer was washed with brine and dried over anhydrous sodium sulfate. After removal of the solvent under reduced pressure, the crude product was purified using silica gel column chromatography (hexanes/ethyl acetate: 1:1→100% ethyl acetate→3:1 ethyl acetate: dichloromethane). The obtained product was further purified by recrystallization from ethyl acetate to give compound 1.13 (1.26 g, 3.51 mmol, 74%). The filtrate was purified again using silica gel chromatography followed by recrystallization to afford additional compound 1.13 (143 mg, 0.40 mmol, 8%).

Compound 1.14. To compound 1.13 (1.26 g, 3.51 mmol) was added THF (11 mL) and lithium hydroxide (1N aqueous solution, 3.68 mL, 3.68 mmol). The reaction was stirred at room temperature for 3 hours. Additional lithium hydroxide (1 mL, 1 mmol) was added and the reaction was stirred overnight. After removal of THF under reduced pressure, HCl (3N aqueous solution) was added until no additional precipitates formed. The product was filtered and rinsed thoroughly with 3N—HCl. After drying under reduced pressure overnight, compound 1.14 (765 mg, 2.31 mmol, 66%) was obtained.

Compound 1.15. To compound 1.14 (248 mg, 0.75 mmol) in DMF (3 mL) was added 3,4-diaminobenzotrifluoride (158 mg, 0.9 mmol), EDC (170 mg, 0.9 mmol), HOBT (122 mg, 0.9 mmol) and Et$_3$N (0.14 mL, 1.0 mmol). The reaction mixture was stirred overnight and then partitioned between CH$_2$Cl$_2$ and 1N HCl. The aqueous layer was extracted with ethyl acetate (2×); the combined organic layers were extracted with 1N HCl, dried over NaHSO$_4$, and concentrated in vacuo to provide compound 1.15.

Compound 1. The residue was heated in AcOH (3 mL) at 80° C. for 1.5 hours. After cooling, the reaction mixture was concentrated and then purified by silica gel chromatography to provide compound 1 (158 mg, 45%). $^1$H NMR (400 MHz, DMSO-D6) δ ppm 1.64 (d, J=6.85 Hz, 3H), 2.57 (t, J=7.58 Hz, 2H), 3.30 (t, J=7.58 Hz, 2H), 5.44 (m, 1H), 7.04 (s, 1H), 7.60 (d, J=8.80 Hz, 1H), 7.81 (d, J=8.80 Hz, 1H), 8.00 (s, 1H), 8.75 (s, 1H), 9.51 (d, J=8.31 Hz, 1H), 11.14 (s, 1H). LCMS: m/z: 472.

Example 2

This example describes the synthesis of

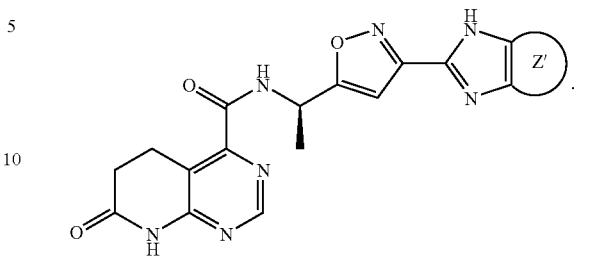

These compounds are prepared according to Example 1 except for using a diamine of the formula

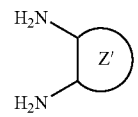

instead of 3,4-diaminobenzotrifluoride (in step for compound 1.15). Illustrative examples of suitable diamines and their resulting compounds are shown in Table 1.

TABLE 1

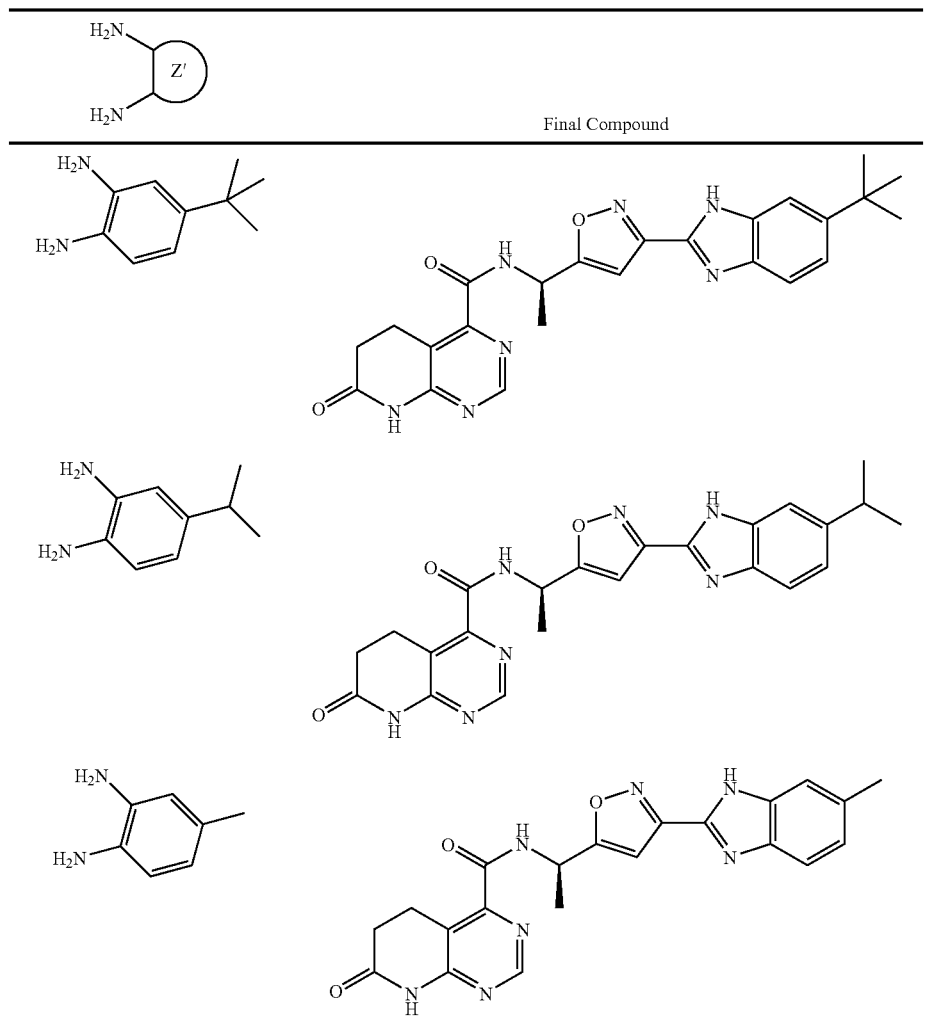

TABLE 1-continued
| 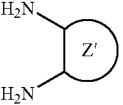 | |
|---|---|
| | Final Compound |
| 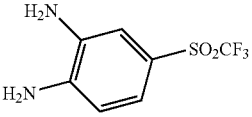 | 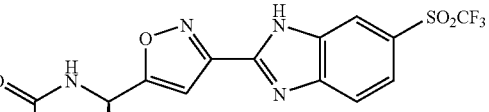 |
| 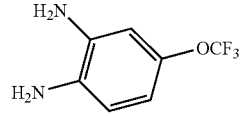 | 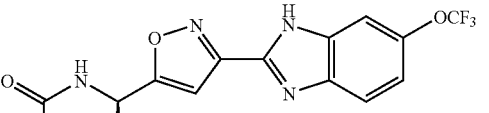 |
| 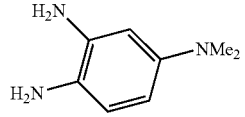 | 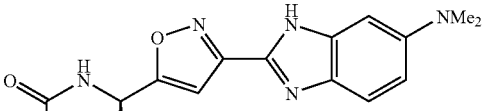 |
| 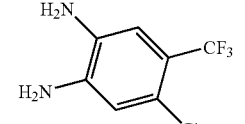 | 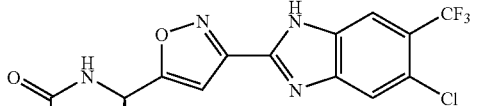 |
| 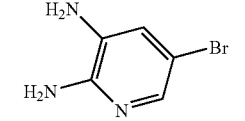 | 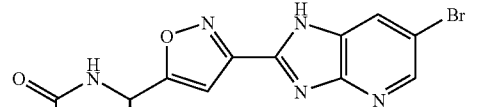 |

TABLE 1-continued
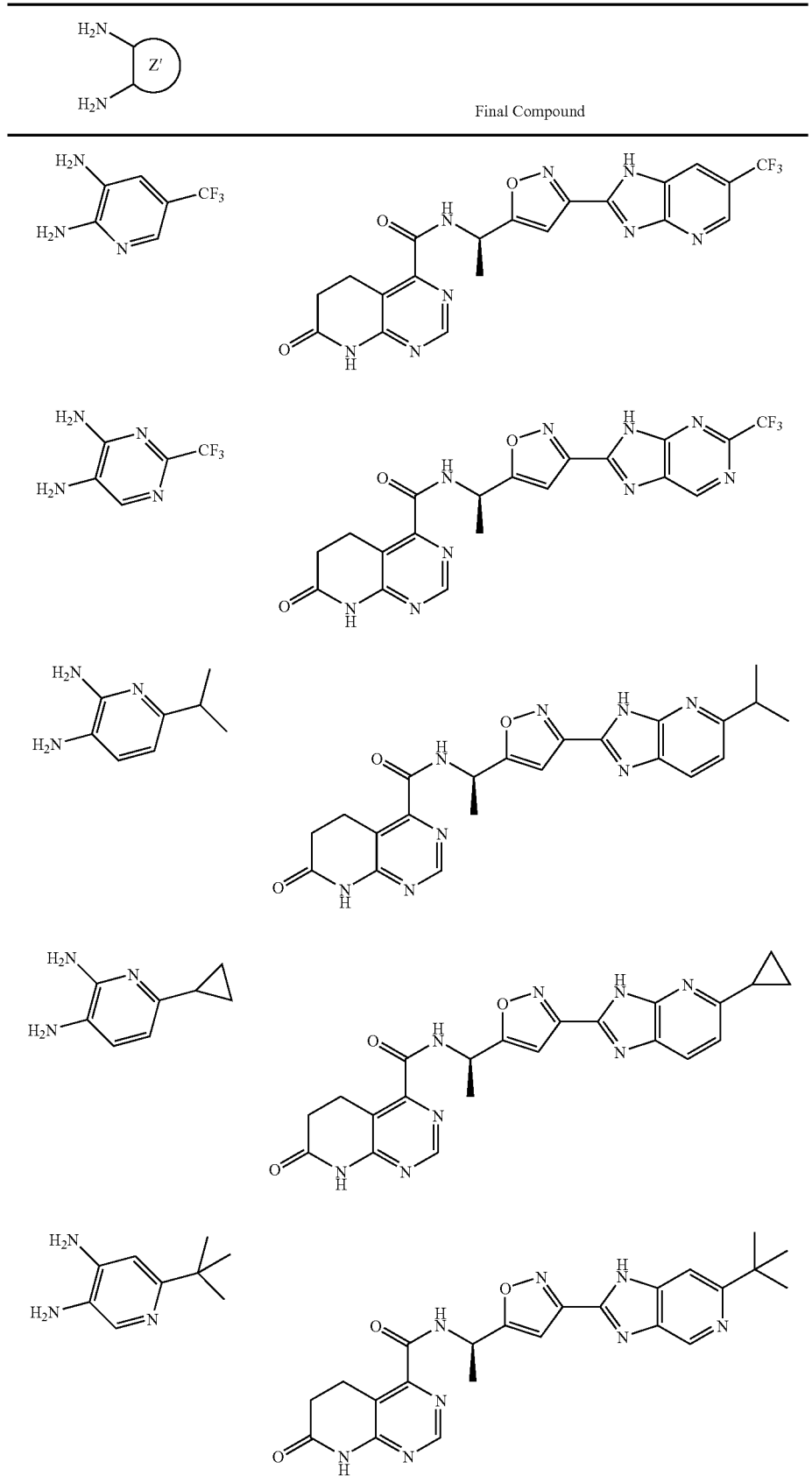

TABLE 1-continued
| 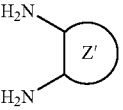 | |
|---|---|
| | Final Compound |
| 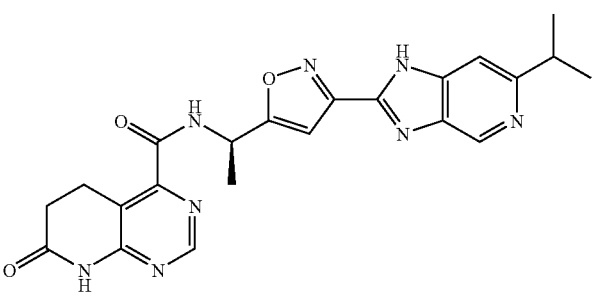 | 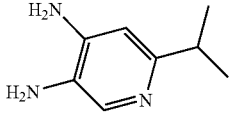 |
| 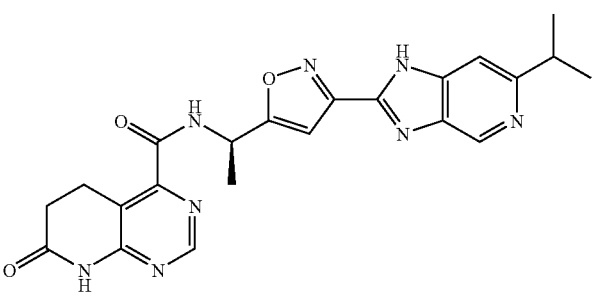 | 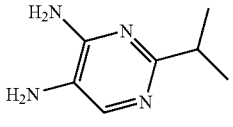 |
| 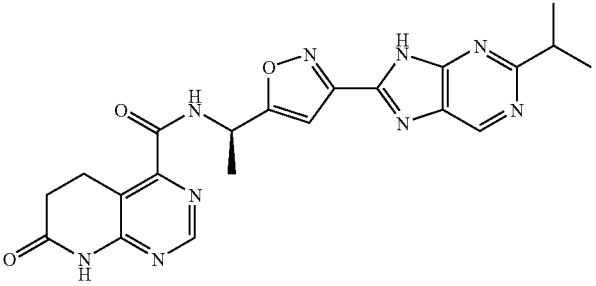 | 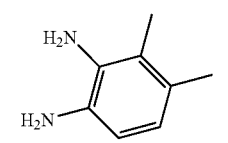 |
| 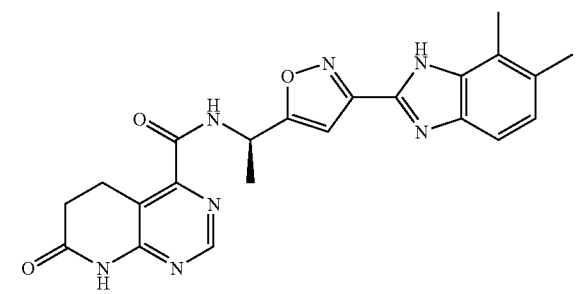 | 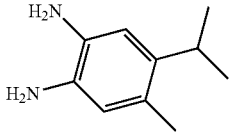 |

TABLE 1-continued

Example 3

This example describes the synthesis of 3

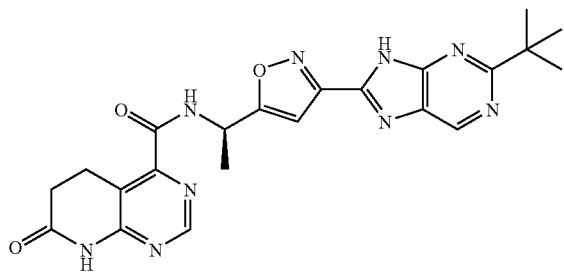

which is prepared according to Scheme B and the protocol below.

Scheme B

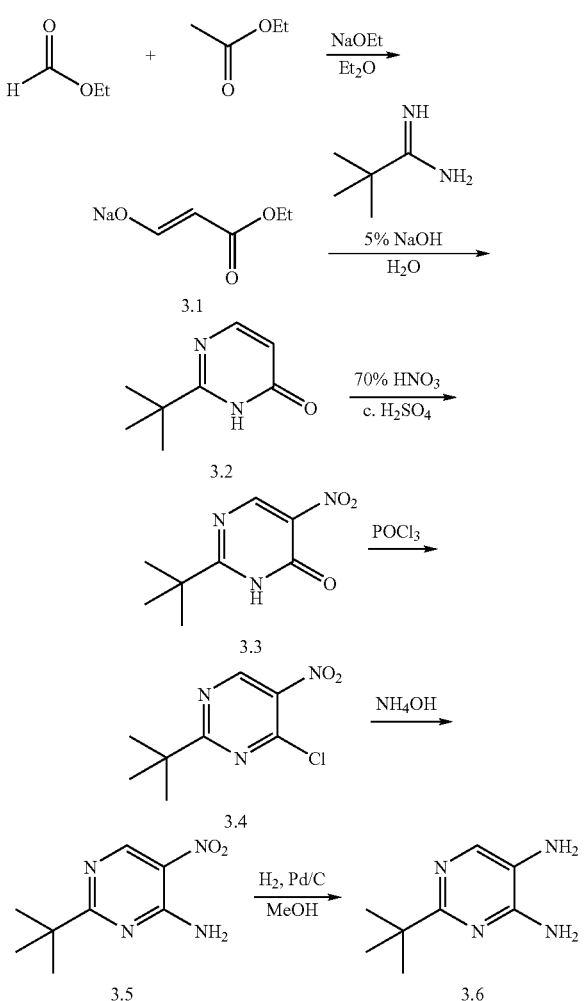

Compound 3.1. To an oven dried 250 mL three neck flask equipped with a reflux condenser and a 50 mL addition funnel, 5.00 g (217 mmol, 1.1 eq.) of sodium metal and toluene (27 mL) were added. The flask was placed in an oil bath (120° C.) and EtOH (16 mL, 283 mmol, 1.2 eq. to Na) was added dropwise through the addition funnel. The reaction mixture was refluxed for 3 hours after the addition, and by that time a thick suspension had formed. After cooling, ether (136 mL) was added resulting in an off-white suspension. A mixture of ethyl formate (15.3 mL, 189 mmol, 1 eq.) and ethyl acetate (18.5 mL, 180 mmol, 1 eq.) was added dropwise. After stirring at room temperature for 3 days, all solvent was removed under reduced pressure, and compound 3.1 was used without further purification.

Compound 3.2. To t-butyl amidine hydrochloride salt (1.38 g, 10.1 mmol) in 5% NaOH/H$_2$O (w/v) (17 mL) was added compound 3.1 (2.76 g, 20.0 mmol, 2 eq.). The reaction mixture was stirred overnight and then acidified to pH=5 with conc. HCl. The solution was extracted with chloroform (3×); the combined organic layer was dried over anhydrous sodium sulfate and concentrated in vacuo. The crude product was purified using silica gel column chromatography eluting with hexanes and ethyl acetate to provide compound 3.2 (0.82 g, 53%).

Compound 3.3. In a microwave vessel, compound 3.2 (123 mg, 0.81 mmol) was added to a solution containing concentrated H$_2$SO$_4$ (0.8 mL) and 70% HNO$_3$ (0.8 mL). The reaction mixture was stirred in the microwave at 140° C. for 10 minutes and then at 150° C. for 10 minutes. The reaction was quenched by addition of ice. Solid NaHCO$_3$ was added until pH~5 was reached and compound 3.3 was extracted with chloroform (5×). The organic layer was dried over anhydrous sodium sulfate. After removal of the solvent, the crude compound 3.3 was directly used in the next step. Yield: 115 mg (~0.584 mmol, ~72%).

Compound 3.4. Compound 3.3 (115 mg, 0.584 mmol) and POCl$_3$ (1 mL) were stirred at reflux for 3 hours. After removal of excess POCl$_3$ under reduced pressure, ice was added and the product was extracted with chloroform. After drying with anhydrous sodium sulfate and removal of the solvent, crude compound 3.4 (110 mg) was obtained and used without further purification.

Compound 3.5. Compound 3.4 was dissolved in MeOH (1 mL) and ammonium hydroxide solution (1.5 mL) was added. The reaction mixture was stirred overnight. After removal of excess ammonia and MeOH, the mixture was extracted with chloroform. After drying with anhydrous sodium sulfate and removal of the solvent, compound 3.5 (89 mg, ~78%) was obtained and used without further purification.

Compound 3.6. To compound 3.5 (89 mg, 0.46 mmol) in MeOH (3 mL) was added 10% Pd/C (wet) (10.3 mg). The reaction was put under an atmosphere of H$_2$ and stirred for 2 hours. The reaction mixture was filtered through a pad of celite and rinsed thoroughly with MeOH. Removal of MeOH afforded compound 3.6 (76 mg, ~100%) which was used without further purification.

Compound 3. Compound 3 was prepared according to Example 1 except for using compound 3.6 instead of 3,4-diaminobenzotrifluoride (in step for compound 1.15).

Example 4

This example describes the synthesis of 4 which was prepared according to Scheme C and the protocol below.

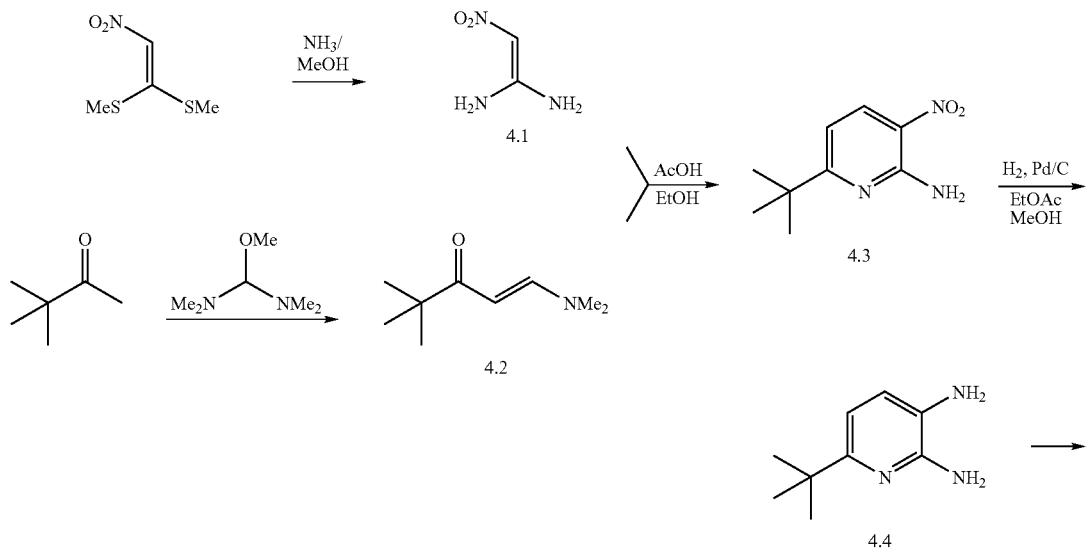

Compound 4.1. 1,1-bis(methylthio)-2-nitroethylene (3.0 g, 18 mmol) in NH$_3$/MeOH (30 mL, 7M) was heated to 50° C. After 18 hours, the reaction mixture was concentrated to obtain an orange solid. Crude product 4.1 (2.42 g, 23 mmol, ~100%) was used in the next step without further purification.

Compound 4.2. Pinacolone (6.2 mL, 50 mmol) and C-methoxy-N,N,N',N'-tetramethyl-methanediamine (10 mL) were heated to 110° C. under N$_2$. After 18 hours, the reaction mixture was concentrated. The crude product was purified by distillation under reduced pressure to afford 4.2 (4.2 g, 53%) as a yellow crystalline solid.

Compound 4.3. Compound 4.1 (0.40 g, 2.9 mmol) and compound 4.2 (0.45 g, 2.9 mmol) in AcOH/EtOH (5 ml, 1:4) were stirred at reflux for 16 hours. The reaction mixture cooled and then concentrated. To the residue was added aqueous sodium hydroxide (1 N) and ethyl acetate. The aqueous layer was extracted with ethyl acetate (3×); the combined organic extracts were washed with brine, dried over anhydrous sodium sulfate, filtered, and concentrated. The residue was purified by silica gel chromatography (100:0→9:1 hexanes/ethyl acetate) to afford compound 4.3 (320 mg, 56%).

Compound 4.4. To compound 4.3 (60 mg, 0.31 mmol) in methanol/ethyl acetate (2 mL, 1:1) at room temperature was added palladium on carbon (10 mg, 10%, wet) and the reaction mixture was put under an atmosphere of hydrogen (balloon). After 4 hours, the reaction mixture was filtered through a pad of celite and rinsed with ethyl acetate. The solvent was removed under reduced pressure. The residue was purified by silica gel chromatography (100:0→19:1 hexanes/ethyl acetate) to afford 4.4 (45 mg, 88%).

Compound 4. Compound 4 is prepared according to Example 1 except for using 4.4 instead of 3,4-diaminobenzotrifluoride (in step for compound 1.15).

Example 5

This example describes the synthesis of

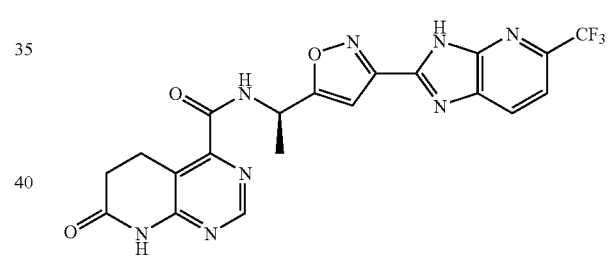

which was prepared according to Scheme D and the protocol below.

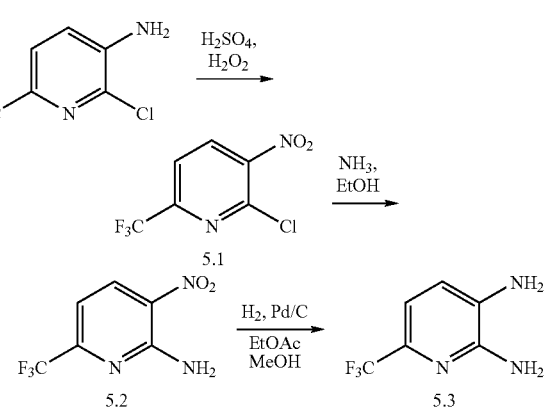

Compound 5.1. To a cooled (0° C.) mixture of fuming sulfuric acid (3.2 mL) and aqueous hydrogen peroxide (50%, 1.6 mL) was added a solution of 3-amino-2-chloro-6-(trifluoromethyl)pyridine (304 mg, 1.55 mmol) in conc. sulfuric acid (4 mL). The reaction was slowly warmed to 25° C. and stirred 20 hours, whereupon the reaction mixture was poured into ice water. The mixture was neutralized with aqueous ammonium hydroxide, and then extracted with ethyl acetate (5×10 mL). The organic layers were dried over anhydrous sodium sulfate and concentrated to afford compound 5.1 (126 mg, 36%) as a yellow solid that was used without further purification.

Compound 5.2. A pressure vessel was charged with compound 5.1 (126 mg, 0.56 mmol) and a saturated solution of ammonia in ethanol (10 mL). The vessel was sealed and the reaction mixture was stirred at room temperature for 15 hours, whereupon the reaction mixture was concentrated. Compound 5.2 (138 mg, >100%) was isolated as a yellow solid, contaminated with inorganic salts.

Compound 5.3. To compound 5.2 (138 mg, <0.67 mmol) in methanol/ethyl acetate (10 mL, 1:1) at room temperature was added palladium on carbon (36 mg, 10%, wet) and the reaction mixture was placed under an atmosphere of hydrogen (balloon). After 1.5 hours, the reaction mixture was filtered through a pad of celite and the filter cake was washed with ethyl acetate and methanol. The solvent was removed under reduced pressure to afford diamine 5.3 (149 mg, >100%) as a yellow film, which was used without further purification.

Compound 5. Compound 5 is prepared according to Example 1 except for using compound 5.3 instead of 3,4-diaminobenzotrifluoride (in step for compound 1.15).

Example 6

This example describes the synthesis of

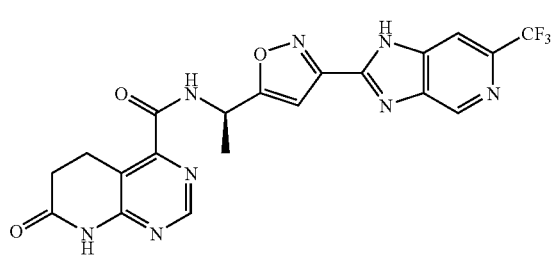

which was prepared according to Scheme E and the protocol below.

Scheme E

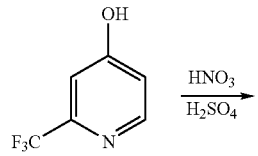

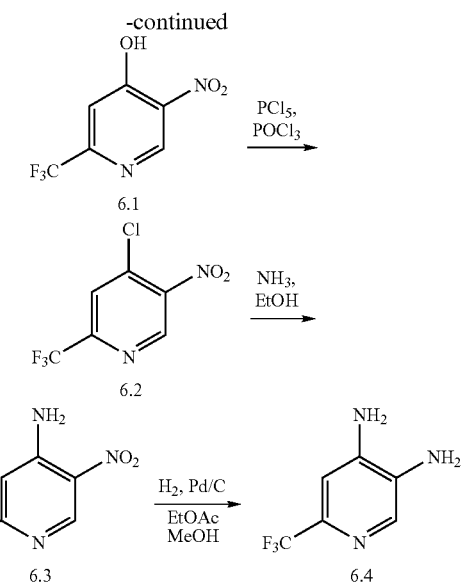

Compound 6.1. 4-Hydroxy-2-(trifluoromethyl)pyridine was prepared according to the reported procedure (Tyvorskii, V. I.; Bobrov, D. N. *Chemistry of Heterocyclic Compounds* 1997 33 (8), 1138-1139). To a cooled (0° C.) solution of 4-hydroxy-2-(trifluoromethyl)pyridine (651 mg, 3.99 mmol) in conc. sulfuric acid (1.6 mL) was added fuming sulfuric acid. Fuming nitric acid (4 mL) was added dropwise over 15 minutes, the pressure vessel was sealed tightly. The reaction mixture was heated to 120° C. and stirred 8 hours, whereupon the reaction mixture was cooled to room temperature and poured into ice water. The mixture was brought to pH=1 by addition of 10 M aqueous sodium hydroxide, then extracted with ethyl acetate (5×40 mL). The organic layers were dried over anhydrous sodium sulfate and concentrated to afford compound 6.1 (570 mg, 69%) as a viscous yellow oil that was used without further purification.

Compound 6.2. A mixture of compound 6.1 (570 mg, 2.74 mmol), phosphorus pentachloride (900 mg, 4.11 mmol, 1.5 equiv), and phosphorus oxychloride (0.38 mL, 4.11 mmol, 1.5 equiv) was heated to 80° C. and stirred 11 hours. After cooling to room temperature, the reaction mixture was transferred to ice cold water and the mixture was extracted with dichloromethane (4×40 mL). The combined organic layers were washed with sat'd aqueous NaHCO₃ (50 mL), water (50 mL), and brine (50 mL), dried over anhydrous sodium sulfate, and concentrated. Compound 6.2 (512 mg, 83%) was isolated as a yellow oil that was used without further purification.

Compound 6.3. A pressure vessel was charged with compound 6.1 (512 mg, 0.51 mmol) and a saturated solution of ammonia in ethanol (15 mL). The vessel was sealed and the reaction mixture was stirred at room temperature for 1.5 hours, whereupon the reaction mixture was concentrated. Compound 6.3 (538 mg, >100%) was isolated as an orange solid, contaminated with inorganic salts.

Compound 6.4. To compound 6.3 (538 mg, <2.6 mmol) in methanol/ethyl acetate (25 mL, 1.5:1) at room temperature was added palladium on carbon (total 245 mg, 10%, wet) portionwise over the course of the reaction. The reaction mixture was stirred under an atmosphere of hydrogen (balloon) for 27 hours. The reaction mixture was filtered through a pad of celite and the filter cake was washed with ethyl acetate and methanol. The solvent was removed under reduced pressure to afford diamine 6.3 (457 mg, >100%) as a yellow film, which was used without further purification.

Compound 6. Compound 6 is prepared according to Example 1 except for using compound 6.4 instead of 3,4-diaminobenzotrifluoride (in step for compound 1.15).

Example 7

This example describes the synthesis of

7

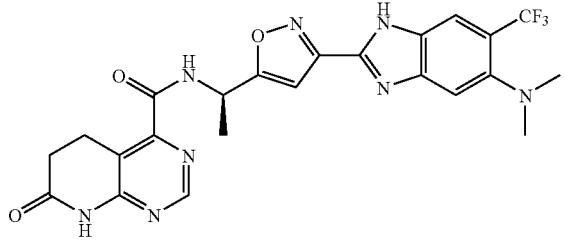

which was prepared according to Scheme F and the protocol below.

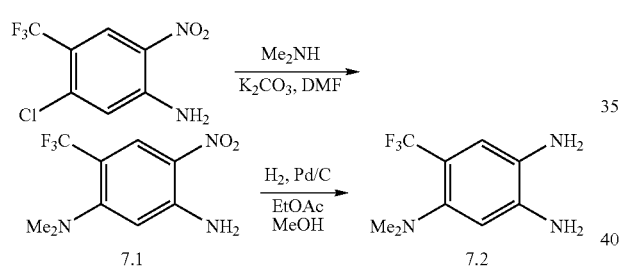

Compound 7.1. A mixture of 5-chloro-2-nitro-4-(trifluoromethyl)aniline (101.5 mg, 0.42 mmol), potassium carbonate (59.0 mg, 0.43 mmol), and dimethylamine (2 M/THF, 220 µL, 0.44 mmol) in DMF (150 µL) was heated in the microwave at 100° C. for 15 minutes, then at 120° C. for 20 minutes. The reaction mixture was concentrated and the crude residue was purified using silica gel column chromatography (5→10→20% EtOAc/hexanes) to afford compound 7.1 (61.7 mg, 59%) as a yellow solid.

Compound 7.2. To compound 7.1 (61.7 mg, 0.248 mmol) in methanol/ethyl acetate (8 mL, 5:3) at room temperature was added palladium on carbon (20 mg, 10%, wet) and the reaction mixture was placed under an atmosphere of hydrogen (balloon). After 2 hours, the reaction mixture was filtered through a pad of celite and the celite pad was washed with methanol and ethyl acetate. The solvent was removed under reduced pressure to afford diamine 7.2 (48 mg, 88%) as a brown film, which was used without further purification.

Compound 7. Compound 7 is prepared according to Example 1 except for using compound 7.2 instead of 3,4-diaminobenzotrifluoride (in step for compound 1.15).

Example 8

This example describes the synthesis of

8

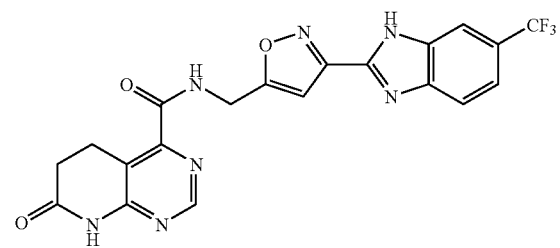

which is prepared according to Example 1 except for using Boc-propargyl amine instead of compound 1.10.

Example 9

This example describes the synthesis of

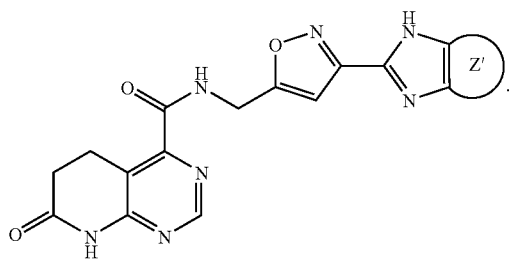

These compounds are prepared according to Example 1 except for using Boc-propargyl amine instead of compound 1.10 and for using diamine of the formula

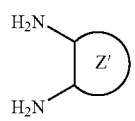

instead of 3,4-diaminobenzotrifluoride (in step for compound 1.15). Illustrative examples of suitable diamines are shown in Table 1.

Example 10

This example describes the synthesis of

10

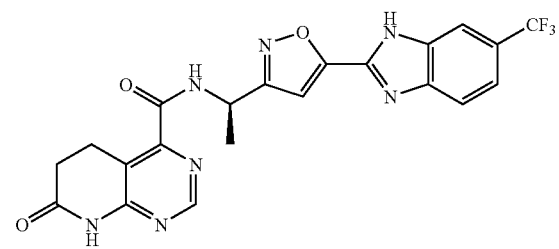

115 which was prepared according to Scheme G and the protocol below.

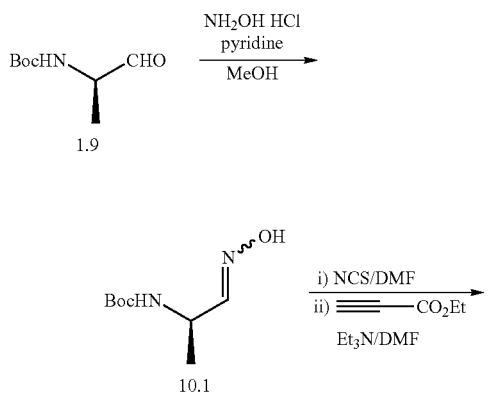

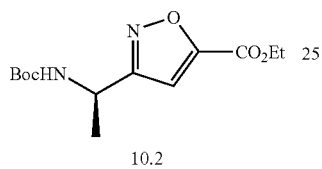

Compound 10.1. Compound 1.9 (2.08 g, <12 mmol), hydroxylamine hydrochloride (852 mg, 12.3 mmol, 1.03) and pyridine (9 mL) were stirred in methanol (45 mL) at room temperature overnight. After evaporation of the solvent, water was added and the product was extracted with methylene chloride three times. The organic layer was dried over anhydrous sodium sulfate. Solvent was removed and pumped overnight to remove pyridine. The crude material, compound 10.1, was used directly in the next reaction. Yield: 2.12 g (<11.3 mmol, 94%).

Compound 10.2. To compound 10.1 (2.12 g, <11.3 mmol) dissolved in 56 mL DMF was added NCS (1.51 g, 11.3 mmol) and the reaction was heated to 60° C. for one hour. After cooling the reaction mixture to 0° C., propynoic acid ethyl ester (2.3 mL, 22.7 mmol) was added all at once. Triethylamine (1.65 mL, 11.8 mmol) in DMF (13 mL) was added to the reaction mixture via an addition funnel over 15 minutes. The reaction mixture was stirred for another 10 minutes. Water (70 mL) and ethyl acetate (50 mL) was added and the layers were separated. The aqueous layer was further extracted with ethyl acetate (50 mL×2). The combined organic layers were washed with water and then with brine, and dried over anhydrous sodium sulfate. After removal of the solvent, the crude product, compound 10.2, was purified using silica gel column chromatography. The product eluted with a gradient of hexanes:ethyl acetate (5:1) to (4:1). Yield: 1.7 g (5.98 mmol, 50% from compound 1.9).

Compound 10. Compound 10 was prepared according to Example 1 except for using compound 10.2 instead of compound 1.11.

116

Example 11

This example describes the synthesis of

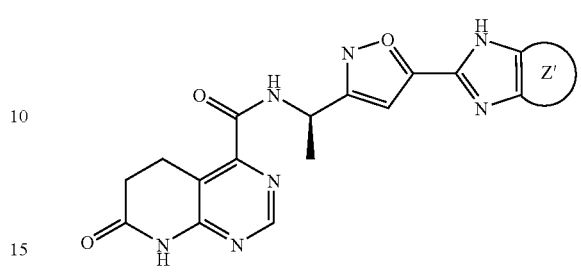

These compounds are prepared according to Example 1 except for using compound 10.2 instead of compound 1.11 and for using diamine of the formula

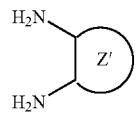

instead of 3,4-diaminobenzotrifluoride (in step for compound 1.15). Illustrative examples of suitable diamines are shown in Table 1.

Example 12

This example describes the synthesis of

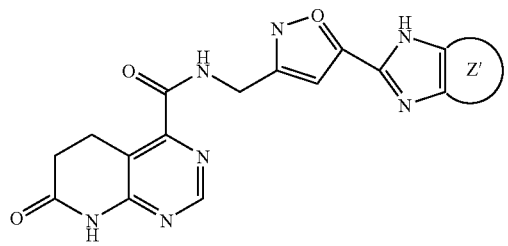

These compounds are prepared according to Example 1 except for using Boc-glycine aldehyde instead of compound 1.9, compound 10.2 instead of compound 1.11, and diamine of the formula

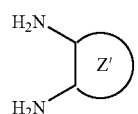

instead of 3,4-diaminobenzotrifluoride (in step for compound 1.15). Illustrative examples of suitable diamines are shown in Table 1.

Example 13

This example describes the synthesis of

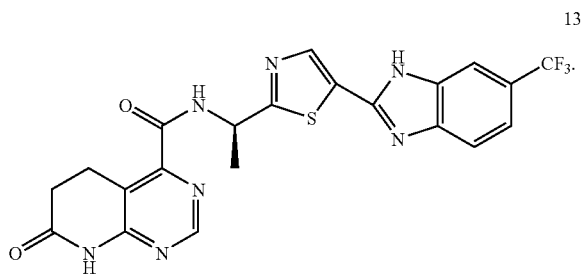

These compounds are prepared according to Scheme H and the protocol below.

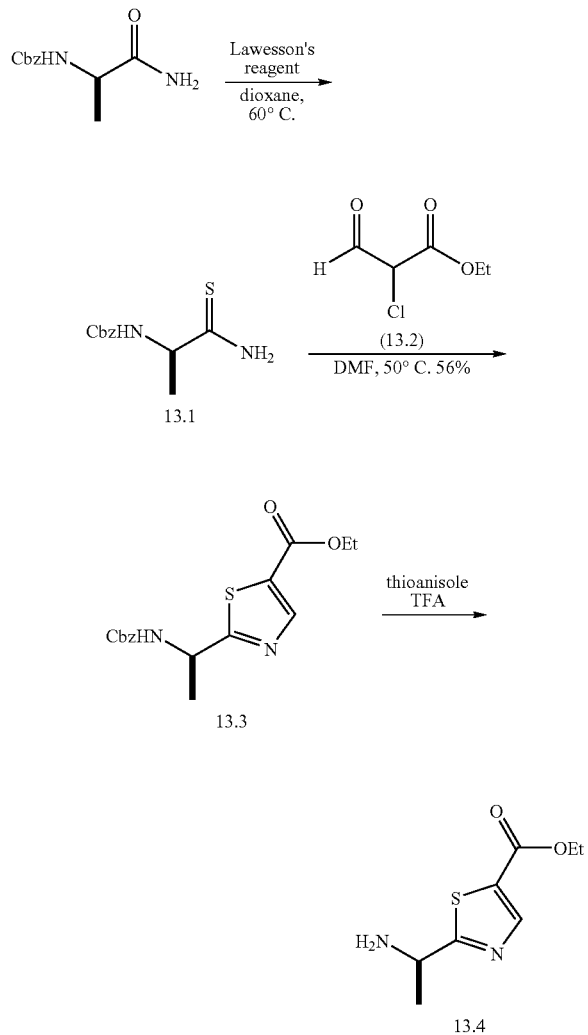

Compound 13.1. To a suspension of Z-D-alanine-NH$_2$ (4.98 g, 22.4 mmol) in dioxane (23 mL) was added Lawesson's reagent (4.98 g, 12.3 mmol, 0.55 equiv). The reaction mixture was heated to 60° C. and stirred for 30 minutes, then cooled to room temperature and stirred an additional 24 hours, whereupon the reaction mixture was concentrated in vacuo. The residue was diluted with a 1:1 mixture of saturated aqueous NaHCO$_3$: H$_2$O (100 mL), then additional saturated aqueous NaHCO$_3$ (100 mL) and EtOAc (100 mL). After separation of the phases, the aqueous phase was extracted with EtOAc (3×100 mL). The combined extracts were washed with brine (100 mL), dried over anhydrous sodium sulfate, and concentrated in vacuo. Purification by flash column chromatography (10→25→50→60% EtOAc/hexanes) afforded compound 13.1 (4.75 g, 90%) as a white solid. LCMS: m/z: 239 (M+1).

Compound 13.2. A flame-dried 1 L 3-neck round bottom flask equipped with an addition funnel and a condenser was charged with dry toluene (45 mL). Sodium metal chunks (8.34 g, 363 mmol, 1.1 equiv) were added, and the mixture was heated to reflux (bath temp. 115° C.). Dry absolute ethanol (30 mL) was added slowly by addition funnel over 30 minutes. The reaction mixture was stirred at 115° C. for an addition 2 hours, then cooled to room temperature. The cooled sodium ethoxide suspension was diluted with ethyl ether (200 mL), then the addition funnel was charged with ethyl chloroacetate (35.3 mL, 330 mmol, 1.0 equiv), ethyl formate (27.0 mL, 330 mmol, 1.0 equiv), and ethyl ether (25 mL). The ethyl chloroacetate/ethyl formate mixture was added slowly over 2.5 hours, and the resultant pale yellow suspension was stirred at room temperature overnight. The reaction mixture was cooled to 0° C., and H$_2$O (150 mL) was gradually added. After separation of the phases, the aqueous layer was acidified to pH 3 with aqueous 1 N HCl (300 mL), and extracted with ether (6×80 mL). The combined organic layers were washed with brine (300 mL), dried over anhydrous sodium sulfate, and concentrated in vacuo. The brownish-red crude oil was purified by distillation under reduced pressure to afford compound 13.2 as a colorless oil (33 g, 68%; lit. boiling point 60° C. @ 12 torr).

Compound 13.3. To a solution of compound 13.1 (1.00 g, 4.2 mmol) in DMF (15 mL) was added compound 13.2 (3.5 g, 5.0 equiv). The reaction mixture was heated to 50° C. and stirred for 3 days, monitoring by LC-MS. After cooling to room temperature, the reaction mixture was diluted with ether (50 mL) then washed with saturated aqueous NaHCO$_3$ (3×100 mL). The combined aqueous washes were extracted with ether (4×25 mL), and the extracts were washed with brine (100 mL), dried over anhydrous sodium sulfate, and concentrated in vacuo. Purification by flash column chromatography (10-20-50% ethyl acetate/hexanes) afforded compound 13.3 (0.81 g, 56%) as a viscous pale yellow oil. LCMS: m/z: 335 (M+1).

Compound 13.4. To thiazole 13.3 (0.20 mmol) in TFA (2.5 mL) was added thioanisole (0.25 mL, 2.0 mmol, 10.0 equiv). After stirring at room temperature overnight, the reaction was judged to be complete by LC-MS analysis. The reaction mixture was concentrated in vacuo (using high vac), diluted with EtOAc (30 mL), and washed with saturated aqueous NaHCO$_3$ (3×50 mL). The combined aqueous washes were extracted with EtOAc (3×25 mL), and the extracts were washed with brine (50 mL), dried over anhydrous sodium sulfate, and concentrated in vacuo to afford amine 13.4, which was used without further purification.

Compound 13. Compound 13 is prepared according to Example 1 except for using 13.4 instead of compound 1.12.

Example 14

This example describes the synthesis of

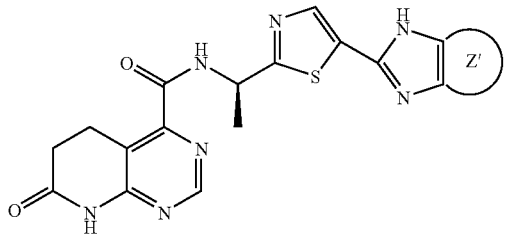

These compounds are prepared according to Example 1 except for using compound 13.4 instead of compound 1.12 and for using diamine of the formula

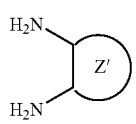

instead of 3,4-diaminobenzotrifluoride (in step for compound 1.15). Illustrative examples of suitable diamines are shown in Table 1.

Example 15

This example describes the synthesis of

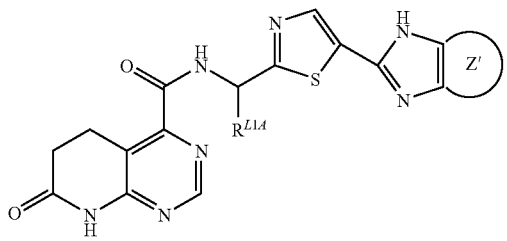

where $R^{L1A}$ is as described previously. These compounds are prepared according to Example 13 except for using

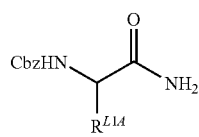

instead of Z-D-alanine-NH$_2$ and for using diamine of the formula

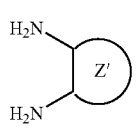

instead of 3,4-diaminobenzotrifluoride (in step for compound 1.15). Illustrative examples of suitable diamines are shown in Table 1.

Example 16

This example describes the synthesis of

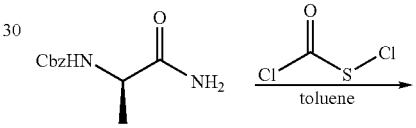

which is prepared according to Scheme I and the protocol below.

Scheme I

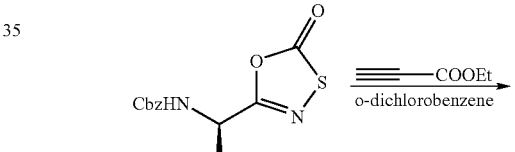

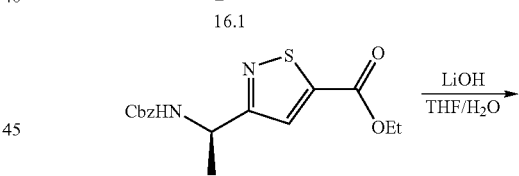

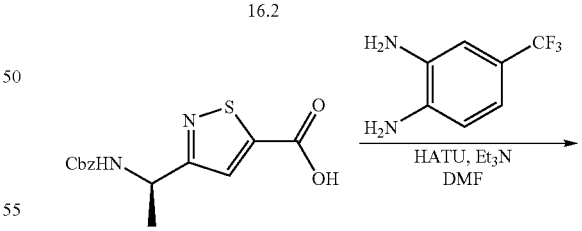

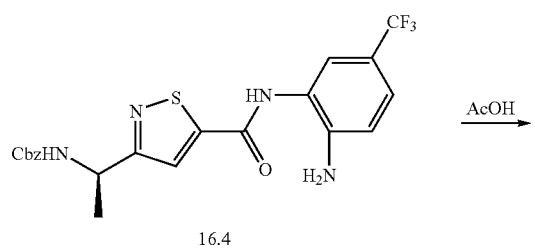

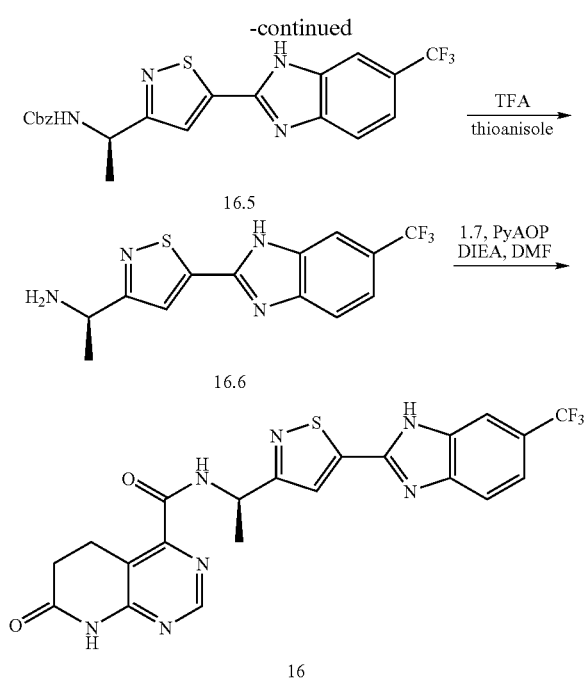

Compound 16.1. To a suspension of Z-D-alanine-NH$_2$ (2.0 g, 8.88 mmol) in toluene (35 mL) was added chlorocarbonyl sulfenyl chloride (1.5 mL, 17.8 mmol, 2 equiv). The reaction mixture was heated to 100° C. and stirred for 4.5 hours, then cooled to room temperature and concentrated in vacuo. The residue was purified by flash column chromatography (10→20% EtOAc/hexanes) to afford compound 16.1 (2.1 g, 84%) as a pale yellow solid.

Compound 16.2. To a solution of compound 16.1 (2.1 g, 7.5 mmol) in o-dichlorobenzene (15 mL) was added ethyl propiolate (3.0 mL, 30 mmol, 4.0 equiv). The reaction mixture was heated to 150° C. and stirred for 3 days, monitoring by LC-MS. After cooling to room temperature, the reaction mixture was diluted with ether (50 mL) then washed with saturated aqueous NaHCO$_3$ (3×100 mL). The combined aqueous washes were extracted with ether (4×25 mL), and the extracts were washed with brine (100 mL), dried over anhydrous sodium sulfate, and concentrated in vacuo. Purification by flash column chromatography (10-20-50% ethyl acetate/hexanes) afforded compound 16.2 (0.81 g, 56%) as a viscous pale yellow oil. LCMS: m/z: 335 (M+1).

Compound 16.3. To a solution of compound 16.2 (1.0 g, 3.0 mmol) in THF (22.5 mL) was added a solution of lithium hydroxide (180 mg, 7.5 mmol, 2.5 equiv) in water (7.5 mL). The reaction was stirred at room temperature for 19 hours, whereupon 1N aqueous HCl was added until a pH of 1 was achieved. The mixture was extracted with ethyl acetate (3×50 mL), and the organic layers were washed with brine (50 mL), dried over anhydrous sodium sulfate, and concentrated to afford acid 16.3 (890 mg, 97%) as a brown residue that was used without further purification.

Compound 16.4. Compound 16.3 (119 mg, 0.39 mmol), 3,4-diaminobenzotrifluoride (75 mg, 0.43 mmol, 1.1 equiv) and HATU (177 mg, 0.47 mmol, 1.2 equiv) were dissolved in DMF (3.5 mL) at room temperature. Triethylamine (0.14 mL, 0.97 mmol, 2.5 equiv) was added and the reaction was stirred for 4.5 hours. The reaction mixture was diluted with ethyl acetate (25 mL) and water (25 mL) the layers were separated. The aqueous layer was extracted with ethyl acetate (3×30 mL), and the combined organic layers were washed with brine (20 mL), dried over anhydrous sodium sulfate, and concentrated to afford compound 16.4 (111 mg, 62%) as a brown residue that was used without further purification.

Compound 16.5. Compound 16.4 was heated in AcOH (1 mL) at 80° C. for 1 hour. After cooling, the reaction mixture was concentrated and then purified by silica gel chromatography (30% EtOAc/hexanes) to provide compound 16.5 (71 mg, 67%) as an off-white solid.

Compound 16.6. To compound 16.5 (71.0 mg, 0.16 mmol) in TFA (2.0 mL) was added thioanisole (0.2 mL, 1.6 mmol, 10.0 equiv). After stirring at room temperature for 17 hours, the reaction mixture was concentrated in vacuo (using high vac), diluted with EtOAc (15 mL), and washed with saturated aqueous NaHCO$_3$ (2×20 mL). The combined aqueous washes were extracted with EtOAc (3×15 mL), and the extracts were washed with brine (30 mL), dried over anhydrous sodium sulfate, and concentrated in vacuo to afford amine 16.6, was used without further purification in the next step.

Compound 16. Compound 16.6 (55 mg, 0.17 mmol, 1.15 equiv), compound 1.7 (28 mg, 0.146 mmol) and PyAOP (91 mg, 0.18 mmol, 1.2 equiv) were dissolved in DMF (2 mL) at room temperature. Diisopropylethylamine (64 µL, 0.37 mmol, 2.5 equiv) was added and the reaction was stirred for 21 hours. The reaction mixture was diluted with ethyl acetate (25 mL) and water (25 mL) the layers were separated. The aqueous layer was extracted with ethyl acetate (3×30 mL), and the combined organic layers were washed with brine (20 mL), dried over anhydrous sodium sulfate, and concentrated. The residue was purified by flash column chromatography (80-100% EtOAc/hexanes) to afford compound 16 (53 mg, 72%) as a white powder.

Example 17

This example describes the synthesis of

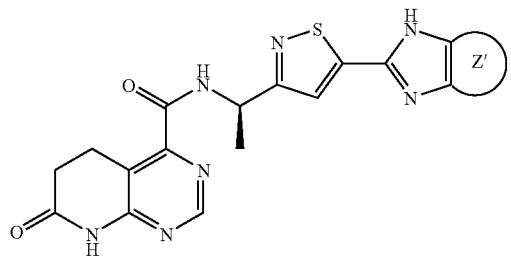

These compounds are prepared according to Example 16 except for using diamine of the formula

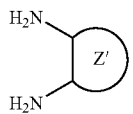

instead of 3,4-diaminobenzotrifluoride (in step for compound 16.4). Illustrative examples of suitable diamines are shown in Table 1.

Example 18

This example describes the synthesis of

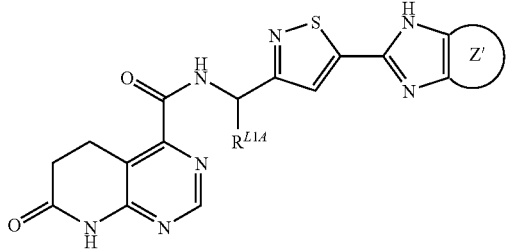

where $R^{L14}$ is as previously described. These compounds are prepared according to Example 16 except for using

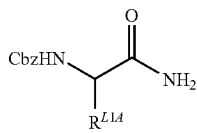

instead of Z-D-alanine-NH$_2$ and for using diamine of the formula

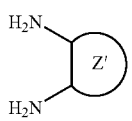

instead of 3,4-diaminobenzotrifluoride (in step for compound 16.4). Illustrative examples of suitable diamines are shown in Table 1.

Example 19

This example describes the synthesis of

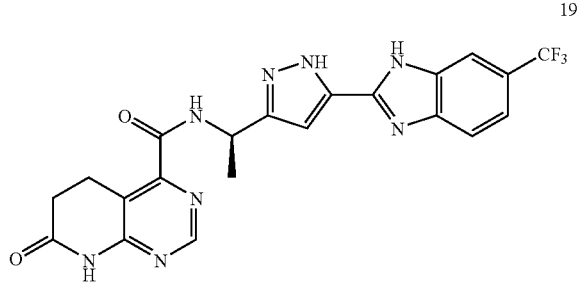

which is prepared according to Scheme J and the protocol below.

Scheme J

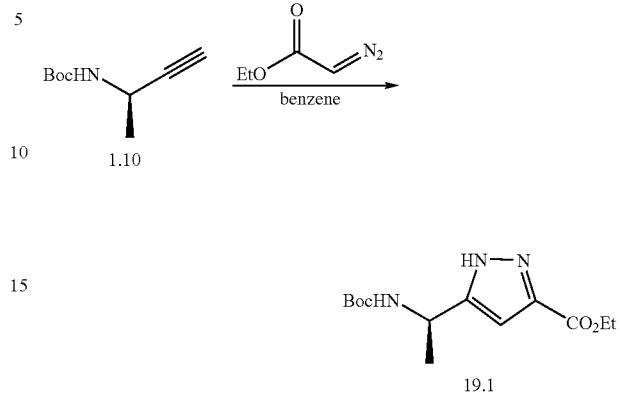

Compound 19.1. Compound 1.10 (283 mg, 1.67 mmol, 1 eq.) and ethyl diazoacetate (208 μL, 2.01 mmol, 1.2 eq.) were dissolved in benzene (0.85 mL) at room temperature. The reaction was microwaved at 140° C. for 80 minutes. The reaction mixture was directly loaded onto a silica gel column. The product was purified using hexanes:ethyl acetate (3:1→2:1→3:2) which afforded 19.1 (208 mg (0.735 mmol, 44%).

Compound 19. Compound 19 is prepared according to Example 1 except for using compound 19.1 instead of compound 1.11.

Example 20

This example describes the synthesis of

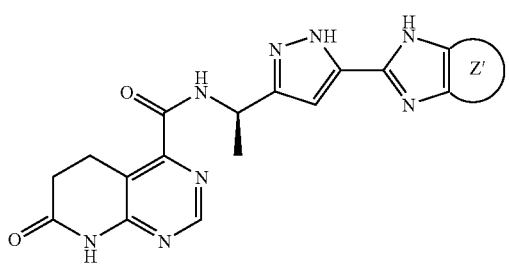

which is prepared according to Example 1 except for using compound 19.1 instead of compound 1.11 and for using diamine of the formula

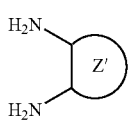

instead of 3,4-diaminobenzotrifluoride (in step for compound 1.15). Illustrative examples of suitable diamines are shown in Table 1.

Example 21

This example describes the synthesis of

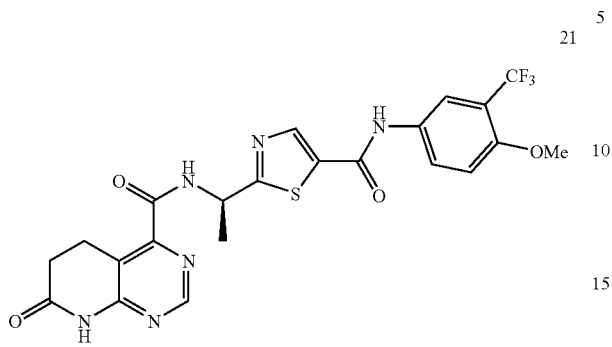

which is prepared according to Example 1 for making compound 1.15 except for using compound 13.4 instead of compound 1.12 and for using 3-methoxy-4-triflouromethylaniline instead of 3,4-diaminobenzotriflouride (in the step for making compound 1.15).

Example 22

This example describes the synthesis of

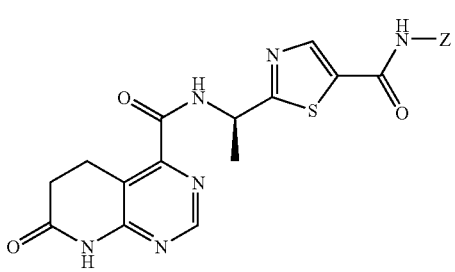

where Z is as previously described. These compounds are made according to Example 21 except for using an amine of the formula $H_2NZ$ instead of 3-methoxy-4-triflouromethylaniline. Illustrative examples of suitable amines and the resulting compounds are shown in Table 2.

TABLE 2

| $H_2NZ$ | Final Compound |
|---|---|

TABLE 2-continued

| H₂NZ | Final Compound |
|---|---|

TABLE 2-continued
| H₂NZ | Final Compound |
|---|---|
| 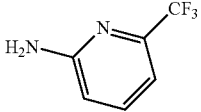 | 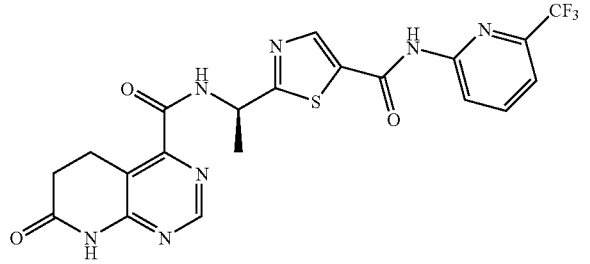 |
| 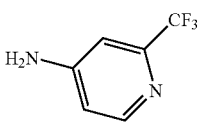 | 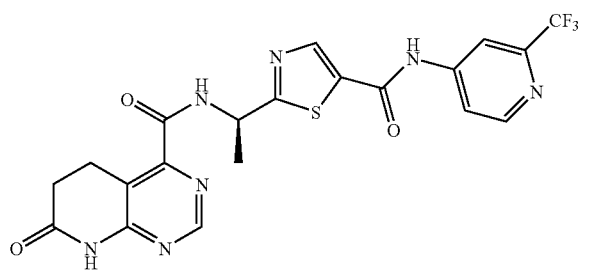 |
| 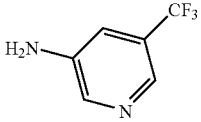 | 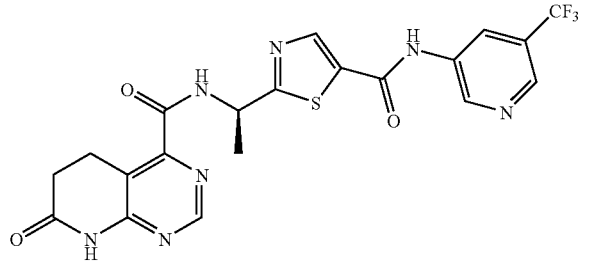 |
| 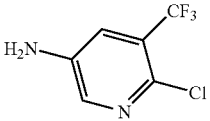 | 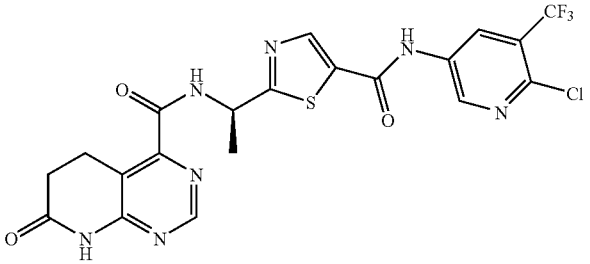 |
| 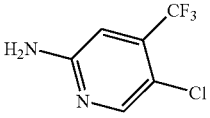 | 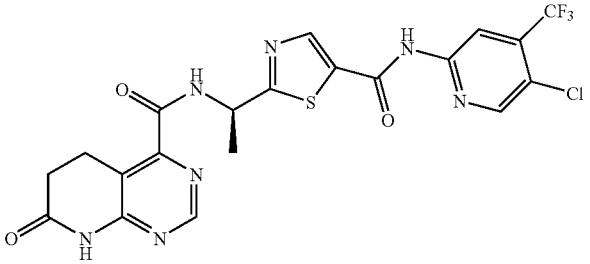 |

TABLE 2-continued
| H₂NZ | Final Compound |
|---|---|
| 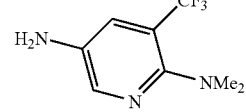 | 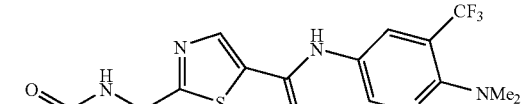 |
| 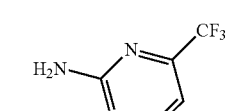 | 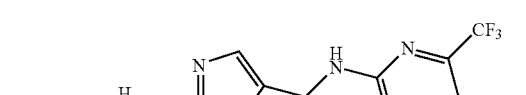 |
| 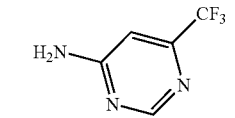 | 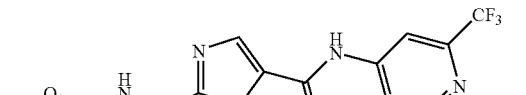 |
|  |  |
| 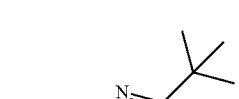 |  |

TABLE 2-continued
| H₂NZ | Final Compound |
|---|---|
| 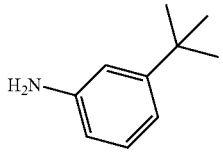 | 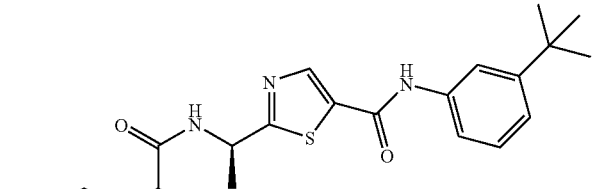 |
| 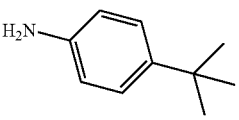 | 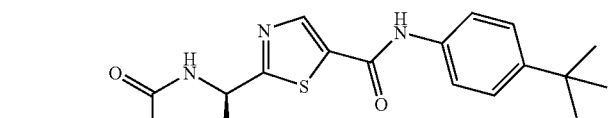 |
| 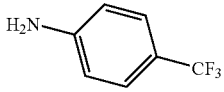 | 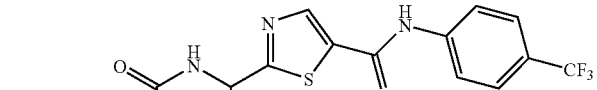 |
| 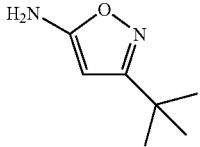 | 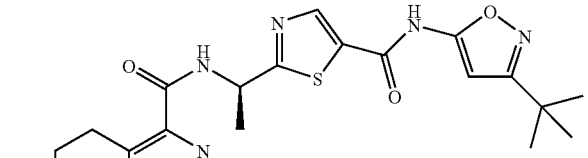 |
| 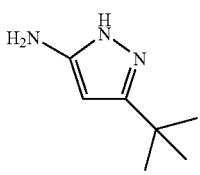 | 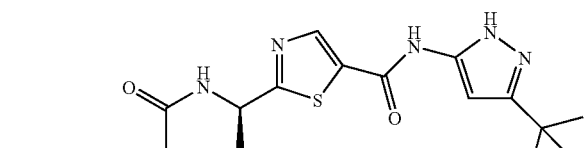 |

TABLE 2-continued

| H₂NZ | Final Compound |
|---|---|
| 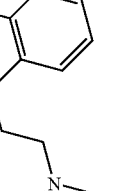 | 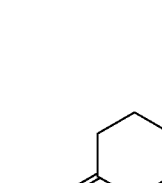 |
| 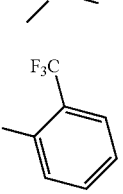 | 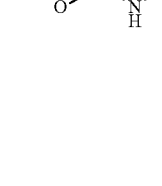 |
|  | 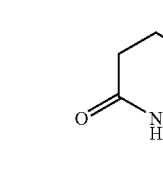 |

Example 23

This example describes the synthesis of

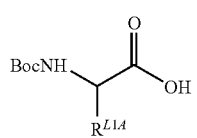

where Z is as previously described. These compounds are made according to Example 1 for making compound 1.15 except for using an amine of the formula H₂NZ instead of 3,4-diaminobenzotrifluoride. Illustrative examples of suitable amines and the resulting compounds are shown in Table 2.

Example 24

This example describes the synthesis of

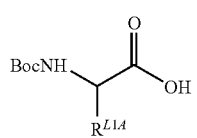

where $R^{L1A}$ and Z are as previously described. These compounds are made according to Example 1 for making compound 1.15 except for using

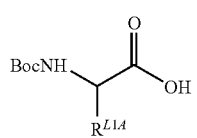

instead of

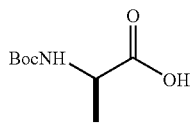

and for using an amine of the formula H₂NZ instead of 3,4-diaminobenzotrifluoride. Illustrative examples of suitable amines and the resulting compounds are shown in Table 2.

Example 25

This example describes the synthesis of

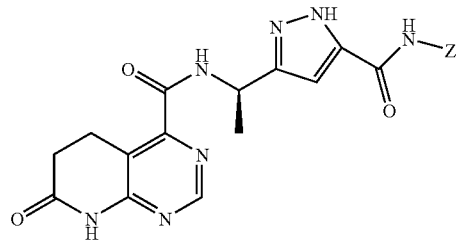

where Z is as previously described. These compounds are made according to Example 1 for making compound 1.15 except for using compound 19.1 instead of compound 1.11 and for using an amine of the formula H₂NZ instead of 3,4-diaminobenzotrifluoride. Illustrative examples of suitable amines and the resulting compounds are shown in Table 2.

Example 26

This example describes the synthesis of

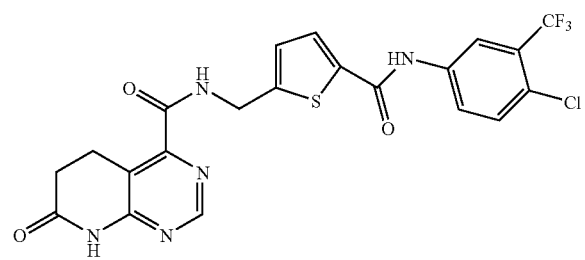

which is prepared according to Scheme K and the protocol below.

Scheme K

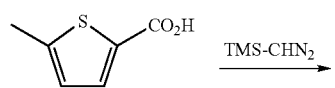

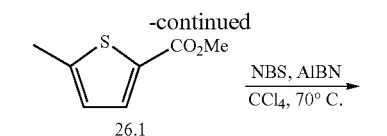

26.1

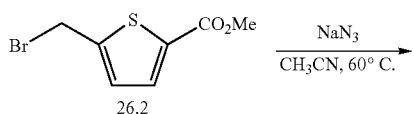

26.2

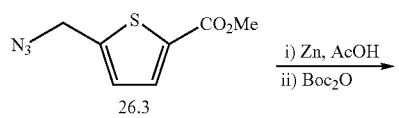

26.3

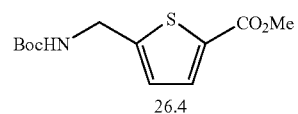

26.4

Compound 26.1. To 5-methyl-thiophene-2-carboxylic acid (2.5 g, 17.6 mmol) in CH₂Cl₂ and MeOH (50 mL, 4:1) was added (trimethylsilyl)diazomethane (9.24 mL, 18.5 mmol, 2.0 M in hexanes) slowly at room temperature. The reaction mixture was stirred at room temperature for 3 hours. Removal of the solvents under reduced pressure provided compound 26.1 (17.95 mmol, 98%) as a white solid. The crude product was used for next step without purification.

Compound 26.2. A mixture of compound 26.1, NBS (6.26 g, 35.2 mmol) and AIBN (0.03 g, 0.18 mmol) in CCl₄ (20 mL) was heated to 80° C. for 2 hours, then cooled to room temperature, filtered, washed with cold CH₂Cl₂/CCl₄ (1:1). The filtrate was concentrated to provide compound 26.2 as major product (90%) and was used in the next step without purification.

Compound 26.3. A mixture of compound 26.2 (41 g, 176 mmol) and sodium azide (22.9 g, 352 mmol) in acetonitrile (150 mL) was stirred at 60° C. for 4 hours. The reaction mixture was cooled and filtered. Removal of the solvent under reduced pressure provided compound 26.3, which was used without additional purification.

Compound 26.4. To a solution of compound 26.3 (176 mmol) in AcOH (100 mL) at 0° C. was added Zn dust (23 g, 352 mmol) in several portions. The reaction mixture was warmed to room temperature and stirred for 3 hours. The reaction mixture was filtered through a pad of celite, and concentrated. The residue was stirred in 4 N HCl overnight during which time the product precipitated. Filtration of the reaction mixture provided the amine HCl salt (24.9 g, 68% from compound 26.2).

A portion of the amine HCl salt (3.13 g, 15.1 mmol) and di-tert-butoxycarbonyl anhydride (3.63 g, 16.9 mmol) were dissolved in CH₂Cl₂ (30 mL) at room temperature. Triethylamine (5.3 mL, 38.0 mmol) was added and the reaction mixture was stirred for 2 hours. Water was added and the aqueous layer was extracted with chloroform (3×). The combined organic layer was dried over Na₂SO₄ and concentrated in vacuo to provide compound 26.4 (3.54 g, 13.0 mmol, 86%).

Compound 26. Compound 26 was prepared according to Example 1 for making compound 1.15 except for using compound 26.4 instead of compound 1.11.

Example 27

This example describes the synthesis of

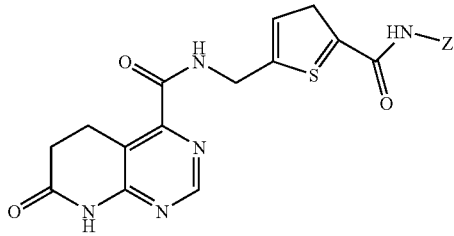

where Z is as previously described. These compounds are prepared according to Example 1 for making compound 1.15 except for using compound 26.4 instead of compound 1.11 and for using an amine of the formula H$_2$NZ instead of 3,4-diaminobenzotrifluoride. Illustrative examples of suitable amines and the resulting compounds are shown in Table 2.

Example 28

This example describes the synthesis of

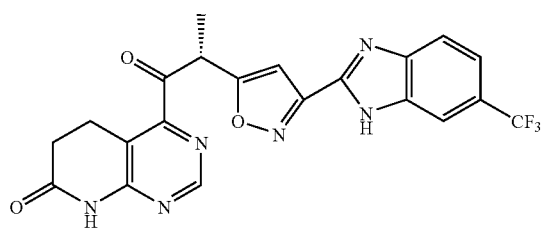

which is prepared according to Scheme L and the protocol below.

Scheme L

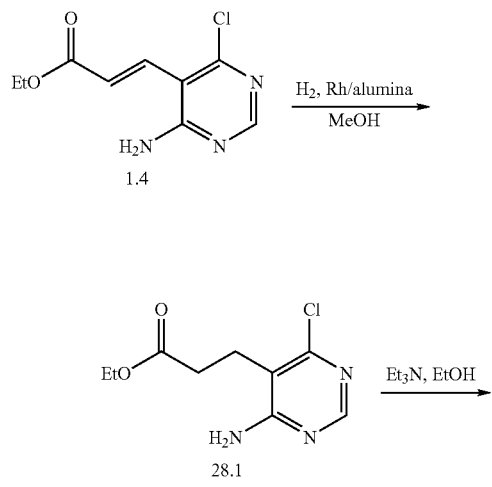

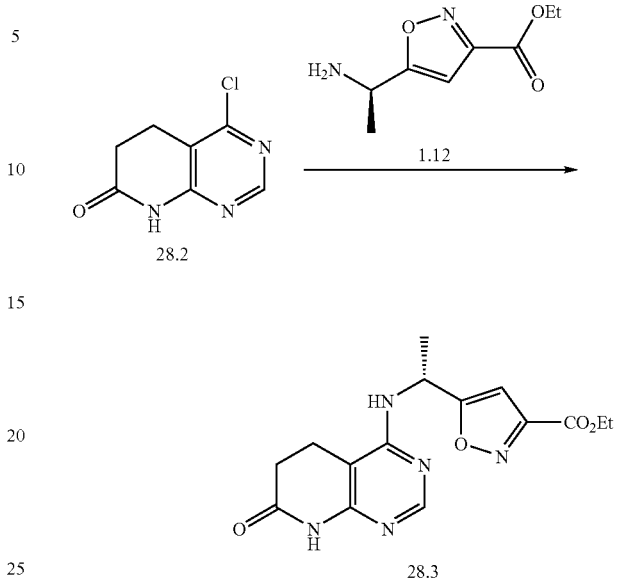

Compound 28.1. To compound 1.4 (1.5 g, 6.6 mmol) in MeOH (60 mL) was added 5% rhodium on alumina (0.8 g). The reaction mixture was stirred vigorously at 45° C. under an atmosphere of nitrogen for 48 hours. The solution was filtered through celite which was then washed with ethyl acetate. Concentration of the filtrate provided compound 28.1 (1.6 g, ~100%) which was used without additional purification.

Compound 28.2. To a sealed tube was added compound 28.1 (~1.6 g, 6.6 mmol), triethylamine (1.4 mL, 10 mmol) and ethanol (40 mL). The reaction mixture was heated at 80° C. for 6 hours, cooled, and then concentrated in vacuo. The residue was partitioned between ethyl acetate and aqueous HCl (0.5 N). The aqueous layer was extracted with ethyl acetate (2×); the combined organic layer was washed with H$_2$O and saturated NaHCO$_3$, dried over Na$_2$SO$_4$, and concentrated. The crude material was purified by silica gel chromatography to provide compound 28.2 (0.6 g, 50% over two steps).

Compound 28.3. To compound 28.2 (91 mg, 0.5 mmol) and compound 1.12 (92 mg, 0.5 mmol) in NMP (1.5 mL) was added triethylamine 0.084 mL, 0.6 mmol). The reaction mixture was heated at 150° C. under microwave irradiation for 30 minutes. The mixture was partitioned between ethyl acetate and H$_2$O followed by extraction with ethyl acetate (3×) and then brine. The combined organic layer was dried over Na$_2$SO$_4$ and concentrated. Purification of the crude material by silica gel chromatography provided compound 28.3 (50 mg, 31%).

Compound 28. Compound 28 was prepared according to Example 1 except for using compound 28.3 instead of compound 1.13.

Example 29

This example describes the synthesis of

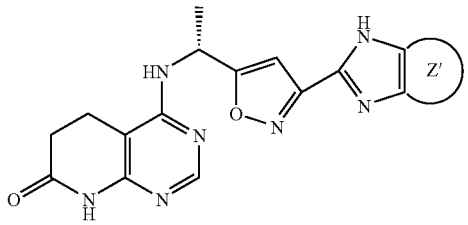

which are prepared according to Example 28 except for using a diamine of the formula

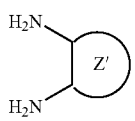

instead of 3,4-diaminobenzotrifluoride (in step for compound 1.15). Illustrative examples of suitable diamines and their resulting compounds are shown in Table 1.

Example 30

This example describes the synthesis of

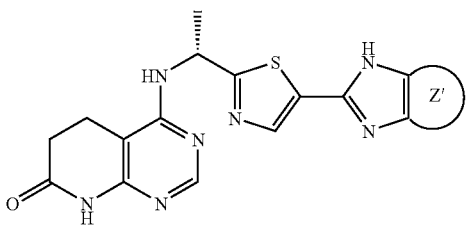

which are prepared according to Example 28 except for using compound 13.4 instead of compound 1.12 and for using a diamine of the formula

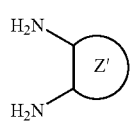

instead of 3,4-diaminobenzotrifluoride (in step for compound 1.15). Illustrative examples of suitable diamines and their resulting compounds are shown in Table 1.

Example 31

This example describes the synthesis of

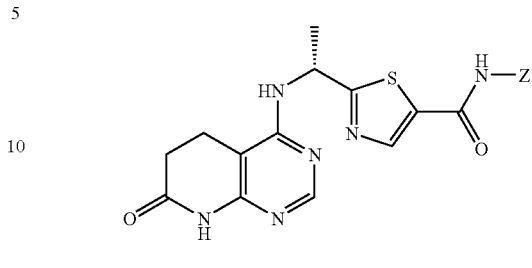

which are prepared according to Example 28 except for using compound 13.4 instead of compound 1.12 and for using an amine of the formula $H_2NZ$ instead of 3,4-diaminobenzotrifluoride for making compound 1.15. Illustrative examples of suitable amines and the resulting compounds are shown in Table 2.

Example 32

This example describes the synthesis of

32

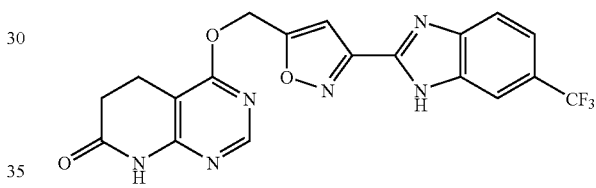

which are prepared according to Scheme M and the protocol below.

Scheme M

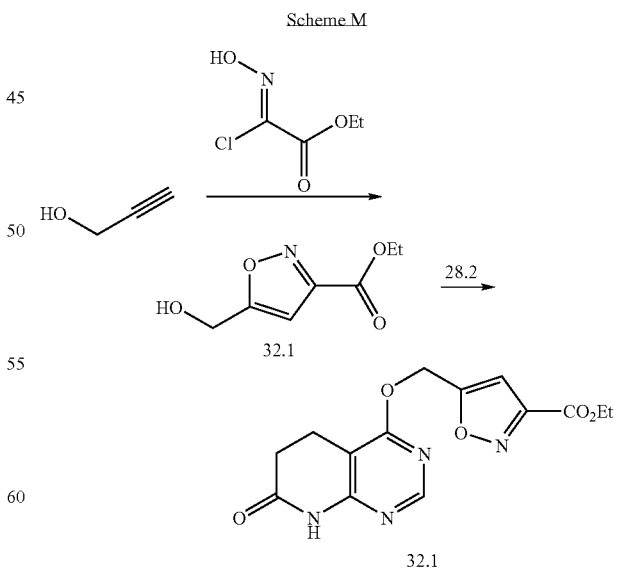

Compound 32.1. Compound 32.1 is prepared according to the procedure for compound 1.11 except for using proparyl alcohol instead of compound 1.10.

Compound 32.2. Compound 32.2 is prepared according to the procedure for compound 28.3 except for using compound 32.1 instead of compound 1.12.

Compound 32. Compound 32 is prepared according to Example 1 except for using compound 32.2 instead of 1.13.

Example 33

This example describes the synthesis of

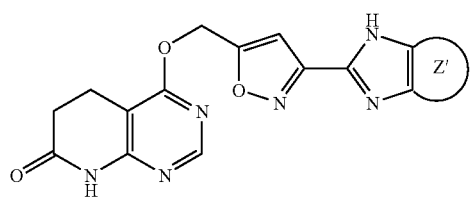

which are prepared according to Example 32 except for using a diamine of the formula

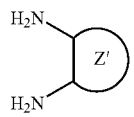

instead of 3,4-diaminobenzotrifluoride (in step for compound 1.15). Illustrative examples of suitable diamines and their resulting compounds are shown in Table 1.

Example 34

This example describes the synthesis of

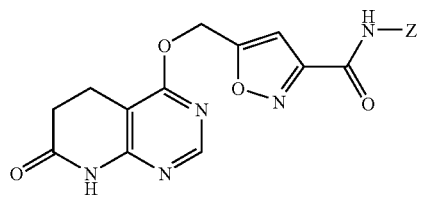

which are prepared according to Example 1 for making compound 1.15 except for using compound 32.2 instead of compound 1.13 and for using an amine of the formula $H_2NZ$ instead of 3,4-diaminobenzotrifluoride. Illustrative examples of suitable amines and the resulting compounds are shown in Table 2.

Example 35

This example describes the synthesis of

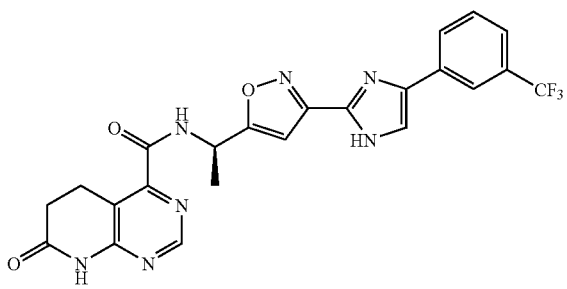

which was prepared according to Scheme N and the protocol below.

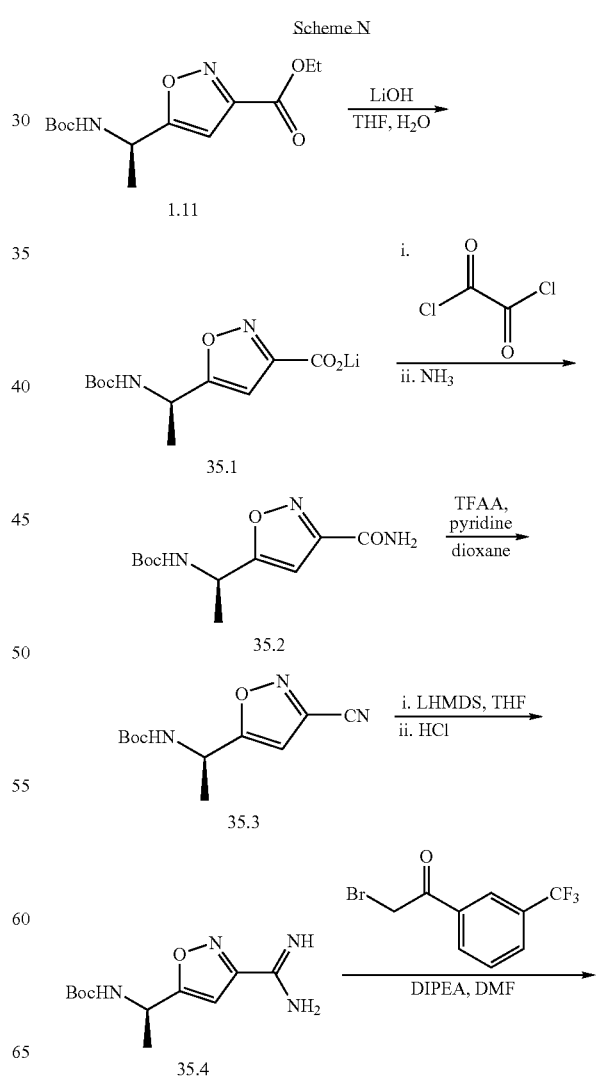

-continued

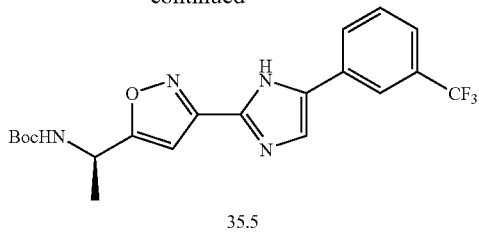

35.5

Compound 35.1. A clear yellow solution of compound 1.11 (2.00 g, 7.00 mmol) in THF (8.4 mL) at room temperature was treated with LiOH (8.4 mL, 8.4 mmol, 1.0 M in H$_2$O) and the reaction progress was monitored by LCMS. After 30 minutes, the reaction mixture was concentrated thoroughly in vacuo to afford compound 35.1 (1.84 g, 100%). LCMS: m/z: 257 (M+1, CO$_2$H).

Compound 35.2. A clear, pale yellow solution of compound 35.1 (1.84 g, 7.00 mmol) in DMF (21 mL) at 0° C. was treated slowly and dropwise with oxalyl chloride (1.00 g, 7.70 mmol), and the reaction progress was monitored by LCMS using aliquots quenched with methyl amine (1.0 M in THF). After 2 hours, the reaction mixture had come gradually to room temperature. The solution was recooled to 0° C. and stirred vigorously as ammonia gas was bubbled into the mixture for 5 minutes, at which time a thick yellow precipitate developed. The reaction mixture was next concentrated thoroughly in vacuo, the solid residue was triturated with ethyl acetate (10 mL) and filtered to remove unwanted salts, and the filtrate was concentrated in vacuo. The residue was purified by silica gel flash column chromatography (60:40→40:60 hexane/ethyl acetate) to afford compound 35.2 (0.52 g, 29%). LCMS: m/z: 156 (M+1-100).

Compound 35.3. A clear, pale yellow solution of compound 35.2 (0.514 g, 2.02 mmol) and pyridine (0.404 g, 5.06 mmol) in dioxane (6.0 mL) at 0° C. was treated slowly and dropwise with TFAA (0.346 g, 2.42 mmol), and the reaction progress was monitored by LCMS. After 30 minutes, the reaction mixture was transferred into saturated aqueous NaHCO$_3$ (20 mL), at which time a precipitate formed. The mixture was treated with ethyl acetate (20 mL), and the solids were removed by filtration. The filtrate was concentrated in vacuo. The residue was purified by silica gel radial chromatography (4:1→6:4 hexane/ethyl acetate) to afford compound 35.3 (0.45 g, 95%). LCMS: m/z: 238 (M+1).

Compound 35.4. A clear, colorless solution of compound 35.3 (0.446 g, 1.88 mmol) in THF (11 mL) at room temperature was treated slowly and dropwise with LHMDS (11.3 mL, 11.3 mmol, 1.0 M THF), and the reaction progress was monitored by LCMS. After 30 minutes, the reaction mixture was treated with 2.0 M HCl (11 mL). After an additional 30 minutes, the reaction mixture was quenched by transferring into saturated NaHCO$_3$ (30 mL), and the resultant mixture was extracted with ethyl acetate (3×). The combined organic extracts were rinsed with brine (30 mL), dried over MgSO$_4$, and concentrated in vacuo. The residue was purified by silica gel radial chromatography (4:1→6:4 hexane/ethyl acetate) to afford compound 35.4 (0.050 g, 10% yield). LCMS: m/z: 255 (M+1).

Compound 35.5. A clear, pale amber solution of compound 35.4 (0.050 g, 0.194 mmol) in DMF (5 mL) was treated with 2-bromo-1-(3-trifluoromethylphenyl)-ethanone (0.0674 g, 1.30 mmol), and the reaction progress was monitored by LCMS. After 2 hours, DIPEA (12.6 mg, 0.097 mmol) was added. After an additional 16 hours, the reaction mixture was diluted with ethyl acetate (50 mL), extracted with 2:1:1 water/saturated NaHCO$_3$/brine (3×), extracted with brine (25 mL), dried over MgSO$_4$, and concentrated in vacuo. The residue was purified by silica gel radial chromatography (4:1→6:4 hexane/ethyl acetate) to afford compound 35.5 (0.040 g, 49%). LCMS: m/z: 422 (M$^+$).

Compound 35. Title compound 35 was prepared according to Example 1 for making compound 1.13 except for using compound 35.5 instead of compound 1.11.

Example 36

This example describes the synthesis of

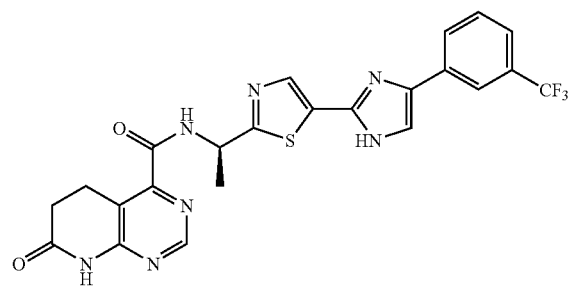

which is prepared according to Example 35 except that compound 13.3 is used instead of compound 1.11.

Example 37

This example describes the synthesis of

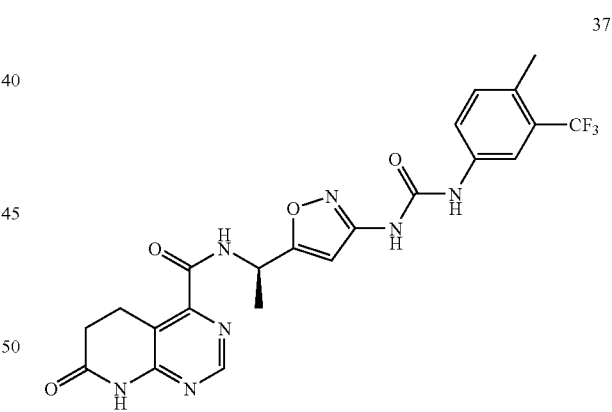

37 which is prepared according to Scheme O and the protocol below.

Scheme O

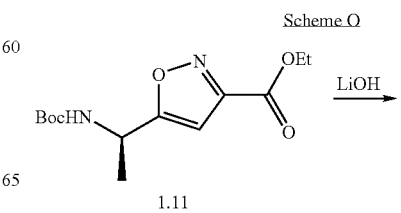

1.11

-continued

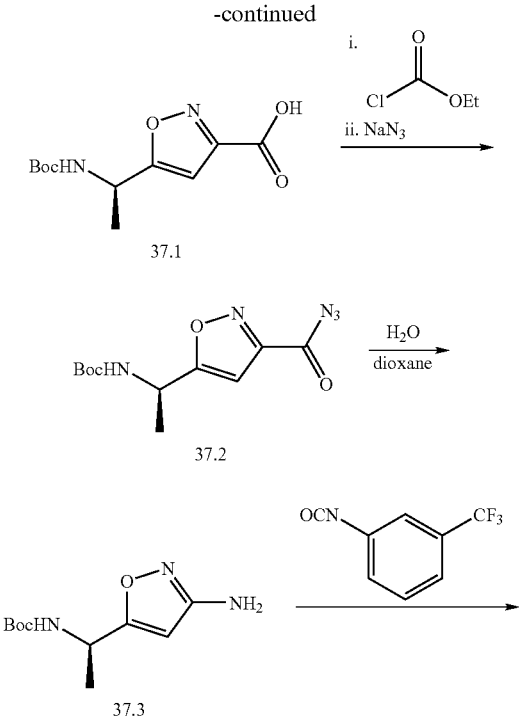

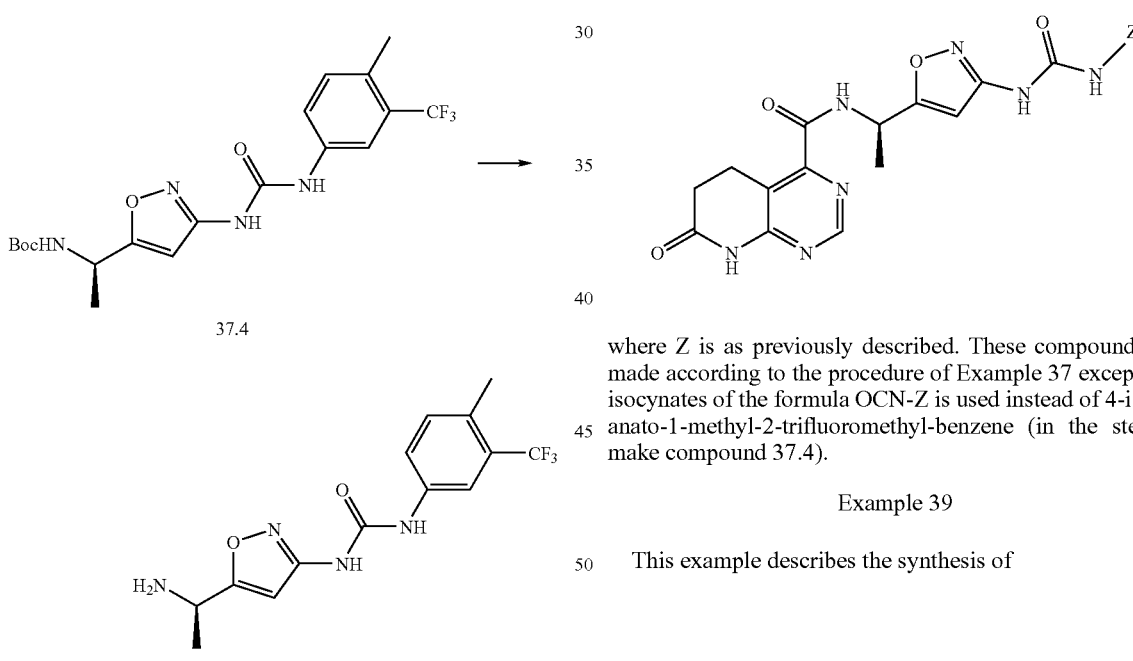

Compound 37.1. Compound 37.1 is prepared according to the procedure to prepare compound 33.3 except for using compound 1.11 instead of compound 33.2.

Compound 37.2. To compound 37.1 (2.26 g, 8.83 mmol) and triethylamine (1.48 mL, 10.6 mmol) in acetone (35 mL) at 0° C. was added dropwise a solution of ethyl chloroformate (1.44 mL, 15 mmol) in acetone (7 mL). After 30 minutes, NaN$_3$ (1.03 g, 15.9 mmol) in water (4.5 mL) was added. The reaction mixture was stirred for 1 hour and then partitioned between CH$_2$Cl$_2$ and water. The organic layer was dried over Na$_2$SO$_4$ and concentrated to afford 37.2 (2.08 g) which was used without additional purification.

Compound 37.3. Compound 37.2 (~2.1 g) was stirred at reflux in dioxane/water (30 mL, 4:1) for 2 hours. The reaction mixture was cooled and then partitioned between dichloromethane and water. The aqueous layer was extracted with CH$_2$Cl$_2$ (2×); the organic layer was dried over Na$_2$SO$_4$ and concentrated. Purification by silica gel chromatography provided compound 37.3 (0.78 g).

Compound 37.4. Compound 37.3 (100 mg, 0.44 mmol), 4-isocyanato-1-methyl-2-trifluoromethyl-benzene (88 mg, 0.44 mmol), and THF (2 mL) were added to a sealed tube and stirred at 65° C. overnight. The reaction mixture was concentrated and the residue was purified by silica gel chromatography (eluting with 5% MeOH/CH$_2$Cl$_2$) to provide compound 37.4 as a white solid.

Compound 37.5. Compound 37.5 is prepared according to Example 1 for making compound 1.12 except that compound 37.4 is used instead of compound 1.11.

Compound 37. Compound 37 is prepared according to Example 1 for making compound 1.13 except for using compound 37.5 instead of compound 1.12.

Example 38

This example describes the synthesis of

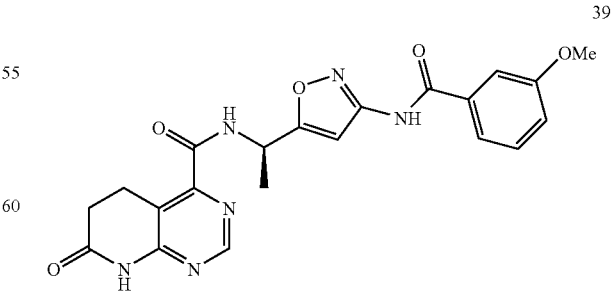

where Z is as previously described. These compounds are made according to the procedure of Example 37 except that isocynates of the formula OCN-Z is used instead of 4-isocyanato-1-methyl-2-trifluoromethyl-benzene (in the step to make compound 37.4).

Example 39

This example describes the synthesis of

39 which is prepared according to Scheme P and the protocol below.

Scheme P

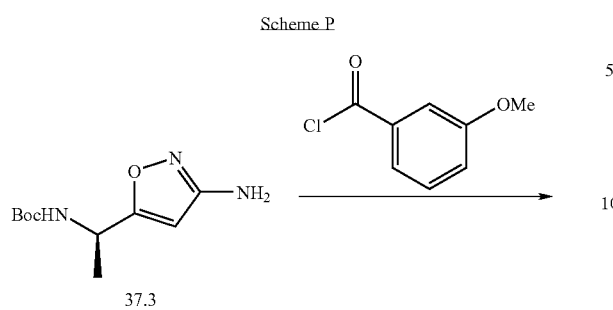

Example 41

This example describes the synthesis of

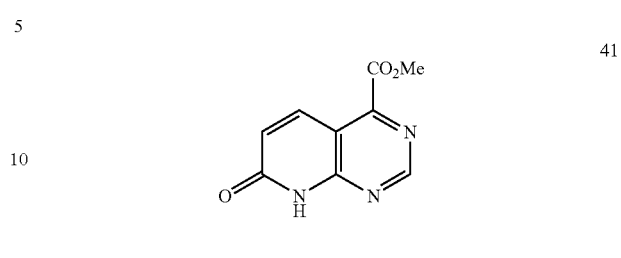

which was prepared according to Scheme Q and the protocol below.

Scheme Q

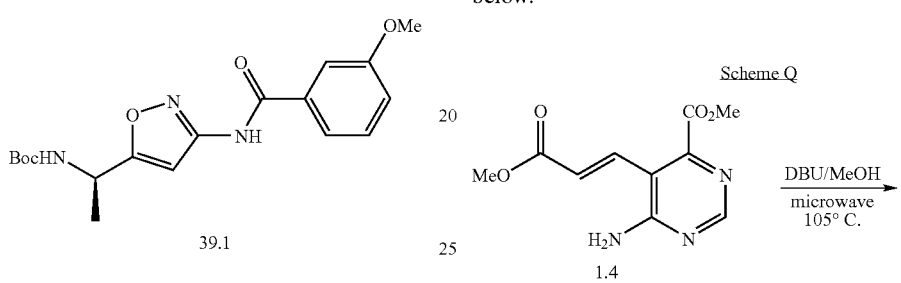

Compound 39.1. To compound 37.3 (87 mg, 0.38 mmol) in $CH_2Cl_2$ (2 mL) at 0° C. was added 3-methoxy-benzoyl chloride (0.11 mL, 0.77 mmol). The reaction mixture was stirred for 3 hours and then partitioned between $CH_2Cl_2$ and 1N HCl. The aqueous layer was extracted with $CH_2Cl_2$ (2×) and then concentrated to provide the bis-acylated material. The crude residue was stirred in 1M LiOH/THF (2 mL, 3:1) for 15 minutes. The solution was neutralized with 1N HCl and the mixture was extracted with ethyl acetate (2×). Purification by silica gel chromatography (eluting with ethyl acetate/hexanes, 3:1) provided compound 39.1 (120 mg) as a white powder.

Compound 39. Compound 39 is prepared according to Example 37 except for using compound 39.1 instead of compound 37.4.

Example 40

This example describes the synthesis of

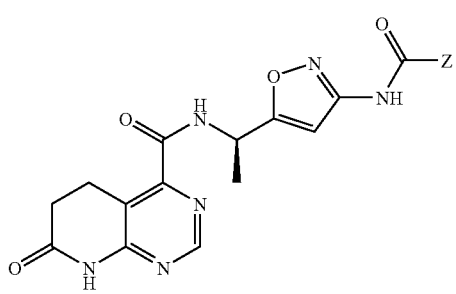

where Z is as described previously. These compounds are prepared according to Example 39 except that an acid chloride of the formula Z(C=O)Cl is used instead of 3-methoxy-benzoyl chloride.

Compound 41. Compound 1.4 (99.3 mg, 0.419 mmol, 1 eq.) was dissolved in MeOH (4 mL). DBU (118 mL, 0.839 mmol, 2 eq.) was added and the reaction was microwaved at 105° C. for 15 minutes. The reaction was neutralized by addition of 3N—HCl (300 μL, 0.900 mmol, 1.07 eq.). The same reaction protocol was repeated three more times using 109 mg, 109 mg and 104 mg of compound 1.4. Ethyl acetate and water were added to the combined reaction mixture. The layers were separated and the product was extracted using ethyl acetate (2×). The combined organic layer was washed with brine and dried over anhydrous sodium sulfate. After removal of the solvent under reduced pressure, the crude product was purified using silica gel column chromatography with a gradient of hexanes:ethyl acetate (2:1→1:4→0:100) followed by ethyl acetate: methanol (10:1) to afford compound 41 (157 mg, 0.763 mmol, 43%).

Example 42

This example describes the synthesis of

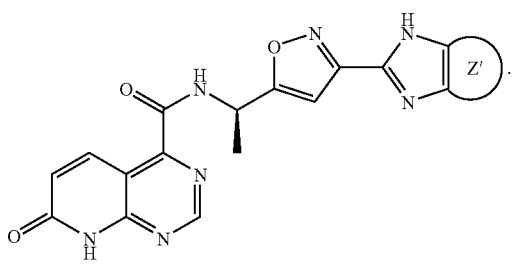

These compounds are prepared according to Example 1 except for using compound 41 instead of compound 1.6 and for using a diamine of the formula

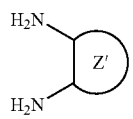

instead of 3,4-diaminobenzotrifluoride (in step for compound 1.15). Illustrative examples of suitable diamines and their resulting compounds are shown in Table 1.

Example 43

This example describes the synthesis of

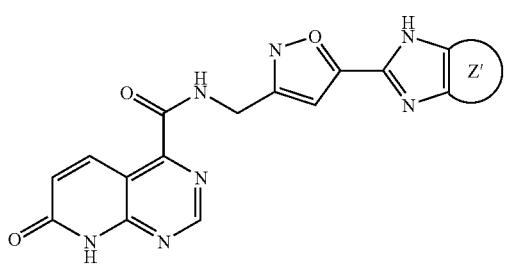

These compounds are prepared according to Example 1 except for using compound 41 instead of compound 1.6, Boc-glycine aldehyde instead of compound 1.9, compound 10.2 instead of compound 1.11, and diamine of the formula

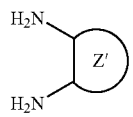

instead of 3,4-diaminobenzotrifluoride (in step for compound 1.15). Illustrative examples of suitable diamines are shown in Table 1.

Example 44

This example describes the synthesis of

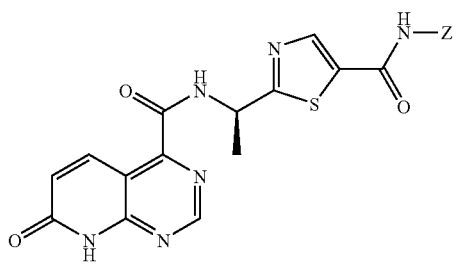

where Z is as previously described. These compounds are prepared according to Example 1 for making compound 1.15 except for using compound 41 instead of compound 1.6, compound 13.4 instead of compound 1.12 and 3-methoxy-4-triflouromethylaniline instead of 3,4-diaminobenzotriflouride (in the step for making compound 1.15).

Example 45

This example describes the synthesis of

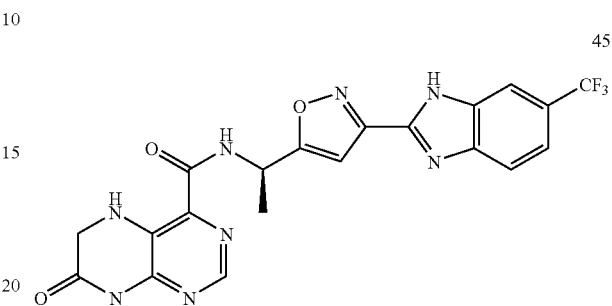

which was prepared according to Scheme R and the protocol below.

Scheme R

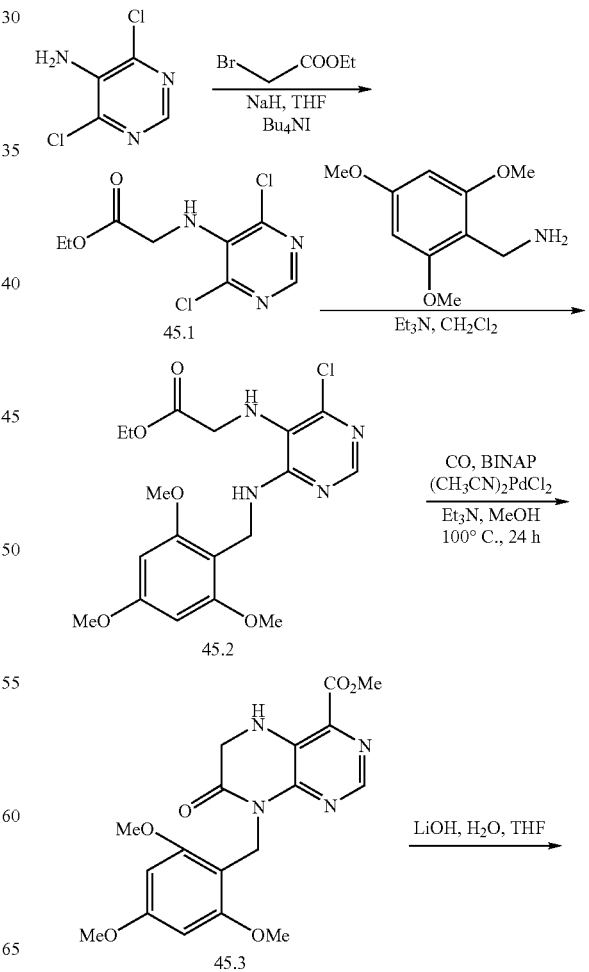

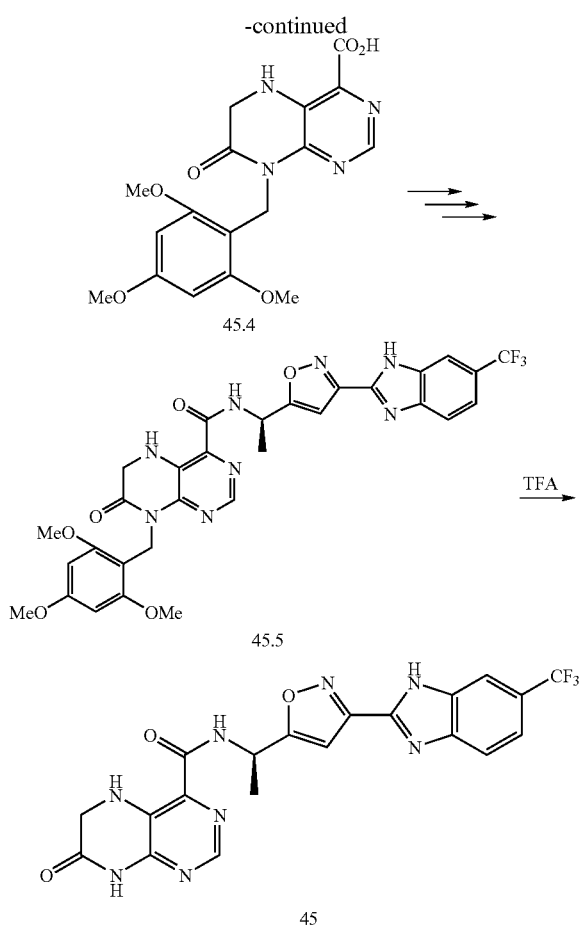

Compound 45.1. To a cooled (0° C.) solution of 4,6-dichloro-5-amino-pyrimidine (5.04 g, 30.8 mmol) in THF (250 mL) was added sodium hydride (1.48 g, 60% in mineral oil, 36.9 mmol, 1.2 equiv). The reaction mixture was stirred for 2 minutes then the ice bath was removed. Ethyl bromoacetate (4.2 mL, 36.9 mmol, 1.2 equiv) was added, followed by tetrabutylammonium iodide (13.9 g, 36.9 mmol, 1.2 equiv). The reaction mixture was stirred at room temperature for 3 days, and the resultant orange suspension was filtered. The filtrate was concentrated to a brown oil. The residue was purified by flash column chromatography (10-25% EtOAc/hexanes), and mixed fractions were isolated and repurified (10-12-100% EtOAc/hexanes) to afford compound 45.1 (5.34 g, 69%) as a pale yellow oil.

Compound 45.2. A 300 mL pressure vessel was charged with compound 45.1 (2.55 g, 10.2 mmol, 1.0 equiv), ethanol (100 mL), trimethoxybenzylamine.HCl (2.67 g, 11.2 mmol, 1.1 equiv), and triethylamine (3.1 mL, 22.4 mmol, 2.2 equiv). The vessel was sealed tightly and the reaction mixture was heated at 70° C. for 16 hours, then heated at 80° C. for an additional 24 hours. After cooling to room temperature, $SiO_2$ gel was added to the reaction mixture and the resultant suspension was concentrated in vacuo. Purification by flash column chromatography (10-30-50% EtOAc/hexanes) afforded compound 45.2 (2.93 g, 70%) as a yellow oil. LCMS: m/z: 411 (M+1).

Compound 45.3. A bomb was charged with bis(acetonitrile)dichloropalladium II (93 mg, 0.36 mmol, 0.05 equiv) and rac-BINAP (0.23 g, 0.36 mmol, 0.05 equiv) followed by a solution of compound 45.2 (2.93 g, 7.13 mmol, 1.0 equiv) in methanol (100 mL). Triethylamine (1.29 mL, 9.27 mmol, 1.3 equiv) was added last. After purging and back-filling the bomb with CO (3×, 50 psi), the bomb was pressurized to 50 psi CO (g). The reaction mixture was stirred at 100° C. for 22 hours, then cooled to rt and the bomb was carefully vented. The reaction mixture contained solid other than palladium by-products so methanol (1 L) and small amounts of DMF were added to attempt to solubilize this solid. The mixture was filtered through celite and concentrated. Purification by flash column chromatography (50-75-100% EtOAc/hexanes) afforded compound 45.3 (1.72 g, 62%) as a yellow solid. LCMS: m/z: 389 (M+1).

Compound 45.4. To a suspension of compound 45.3 (0.53 g, 1.36 mmol) in THF (10.2 mL) was added a solution of LiOH (82 mg, 3.41 mmol, 2.5 equiv) in $H_2O$ (3.4 mL). The reaction mixture was stirred at rt for 20 hours. When LC-MS indicated complete conversion to product, the reaction mixture was treated dropwise with aqueous 1 N HCl (100 mL). The resultant suspension was filtered, washing solid with ether. The solid was collected, triturated in toluene, concentrated, and dried under high vacuum to provide compound 45.4 (0.281 g, 55%) as a pale yellow solid. LC-MS: m/z: 375 (M+1).

Compound 45.5. Compound 45.5 is prepared according to Example 1 except for using compound 45.4 instead of compound 1.7.

Compound 45. To a solution of compound 45.5 (160 mg, 0.25 mmol) in dichloromethane (6 mL) was added triethylsilane (0.2 mL, 1.2 mmol, 5 equiv) and trifluoroacetic acid (2 mL). The resultant solution was stirred 3.5 hours, whereupon the reaction mixture was concentrated in vacuo and the residue was diluted with EtOAc (30 mL). After washing with aqueous saturated $NaHCO_3$ (2×50 mL), the combined aqueous layers were extracted with EtOAc (4×30 mL), the extracts were washed with brine (50 mL), dried over anhydrous sodium sulfate and filtered. The organic layer was adsorbed onto $SiO_2$ gel. Purification by flash column chromatography (80-100% EtOAc/hexanes) afforded compound 45 (80 mg, 69%) as a peach solid. LCMS: m/z: 473 (M+1).

Example 46

This example describes the synthesis of

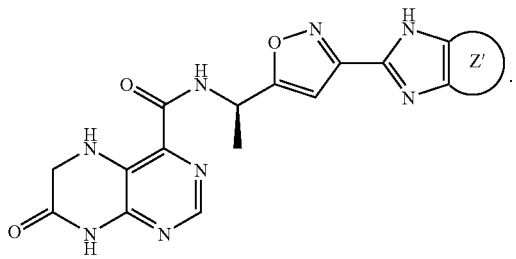

These compounds are prepared according to Example 45 except for using a diamine of the formula

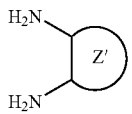

instead of 3,4-diaminobenzotrifluoride (in step for compound 1.15). Illustrative examples of suitable diamines are shown in Table 1.

Example 47

This example describes the synthesis of

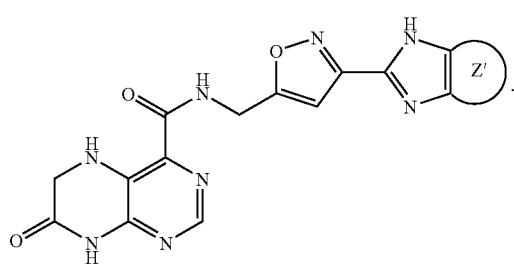

These compounds are prepared according to Scheme S and the protocol below.

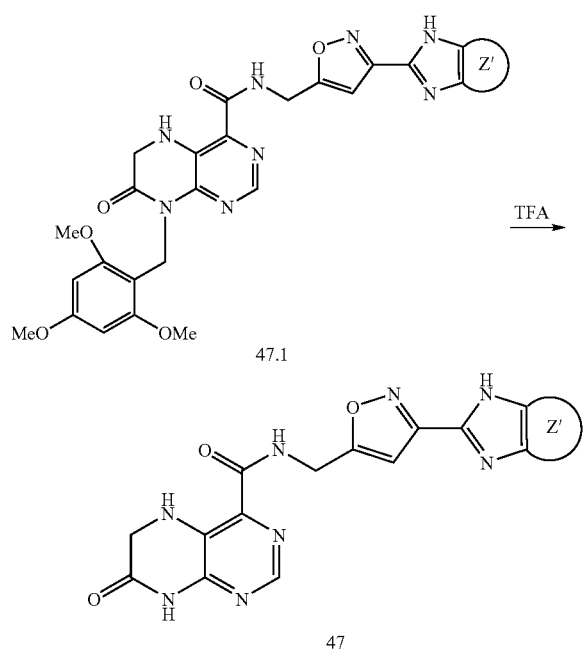

Compound 47.1. Compound 47.1 is prepared according to Example 1 except for using compound 45.4 instead of compound 1.7, Boc-glycine aldehyde instead of compound 1.9, and a diamine of the formula

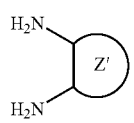

instead of 3,4-diaminobenzotrifluoride (in step for compound 1.15). Illustrative examples of suitable diamines are shown in Table 1.

Compound 47. Compound 47 is prepared according to Example 45 for making compound 45 except for using compound 47.1 instead of compound 45.5.

Example 48

This example describes the synthesis of

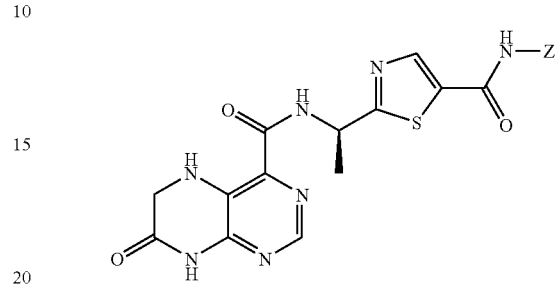

where Z is as previously described. These compounds are prepared according to Scheme T and the protocol below.

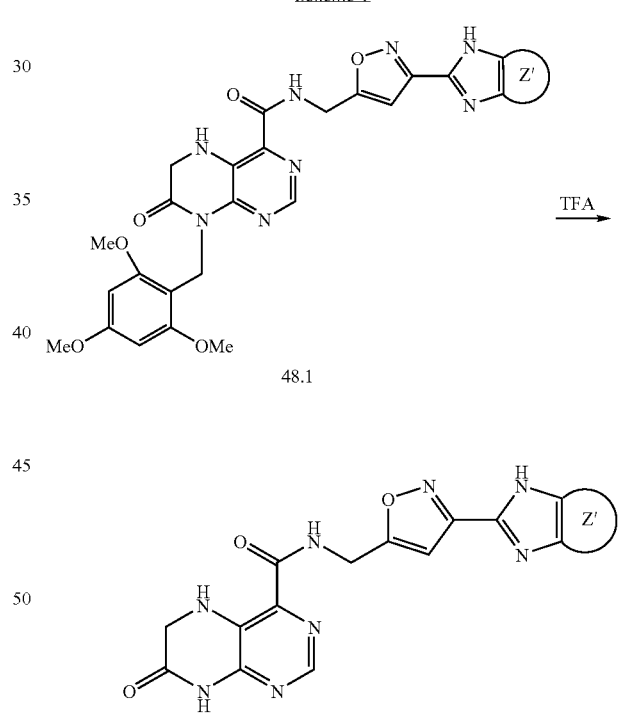

Compound 48.1. Compound 48.1 is prepared according to Example 1 for making compound 1.15 except for using compound 45.4 instead of compound 1.7, compound 13.4 instead of compound 1.12 and 3-methoxy-4-triflouromethylaniline instead of 3,4-diaminobenzotrifluoride (in the step for making compound 1.15).

Compound 48. Compound 48 is prepared according to Example 45 for making compound 45 except for using compound 48.1 instead of compound 45.5.

Example 49

This example describes the synthesis of

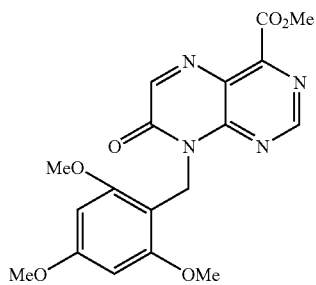

which is prepared according to Scheme U and the protocol below.

Scheme U

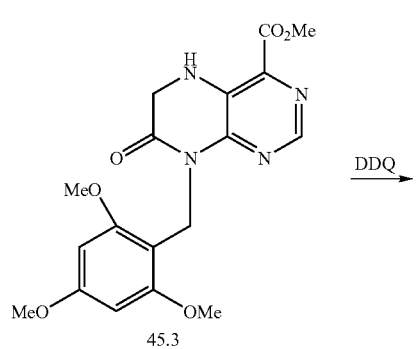

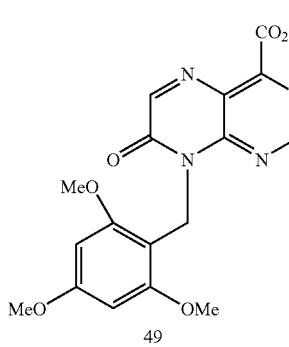

Compound 49. To a solution of compound 45.3 (388 mg, 1 mmol) in toluene (10 mL) was added DDQ (230 mg, 1 mmol). The reaction mixture was heated to reflux for 7 hours and then cooled to room temperature. The mixture was filtered and the solid was purified by silica gel chromatography to provide compound 49 (205 mg, 53%).

Example 50

This example describes the synthesis of

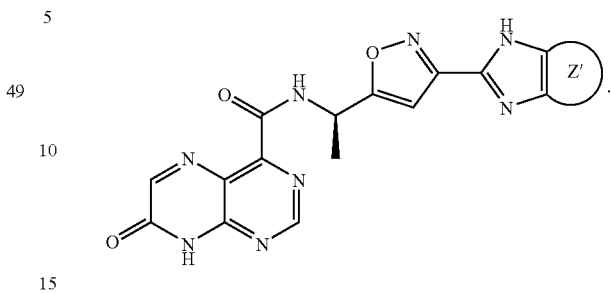

These compounds are prepared according to Example 1 except for using compound 49 instead of compound 1.7 and for using a diamine of the formula

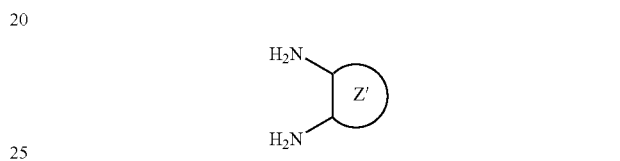

instead of 3,4-diaminobenzotrifluoride (in step for compound 1.15). Illustrative examples of suitable diamines are shown in Table 1.

Example 51

This example describes the synthesis of

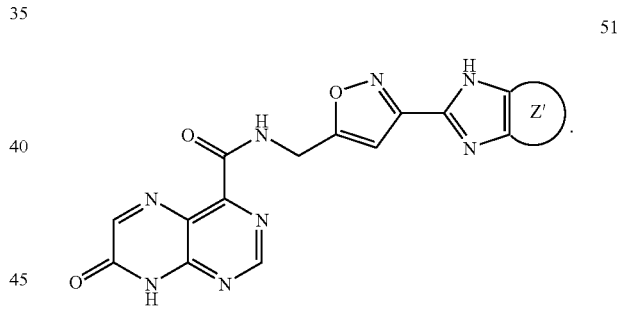

These compounds are prepared according to Scheme V and the protocol below.

Scheme V

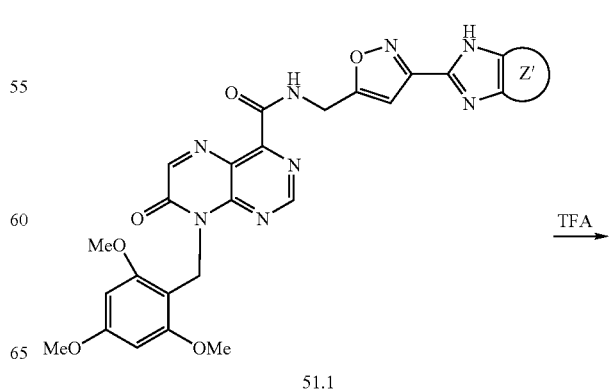

-continued

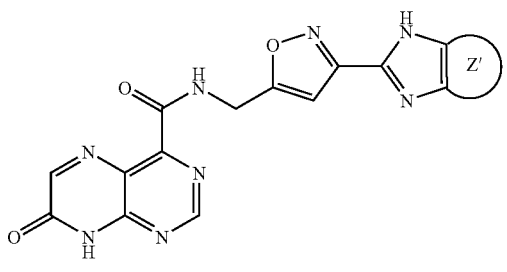

51

Compound 51.1. Compound 51.1 is prepared according to Example 1 except for using compound 49 instead of compound 1.7, Boc-glycine aldehyde instead of compound 1.9, and a diamine of the formula

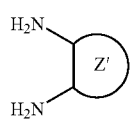

instead of 3,4-diaminobenzotrifluoride (in step for compound 1.15). Illustrative examples of suitable diamines are shown in Table 1.

Compound 51. Compound 51 is prepared according to Example 45 for making compound 45 except for using compound 51.1 instead of compound 45.5.

Example 52

This example describes the synthesis of

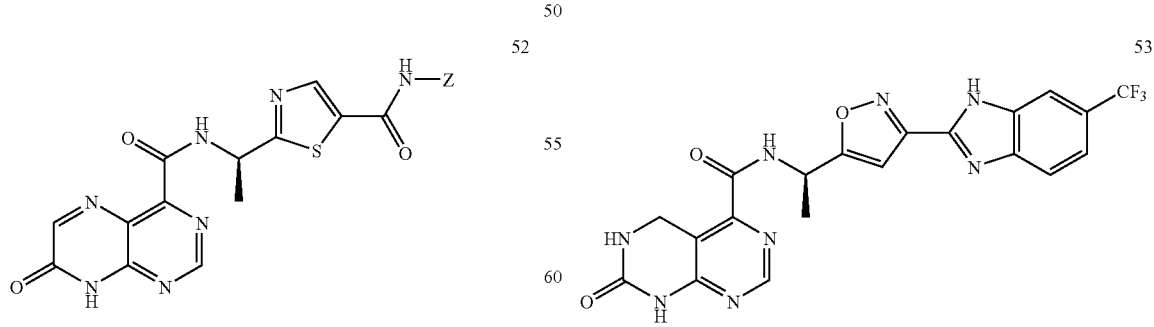

where Z is as previously described. These compounds are prepared according to Scheme W and the protocol below.

Scheme W

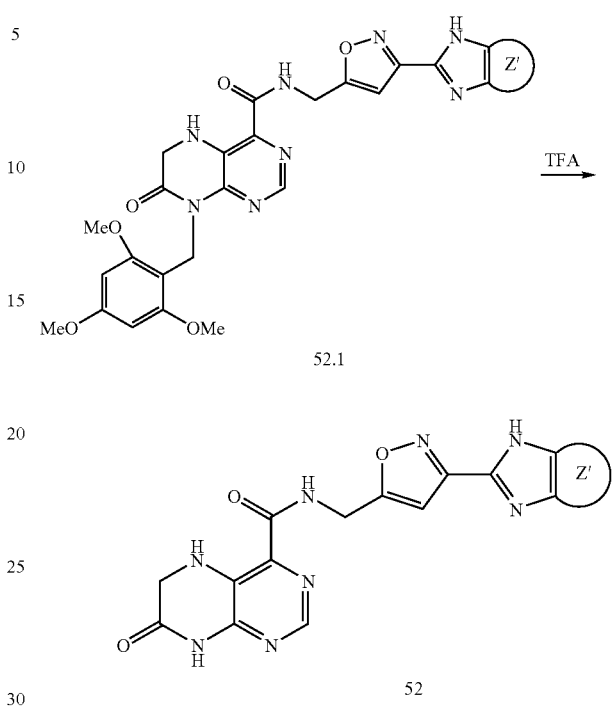

Compound 52.1. Compound 53.1 is prepared according to Example 1 for making compound 1.15 except for using compound 49 instead of compound 1.7, compound 13.4 instead of compound 1.12 and 3-methoxy-4-triflouromethylaniline instead of 3,4-diaminobenzotriflouride (in the step for making compound 1.15).

Compound 52. Compound 52 is prepared according to Example 45 for making compound 45 except for using compound 52.1 instead of compound 45.5.

Example 53

This example describes the synthesis of which is prepared according to Scheme X and the protocol below.

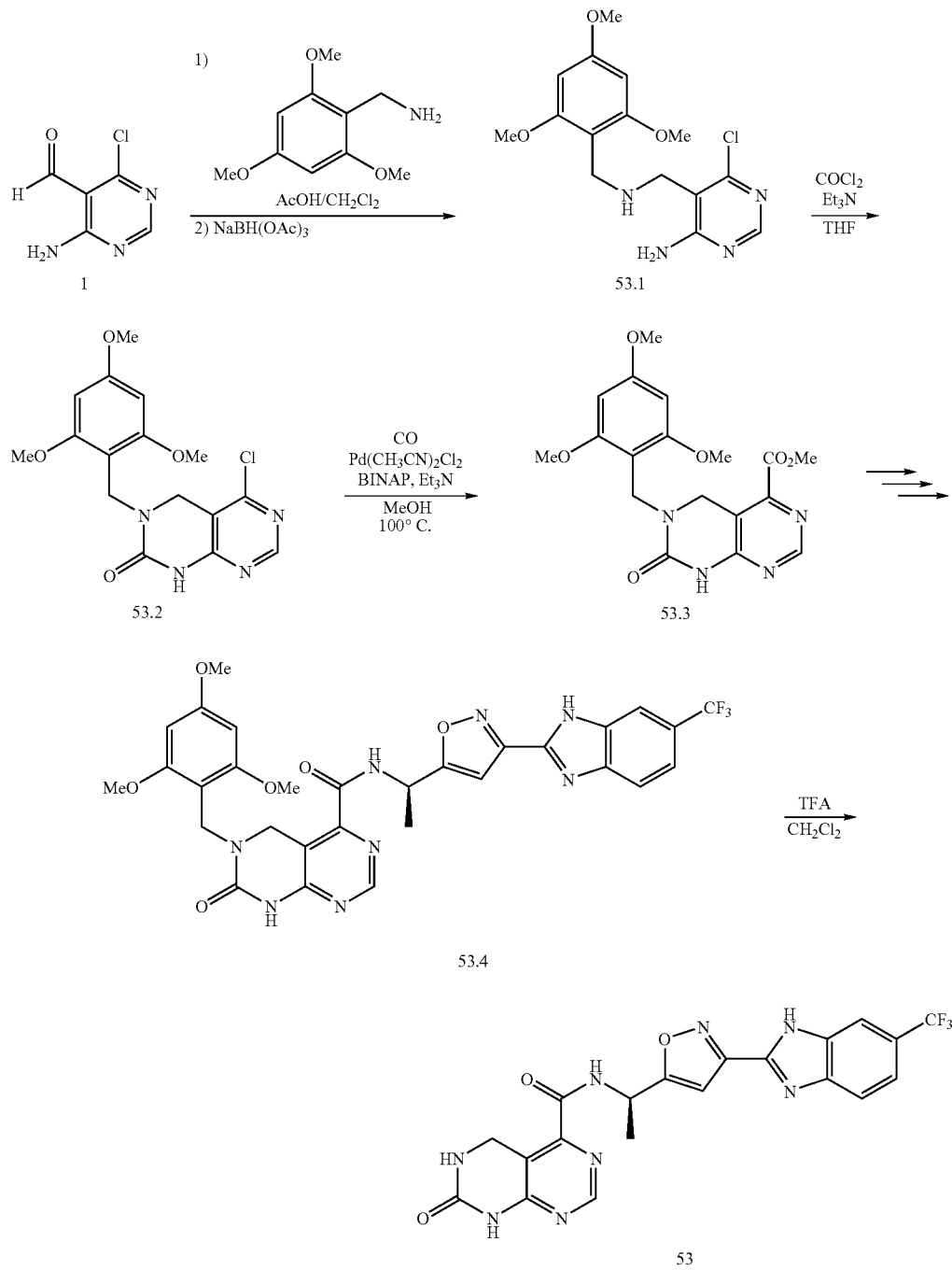

Compound 53.1. Compound 1.2 (249 mg, 1.58 mmol, 1 eq.) and 2,4,6-trimethoxybenzylamine (free-based by saturated sodium bicarbonate wash) (313 mg, 1.59 mmol, 1 eq.) were dissolved in dichloromethane (3 mL) at room temperature. Acetic acid (91 µL, 1.58 mmol, 1 eq.) was added and the reaction mixture was heated in a microwave at 100° C. for 5 minutes. Sodium triacetoxyborohydride (410 mg, 1.94 mmol, 1.2 eq.) was added at room temperature and the reaction was stirred overnight. Saturated sodium bicarbonate solution and ethyl acetate were added to the reaction mixture and the layers were separated. The product was extracted twice more with ethyl acetate. The combined organic layers were washed with saturated sodium bicarbonate solution, brine, and then dried over anhydrous sodium sulfate. After removal of the solvent under reduced pressure, the crude product was purified using silica gel column chromatography with a gradient of hexanes/ethyl acetate (1:1→1:2→1:4→0:100) followed by ethyl acetate/methanol (50:1) to afford compound 53.1 (287 mg, 0.846 mmol, 54%).

Compound 53.2. Compound 53.1 (109 mg, 0.321 mmol, 1 eq.) was dissolved in THF (3 mL) and triethylamine (224 µL, 1.61 mmol, 5 eq.) was added at room temperature. The reaction mixture was cooled to −78° C. and phosgene (20% solution in toluene, 340 µL, 0.643 mmol, 2 eq.) was added. The reaction was gradually warmed to room temperature. Nitrogen was blown into the reaction mixture to remove any excess phosgene. The reaction was heated in a microwave at 120° C. for 5 minutes. Water and ethyl acetate were added to the reaction mixture and the layers were separated. The product was extracted with ethyl acetate (2×). The combined organic layers were dried over anhydrous sodium sulfate. After removal of the solvent under reduced pressure, the crude material was purified using silica gel column chromatography with a gradient of hexanes/ethyl acetate (1:1→1:2→1:4) to afford compound 53.2 (59.3 mg, 0.163 mmol, 51%).

Compound 53.3. Compound 53.3 is prepared according to Example 1 for making compound 1.4 except for using compound 53.2 instead of compound 1.3.

Compound 53.4. Compound 53.4 is prepared according to Example 1 except for using compound 53.3 instead of compound 1.6.

Compound 53. Compound 53.4 (53.7 mg, 0.0823 mmol) was dissolved in dichloromethane (3 mL) at room temperature. Trifluoroacetic acid (1 mL) was added at room temperature and the reaction was stirred for 0.5 hour. The reaction mixture was azeotroped with toluene. Saturated sodium bicarbonate solution and ethyl acetate were added and the layers were separated. The product was extracted with ethyl acetate (2×). A small amount of methanol was added to ethyl acetate to facilitate extraction. The combined organic layers were washed with brine and dried over anhydrous sodium sulfate. After removal of the solvent under reduced pressure, the crude material was purified using silica gel column chromatography with a gradient of hexanes/ethyl acetate (1:1→1:2→1:4→0:100) followed by ethyl acetate/methanol (25:1) to afford compound 53 (28.3 mg, 0.0600 mmol, 73%).

Example 54

This example describes the synthesis of

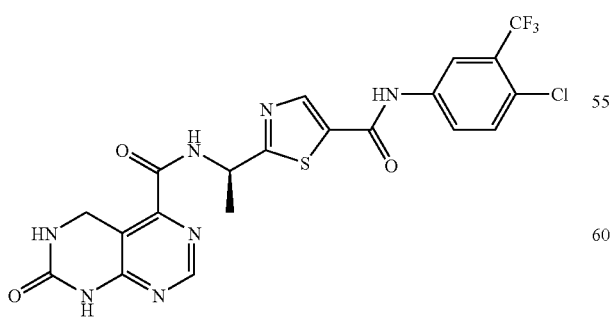

54 which was prepared according to Example 53 except for using compound 13.4 instead of compound 1.12.

Example 55

This example describes the synthesis of

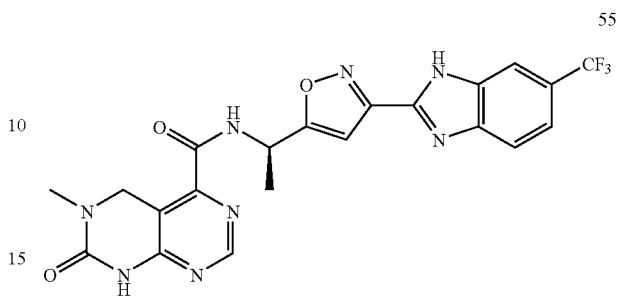

55 which is prepared according to Scheme Y and the protocol below.

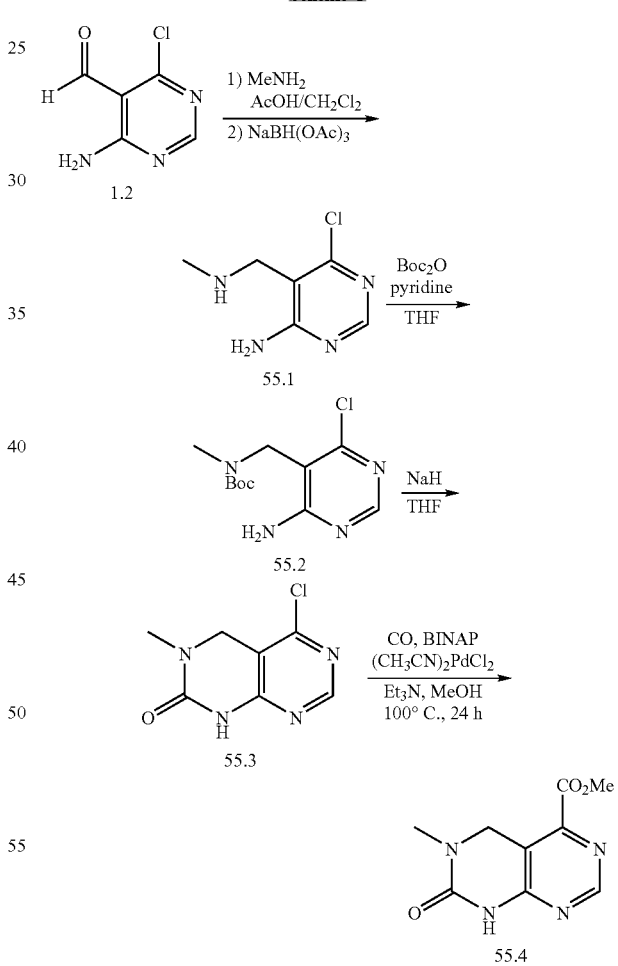

Compound 55.1. Compound 55.1 is prepared according to Example 53 for making compound 55.1 except for using methylamine instead of 2,4,6-trimethoxybenzylamine.

Compound 55.2. Compound 55.1 (214 mg, 1.24 mmol) was dissolved in THF (2 mL) at room temperature. Pyridine (0.52 mL, 6.43 mmol) and Boc$_2$O (343 mg, 1.56 mmol) was added and the reaction was stirred for 1 hour. Saturated sodium bicarbonate solution and ethyl acetate were added to the reaction mixture and the layers were separated. The product was extracted twice more with ethyl acetate. The combined organic layers were washed once with brine and dried over anhydrous sodium sulfate. After removal of the solvent under reduced pressure, the crude material was purified using silica gel column chromatography with a gradient of hexanes/ethyl acetate (4:1→2:1) to afford compound 55.2 (141 mg, 0.516 mmol, 42%).

Compound 55.3. Sodium hydride (60% in mineral oil, 30.4 mg, 0.760 mmol, 2 eq.) was rinsed once with hexanes. THF (1.5 mL) was added, followed by compound 55.2 (100 mg, 0.368 mmol, 1 eq.) as a THF (2 mL) solution. After stirring for 5 minutes at room temperature, the reaction was heated at 70° C. for 4 hours. Brine and ethyl acetate were added to the reaction mixture and the layers were separated. The product was extracted with ethyl acetate (2×). The combined organic layers were dried over anhydrous sodium sulfate. Solvent was removed under reduced pressure to afford the crude product 55.3 (73.9 mg, ~100%), which was used without further purification.

Compound 55.4. Compound 55.4 is prepared according to Example 1 for making compound 1.4 except for using compound 55.3 instead of compound 1.3.

Compound 55. Compound 55 is prepared according to Example 53 except for using compound 55.4 instead of compound 53.3.

Example 56

This example describes the synthesis of

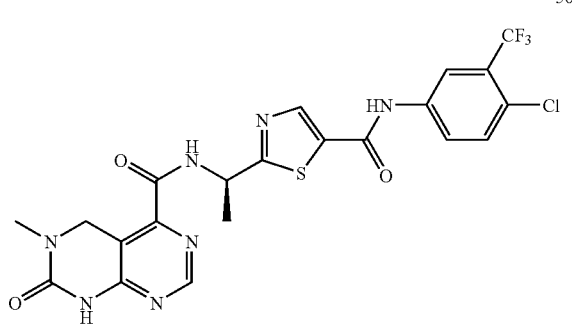

56 which is prepared according to Example 54 except for using compound 55.4 instead of compound 53.3.

Example 57

To assess PK and PD response to compound treatment, 2×10⁶ WM-266-4 human melanoma cells (ATCC #CRL-1676; V600D Raf B) were implanted, with matrigel (BD Biosciences), in the right flank of athymic nude female mice (Harlan Sprague Dawley). When tumors reached an average size of 500 mg (approximately three weeks post implantation), test compound suspended in dosing vehicle (1/3/6 DMSO/PEG400/saline) was administered by a single oral gavage. Treated mice were then sacrificed at 1, 3, and 8 hours post dosing and terminal endpoints (plasma drug concentration, tumor drug concentration, and tumor levels of phosphorylated ERK) were collected.

Drug concentrations were assessed by LC-MS/MS either from plasma or from freshly excised tumors (a portion of the same tumor sample used for quantifying phosphorylated ERK as described below) following homogenization in PBS (tumor tissue) and extraction with 3× (v/v) 50% acetonitrile. FIG. 1 shows the plasma and tumor concentration of an illustrative compound of the invention.

Example 58

Figure 2:
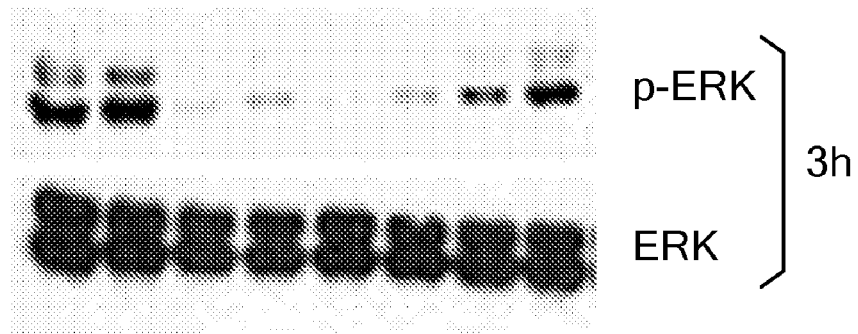
FIG. 2 depicts exemplary western analysis of WM-266-4 xenograft tumor tissue. Tumors were excised and proteins extracted at 3, 8, and 16 hours following a single oral dose containing vehicle alone (lanes 1 and 2) or 100 (lanes 3 and 4), 50 (lanes 5 and 6), or 25 (lanes 7 and 8) mg/kg compound X. ERK and phospho-ERK levels were then assessed by Western blot analysis
Figure 2:
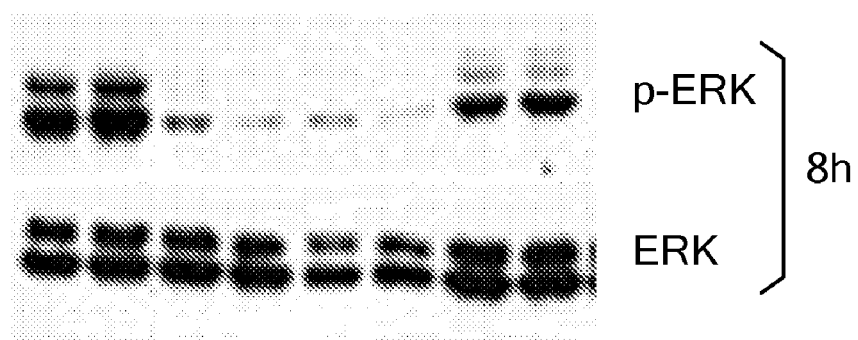
Figure 2:
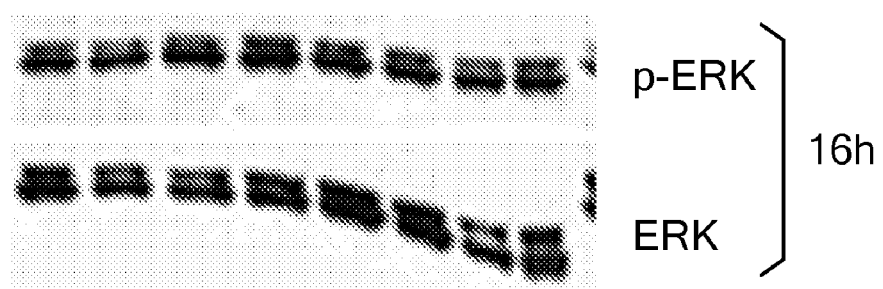

Tumor levels of phosphorylated ERK were assessed by first grinding freshly harvested tumor samples in liquid nitrogen and then reconstituting the ground tissue in cell extraction buffer (10 mM Tris HCl pH7.4, 100 mM NaCl, 1 mM EDTA, 1 mM EGTA, 1 mM NaF, 20 mM $Na_4P_2O_7$, 2 mM $Na_4VO_4$, 1% Triton X-100, 10% Glycerol, 0.1% SDS) containing freshly added phosphatase and protease inhibitors (1:100 of 100 mM PMSF, Sigma Phosphatase Inhibitor Cocktail I (Cat #P-2850), and Sigma Phosphatase Inhibitor Cocktail II (Cat #P-5726), and 1:1000 of Sigma Protease Inhibitor Cocktail (Cat #P-2714)). ERK and phospho-ERK levels were assessed by standard Western analyses using antibodies against ERK (Cell Signaling #9102) and phosphorylated ERK (Cell Signaling #9101). FIG. 2 shows the tumor levels of phosphorylated ERK treated with an illustrative compound of the invention.

Example 59

Figure 3:
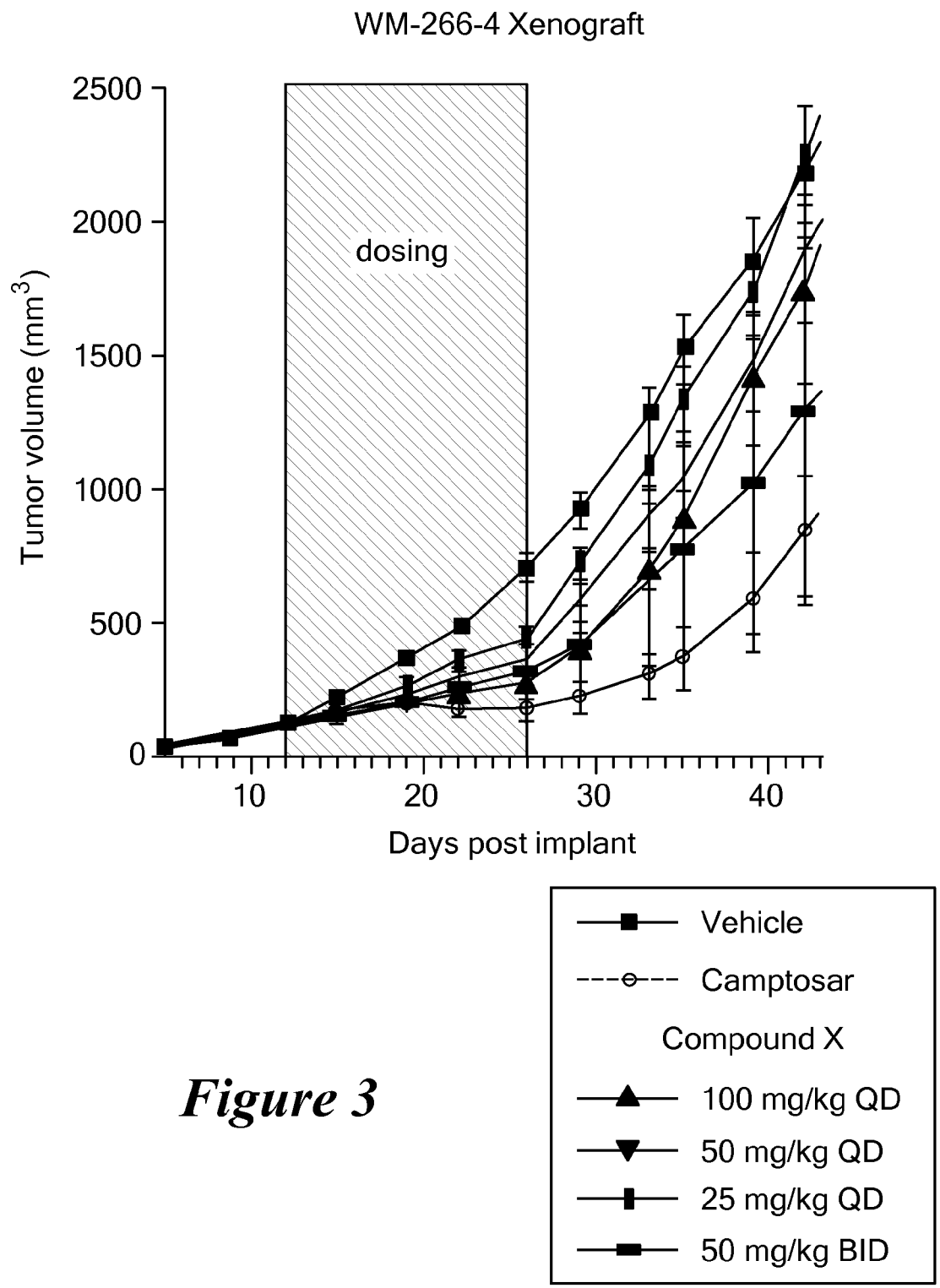
FIG. 3 depicts exemplary growth rates of WM-266-4 melanoma tumor xenografts in mice treated for two weeks with 25, 50, or 100 mg/kg QD compound X, 50 mg/kg BID compound X, 10 mg/kg QD Camptosar, or dosing vehicle alone.

2×10⁶ WM-266-4 human melanoma cells were implanted in the right flank of nude mice as described previously. When tumors reached an average size of 200 mg (approximately two weeks post implantation), test compound suspended in dosing vehicle (1/3/6 DMSO/PEG400/saline), was administered by oral gavage either QD×14 or BID×14. Alternatively, a control compound (e.g., 10 mg/kg Camptosar) was administered by IP injection on a QD×10 (M-F) schedule. Body weight and tumor size were recorded two times per week throughout the duration of the study. FIG. 3 shows the tumor growth rate curves for mice treated with an illustrative compound of the invention.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

What is claimed is:

1. A compound having the structure:

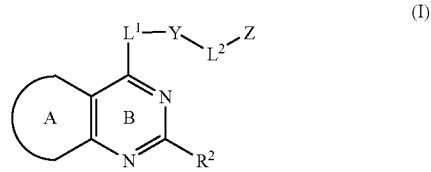

(I)

or pharmaceutically acceptable salt thereof;

wherein A-B together represent:

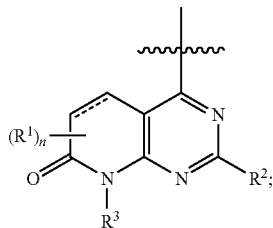

----- represents a single or double bond as valency permits;

n is an integer from 0-4;

$R^1$ and $R^2$ are independently hydrogen, halogen, cyano, nitro, or an aliphatic, heteroaliphatic, alicyclic, heteroalicyclic, aromatic or heteroaromatic moiety;

$R^3$ is hydrogen, or an aliphatic, heteroaliphatic, alicyclic, heteroalicyclic, aromatic or heteroaromatic moiety;

$L^1$ is —O—, —S—, —$NR^{L1A}$— or a substituted or unsubstituted $C_{1-6}$alkylene or $C_{2-6}$alkenylene chain wherein up to two non-adjacent methylene units are independently optionally replaced by —C(=O)—, —$CO_2$—, —C(=O)C(=O)—, —C(=O)$NR^{L1A}$—, —OC(=O)—, —OC(=O)$NR^{L1A}$—, —$NR^{L1A}NR^{L1B}$—, —$NR^{L1A}NR^{L1B}$C(=O)—, —$NR^{L1A}$C(=O)—, —$NR^{L1A}CO_2$—, —$NR^{L1A}$C(=O)$NR^{L1B}$—, —S(=O)—, —$SO_2$—, —$NR^{L1A}SO_2$—, —$SO_2NR^{L1A}$—, —$NR^{L1A}SO_2NR^{L1B}$—, —O—, —S—, or —$NR^{L1A}$—; wherein each occurrence of $R^{L1A}$ and $R^{L1B}$ is independently hydrogen, alkyl, heteroalkyl, heterocyclyl, aromatic, heteroaromatic or acyl;

$L^2$ is a single bond, —O—, —S—, —$NR^{L2A}$—, a heteroalicyclic or heteroaromatic moiety, or a substituted or unsubstituted $C_{1-6}$alkylene or $C_{2-6}$alkenylene chain wherein up to two non-adjacent methylene units are independently optionally replaced by —C(=O)—, —$CO_2$—, —C(=O)C(=O)—, —C(=O)$NR^{L2A}$—, —OC(=O)—, —OC(=O)$NR^{L2A}$—, —$NR^{L2A}NR^{L2B}$—, —$NR^{L2A}NR^{L2B}$C(=O)—, —$NR^{L2A}$C(=O)—, —$NR^{L2A}CO_2$—, —$NR^{L2A}$C(=O)$NR^{L2B}$—, —S(=O)—, —$SO_2$—, —$NR^{L2A}SO_2$—, —$SO_2NR^{L2A}$—, —$NR^{L2A}SO_2NR^{L2B}$—, —O—, —S—, or —$NR^{L2A}$—; wherein each occurrence of $R^{L2A}$ and $R^{L2B}$ is independently hydrogen, alkyl, heteroalkyl, heterocyclyl, aromatic, heteroaromatic or acyl;

Y is a divalent cycloalkyl, cycloalkenyl, heterocyclic, aryl or heteroaryl moiety; and Z is an aliphatic, heteroaliphatic, alicyclic, heteroalicyclic, aromatic or heteroaromatic moiety.

2. The compound of claim 1 having the structure:

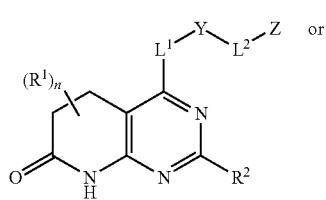

-continued

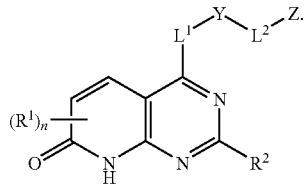

3. A compound having the structure

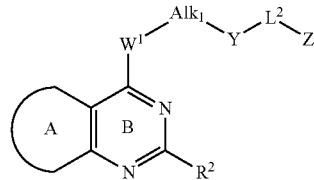

or pharmaceutically acceptable salt thereof;

wherein A-B together represent:

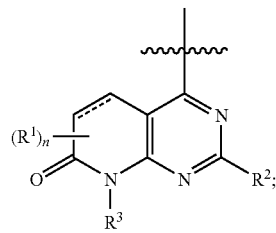

----- represents a single or double bond as valency permits;

n is an integer from 0-4;

$R^1$ and $R^2$ are independently hydrogen, halogen, cyano, nitro, or an aliphatic, heteroaliphatic, alicyclic, heteroalicyclic, aromatic or heteroaromatic moiety;

$R^3$ is hydrogen, or an aliphatic, heteroaliphatic, alicyclic, heteroalicyclic, aromatic or heteroaromatic moiety;

$W^1$ is —O—, —S—, —N($R^{W1}$)—, —C(=O)—, —N($R^{W1}$)C(=O) or —C(=O)N($R^{W1}$)—, where $R^{W1}$ is hydrogen, aliphatic, heteroaliphatic, alicyclic, heteroalicyclic, aromatic, heteroaromatic, or acyl; and $Alk_1$ is a $C_{1-6}$alkylene or $C_{2-6}$alkenylene moiety;

$L^2$ is a single bond, —O—, —S—, —$NR^{L2A}$—, a heteroalicyclic or heteroaromatic moiety, or a substituted or unsubstituted $C_{1-6}$alkylene or $C_{2-6}$alkenylene chain wherein up to two non-adjacent methylene units are independently optionally replaced by —C(=O)—, —$CO_2$—, —C(=O)C(=O)—, —C(=O)$NR^{L2A}$—, —OC(=O)—, —OC(=O)$NR^{L2A}$—, —$NR^{L2A}NR^{L2B}$—, —$NR^{L2A}NR^{L2B}$C(=O)—, —$NR^{L2A}$C(=O)—, —$NR^{L2A}CO_2$—, —$NR^{L2A}$C(=O)$NR^{L2B}$—, —S(=O)—, —$SO_2$—, —$NR^{L2A}SO_2$—, —$SO_2NR^{L2A}$—, —$NR^{L2A}SO_2NR^{L2B}$—, —O—, —S—, or —$NR^{L2A}$—; wherein each occurrence of $R^{L2A}$ and $R^{L2B}$ is independently hydrogen, alkyl, heteroalkyl, heterocyclyl, aromatic, heteroaromatic or acyl;

Y is a divalent cycloalkyl, cycloalkenyl, heterocyclic, aryl or heteroaryl moiety; and Z is an aliphatic, heteroaliphatic, alicyclic, heteroalicyclic, aromatic or heteroaromatic moiety.

4. A compound having the structure:

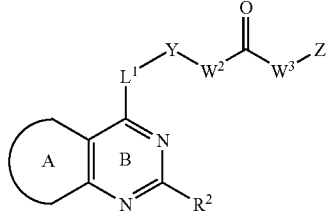

or pharmaceutically acceptable salt thereof;
wherein A-B together represent:

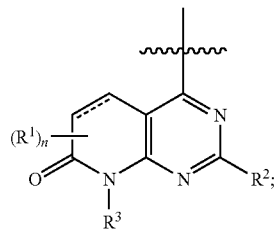

----- represents a single or double bond as valency permits;

n is an integer from 0-4;

$R^1$ and $R^2$ are independently hydrogen, halogen, cyano, nitro, or an aliphatic, heteroaliphatic, alicyclic, heteroalicyclic, aromatic or heteroaromatic moiety;

$R^3$ is hydrogen, or an aliphatic, heteroaliphatic, alicyclic, heteroalicyclic, aromatic or heteroaromatic moiety;

$L^1$ is —O—, —S—, —NR$^{L1A}$— or a substituted or unsubstituted $C_{1-6}$alkylene or $C_{2-6}$alkenylene chain wherein up to two non-adjacent methylene units are independently optionally replaced by —C(=O)—, —CO$_2$—, —C(=O)C(=O)—, —C(=O)NR$^{L1A}$—, —OC(=O)—, —OC(=O)NR$^{L1A}$—, —NR$^{L1A}$NR$^{L1B}$—, —NR$^{L1A}$NR$^{L1B}$C(=O)—, —NR$^{L1A}$C(=O)—, —NR$^{L1A}$CO$_2$—, —NR$^{L1A}$C(=O)NR$^{L1B}$—, —S(=O)—, —SO$_2$—, —NR$^{L1A}$SO$_2$—, —SO$_2$NR$^{L1A}$—, —NR$^{L1A}$SO$_2$NR$^{L1B}$—, —O—, —S—, or —NR$^{L1A}$—; wherein each occurrence of R$^{L1A}$ and R$^{L1B}$ is independently hydrogen, alkyl, heteroalkyl, heterocyclyl, aromatic, heteroaromatic or acyl;

$W^2$ and $W^3$ are independently a single bond, —O— or —N(R$^W$)—, where R$^W$ is hydrogen, aliphatic, heteroaliphatic, alicyclic, heteroalicyclic, aromatic or heteroaromatic Y is a divalent cycloalkyl, cycloalkenyl, heterocyclic, aryl or heteroaryl moiety; and Z is an aliphatic, heteroaliphatic, alicyclic, heteroalicyclic, aromatic or heteroaromatic moiety.

5. The compound of claim 1 having the structure:

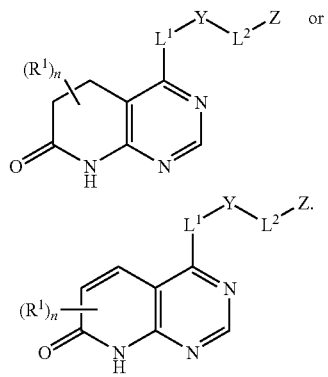

6. A compound having the structure:

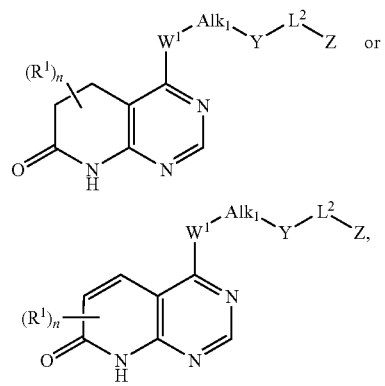

or a pharmaceutically acceptable salt thereof, wherein:

n is an integer from 0-4;

$R^1$ is hydrogen, halogen, cyano, nitro, or an aliphatic, heteroaliphatic, alicyclic, heteroalicyclic, aromatic or heteroaromatic moiety;

$W^1$ is —O—, —N(R$^{W1}$)—, —C(=O)— or —C(=O)N(R$^{W1}$)—, where R$^{W1}$ is hydrogen, alkyl, cycloalkyl, heteroalkyl, aryl, heteroaryl, -(alkyl)aryl, -(alkyl)heteroaryl or acyl; and Alk$_1$ is a substituted or unsubstituted $C_{1-6}$alkylene or $C_{2-6}$alkenylene chain wherein up to two non-adjacent methylene units are independently optionally replaced by —C(=O)—, —CO$_2$—, —C(=O)C(=O)—, —C(=O)NR$^{L1A}$—, —OC(=O)—, —OC(=O)NR$^{L1A}$—, —NR$^{L1A}$NR$^{L1B}$—, —NR$^{L1A}$NR$^{L1B}$C(=O)—, —NR$^{L1A}$C(=O)—, —NR$^{L1A}$CO$_2$—, —NR$^{L1A}$C(=O)NR$^{L1B}$—, —S(=O)—, —SO$_2$—, —NR$^{L1A}$SO$_2$—, —SO$_2$NR$^{L1A}$—, —NR$^{L1A}$SO$_2$NR$^{L1B}$—, —O—, —S—, or —NR$^{L1A}$—; wherein each occurrence of R$^{L1A}$ and R$^{L1B}$ is independently hydrogen, alkyl, heteroalkyl, heterocyclyl, aromatic, heteroaromatic or acyl;

$L^2$ is a single bond, —O—, —S—, —NR$^{L2A}$—, a heteroalicyclic or heteroaromatic moiety, or a substituted or unsubstituted $C_{1-6}$alkylene or $C_{2-6}$alkenylene chain wherein up to two non-adjacent methylene units are independently optionally replaced by —C(=O)—, —CO$_2$—, —C(=O)C(=O)—, —C(=O)NR$^{L2A}$—, —OC(=O)—, —OC(=O)NR$^{L2A}$—, —NR$^{L2A}$NR$^{L2B}$—, —NR$^{L2A}$NR$^{L2B}$C(=O)—, —NR$^{L2A}$C(=O)—, —NR$^{L2A}$CO$_2$—, —NR$^{L2A}$C(=O)NR$^{L2B}$—, —S(=O)—, —SO$_2$—, —NR$^{L2A}$SO$_2$—, —SO$_2$NR$^{L2A}$—, —NR$^{L2A}$SO$_2$NR$^{L2B}$—, —O—, —S—, or —NR$^{L2A}$—; wherein each occurrence of R$^{L2A}$ and R$^{L2B}$ is independently hydrogen, alkyl, heteroalkyl, heterocyclyl, aromatic, heteroaromatic or acyl;

Y is a divalent cycloalkyl, cycloalkenyl, heterocyclic, aryl or heteroaryl moiety; and Z is an aliphatic, heteroaliphatic, alicyclic, heteroalicyclic, aromatic or heteroaromatic moiety.

7. The compound of claim 6, wherein

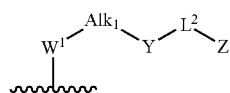

has one of the structures:

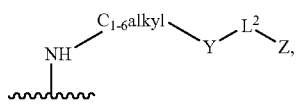
(a)

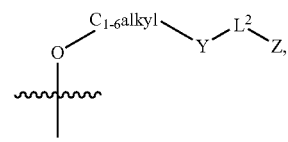
(b)

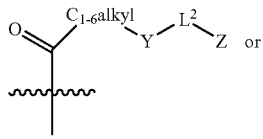
(c)

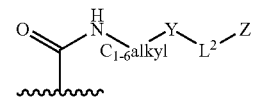
(d)

wherein the C$_{1-6}$alkyl moiety may be substituted or unsubstituted.

8. A compound having the structure:

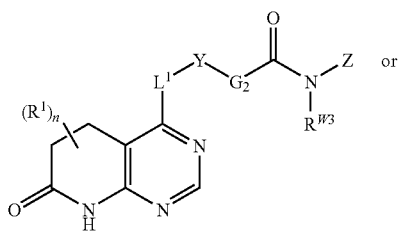

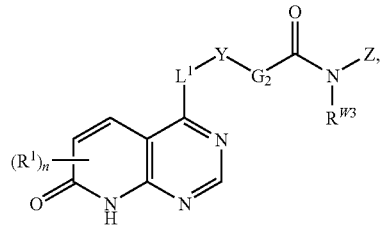

or a pharmaceutically acceptable salt thereof, wherein:

n is an integer from 0-4;

R$^1$ is hydrogen, halogen, cyano, nitro, or an aliphatic, heteroaliphatic, heteroalicyclic, aromatic or heteroaromatic moiety;

L$^1$ is —O—, —S—, —NR$^{L1A}$— or a substituted or unsubstituted C$_{1-6}$alkylene or C$_{2-6}$alkenylene chain wherein up to two non-adjacent methylene units are independently optionally replaced by —C(=O)—, —CO$_2$—, —C(=O)C(=O)—, —C(=O)NR$^{L1A}$—, —OC(=O)—, —OC(=O)NR$^{L1A}$—, —NR$^{L1A}$NR$^{L1B}$—, —NR$^{L1A}$NR$^{L1B}$C(=O)—, —NR$^{L1A}$C(=O)—, —NR$^{L1A}$CO$_2$—, —NR$^{L1A}$C(=O)NR$^{L1B}$—, —S(=O)—, —SO$_2$—, —NR$^{L1A}$SO$_2$—, —SO$_2$NR$^{L1A}$—, —NR$^{L1A}$SO$_2$NR$^{L1B}$—, —O—, —S—, or —NR$^{L1A}$—; wherein each occurrence of R$^{L1A}$ and R$^{L1B}$ is independently hydrogen, alkyl, heteroalkyl, heterocyclyl, aromatic, heteroaromatic or acyl;

G$_2$ is a single bond, O or NR$^{G2}$; and R$^{W3}$ and R$^{G2}$ are independently hydrogen, lower alkyl, lower heteroalkyl, aryl, heteroaryl, -(alkyl)aryl, -(alkyl)heteroaryl or acyl-;

Y is a divalent cycloalkyl, cycloalkenyl, heterocyclic, aryl or heteroaryl moiety; and Z is an aliphatic, heteroaliphatic, alicyclic, heteroalicyclic, aromatic or heteroaromatic moiety.

9. The compound of claim 8, wherein -G$_2$C(=O)N(R$^{W3}$)— is —C(=O)NH—.

10. A compound having the structure:

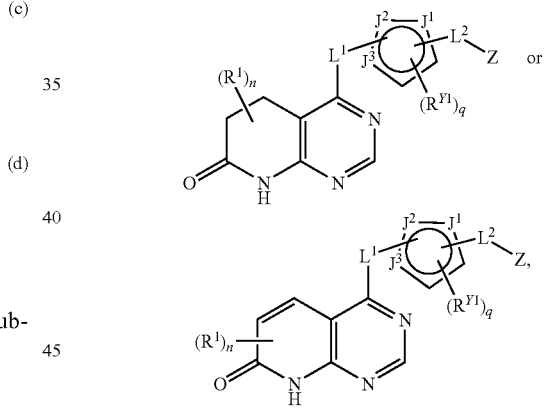

or a pharmaceutically acceptable salt thereof, wherein:

n is an integer from 0-4;

R$^1$ is hydrogen, halogen, cyano, nitro, or an aliphatic, heteroaliphatic, alicyclic, heteroalicyclic, aromatic or heteroaromatic moiety;

L$^1$ is —O—, —S—, —NR$^{L1A}$— or a substituted or unsubstituted C$_{1-6}$alkylene or C$_{2-6}$alkenylene chain wherein up to two non-adjacent methylene units are independently optionally replaced by —C(=O)—, —CO$_2$—, —C(=O)C(=O)—, —C(=O)NR$^{L1A}$—, —OC(=O)—, —OC(=O)NR$^{L1A}$—, —NR$^{L1A}$NR$^{L1B}$—, —NR$^{L1A}$NR$^{L1B}$C(=O)—, —NR$^{L1A}$C(=O)—, —NR$^{L1A}$CO$_2$—, —NR$^{L1A}$C(=O)NR$^{L1B}$—, —S(=O)—, —SO$_2$—, —NR$^{L1A}$SO$_2$—, —SO$_2$NR$^{L1A}$—, —NR$^{L1A}$SO$_2$NR$^{L1B}$—, —O—, —S—, or —NR$^{L1A}$—; wherein each occurrence of R$^{L1A}$ and R$^{L1B}$ is independently hydrogen, alkyl, heteroalkyl, heterocyclyl, aromatic, heteroaromatic or acyl;

L² is a single bond, —O—, —S—, —NR^{L2A}—, a heteroalicyclic or heteroaromatic moiety, or a substituted or unsubstituted C$_{1-6}$alkylene or C$_{2-6}$alkenylene chain wherein up to two non-adjacent methylene units are independently optionally replaced by —C(=O)—, —CO$_2$—, —C(=O)C(=O)—, —C(=O)NR^{L2A}—, —OC(=O)—, —OC(=O)NR^{L2A}—, —NR^{L2A}NR^{L2B}—, —NR^{L2A}NR^{L2B}C(=O)—, —NR^{L2A}C(=O)—, —NR^{L2A}CO$_2$—, —NR^{L2A}C(=O)NR^{L2B}—, —S(=O)—, —SO$_2$—, —NR^{L2A}SO$_2$—, —SO$_2$NR^{L2A}—, —NR^{L2A}SO$_2$NR^{L2B}—, —O—, —S—, or —NR^{L2A}—; wherein each occurrence of R^{L2A} and R^{L2B} is independently hydrogen, alkyl, heteroalkyl, heterocyclyl, aromatic, heteroaromatic or acyl;

q is an integer from 0-2;

J¹, J² and J³ are independently O, S, N, NR^{Y1} or CR^{Y1}; wherein each occurrence of R^{Y1} is independently hydrogen, alkyl, heteroalkyl, aryl, heteroaryl, -(alkyl)aryl or -(alkyl)heteroaryl, —OR^{Y3}, —SR^{Y3}, —NR^{Y2}R^{Y3}, —SO$_2$NR^{Y2}R^{Y3}, —C(=O)NR^{Y2}R^{Y3}, halogen, —CN, —NO$_2$, —C(=O)OR^{Y3}, —N(R^{Y2})C(=O)R^{Y3}, wherein each occurrence of R^{Y2} and R^{Y3} is independently hydrogen, lower alkyl, lower heteroalkyl, aryl, heteroaryl, -(alkyl)aryl, -(alkyl)heteroaryl or acyl, or R^{Y2} and R^{Y3} taken together with the nitrogen atom to which they are attached form a 5-6 membered heterocyclic ring; and Z is an aliphatic, heteroaliphatic, alicyclic, heteroalicyclic, aromatic or heteroaromatic moiety.

11. The compound of claim 10, wherein

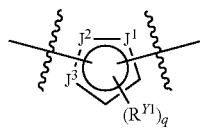

has one of the following structures:

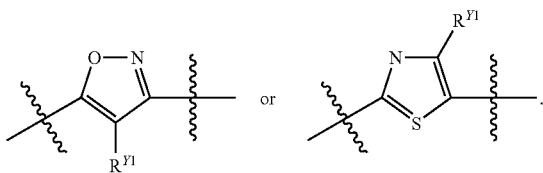

12. A compound having the structure:

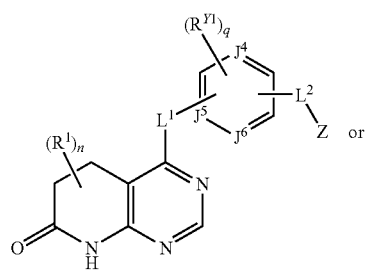

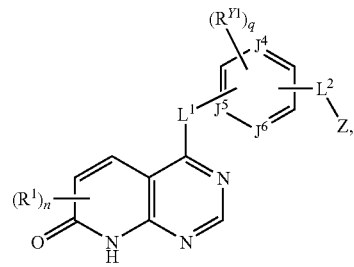

or a pharmaceutically acceptable salt thereof, wherein:

n is an integer from 0-4;

R¹ is hydrogen, halogen, cyano, nitro, or an aliphatic, heteroaliphatic, alicyclic, heteroalicyclic, aromatic or heteroaromatic moiety;

L¹ is —O—, —S—, —NR^{L1A}— or a substituted or unsubstituted C$_{1-6}$alkylene or C$_{2-6}$alkenylene chain wherein up to two non-adjacent methylene units are independently optionally replaced by —C(=O)—, —CO$_2$—, —C(=O)C(=O)—, —C(=O)NR^{L1A}—, —OC(=O)—, —OC(=O)NR^{L1A}—, —NR^{L1A}NR^{L1B}—, —NR^{L1A}NR^{L1B}C(=O)—, —NR^{L1A}C(=O)—, —NR^{L1A}CO$_2$—, —NR^{L1A}C(=O)NR^{L1B}—, —S(=O)—, —SO$_2$—, —NR^{L1A}SO$_2$—, —SO$_2$NR^{L1A}—, —NR^{L1A}SO$_2$NR^{L1B}—, —O—, —S—, or —NR^{L1A}—; wherein each occurrence of R^{L1A} and R^{L1B} is independently hydrogen, alkyl, heteroalkyl, heterocyclyl, aromatic, heteroaromatic or acyl;

L² is a single bond, —O—, —S—, —NR^{L2A}—, a heteroalicyclic or heteroaromatic moiety, or a substituted or unsubstituted C$_{1-6}$alkylene or C$_{2-6}$alkenylene chain wherein up to two non-adjacent methylene units are independently optionally replaced by —C(=O)—, —CO$_2$—, —C(=O)C(=O)—, —C(=O)NR^{L2A}—, —OC(=O)—, —OC(=O)NR^{L2A}—, —NR^{L2A}NR^{L2B}—, —NR^{L2A}NR^{L2B}C(=O)—, —NR^{L2A}C(=O)—, —NR^{L2A}CO$_2$—, —NR^{L2A}C(=O)NR^{L2B}—, —S(=O)—, —SO$_2$—, —NR^{L2A}SO$_2$—, —SO$_2$NR^{L2A}—, —NR^{L2A}SO$_2$NR^{L2B}—, —O—, —S—, or —NR^{L2A}—; wherein each occurrence of R^{L2A} and R^{L2B} is independently hydrogen, alkyl, heteroalkyl, heterocyclyl, aromatic, heteroaromatic or acyl;

q is an integer from 0-3;

J⁴, J⁵ and J⁶ are independently N or CR^{Y1}; wherein each occurrence of R^{Y1} is independently hydrogen, alkyl, heteroalkyl, aryl, heteroaryl, -(alkyl)aryl or -(alkyl)heteroaryl, —OR^{Y3}, —SR^{Y3}, —NR^{Y2}R^{Y3}, —SO$_2$NR^{Y2}R^{Y3}, —C(=O)NR^{Y2}R^{Y3}, halogen, —CN, —NO$_2$, —C(=O)OR^{Y3}, —N(R^{Y2})C(=O)R^{Y3}, wherein each occurrence of R^{Y2} and R^{Y3} is independently hydrogen, lower alkyl, lower heteroalkyl, aryl, heteroaryl, -(alkyl)aryl, -(alkyl)heteroaryl or acyl, or R^{Y2} and R^{Y3} taken together with the nitrogen atom to which they are attached form a 5-6 membered heterocyclic ring; and Z is an aliphatic, heteroaliphatic, alicyclic, heteroalicyclic, aromatic or heteroaromatic moiety.

13. The compound of claim 12, wherein

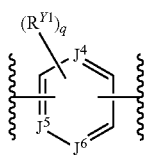

has the structure:

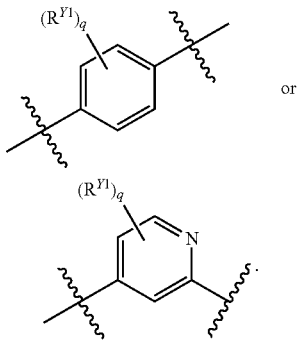

14. A compound having the structure:

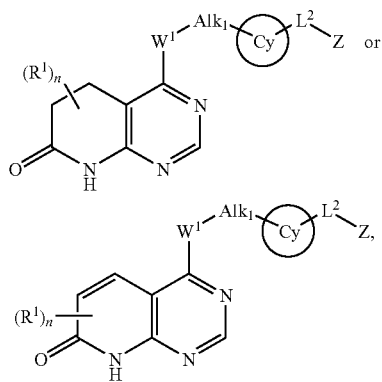

or a pharmaceutically acceptable salt thereof, wherein:
Cy is

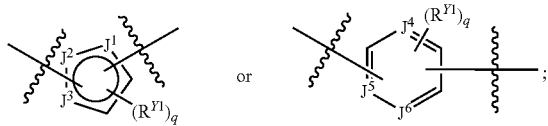

q is an integer from 0-3;

$J^4$, $J^5$ and $J^6$ are independently N or $CR^{Y1}$; wherein each occurrence of $R^{Y1}$ is independently hydrogen, alkyl, heteroalkyl, aryl, heteroaryl, -(alkyl)aryl or -(alkyl)heteroaryl, —$OR^{Y3}$, —$SR^{Y3}$, —$NR^{Y2}R^{Y3}$, —$SO_2NR^{Y2}R^{Y3}$, —C(=O)$NR^{Y2}R^{Y3}$, halogen, —CN, —$NO_2$, —C(=O)$OR^{Y3}$, —N($R^{Y2}$)C(=O)$R^{Y3}$, wherein each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or $R^{Y2}$ and $R^{Y3}$ taken together with the nitrogen atom to which they are attached form a 5-6 membered heterocyclic ring;

n is an integer from 0-4;

$R^1$ is hydrogen, halogen, cyano, nitro, or an aliphatic, heteroaliphatic, alicyclic, heteroalicyclic, aromatic or heteroaromatic moiety;

$L^2$ is a single bond, —O—, —S—, —$NR^{L2A}$—, a heteroalicyclic or heteroaromatic moiety, or a substituted or unsubstituted $C_{1-6}$alkylene or $C_{2-6}$alkenylene chain wherein up to two non-adjacent methylene units are independently optionally replaced by —C(=O)—, —$CO_2$—, —C(=O)C(=O)—, —C(=O)$NR^{L2A}$—, —OC(=O)—, —OC(=O)$NR^{L2A}$—, —$NR^{L2A}NR^{L2B}$—, —$NR^{L2A}NR^{L2B}$C(=O)—, —$NR^{L2A}$C(=O)—, —$NR^{L2A}CO_2$—, —$NR^{L2A}$C(=O)$NR^{L2B}$—, —S(=O)—, —$SO_2$—, —$NR^{L2A}SO_2$—, —$SO_2NR^{L2A}$—, —$NR^{L2A}SO_2NR^{L2B}$—, —O—, —S—, or —$NR^{L2A}$—; wherein each occurrence of $R^{L2A}$ and $R^{L2B}$ is independently hydrogen, alkyl, heteroalkyl, heterocyclyl, aromatic, heteroaromatic or acyl;

Z is an aliphatic, heteroaliphatic, alicyclic, heteroalicyclic, aromatic or heteroaromatic moiety; and $W^1$ is —O—, —N($R^{W1}$)—, —C(=O)— or —C(=O)N($R^{W1}$)—, where $R^{W1}$ is hydrogen, alkyl, cycloalkyl, heteroalkyl, aryl, heteroaryl, -(alkyl)aryl, -(alkyl)heteroaryl or acyl; and $Alk_1$ is a substituted or unsubstituted $C_{1-6}$alkylene or $C_{2-6}$alkenylene chain wherein up to two non-adjacent methylene units are independently optionally replaced by —C(=O)—, —$CO_2$—, —C(=O)C(=O)—, —C(=O)$NR^{L1A}$—, —OC(=O)—, —OC(=O)$NR^{L1A}$—, —$NR^{L1A}NR^{L1B}$—, —$NR^{L1A}NR^{L1B}$C(=O)—, —$NR^{L1A}$C(=O)—, —$NR^{L1A}CO_2$—, —$NR^{L1A}$C(=O)$NR^{L1B}$—, —S(=O)—, —$SO_2$—, —$NR^{L1A}SO_2$—, —$SO_2NR^{L1A}$—, —$NR^{L1A}SO_2NR^{L1B}$—, —O—, —S—, or —$NR^{L1A}$—; wherein each occurrence of $R^{L1A}$ and $R^{L1B}$ is independently hydrogen, alkyl, heteroalkyl, heterocyclyl, aromatic, heteroaromatic or acyl; q is an integer from 0-3; $J^1$, $J^2$ and $J^3$ are independently O, S, N, $NR^{Y1}$ or $CR^{Y1}$.

15. A compound having the structure:

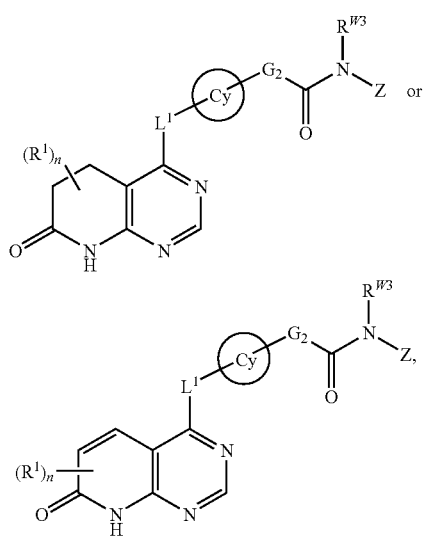

or a pharmaceutically acceptable salt thereof, wherein:

Cy is

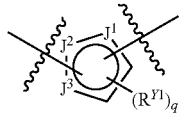 or 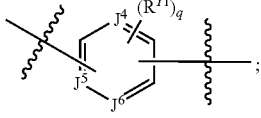;

q is an integer from 0-3;

$J^1$, $J^2$ and $J^3$ are independently O, S, N, $NR^{Y1}$ or $CR^{Y1}$; $J^4$, $J^5$ and $J^6$ are independently N or $CR^{Y1}$; wherein each occurrence of $R^{Y1}$ is independently hydrogen, alkyl, heteroalkyl, aryl, heteroaryl, -(alkyl)aryl or -(alkyl)heteroaryl, $-OR^{Y3}$, $-SR^{Y3}$, $-NR^{Y2}R^{Y3}$, $-SO_2NR^{Y2}R^{Y3}$, $-C(=O)NR^{Y2}R^{Y3}$, halogen, $-CN$, $-NO_2$, $-C(=O)OR^{Y3}$, $-N(R^{Y2})C(=O)R^{Y3}$, wherein each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or $R^{Y2}$ and $R^{Y3}$ taken together with the nitrogen atom to which they are attached form a 5-6 membered heterocyclic ring; $G_2$ is a single bond, O or $NR^{G2}$; and $R^{W3}$ and $R^{G2}$ are independently hydrogen, lower alkyl, lower heteroalkyl, aryl, heteroaryl, -(alkyl)aryl, -(alkyl)heteroaryl or acyl;

n is an integer from 0-4;

$R^1$ is hydrogen, halogen, cyano, nitro, or an aliphatic, heteroaliphatic, heteroalicyclic, aromatic or heteroaromatic moiety;

$L^1$ is $-O-$, $-S-$, $-NR^{L1A}-$ or a substituted or unsubstituted $C_{1-6}$alkylene or $C_{2-6}$alkenylene chain wherein up to two non-adjacent methylene units are independently optionally replaced by $-C(=O)-$, $-CO_2-$, $-C(=O)C(=O)-$, $-C(=O)NR^{L1A}-$, $-OC(=O)-$, $-OC(=O)NR^{L1A}-$, $-NR^{L1A}NR^{L1B}C(=O)-$, $-NR^{L1A}C(=O)-$, $-NR^{L1A}CO_2-$, $-NR^{L1A}C(=O)NR^{L1B}-$, $-S(=O)-$, $-SO_2-$, $-NR^{L1A}SO_2-$, $-SO_2NR^{L1A}-$, $-NR^{L1A}SO_2NR^{L1B}-$, $-O-$, $-S-$, or $-NR^{L1A}-$; wherein each occurrence of $R^{L1A}$ and $R^{L1B}$ is independently hydrogen, alkyl, heteroalkyl, heterocyclyl, aromatic, heteroaromatic or acyl; and Z is an aliphatic, heteroaliphatic, alicyclic, heteroalicyclic, aromatic or heteroaromatic moiety.

16. A compound having the structure:

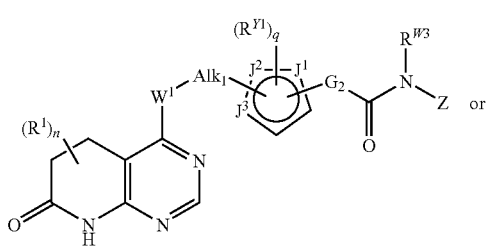 or

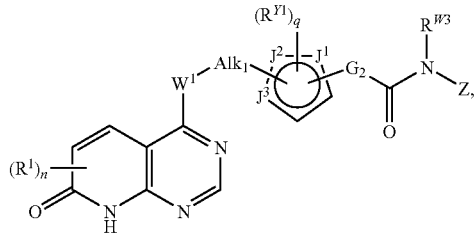

or a pharmaceutically acceptable salt thereof, wherein:

$W^1$ is $-O-$, $-N(R^{W1})-$, $-C(=O)-$ or $-C(=O)N(R^{W1})-$, where $R^{W1}$ is hydrogen, alkyl, cycloalkyl, heteroalkyl, aryl, heteroaryl, -(alkyl)aryl, -(alkyl)heteroaryl or acyl; and $Alk_1$ is a substituted or unsubstituted $C_{1-6}$alkylene or $C_{2-6}$alkenylene chain wherein up to two non-adjacent methylene units are independently optionally replaced by $-C(=O)-$, $-CO_2-$, $-C(=O)C(=O)-$, $-C(=O)NR^{L1A}-$, $-OC(=O)-$, $-OC(=O)NR^{L1A}-$, $-NR^{L1A}NR^{L1B}-$, $-NR^{L1A}NR^{L1B}C(=O)-$, $-NR^{L1A}C(=O)-$, $-NR^{L1A}CO_2-$, $-NR^{L1A}C(=O)NR^{L1B}-$, $-S(=O)-$, $-SO_2-$, $-NR^{L1A}SO_2-$, $-SO_2NR^{L1A}-$, $-NR^{L1A}SO_2NR^{L1B}-$, $-O-$, $-S-$, or $-NR^{L1A}-$; wherein each occurrence of $R^{L1A}$ and $R^{L1B}$ is independently hydrogen, alkyl, heteroalkyl, heterocyclyl, aromatic, heteroaromatic or acyl; q is an integer from 0-3; $J^1$, $J^2$ and $J^3$ are independently O, S, N, $NR^{Y1}$ or $CR^{Y1}$; wherein each occurrence of $R^{Y1}$ is independently hydrogen, alkyl, heteroalkyl, aryl, heteroaryl, -(alkyl)aryl or -(alkyl)heteroaryl, $-OR^{Y3}$, $-SR^{Y3}$, $-NR^{Y2}R^{Y3}$, $-SO_2NR^{Y2}R^{Y3}$, $-C(=O)NR^{Y2}R^{Y3}$, halogen, $-CN$, $-NO_2$, $-C(=O)OR^{Y3}$, $-N(R^{Y2})C(=O)R^{Y3}$, wherein each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or $R^{Y2}$ and $R^{Y3}$ taken together with the nitrogen atom to which they are attached form a 5-6 membered heterocyclic ring; $G_2$ is a single bond, O or $NR^{G2}$; and $R^{W3}$ and $R^{G2}$ are independently hydrogen, lower alkyl, lower heteroalkyl, aryl, heteroaryl, -(alkyl)aryl, -(alkyl)heteroaryl or acyl n is an integer from 0-4;

$R^1$ is hydrogen, halogen, cyano, nitro, or an aliphatic, heteroaliphatic, alicyclic, heteroalicyclic, aromatic or heteroaromatic moiety; and Z is an aliphatic, heteroaliphatic, alicyclic, heteroalicyclic, aromatic or heteroaromatic moiety.

17. The compound of claim 16, wherein

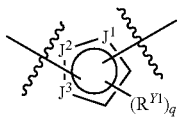

has one of the following structures:

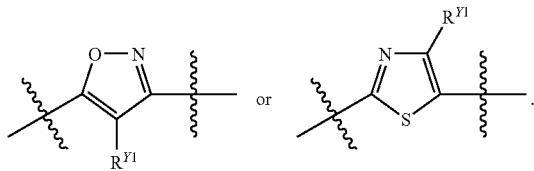

18. A compound having the structure:

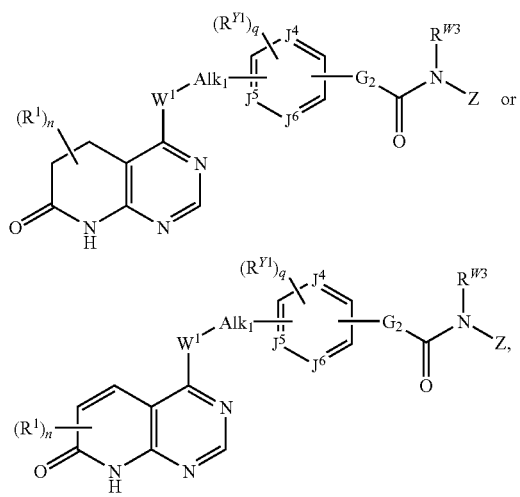

or a pharmaceutically acceptable salt thereof, wherein:
$W^1$ is —O—, —N($R^{W1}$)—, —C(=O)— or —C(=O)N($R^{W1}$)—, where $R^{W1}$ is hydrogen, alkyl, cycloalkyl, heteroalkyl, aryl, heteroaryl, -(alkyl)aryl, -(alkyl)heteroaryl or acyl; and $Alk_1$ is a substituted or unsubstituted $C_{1-6}$alkylene or $C_{2-6}$alkenylene chain wherein up to two non-adjacent methylene units are independently optionally replaced by —C(=O)—, —CO$_2$—, —C(=O)C(=O)—, —C(=O)NR$^{L1A}$—, —OC(=O)—, —OC(=O)NR$^{L1A}$—, —NR$^{L1A}$NR$^{L1B}$—, —NR$^{L1A}$NR$^{L1B}$C(=O)—, —NR$^{L1A}$C(=O)—, —NR$^{L1A}$CO$_2$—, —NR$^{L1A}$C(=O)NR$^{L1B}$—, —S(=O)—, —SO$_2$—, —NR$^{L1A}$SO$_2$—, —SO$_2$NR$^{L1A}$—, —NR$^{L1A}$SO$_2$NR$^{L1B}$—, —O—, —S—, or —NR$^{L1A}$—; wherein each occurrence of $R^{L1A}$ and $R^{L1B}$ is independently hydrogen, alkyl, heteroalkyl, heterocyclyl, aromatic, heteroaromatic or acyl; q is an integer from 0-3; $J^4$, $J^5$ and $J^6$ are independently N or CR$^{Y1}$; wherein each occurrence of $R^{Y1}$ is independently hydrogen, alkyl, heteroalkyl, aryl, heteroaryl, -(alkyl)aryl or -(alkyl)heteroaryl, —OR$^{Y3}$, —SR$^{Y3}$, —NR$^{Y2}$R$^{Y3}$, —SO$_2$NR$^{Y2}$R$^{Y3}$, —C(=O)NR$^{Y2}$R$^{Y3}$, halogen, —CN, —NO$_2$, —C(=O)OR$^{Y3}$, —N(R$^{Y2}$)C(=O)R$^{Y3}$, wherein each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or $R^{Y2}$ and $R^{Y3}$ taken together with the nitrogen atom to which they are attached form a 5-6 membered heterocyclic ring; $G_2$ is a single bond, O or NR$^{G2}$; and $R^{W3}$ and $R^{G2}$ are independently hydrogen, lower alkyl, lower heteroalkyl, aryl, heteroaryl, -(alkyl)aryl, -(alkyl)heteroaryl or acyl n is an integer from 0-4;

$R^1$ is hydrogen, halogen, cyano, nitro, or an aliphatic, heteroaliphatic, alicyclic, heteroalicyclic, aromatic or heteroaromatic moiety; and Z is an aliphatic, heteroaliphatic, alicyclic, heteroalicyclic, aromatic or heteroaromatic moiety.

19. The compound of claim 18, wherein

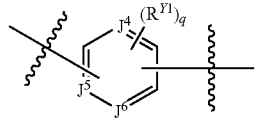

has the structure:

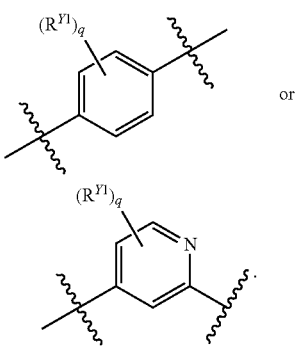

20. A compound having the structure:

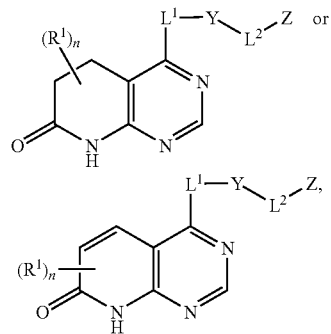

or a pharmaceutically acceptable salt thereof, wherein:
$L^2$ is a single bond and Z is:

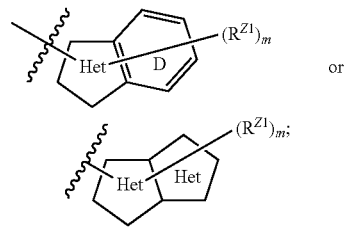

n is an integer from 0-4;
$R^1$ is hydrogen, halogen, cyano, nitro, or an aliphatic, heteroaliphatic, alicyclic, heteroalicyclic, aromatic or heteroaromatic moiety;

L¹ is —O—, —S—, —NR^{L1A}— or a substituted or unsubstituted $C_{1-6}$alkylene or $C_{2-6}$alkenylene chain wherein up to two non-adjacent methylene units are independently optionally replaced by —C(=O)—, —CO₂—, —C(=O)C(=O)—, —C(=O)NR^{L1A}—, —OC(=O)—, —OC(=O)NR^{L1A}—, —NR^{L1A}NR^{L1B}—, —NR^{L1A}NR^{L1B}C(=O)—, —NR^{L1A}C(=O)—, —NR^{L1A}CO₂—, —NR^{L1A}C(=O)NR^{L1B}—, —S(=O)—, —SO₂—, —NR^{L1A}SO₂—, —SO₂NR^{L1A}—, —NR^{L1A}SO₂NR^{L1B}—, —O—, —S—, or —NR^{L1A}—; wherein each occurrence of R^{L1A} and R^{L1B} is independently hydrogen, alkyl, heteroalkyl, heterocyclyl, aromatic, heteroaromatic or acyl;

L² is absent, —O—, —S—, —NR^{L2A}—, a heteroalicyclic or heteroaromatic moiety, or a substituted or unsubstituted $C_{1-6}$alkylene or $C_{2-6}$alkenylene chain wherein up to two non-adjacent methylene units are independently optionally replaced by —C(=O)—, —CO₂—, —C(=O)C(=O)—, —C(=O)NR^{L2A}—, —OC(=O)—, —OC(=O)NR^{L2A}—, —NR^{L2A}NR^{L2B}—, —NR^{L2A}NR^{L2B}C(=O)—, —NR^{L2A}C(=O)—, —NR^{L2A}CO₂—, —NR^{L2A}C(=O)NR^{L2B}—, —S(=O)—, —SO₂—, —NR^{L2A}SO₂—, —SO₂NR^{L2A}—, —NR^{L2A}SO₂NR^{L2B}—, —O—, —S—, or —NR^{L2A}—; wherein each occurrence of R^{L2A} and R^{L2B} is independently hydrogen, alkyl, heteroalkyl, heterocyclyl, aromatic, heteroaromatic or acyl;

Y is a divalent cycloalkyl, cycloalkenyl, heterocyclic, aryl or heteroaryl moiety;

the "D" cyclic moiety is a 6-membered aromatic ring comprising from 0-4 nitrogen atoms; each "Het" moiety independently represents a fully or partially saturated or unsaturated 5-membered ring comprising 1-4 heteroatoms selected from N, O and S; m is an integer from 0-6; and each occurrence of R^{Z1} is independently hydrogen, alkyl, heteroalkyl, aryl, heteroaryl, -(alkyl)aryl, -(alkyl)heteroaryl, —OR^{Z2}, —SR^{Z2}, —N(R^{Z2})₂, —SO₂N(R^{Z2})₂, —SO₂R^{Z4}, —C(=O)N(R^{Z2})₂, halogen, —CN, —NO₂, —C(=O)OR^{Z2}, —N(R^{Z2})C(=O)R^{Z3} or —N(R^{Z2})SO₂R^{Z4}; wherein each occurrence of R^{Z2} and R^{Z3} is independently hydrogen, lower alkyl, lower heteroalkyl, aryl, heteroaryl, -(alkyl)aryl, -(alkyl)heteroaryl, acyl; or any two occurrences of R^{Z2}, taken together with the nitrogen atom to which they are attached (e.g., N(R^{Z2})₂), form a substituted or unsubstituted heterocyclic moiety; and R^{Z4} is alkyl, heteroalkyl, aryl, heteroaryl, -(alkyl)aryl, or -(alkyl)heteroaryl; and wherein any two adjacent occurrence of R^{Z1} may form a fused 5- to 6-membered aryl, heteroaryl or heterocyclic ring.

21. The compound of claim 20, wherein L² is a single bond and Z is a moiety having one of the following structures:

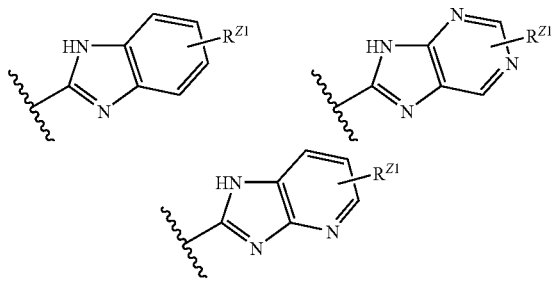

wherein R^{Z1} is hydrogen, halogen, lower alkyl, lower heteroalkyl, lower haloalkyl, aryl, heteroaryl, —OR^{Z2}, —SR^{Z2} or —N(R^{Z2})₂; wherein each occurrence of R^{Z2} is independently hydrogen, lower alkyl, lower heteroalkyl, aryl, heteroaryl, -(alkyl)aryl, -(alkyl)heteroaryl, acyl; or any two occurrences of R^{Z2}, taken together with the nitrogen atom to which they are attached form a substituted or unsubstituted heterocyclic moiety.

22. The compound of claim 21, wherein L² is a single bond and Z is a moiety having one of the following structures:

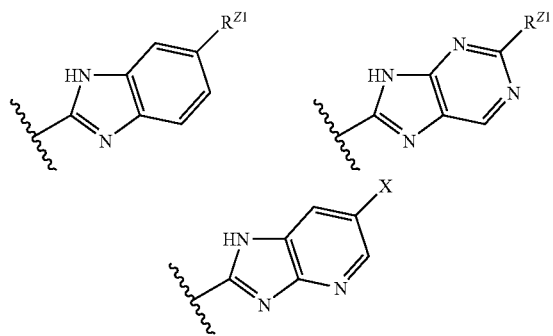

wherein X is halogen and R^{Z1} is halogen, lower alkyl or lower haloalkyl.

23. The compound of claim 22 wherein R^{Z1} is —CF₃ or tent-butyl, and X is F or Cl.

24. The compound of claim 21 wherein Z is a moiety having one of the following structures:

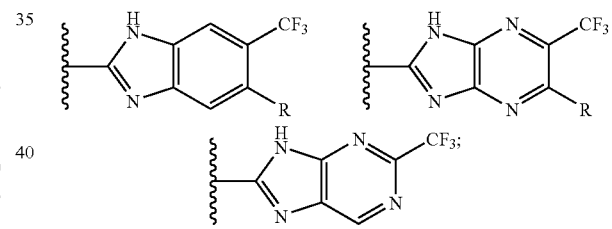

wherein R is —CF₃ or tert-butyl.

25. A compound having the structure:

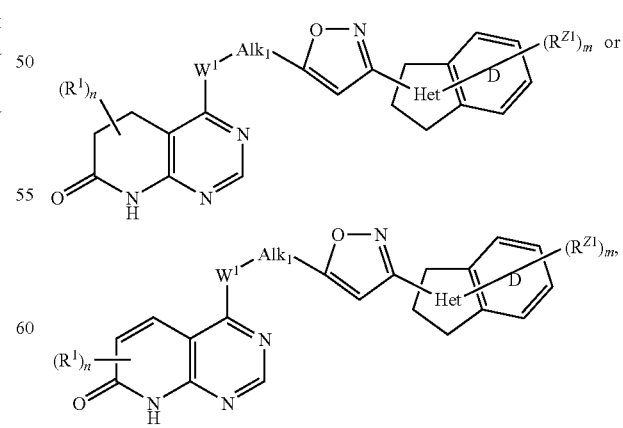

or a pharmaceutically acceptable salt thereof, wherein:
n is an integer from 0-4;

$R^1$ is hydrogen, halogen, cyano, nitro, or an aliphatic, heteroaliphatic, heteroalicyclic, aromatic or heteroaromatic moiety;

$W^1$ is —O—, —N($R^{W1}$)—, —C(=O)— or —C(=O)N($R^{W1}$)—, where $R^{W1}$ is hydrogen, alkyl, cycloalkyl, heteroalkyl, aryl, heteroaryl, -(alkyl)aryl, -(alkyl)heteroaryl or acyl; and $Alk_1$ is a substituted or unsubstituted $C_{1-6}$alkylene or $C_{2-6}$alkenylene chain wherein up to two non-adjacent methylene units are independently optionally replaced by —C(=O)—, —CO$_2$—, —C(=O)C(=O)—, —C(=O)N$R^{L1A}$—, —OC(=O)—, —OC(=O)N$R^{L1A}$—, —N$R^{L1A}$N$R^{L1B}$—, —N$R^{L1A}$N$R^{L1B}$C(=O)—, —N$R^{L1A}$C(=O)—, —N$R^{L1A}$CO$_2$—, —N$R^{L1A}$C(=O)N$R^{L1B}$—, —S(=O)—, —SO$_2$—, —N$R^{L1A}$SO$_2$—, —SO$_2$N$R^{L1A}$—, —N$R^{L1A}$SO$_2$N$R^{L1B}$—, —O—, —S—, or —N$R^{L1A}$—; wherein each occurrence of $R^{L1A}$ and $R^{L1B}$ is independently hydrogen, alkyl, heteroalkyl, heterocyclyl, aromatic, heteroaromatic or acyl;

the "D" cyclic moiety is a 6-membered aromatic ring comprising from 0-4 nitrogen atoms;

each "Het" moiety independently represents a fully or partially saturated or unsaturated 5-membered ring comprising 1-4 heteroatoms selected from N, O and S; m is an integer from 0-6; and each occurrence of $R^{Z1}$ is independently hydrogen, alkyl, heteroalkyl, aryl, heteroaryl, -(alkyl)aryl, -(alkyl)heteroaryl, —O$R^{Z2}$, —S$R^{Z2}$, —N($R^{Z2}$)$_2$, —SO$_2$N($R^{Z2}$)$_2$, —SO$_2$$R^{Z4}$, —C(=O)N($R^{Z2}$)$_2$, halogen, —CN, —NO$_2$, —C(=O)O$R^{Z2}$, —N($R^{Z2}$)C(=O)$R^{Z3}$ or —N($R^{Z2}$)SO$_2$$R^{Z4}$; wherein each occurrence of $R^{Z2}$ and $R^{Z3}$ is independently hydrogen, lower alkyl, lower heteroalkyl, aryl, heteroaryl, -(alkyl)aryl, -(alkyl)heteroaryl, acyl; or any two occurrences of $R^{Z2}$, taken together with the nitrogen atom to which they are attached (e.g., N($R^{Z2}$)$_2$), form a substituted or unsubstituted heterocyclic moiety; and $R^{Z4}$ is alkyl, heteroalkyl, aryl, heteroaryl, -(alkyl)aryl, or -(alkyl)heteroaryl; and wherein any two adjacent occurrence of $R^{Z1}$ may form a fused 5- to 6-membered aryl, heteroaryl or heterocyclic ring.

26. The compound of claim 25 having the structure:

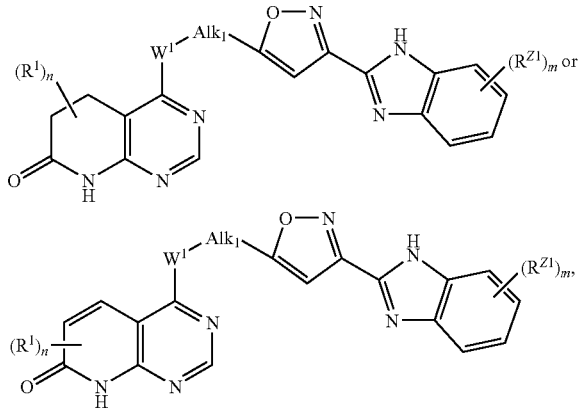

wherein $W^1$ is —O—, —N($R^{W1}$)—, —C(=O)— or —C(=O)N($R^{W1}$)—, where $R^{W1}$ is hydrogen, alkyl, cycloalkyl, heteroalkyl, aryl, heteroaryl, -(alkyl)aryl, -(alkyl)heteroaryl or acyl; and $Alk_1$ is a substituted or unsubstituted $C_{1-6}$alkylene or $C_{2-6}$alkenylene chain wherein up to two non-adjacent methylene units are independently optionally replaced by —C(=O)—, —CO$_2$—, —C(=O)C(=O)—, C(=O)N$R^{L1A}$—, —OC(=O)—, —OC(=O)N$R^{L1A}$—, —N$R^{L1A}$N$R^{L1B}$—, —N$R^{L1A}$N$R^{L1B}$C(=O)—, —N$R^{L1A}$C(=O)—, —N$R^{L1A}$CO$_2$—, —N$R^{L1A}$C(=O)N$R^{L1B}$—, —S(=O)—, —SO$_2$—, —N$R^{L1A}$SO$_2$—, —SO$_2$N$R^{L1A}$—, —N$R^{L1A}$SO$_2$N$R^{L1B}$—, —O—, —S—, or —N$R^{L1A}$—; wherein each occurrence of $R^{L1A}$ and $R^{L1B}$ is independently hydrogen, alkyl, heteroalkyl, heterocyclyl, aromatic, heteroaromatic or acyl; m is an integer from 0 to 3; each occurrence of $R^{Z1}$ is independently hydrogen, alkyl, heteroalkyl, aryl, heteroaryl, -(alkyl)aryl or -(alkyl)heteroaryl, —O$R^{Z2}$, —S$R^{Z2}$, —N$R^{Z2}$$R^{Z3}$, —SO$_2$N$R^{Z2}$$R^{Z3}$, —SO$_2$$R^{Z4}$, —C(=O)N$R^{Z2}$$R^{Z3}$, halogen, —CN, —NO$_2$, —C(=O)O$R^{Z3}$, —N($R^{Z2}$)C(=O)$R^{Z3}$, wherein each occurrence of $R^{Z2}$ and $R^{Z3}$ is independently hydrogen, lower alkyl, lower heteroalkyl, aryl, heteroaryl, -(alkyl)aryl, -(alkyl)heteroaryl or acyl, or $R^{Z2}$ and $R^{Z3}$ taken together with the nitrogen or carbon atom to which they are attached form a 5-6 membered heterocyclic, aryl or heteroaryl ring; and $R^{Z4}$ is alkyl, heteroalkyl, aryl, heteroaryl, -(alkyl)aryl, or -(alkyl)heteroaryl.

27. The compound of claim 26 wherein the compound has one of the following structures:

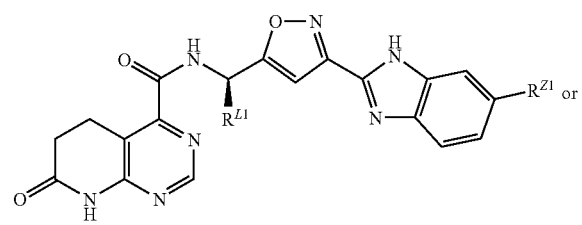

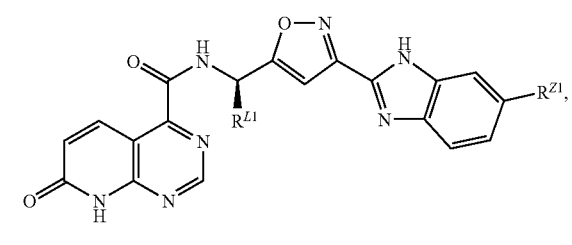

wherein $R^{Z1}$ is lower alkyl, lower diaminoalkyl or lower alkyl and $R^{L1}$ is lower alkyl.

28. The compound of claim 27 wherein $R^{Z1}$ is —CF$_3$ and $R^{L1}$ is methyl.

29. The compound of claim 25 having the structure:

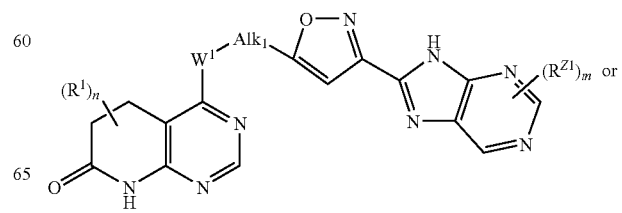

-continued

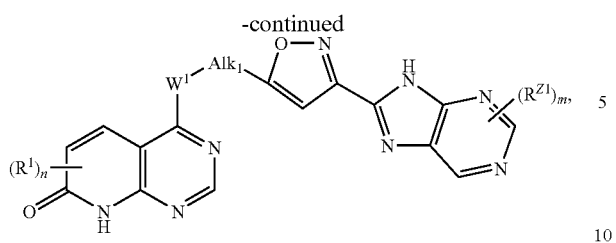

wherein W¹ is —O—, —N(R^W1)—, —C(=O)— or C(=O)N(R^W1)—, where R^W1 is hydrogen, alkyl, cycloalkyl, heteroalkyl, aryl, heteroaryl, -(alkyl)aryl, -(alkyl)heteroaryl or acyl; and $Alk_1$ is a substituted or unsubstituted $C_{1-6}$alkylene or $C_{2-6}$alkenylene chain wherein up to two non-adjacent methylene units are independently optionally replaced by —C(=O)—, —CO₂—, —C(=O)C(=O)—, —C(=O)NR^{L1A}—, —OC(=O)—, —OC(=O)NR^{L1A}—, —NR^{L1A}NR^{L1B}—, —NR^{L1A}NR^{L1B}C(=O)—, —NR^{L1A}C(=O)—, —NR^{L1A}CO₂—, —NR^{L1A}C(=O)NR^{L1B}—, —S(=O)—, —SO₂—, —NR^{L1A}SO₂—, —SO₂NR^{L1A}—, —NR^{L1A}SO₂NR^{L1B}—, —O—, —S—, or —NR^{L1A}—; wherein each occurrence of R^{L1A} and R^{L1B} is independently hydrogen, alkyl, heteroalkyl, heterocyclyl, aromatic, heteroaromatic or acyl; m is an integer from 0 to 3; each occurrence of R^{Z1} is independently hydrogen, alkyl, heteroalkyl, aryl, heteroaryl, -(alkyl)aryl or -(alkyl)heteroaryl, —OR^{Z2}, —SR^{Z2}, —NR^{Z2}R^{Z3}, —SO₂NR^{Z2}R^{Z3}, —SO₂R^{Z4}, —C(=O)NR^{Z2}R^{Z3}, halogen, —CN, —NO₂, —C(=O)OR^{Z3}, —N(R^{Z2})C(=O)R^{Z3}, wherein each occurrence of R^{Z2} and R^{Z3} is independently hydrogen, lower alkyl, lower heteroalkyl, aryl, heteroaryl, -(alkyl)aryl, -(alkyl)heteroaryl or acyl, or R^{Z2} and R^{Z3} taken together with the nitrogen or carbon atom to which they are attached form a 5-6 membered heterocyclic, aryl or heteroaryl ring; and R^{Z4} is alkyl, heteroalkyl, aryl, heteroaryl, -(alkyl)aryl, or -(alkyl)heteroaryl.

30. The compound of claim 29 wherein the compound has one of the following structures:

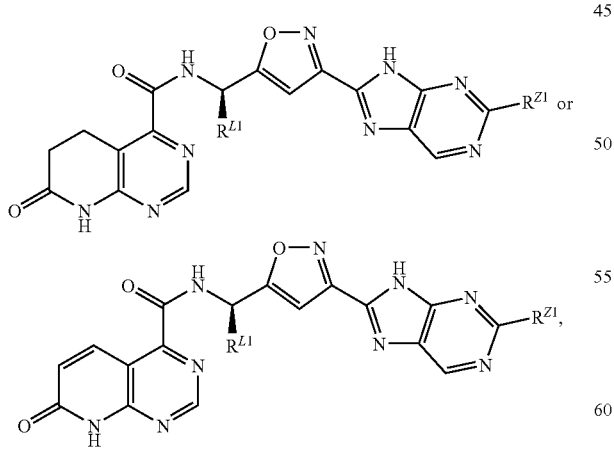

wherein R^{Z1} is lower alkyl or lower haloalkyl and R^{L1} is lower alkyl.

31. The compound of claim 30 wherein R^{Z1} is t-Bu and R^{L1} is methyl.

32. The compound of claim 16 having the structure:

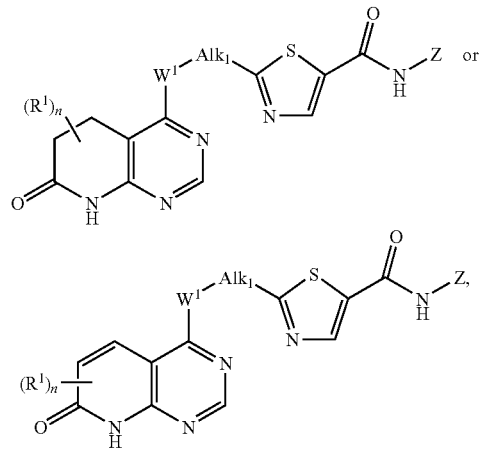

wherein:
Z is an aryl, heteroaryl or heterocyclic moiety;
W¹ is —O—, —N(R^{W1})—, —C(=O)— or C(=O)N(R^{W1})—, where R^{W1} is hydrogen, alkyl, cycloalkyl, heteroalkyl, aryl, heteroaryl, -(alkyl)aryl, -(alkyl)heteroaryl or acyl; and $Alk_1$ is a substituted or unsubstituted $C_{1-6}$alkylene or $C_{2-6}$alkenylene chain wherein up to two non-adjacent methylene units are independently optionally replaced by —C(=O)—, —CO₂—, —C(=O)C(=O)—, —C(=O)NR^{L1A}—, —OC(=O)—, —OC(=O)NR^{L1A}—, —NR^{L1A}NR^{L1B}—, —NR^{L1A}NR^{L1B}C(=O)—, —NR^{L1A}C(=O)—, —NR^{L1A}CO₂—, —NR^{L1A}C(=O)NR^{L1B}—, —S(=O)—, —SO₂—, —NR^{L1A}SO₂—, —SO₂NR^{L1A}—, —NR^{L1A}SO₂NR^{L1B}—, —O—, —S—, or —NR^{L1A}—; wherein each occurrence of R^{L1A} and R^{L1B} is independently hydrogen, alkyl, heteroalkyl, heterocyclyl, aromatic, heteroaromatic or acyl.

33. The compound of claim 32 having the structure:

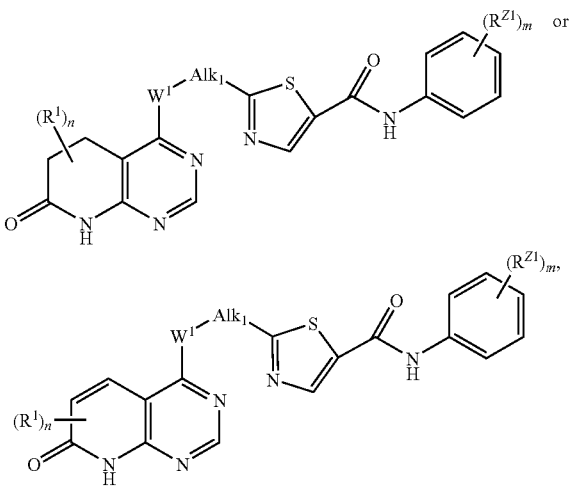

wherein W$^1$ is —O—, —N(R$^{W1}$)—, —C(=O)— or —C(=O)N(R$^{W1}$)—, where R$^{W1}$ is hydrogen, alkyl, cycloalkyl, heteroalkyl, aryl, heteroaryl, -(alkyl)aryl, -(alkyl)heteroaryl or acyl; and Alk$_1$ is a substituted or unsubstituted C$_{1-6}$alkylene or C$_{2-6}$alkenylene chain wherein up to two non-adjacent methylene units are independently optionally replaced by —C(=O)—, —CO$_2$—, —C(=O)C(=O)—, —C(=O)NR$^{L1A}$—, —OC(=O)—, —OC(=O)NR$^{L1A}$—, —NR$^{L1A}$NR$^{L1B}$—, —NR$^{L1A}$NR$^{L1B}$C(=O)—, —NRC(=O)—, —NR$^{L1A}$CO$_2$—, —NR$^{L1A}$C(=O)NR$^{L1B}$—, —S(=O)—, —SO$_2$—, —NR$^{L1A}$SO$_2$—, —SO$_2$NR$^{L1A}$—, —NR$^{L1A}$SO$_2$NR$^{L1B}$—, —O—, —S—, or —NR$^{L1A}$—; wherein each occurrence of R$^{L1A}$ and R$^{L1B}$ is independently hydrogen, alkyl, heteroalkyl, heterocyclyl, aromatic, heteroaromatic or acyl; m is an integer from 0 to 3; each occurrence of R$^{Z1}$ is independently hydrogen, alkyl, heteroalkyl, aryl, heteroaryl, -(alkyl)aryl, -(alkyl)heteroaryl, —OR$^{Z2}$, —SR$^{Z2}$, —NR$^{Z2}$R$^{Z3}$, —SO$_2$NR$^{Z2}$R$^{Z3}$, —SO$_2$R$^{Z4}$, —C(=O)NR$^{Z2}$R$^{Z3}$, halogen, —CN, —NO$_2$, —C(=O)OR$^{Z3}$, or —N(R$^{Z2}$)C(=O)R$^{Z3}$, wherein each occurrence of R$^{Z2}$ and R$^{Z3}$ is independently hydrogen, lower alkyl, lower heteroalkyl, aryl, heteroaryl, -(alkyl)aryl, -(alkyl)heteroaryl or acyl, or R$^{Z2}$ and R$^{Z3}$ taken together with the nitrogen or carbon atom to which they are attached form a 5-6 membered heterocyclic, aryl or heteroaryl ring; and R$^{Z4}$ is alkyl, heteroalkyl, aryl, heteroaryl, -(alkyl)aryl, or -(alkyl)heteroaryl.

34. The compound of claim 33 wherein the compound has one of the following structures:

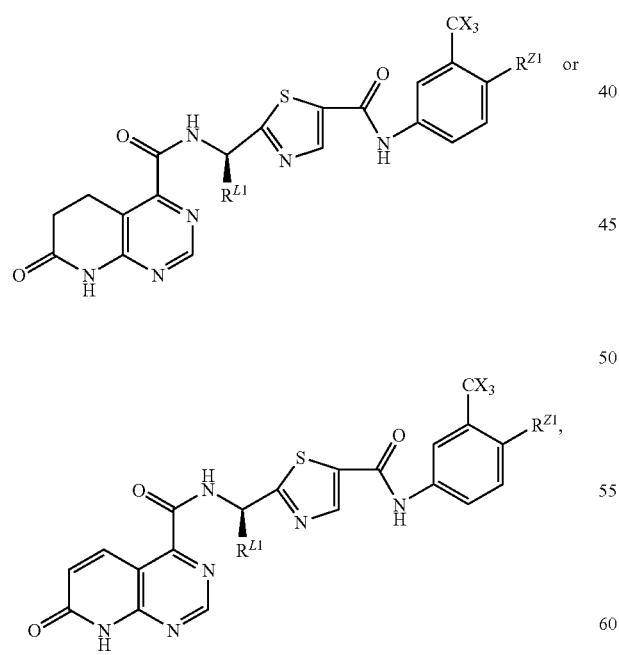

wherein R$^{Z1}$ is halogen or lower alkyl, X is halogen and R$^{L1}$ is lower alkyl.

35. The compound of claim 34 wherein R$^{Z1}$ is Cl or methyl and R$^{L1}$ is methyl.

36. The compound of claim 16 having the structure:

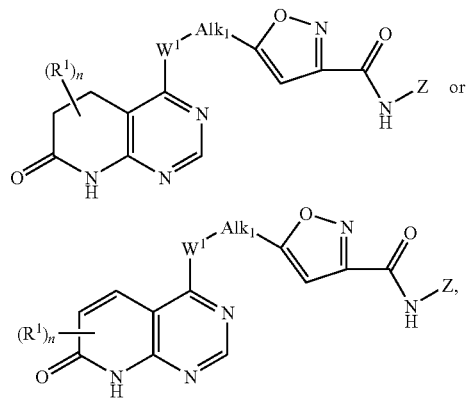

wherein:
Z is an aryl, heteroaryl or heterocyclic moiety;
W$^1$ is —O—, —N(R$^{W1}$)—, —C(=O)— or —C(=O)N(R$^{W1}$)—, where R$^{W1}$ is hydrogen, alkyl, cycloalkyl, heteroalkyl, aryl, heteroaryl, -(alkyl)aryl, -(alkyl)heteroaryl or acyl; and
Alk$_1$ is a substituted or unsubstituted C$_{1-6}$alkylene or C$_{2-6}$alkenylene chain wherein up to two non-adjacent methylene units are independently optionally replaced by —C(=O)—, —CO$_2$—, —C(=O)C(=O)—, —C(=O)NR$^{L1A}$—, —OC(=O)—, —OC(=O)NR$^{L1A}$—, —NR$^{L1A}$NR$^{L1B}$—, —NR$^{L1A}$NR$^{L1B}$C(=O)—, —NR$^{L1A}$C(=O)—, —NR$^{L1A}$CO$_2$—, —NR$^{L1A}$C(=O)NR$^{L1B}$—, —S(=O)—, —SO$_2$—, —NR$^{L1A}$SO$_2$—, —SO$_2$NR$^{L1A}$—, —NR$^{L1A}$SO$_2$NR$^{L1B}$—, —O—, —S—, or —NR$^{L1A}$—; wherein each occurrence of R$^{L1A}$ and R$^{L1B}$ is independently hydrogen, alkyl, heteroalkyl, heterocyclyl, aromatic, heteroaromatic or acyl.

37. The compound of claim 36 having the structure:

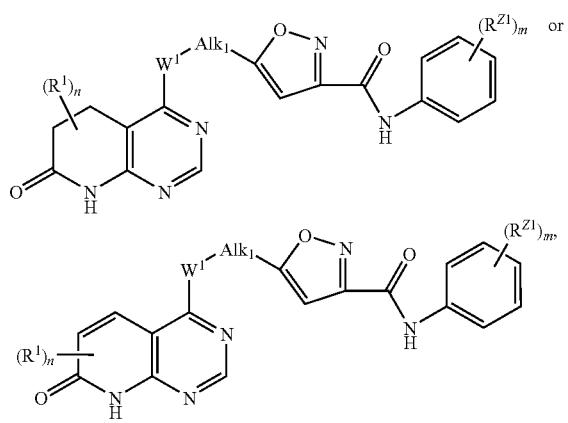

wherein:
n is an integer from 0-4;
R$^1$ is hydrogen, halogen, cyano, nitro, or an aliphatic, heteroaliphatic, alicyclic, heteroalicyclic, aromatic or heteroaromatic moiety;

W¹ is —O—, —N(R^{W1})—, —C(=O)— or —C(=O)N(R^{W1})—, where R^{W1} is hydrogen, alkyl, cycloalkyl, heteroalkyl, aryl, heteroaryl, -(alkyl)aryl, -(alkyl)heteroaryl or acyl; and Alk₁ is a substituted or unsubstituted $C_{1-6}$alkylene or $C_{2-6}$alkenylene chain wherein up to two non-adjacent methylene units are independently optionally replaced by —C(=O)—, —CO₂—, —C(=O)C(=O)—, —C(=O)NR^{L1A}—, —OC(=O)—, —OC(=O)NR^{L1A}—, —NR^{L1A}NR^{L1B}—, —NR^{L1A}NR^{L1B}C(=O)—, —NR^{L1A}C(=O)—, —NR^{L1A}CO₂—, —NR^{L1A}C(O)NR^{L1B}—, —S(=O)—, —SO₂—, —NR^{L1A}SO₂NR^{L1A}—, —NR^{L1A}SO₂NR^{L1B}—, —O—, —S—, or —NR^{L1A}—; wherein each occurrence of R^{L1A} and R^{L1B} is independently hydrogen, alkyl, heteroalkyl, heterocyclyl, aromatic, heteroaromatic or acyl; m is an integer from 0 to 3; each occurrence of $R^{Z1}$ is independently hydrogen, alkyl, heteroalkyl, aryl, heteroaryl, -(alkyl)aryl or -(alkyl)heteroaryl, —OR^{Z2}, —SR^{Z2}, —NR^{Z2}R^{Z3}, —SO₂NR^{Z2}R^{Z3}, —SO₂R^{Z4}, —C(=O)NR^{Z2}R^{Z3}, halogen, —CN, —NO₂, —C(=O)OR^{Z3}, —N(R^{Z2})C(=O)R^{Z3}, wherein each occurrence of R^{Z2} and R^{Z3} is independently hydrogen, lower alkyl, lower heteroalkyl, aryl, heteroaryl, -(alkyl)aryl, -(alkyl)heteroaryl or acyl, or R^{Z2} and R^{Z3} taken together with the nitrogen or carbon atom to which they are attached form a 5-6 membered heterocyclic, aryl or heteroaryl ring; and R^{Z4} is alkyl, heteroalkyl, aryl, heteroaryl, -(alkyl)aryl, or -(alkyl)heteroaryl.

38. The compound of claim 37 having the structure:

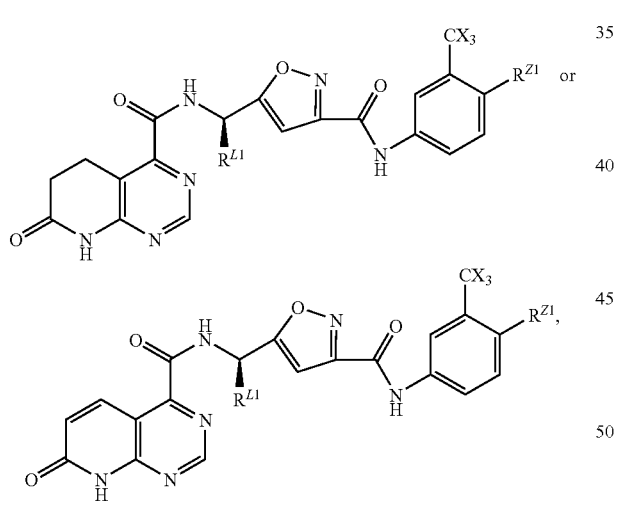

wherein $R^{Z1}$ is halogen or lower alkyl, X is halogen and $R^{L1}$ is lower alkyl.

39. The compound of claim 37 wherein $R^{Z1}$ is Cl or methyl and $R^{L1}$ is methyl.

40. The compound of claim 1 wherein n is 1 and R¹ is hydrogen, halogen, heterocyclyl, aryl or heteroaryl.

41. The compound of claim 1 wherein n is 0 and R¹ is hydrogen, halogen, heterocyclyl, aryl or heteroaryl.

42. The compound of claim 20, 25, 26, 29, 33 or 37 wherein m is 1 and $R^{Z1}$ is halogen, lower alkyl or lower haloalkyl.

43. The compound of claim 1 wherein Z is one of the following structures:

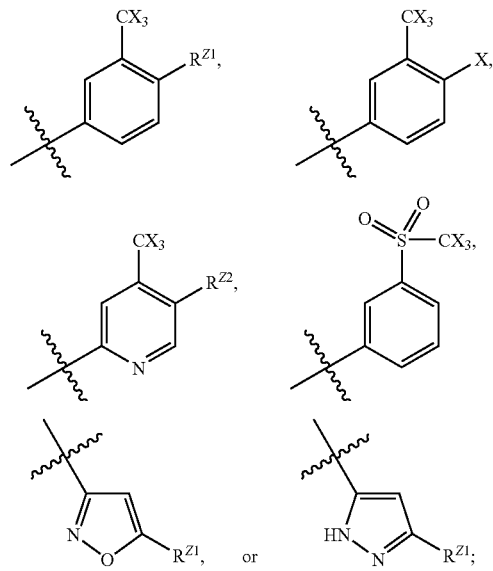

wherein X is halogen; $R^{Z1}$ is substituted or unsubstituted lower alkyl; and $R^{Z2}$ is hydrogen, halogen or substituted or unsubstituted lower alkyl.

44. The compound of claim 43 wherein Z is one of the following structures:

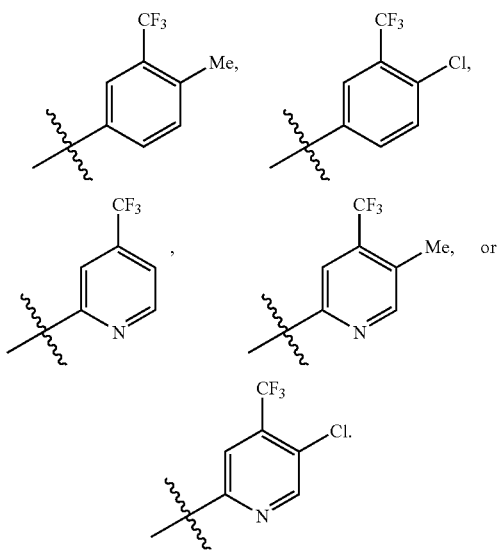

45. The compound of claim 1 wherein L² is a single bond and Z is a moiety having one of the following structures:

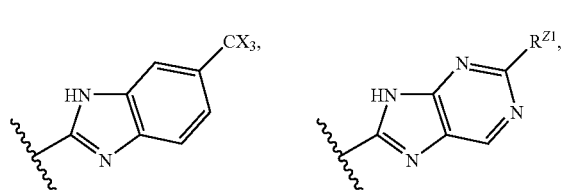

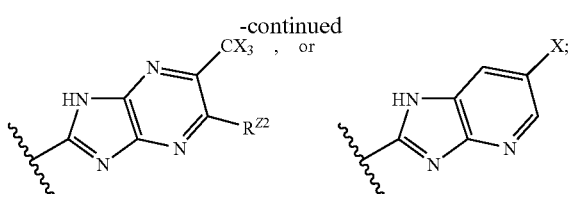

wherein $R^{Z1}$ is lower alkyl; X is halogen; and $R^{Z2}$ is —$CX_3$ or lower alkyl.

46. The compound of claim 45 wherein $L^2$ is a single bond and Z is a moiety having one of the following structures:

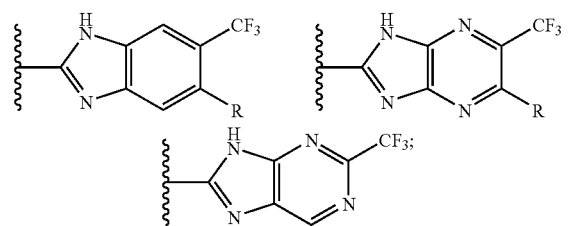

wherein R is —$CF_3$ or tert-butyl.

47. The compound of claim 14 or 15 wherein Cy has one of the following structures:

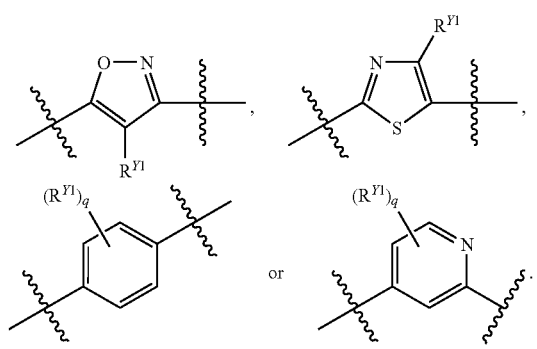

48. The compound of claim 3 wherein —$W^1$-$Alk_1$- is —$NHC_{1-6}alkyl$-, —$OC_{1-6}alkyl$-, —$C(=O)C_{1-6}alkyl$- or —$C(=O)NHC_{1-6}alkyl$-; wherein the $C_{1-6}alkyl$ moiety may be substituted or unsubstituted.

49. The compound of claim 7 or 48 wherein the $C_{1-6}alkyl$ is —$CH_2$— or —$CH(R^{L1})$—; wherein $R^{L1}$ is lower alkyl.

50. The compound of claim 49 wherein the $C_{1-6}alkyl$ is —$CH_2$— or —$CH(R^{L1})$—; wherein $R^{L1}$ is methyl.

51. The compound of claim 8, wherein -$G_2C(=O)N(R^{W3})$— is —$C(=O)NH$—, —$OC(=O)NH$—, or —$NHC(=O)NH$—.

52. The compound of claim 51 wherein -$G_2C(=O)N(R^{W2})$— is —$C(=O)NH$—.

53. A composition comprising a compound of claim 1, and a pharmaceutically acceptable carrier, adjuvant, or vehicle.

54. The composition of claim 53, additionally comprising a therapeutic agent selected from mechlorethamine, chlorambucil, cyclophosphamide, melphalan, ifosfamide, methotrexate, 6-mercaptopurine, 5-fluorouracil, cytarabine, gemcitabine, vinblastine, vincristine, vinorelbine, paclitaxel, etoposide, irinotecan, topotecan, antibiotics, carmustine, lomustine, cisplatin, carboplatin, asparaginase, tamoxifen, leuprolide, flutamide, megestrol, imatinib mesylate, doxorubicin, dexamethasone, interferons, interleukins, antiemetics, corticosteroids, IL-1RA, azathioprine, sulfasalazine, acetylcholinesterase inhibitors, MAO inhibitors, anti-convulsants, riluzole, beta-blockers, ACE inhibitors, calcium channel blockers, statins, cholestyramine, anti-viral agents, anti-leukemic agents, growth factors, gamma globulin, cyclosporin, tacrolimus, rapamycin, and mycophenolate mofetil.

55. The compound according to claim 1, wherein:
Y is

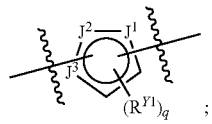

q is an integer from 0-2; and
$J^1$, $J^2$ and $J^3$ are independently O, S, N, $NR^{Y1}$ or $CR^{Y1}$; wherein each occurrence of $R^{Y1}$ is independently hydrogen, alkyl, heteroalkyl, aryl, heteroaryl, -(alkyl)aryl or -(alkyl)heteroaryl, —$OR^{Y3}$, —$SR^{Y3}$, —$NR^{Y2}R^{Y3}$, —$SO_2NR^{Y2}R^{Y3}$, —$C(=O)NR^{Y2}R^{Y3}$, halogen, —CN, —$NO_2$, —$C(=O)OR^{Y3}$, —$N(R^{Y2})C(=O)R^{Y3}$, wherein each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or $R^{Y2}$ and $R^{Y3}$ taken together with the nitrogen atom to which they are attached form a 5-6 membered heterocyclic ring.

56. The compound according to claim 1, wherein:
Y is

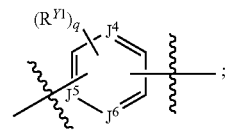

q is an integer from 0-3; and
$J^4$, $J^5$ and $J^6$ are independently N or $CR^{Y1}$; wherein each occurrence of $R^{Y1}$ is independently hydrogen, alkyl, heteroalkyl, aryl, heteroaryl, -(alkyl)aryl or -(alkyl)heteroaryl, —$OR^{Y3}$, —$SR^{Y3}$, —$NR^{Y2}R^{Y3}$, —$SO_2NR^{Y2}R^{Y3}$, —$C(=O)NR^{Y2}R^{Y3}$, halogen, —CN, —$NO_2$, —$C(=O)OR^{Y3}$, —$N(R^{Y2})C(=O)R^{Y3}$, wherein each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or $R^{Y2}$ and $R^{Y3}$ taken together with the nitrogen atom to which they are attached form a 5-6 membered heterocyclic ring.

57. The compound according to claim 6, wherein:
Y is a divalent Cy moiety;
Cy is

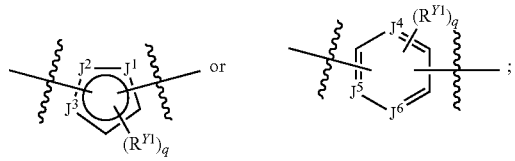

q is an integer from 0-3;

$J^1$, $J^2$ and $J^3$ are independently O, S, N, $NR^{Y1}$ or $CR^{Y1}$; $J^4$, $J^5$ and $J^6$ are independently N or $CR^{Y1}$; wherein each occurrence of $R^{Y1}$ is independently hydrogen, alkyl, heteroalkyl, aryl, heteroaryl, -(alkyl)aryl or -(alkyl)heteroaryl, $-OR^{Y3}$, $-SR^{Y3}$, $-NR^{Y2}R^{Y3}$, $-SO_2NR^{Y2}R^{Y3}$, $-C(=O)NR^{Y2}R^{Y3}$, halogen, $-CN$, $-NO_2$, $-C(=O)OR^{Y3}$, $-N(R^{Y2})C(=O)R^{Y3}$, wherein each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or $R^{Y2}$ and $R^{Y3}$ taken together with the nitrogen atom to which they are attached form a 5-6 membered heterocyclic ring; $G_2$ is a single bond, O or $NR^{G2}$; and $R^{W3}$ and $R^{G2}$ are independently hydrogen, lower alkyl, lower heteroalkyl, aryl, heteroaryl, -(alkyl)aryl, -(alkyl)heteroaryl or acyl; and $J^4$, $J^5$ and $J^6$ are independently N or $CR^{Y1}$; wherein each occurrence of $R^{Y1}$ is independently hydrogen, alkyl, heteroalkyl, aryl, heteroaryl, -(alkyl)aryl or -(alkyl)heteroaryl, $-OR^{Y3}$, $-SR^{Y3}$, $-NR^{Y2}R^{Y3}$, $-SO_2NR^{Y2}R^{Y3}$, $-C(=O)NR^{Y2}R^{Y3}$, halogen, $-CN$, $-NO_2$, $-C(=O)OR^{Y3}$, $-N(R^{Y2})C(=O)R^{Y3}$, wherein each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or $R^{Y2}$ and $R^{Y3}$ taken together with the nitrogen atom to which they are attached form a 5-6 membered heterocyclic ring.

58. The compound according to claim 8, wherein:
Y is a divalent Cy moiety;
Cy is

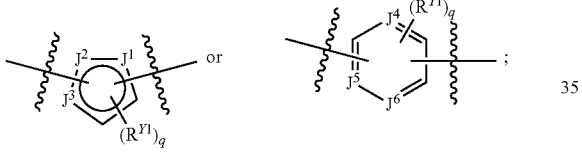

q is an integer from 0-3; and
$J^1$, $J^2$ and $J^3$ are independently O, S, N, $NR^{Y1}$ or $CR^{Y1}$; $J^4$, $J^5$ and $J^6$ are independently N or $CR^{Y1}$; wherein each occurrence of $R^{Y1}$ is independently hydrogen, alkyl, heteroalkyl, aryl, heteroaryl, -(alkyl)aryl or -(alkyl)heteroaryl, $-OR^{Y3}$, $-SR^{Y3}$, $-NR^{Y2}R^{Y3}$, $-SO_2NR^{Y2}R^{Y3}$, $-C(=O)NR^{Y2}R^{Y3}$, halogen, $-CN$, $-NO_2$, $-C(=O)OR^{Y3}$, $-N(R^{Y2})C(=O)R^{Y3}$, wherein each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or $R^{Y2}$ and $R^{Y3}$ taken together with the nitrogen atom to which they are attached form a 5-6 membered heterocyclic ring; and $G_2$ is a single bond, O or $NR^{G2}$.

59. The compound according to claim 1, wherein:
$L^2$ is a single bond;
Z is:

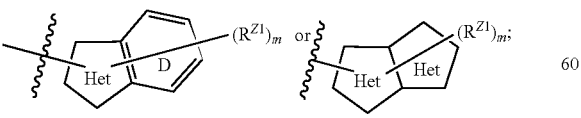

the "D" cyclic moiety is a 6-membered aromatic ring comprising from 0-4 nitrogen atoms;
each "Het" moiety independently represents a fully or partially saturated or unsaturated 5-membered ring comprising 1-4 heteroatoms selected from N, O and S; m is an integer from 0-6; and
each occurrence of $R^{Z1}$ is independently hydrogen, alkyl, heteroalkyl, aryl, heteroaryl, -(alkyl)aryl, -(alkyl)heteroaryl, $-OR^{Z2}$, $-SR^{Z2}$, $-N(R^{Z2})_2$, $-SO_2N(R^{Z2})_2$, $-SO_2R^{Z4}$, $-C(=O)N(R^{Z2})_2$, halogen, $-CN$, $-NO_2$, $-C(=O)OR^{Z2}$, $-N(R^{Z2})C(=O)R^{Z3}$ or $-N(R^{Z2})SO_2R^{Z4}$; wherein each occurrence of $R^{Z2}$ and $R^{Z3}$ is independently hydrogen, lower alkyl, lower heteroalkyl, aryl, heteroaryl, -(alkyl)aryl, -(alkyl)heteroaryl, acyl; or any two occurrences of $R^{Z2}$, taken together with the nitrogen atom to which they are attached form a substituted or unsubstituted heterocyclic moiety; and $R^{Z4}$ is alkyl, heteroalkyl, aryl, heteroaryl, -(alkyl)aryl, or -(alkyl)heteroaryl; and wherein any two adjacent occurrence of $R^{Z1}$ may form a fused 5- to 6-membered aryl, heteroaryl or heterocyclic ring.

60. The compound according to claim 14, wherein:
Cy is

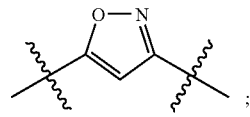

$L^2$ is a single bond; and
Z is

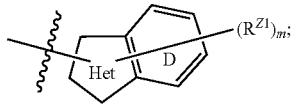

the "D" cyclic moiety is a 6-membered aromatic ring comprising from 0-4 nitrogen atoms;
each "Het" moiety independently represents a fully or partially saturated or unsaturated 5-membered ring comprising 1-4 heteroatoms selected from N, O and S; m is an integer from 0-6; and
each occurrence of $R^{Z1}$ is independently hydrogen, alkyl, heteroalkyl, aryl, heteroaryl, -(alkyl)aryl, -(alkyl)heteroaryl, $-OR^{Z2}$, $-SR^{Z2}$, $-N(R^{Z2})_2$, $-SO_2N(R^{Z2})_2$, $-SO_2R^{Z4}$, $-C(=O)N(R^{Z2})_2$, halogen, $-CN$, $-NO_2$, $-C(=O)OR^{Z2}$, $-N(R^{Z2})C(=O)R^{Z3}$ or $-N(R^{Z2})SO_2R^{Z4}$; wherein each occurrence of $R^{Z2}$ and $R^{Z3}$ is independently hydrogen, lower alkyl, lower heteroalkyl, aryl, heteroaryl, -(alkyl)aryl, -(alkyl)heteroaryl, acyl; or any two occurrences of $R^{Z2}$, taken together with the nitrogen atom to which they are attached form a substituted or unsubstituted heterocyclic moiety; and $R^{Z4}$ is alkyl, heteroalkyl, aryl, heteroaryl, -(alkyl)aryl, or -(alkyl)heteroaryl; and wherein any two adjacent occurrence of $R^{Z1}$ may form a fused 5- to 6-membered aryl, heteroaryl or heterocyclic ring.

* * * * *